US009551009B2

(12) United States Patent
Fontayne et al.

(10) Patent No.: US 9,551,009 B2
(45) Date of Patent: Jan. 24, 2017

(54) TRANSCRIPTION UNIT AND USE THEREOF IN EXPRESSION VECTORS

(71) Applicant: LABORATOIRE FRANCAIS DU FRACTIONNEMENT ET DES BIOTECHNOLOGIES, Courtaboeuf (FR)

(72) Inventors: Alexandre Fontayne, La Madeleine (FR); Francois Coutard, Ales (FR)

(73) Assignee: LABORATOIRE FRANCAIS DU FRACTIONNEMENT ET DES BIOTECHNOLOGIES, Courtaboeuf (FR)

( * ) Notice: Subject to any disclaimer, the term of this patent is extended or adjusted under 35 U.S.C. 154(b) by 0 days.

(21) Appl. No.: 14/354,331

(22) PCT Filed: Oct. 29, 2012

(86) PCT No.: PCT/FR2012/052496
§ 371 (c)(1),
(2) Date: Apr. 25, 2014

(87) PCT Pub. No.: WO2013/061010
PCT Pub. Date: May 2, 2013

(65) Prior Publication Data
US 2014/0242638 A1 Aug. 28, 2014

(30) Foreign Application Priority Data
Oct. 28, 2011 (FR) .................................... 11 59864

(51) Int. Cl.
C12N 15/85 (2006.01)
C07K 16/28 (2006.01)
C12P 21/00 (2006.01)

(52) U.S. Cl.
CPC ........... *C12N 15/85* (2013.01); *C07K 16/2869* (2013.01); *C07K 16/2887* (2013.01); *C07K 16/2896* (2013.01); *C12P 21/00* (2013.01); *C12N 2830/15* (2013.01); *C12N 2830/42* (2013.01)

(58) Field of Classification Search
None
See application file for complete search history.

(56) References Cited

U.S. PATENT DOCUMENTS

| 5,024,939 | A * | 6/1991 | Gorman ........................ 435/69.1 |
| 2004/0091913 | A1* | 5/2004 | Livingston et al. .............. 435/6 |
| 2004/0110921 | A1* | 6/2004 | Orita et al. .................... 530/350 |
| 2008/0250514 | A1* | 10/2008 | Tsunoda et al. ................ 800/13 |
| 2009/0083866 | A1* | 3/2009 | Gu et al. .......................... 800/3 |
| 2009/0170727 | A1* | 7/2009 | Reed ............................... 506/26 |
| 2009/0271884 | A1* | 10/2009 | Poueymirou et al. .......... 800/21 |
| 2012/0258096 | A1 | 10/2012 | Beliard et al. |
| 2012/0309050 | A1* | 12/2012 | Kumon et al. ............... 435/69.1 |

FOREIGN PATENT DOCUMENTS

| EP | 1 405 908 A1 | 4/2004 |
| WO | 01/77181 A2 | 10/2001 |
| WO | 03/106658 A1 | 12/2003 |
| WO | 2004/050879 A1 | 6/2004 |
| WO | 2006/022944 A2 | 3/2006 |
| WO | 2009/042971 A2 | 4/2009 |
| WO | 2011/110864 A1 | 9/2011 |

OTHER PUBLICATIONS

Foecking M K et al.: "Powerful and versatile enhancer-promoter unit for mammalian expression vectors", Gene. Elsevier. Amsterdam. NL. vo 1. 45. No. 1. Jan. 1, 1986 (Jan. 1, 1986). pp. 101-105. XP025688566. ISSN: 0378-1119. DOI: 10.1016/0378-1119(86)90137-X [retrieved on Jan. 1, 1986] p. 104.
Liu H et al.: "Genomic organization and characterization of promoter function of the human CDK9 gene", Gene. Elsevier. Amsterdam. NL. vol. 252. No. 1-2. Jul. 11, 2000 (Jul. 11, 2000). pp. 51-59, XP004210154 ISSN: 0378-1119. DOI: 10.1016/S0378-1119(00)00215-8 p. 58; figure 4.
Liu H et al.: "Isolation and characterization of the human cyclin TI promoter", Gene. Elsevier. Amsterdam. NL. vol. 252. No. 1-2. Jul. 11, 2000 (Jul. 11, 2000). pp. 39-49, XP004210153, ISSN: 0378-1119. DOI: 10.1016/0378-1119(00)00214-6 figure 5.
Giulia De Falco et al.: "Cdk9/Cycl in T1 complex: A key player during the activation/differentiation process of normal lymphoid B cell S", Journal of Cellular Physiology, vol. 215. No. 1. Apr. 1, 2008 (Apr. 1, 2008) pp. 276-282. XP055051946, ISSN: 0021-9541. DOI: 10.1002/jcp.21311 p. 278.
R. E. Rhoads: "Internal Initiation of Translation Directed by the 5'-Untranslated Region of the mRNA for eIF4G, a Factor Involved in the Picornavirus-induced Switch from Cap-dependent to Internal Initiation", Journal of Biological Chemistry, vol. 271, No. 2, Jan. 12, 1996 (Jan. 12, 1996), pp. 623-626, XP055028850, ISSN: 0021-9258, DOI: 10.1074/jbc.271.2.623 figures 1-3.
Yoo E M et al.: "Myeloma expression systems", Journal of Immunological Methods, Elsevier Science Publishers B.V.,Amsterdam, NL, vol. 261, No. 1-2, Mar. 1, 2002 (Mar. 1, 2002), pp. 1-20, XP004341264, ISSN: 0022-1759 the whole document.
International Search Report, dated Feb. 15, 2013, from corresponding PCT application.
FR Search Report, dated Jun. 5, 2012, from corresponding FR application.

* cited by examiner

*Primary Examiner* — Addison D Ault
(74) *Attorney, Agent, or Firm* — Young & Thompson

(57) ABSTRACT

A transcription unit constituted by a polynucleotide including the hCMVie virus enhancer, the enhancer having the nucleotide sequence SEQ ID NO: 1, or a nucleotide acid having at least 70% sequence identity with the sequence SEQ ID NO: 1 and essentially having transcription activation properties, and the promoter region of Cyclin-Dependent Kinase 9 (CDK9), the promoter region having the nucleotide sequence SEQ ID NO: 2, or a nucleotide acid having at least 70% sequence identity with the sequence SEQ ID NO: 2 and essentially having a promoter activity.

8 Claims, 25 Drawing Sheets

SEQUENCE LISTING

<160> NUMBER OF SEQ ID NOS: 71

<210> SEQ ID NO 1
<211> LENGTH: 306

```
<212> TYPE: DNA
<213> ORGANISM: Artificial Sequence
<220> FEATURE:
<223> OTHER INFORMATION: CMV

<400> SEQUENCE: 1
gcgttacata acttacggta aatggcccgc ctggctgacc gcccaacgac ccccgcccat    60
tgacgtcaat aatgacgtat gttcccatag taacgccaat agggactttc cattgacgtc   120
aatgggtgga gtatttacgg taaactgccc acttggcagt acatcaagtg tatcatatgc   180
caagtacgcc ccctattgac gtcaatgacg gtaaatggcc cgcctggcat tatgcccagt   240
acatgacctt atgggacttt cctacttggc agtacatcta cgtattagtc atcgctatta   300
ccatgg                                                             306

<210> SEQ ID NO 2
<211> LENGTH: 352
<212> TYPE: DNA
<213> ORGANISM: Artificial Sequence
<220> FEATURE:
<223> OTHER INFORMATION: CDK9

<400> SEQUENCE: 2
catgcagcgg gacgcgccac cccgagcccc agctccggcg ccccggctcc ccgcgccccc    60
gatcggggcc gccgctagta gtggcggcgg cggaggcggg ggcagcggcg gcggcggcgg   120
aggcgcctct gcagctccgg ctcccccctgg cctctcggga actacaagtc caggggggcc   180
tggcggtggg cggcgggcgg aagaggcggg gtcggcgccg cgaggccgga agtggccgtg   240
gaggcggaag tggcgcggcc gcggaggggc ctggagtgcg gcggcggcgg gacccggagc   300
aggagcggcg gcagcagcga ctggggcgg cggcggcgcg ttggaggcgg cc           352

<210> SEQ ID NO 3
<211> LENGTH: 267
<212> TYPE: DNA
<213> ORGANISM: Artificial Sequence
<220> FEATURE:
<223> OTHER INFORMATION: U1

<400> SEQUENCE: 3
ggctcgcatc tctccttcac gcgcccgccg ccctacctga ggccgccatc cacgccggtt    60
gagtcgcgtt ctgccgcctc ccgcctgtgg tgcctcctga actgcgtccg ccgtctaggt   120
aagtttaaag ctcaggtcga gaccgggcct ttgtccggcg ctcccttgga gcctacctag   180
actcagccgg ctctccacgc tttgcctgac cctgcttgct caactctacg tctttgtttc   240
gttttctgtt ctgcgccgtt acagatc                                      267

<210> SEQ ID NO 4
<211> LENGTH: 653
<212> TYPE: DNA
<213> ORGANISM: Artificial Sequence
<220> FEATURE:
<223> OTHER INFORMATION: U2

<400> SEQUENCE: 4
cagagtaatg acatggttcc ttccatcctc caaaggtgac caataatagt ttgtaagtat    60
cattatgaac taatgaattt tcaacatatt tgatatattt caatccattg ccatcattgt   120
tcttatcgat atttgagttg gctcactttg ccagtaagag tctattcaaa ttggcttctg   180
agtccatttg acacaacacc tttgatcttt gacagttttcc ttggttttag gtgctagatg   240
```

```
atttctcagg ctcaccttag acatttcctg ccacagactt agaatcagcc atttctctaa      300
ggaccctgat tccatttcat gagaaatgat agagaccaca atcaaaacaa gtcatgaatt      360
tatactgata ttttcaattc aaattaaaga tgaggttttt gctaaatttt tttgagttta      420
tatttgtatg tcttatgctg aaaaatcttg tttcctaatt agtaacataa ttattcattt      480
gatgggtaaa tattttaggg ccgattcttt ggttttatag ccaagatacc ctgttgataa      540
agtcttgtgg gagcaattat aagactggct tattttgaag cttttta aaa aagacatcct     600 tacctgtttt aactgtagat tatattaact taaataggta cagcccacgc ttg            653
```

<210> SEQ ID NO 5
<211> LENGTH: 314
<212> TYPE: DNA
<213> ORGANISM: Artificial Sequence
<220> FEATURE:
<223> OTHER INFORMATION: U3

<400> SEQUENCE: 5

```
gctggtgggt agggatgagg gagggagggg cattgtgatg tacagggctg ctctgtgaga       60
tcaagggtct cttaagggtg ggagctgggg cagggactac gagagcagcc agatgggctg      120
aaagtggaac tcaaggggtt tctggcacct acctacctgc ttcccgctgg ggggtgggga      180
gttggcccag agtcttaaga ttggggcagg gtggagaggt gggctcttcc tgcttcccac      240
tcatcttata gctttctttc cccagatccg aattcgagat ccaaaccaag gaggaaagga      300
tatcacagag gaga                                                        314
```

<210> SEQ ID NO 6
<211> LENGTH: 933
<212> TYPE: DNA
<213> ORGANISM: Artificial Sequence
<220> FEATURE:
<223> OTHER INFORMATION: U1U2

<400> SEQUENCE: 6

```
ggctcgcatc tctccttcac gcgcccgccg ccctacctga ggccgccatc cacgccggtt       60
gagtcgcgtt ctgccgcctc ccgcctgtgg tgcctcctga actgcgtccg ccgtctaggt      120
aagtttaaag ctcaggtcga gaccgggcct ttgtccggcg ctcccttgga gcctacctag      180
actcagccgg ctctccacgc tttgcctgac cctgcttgct caactctacg tctttgtttc      240
gttttctgtt ctgcgccgtt acagatcact agtgtttaaa cagagtaatg acatggttcc      300
ttccatcctc caaaggtgac caataatagt ttgtaagtat cattatgaac taatgaattt      360
tcaacatatt tgatatattt caatccattg ccatcattgt tcttatcgat atttgagttg      420
gctcactttg ccagtaagag tctattcaaa ttggcttctg agtccatttg acacaacacc      480
tttgatcttt gacagtttcc ttggttttag gtgctagatg atttctcagg ctcaccttag      540
acatttcctg ccacagactt agaatcagcc atttctctaa ggaccctgat tccatttcat      600
gagaaatgat agagaccaca atcaaaacaa gtcatgaatt tatactgata ttttcaattc      660
aaattaaaga tgaggttttt gctaaatttt tttgagttta tatttgtatg tcttatgctg      720
aaaaatcttg tttcctaatt agtaacataa ttattcattt gatgggtaaa tattttaggg      780
ccgattcttt ggttttatag ccaagatacc ctgttgataa agtcttgtgg gagcaattat      840
aagactggct tattttgaag cttttta aaa aagacatcct tacctgtttt aactgtagat     900
tatattaact taaataggta cagcccacgc ttg                                   933
```

<210> SEQ ID NO 7
<211> LENGTH: 591
<212> TYPE: DNA
<213> ORGANISM: Artificial Sequence
<220> FEATURE:
<223> OTHER INFORMATION: U1U3

<400> SEQUENCE: 7

```
ggctcgcatc tctccttcac gcgcccgccg ccctacctga ggccgccatc cacgccggtt      60
gagtcgcgtt ctgccgcctc ccgcctgtgg tgcctcctga actgcgtccg ccgtctaggt     120
aagtttaaag ctcaggtcga gaccgggcct tgtccggcg ctcccttgga gcctacctag      180
actcagccgg ctctccacgc tttgcctgac cctgcttgct caactctacg tctttgtttc     240
gttttctgtt ctgcgccgtt acagatcact agttaacgct ggtgggtagg gatgagggag     300
ggaggggcat tgtgatgtac agggctgctc tgtgagatca agggtctctt aagggtggga     360 gctgggcag ggactacgag agcagccaga tgggctgaaa gtggaactca aggggtttct      420
ggcacctacc tacctgcttc ccgctggggg gtggggagtt ggcccagagt cttaagattg     480
gggcagggtg gagaggtggg ctcttcctgc ttcccactca tcttatagct ttctttcccc     540
agatccgaat tcgagatcca aaccaaggag gaaaggatat cacagaggag a              591
```

<210> SEQ ID NO 8
<211> LENGTH: 977
<212> TYPE: DNA
<213> ORGANISM: Artificial Sequence
<220> FEATURE:
<223> OTHER INFORMATION: U2U3

<400> SEQUENCE: 8

```
cagagtaatg acatggttcc ttccatcctc caaaggtgac caataatagt ttgtaagtat      60
cattatgaac taatgaattt tcaacatatt tgatatattt caatccattg ccatcattgt     120
tcttatcgat atttgagttg gctcactttg ccagtaagag tctattcaaa ttggcttctg     180
agtccatttg acacaacacc tttgatcttt gacagtttcc ttggttttag gtgctagatg     240
atttctcagg ctcaccttag acatttcctg ccacagactt agaatcagcc atttctctaa     300
ggaccctgat tccatttcat gagaaatgat agagaccaca atcaaaacaa gtcatgaatt     360
tatactgata ttttcaattc aaattaaaga tgaggttttt gctaaatttt tttgagttta     420
tatttgtatg tcttatgctg aaaaatcttg tttcctaatt agtaacataa ttattcattt     480
gatgggtaaa tattttaggg ccgattcttt ggttttatag ccaagatacc ctgttgataa     540
agtcttgtgg gagcaattat aagactggct tatttttgaag cttttttaaaa aagacatcct    600 tacctgtttt aactgtagat tatattaact taaataggta cagcccacgc ttgactagtt     660
aacgctggtg gtagggatg agggaggag gggcattgtg atgtacaggg ctgctctgtg      720
agatcaaggg tctcttaagg gtgggagctg ggcagggac tacgagagca gccagatggg      780
ctgaaagtgg aactcaaggg gtttctggca cctacctacc tgcttcccgc tggggggtgg     840
ggagttggcc cagagtctta agattgggc agggtggaga ggtgggctct tcctgcttcc     900
cactcatctt atagctttct ttccccagat ccgaattcga gatccaaacc aaggaggaaa     960
ggatatcaca gaggaga                                                   977
```

<210> SEQ ID NO 9
<211> LENGTH: 1257
<212> TYPE: DNA
<213> ORGANISM: Artificial Sequence
<220> FEATURE:

<223> OTHER INFORMATION: U1U2U3

<400> SEQUENCE: 9

```
ggctcgcatc tctccttcac gcgcccgccg ccctacctga ggccgccatc cacgccggtt      60
gagtcgcgtt ctgccgcctc ccgcctgtgg tgcctcctga actgcgtccg ccgtctaggt     120
aagtttaaag ctcaggtcga gaccgggcct ttgtccggcg ctcccttgga gcctacctag     180
actcagccgg ctctccacgc tttgcctgac cctgcttgct caactctacg tctttgtttc     240
gttttctgtt ctgcgccgtt acagatcact agtgtttaaa cagagtaatg acatggttcc     300
ttccatcctc caaaggtgac caataatagt ttgtaagtat cattatgaac taatgaattt     360
tcaacatatt tgatatattt caatccattg ccatcattgt tcttatcgat atttgagttg     420
gctcactttg ccagtaagag tctattcaaa ttggcttctg agtccatttg acacaacacc     480
tttgatcttt gacagtttcc ttggttttag gtgctagatg atttctcagg ctcaccttag     540
acatttcctg ccacagactt agaatcagcc atttctctaa ggaccctgat tccatttcat     600
gagaaatgat agagaccaca atcaaaacaa gtcatgaatt tatactgata ttttcaattc     660
aaattaaaga tgaggttttt gctaaatttt tttgagttta tatttgtatg tcttatgctg     720
aaaaatcttg tttcctaatt agtaacataa ttattcattt gatgggtaaa tattttaggg     780
ccgattcttt ggttttatag ccaagatacc ctgttgataa agtcttgtgg gagcaattat     840
aagactggct tattttgaag ctttttaaaa aagacatcct tacctgtttt aactgtagat     900
tatattaact taaataggta cagcccacgc ttgactagtt aacgctggtg ggtagggatg     960
agggagggag gggcattgtg atgtacaggg ctgctctgtg agatcaaggg tctcttaagg    1020
gtgggagctg gggcagggac tacgagagca gccagatggg ctgaaagtgg aactcaaggg    1080
gtttctggca cctacctacc tgcttcccgc tggggggtgg ggagttggcc cagagtctta    1140
agattggggc agggtggaga ggtgggctct tcctgcttcc cactcatctt atagctttct    1200
ttccccagat ccgaattcga gatccaaacc aaggaggaaa ggatatcaca gaggaga       1257
```

<210> SEQ ID NO 10
<211> LENGTH: 939
<212> TYPE: DNA
<213> ORGANISM: Artificial Sequence
<220> FEATURE:
<223> OTHER INFORMATION: EF1A

<400> SEQUENCE: 10

```
gtaagtgccg tgtgtggttc ccgcgggcct ggcctcttta cgggttatgg cccttgcgtg      60
ccttgaatta cttccacctg gctgcagtac gtgattcttg atcccgagct tcgggttgga     120
agtgggtggg agagttcgag gccttgcgct taaggagccc cttcgcctcg tgcttgagtt     180
gaggcctggc ctgggcgctg gggccgccgc gtgcgaatct ggtggcacct tcgcgcctgt     240
ctcgctgctt tcgataagtc tctagccatt taaaattttt gatgacctgc tgcgacgctt     300
tttttctggc aagatagtct tgtaaatgcg ggccaagatc tgcacactgg tatttcggtt     360
tttgggccg cgggcggcga cggggcccgt gcgtcccagc gcacatgttc ggcgaggcgg     420
ggcctgcgag cgcggccacc gagaatcgga cggggggtagt ctcaagctgg ccggcctgct     480
ctggtgcctg gcctcgcgcc gccgtgtatc gccccgccct gggcggcaag gctggcccgg     540
tcggcaccag ttgcgtgagc ggaaagatgg ccgcttcccg gccctgctgc agggagctca     600
aaatggagga cgcggcgctc gggagagcgg gcgggtgagt cacccacaca aaggaaaagg     660
gcctttccgt cctcagccgt cgcttcatgt gactccacgg agtaccgggc gccgtccagg     720
```

```
cacctcgatt agttctcgag cttttggagt acgtcgtctt taggttgggg ggaggggttt      780
tatgcgatgg agtttcccca cactgagtgg gtggagactg aagttaggcc agcttggcac      840
ttgatgtaat tctccttgga atttgccctt tttgagtttg gatcttggtt cattctcaag      900
cctcagacag tggttcaaag ttttttttctt ccatttcag                            939
```

<210> SEQ ID NO 11
<211> LENGTH: 351
<212> TYPE: DNA
<213> ORGANISM: Artificial Sequence
<220> FEATURE:
<223> OTHER INFORMATION: MROSA

<400> SEQUENCE: 11

```
gtagggatc gggactctgg cgggagggcg gcttggtgcg tttgcgggga tgggcggccg       60
cggcaggccc tccgagcgtg gtggagccgt tctgtgagac agccgggtac gagtcgtgac     120
gctggaaggg gcaagcgggt ggtgggcagg aatgcggtcc gccctgcagc aaccggaggg     180
ggagggagaa gggagcggaa aagtctccac cggacgcggc catggctcgg gggggggggg     240
gcagcggagg agcgcttccg gccgacgtct cgtcgctgat tggcttctttt tcctcccgcc     300 gtgtgtgaaa acacaattgt actaaccttc ttctcttttcc tctcctgaca g             351
```

<210> SEQ ID NO 12
<211> LENGTH: 288
<212> TYPE: DNA
<213> ORGANISM: Artificial Sequence
<220> FEATURE:
<223> OTHER INFORMATION: HTLV-1

<400> SEQUENCE: 12

```
ggctcgcatc tctccttcac gcgcccgccg ccctacctga ggccgccatc cacgccggtt      60
gagtcgcgtt ctgccgcctc ccgcctgtgg tgcctcctga actgcgtccg ccgtctaggt     120
aagtttaaag ctcaggtcga gaccgggcct ttgtccggcg ctcccttgga gcctacctag     180
actcagccgg ctctccacgc tttgcctgac cctgcttgct caactctacg tctttgtttc     240
gttttctgtt ctgcgccgtt acagatccaa gctgtgaccg gcgcctac                  288
```

<210> SEQ ID NO 13
<211> LENGTH: 133
<212> TYPE: DNA
<213> ORGANISM: Artificial Sequence
<220> FEATURE:
<223> OTHER INFORMATION: PCINEO

<400> SEQUENCE: 13

```
gtaagtatca aggttacaag acaggtttaa ggagaccaat agaaactggg cttgtcgaga      60
cagagaagac tcttgcgttt ctgataggca cctattggtc ttactgacat ccactttgcc     120
tttctctcca cag                                                        133
```

<210> SEQ ID NO 14
<211> LENGTH: 951
<212> TYPE: DNA
<213> ORGANISM: Artificial Sequence
<220> FEATURE:
<223> OTHER INFORMATION: artificial sequence

<400> SEQUENCE: 14

```
gcgttacata acttacggta aatggcccgc ctggctgacc gcccaacgac ccccgcccat       60
```

| | |
|---|---|
| tgacgtcaat aatgacgtat gttcccatag taacgccaat agggactttc cattgacgtc | 120 |
| aatgggtgga gtatttacgg taaactgccc acttggcagt acatcaagtg tatcatatgc | 180 |
| caagtacgcc ccctattgac gtcaatgacg gtaaatggcc cgcctggcat tatgcccagt | 240 |
| acatgacctt atgggacttt cctacttggc agtacatcta cgtattagtc atcgctatta | 300 |
| ccatggcccg ggtcgcgaca tgcagcggga cgcgccaccc cgagcccag ctccggcgcc | 360 |
| ccggctcccc gcgccccga tcggggccgc cgctagtagt ggcggcggcg gaggcggggg | 420 |
| cagcggcggc ggcggcggag gcgcctctgc agctccggct ccccctggcc tctcgggaac | 480 |
| tacaagtccc aggggggcctg gcggtgggcg gcgggcggaa gaggcggggt cggcgccgcg | 540 |
| aggccggaag tggccgtgga ggcggaagtg gcgcggccgc ggaggggcct ggagtgcggc | 600 |
| ggcggcggga cccggagcag gagcggcggc agcagcgact gggggcggcg gcggcgcgtt | 660 |
| ggaggcggcc ggatccgttt aaacggctcg catctctcct tcacgcgccc gccgccctac | 720 |
| ctgaggccgc catccacgcc ggttgagtcg cgttctgccg cctcccgcct gtggtgcctc | 780 |
| ctgaactgcg tccgccgtct aggtaagttt aaagctcagg tcgagaccgg gcctttgtcc | 840 |
| ggcgctccct tggagcctac ctagactcag ccggctctcc acgctttgcc tgaccctgct | 900 |
| tgctcaactc tacgtctttg tttcgttttc tgttctgcgc cgttacagat c | 951 |

```
<210> SEQ ID NO 15
<211> LENGTH: 1336
<212> TYPE: DNA
<213> ORGANISM: Artificial Sequence
<220> FEATURE:
<223> OTHER INFORMATION: artificial sequence

<400> SEQUENCE: 15
```

| | |
|---|---|
| gcgttacata acttacggta aatggcccgc ctggctgacc gcccaacgac ccccgcccat | 60 |
| tgacgtcaat aatgacgtat gttcccatag taacgccaat agggactttc cattgacgtc | 120 |
| aatgggtgga gtatttacgg taaactgccc acttggcagt acatcaagtg tatcatatgc | 180 |
| caagtacgcc ccctattgac gtcaatgacg gtaaatggcc cgcctggcat tatgcccagt | 240 |
| acatgacctt atgggacttt cctacttggc agtacatcta cgtattagtc atcgctatta | 300 |
| ccatggcccg ggtcgcgaca tgcagcggga cgcgccaccc cgagcccag ctccggcgcc | 360 |
| ccggctcccc gcgccccga tcggggccgc cgctagtagt ggcggcggcg gaggcggggg | 420 |
| cagcggcggc ggcggcggag gcgcctctgc agctccggct ccccctggcc tctcgggaac | 480 |
| tacaagtccc aggggggcctg gcggtgggcg gcgggcggaa gaggcggggt cggcgccgcg | 540 |
| aggccggaag tggccgtgga ggcggaagtg gcgcggccgc ggaggggcct ggagtgcggc | 600 |
| ggcggcggga cccggagcag gagcggcggc agcagcgact gggggcggcg gcggcgcgtt | 660 |
| ggaggcggcc ggatccgttt aaacagagta atgacatggt tccttccatc ctccaaaggt | 720 |
| gaccaataat agtttgtaag tatcattatg aactaatgaa ttttcaacat atttgatata | 780 |
| tttcaatcca ttgccatcat tgttcttatc gatatttgag ttggctcact ttgccagtaa | 840 |
| gagtctattc aaattggctt ctgagtccat ttgacacaac acctttgatc tttgacagtt | 900 |
| tccttggttt taggtgctag atgatttctc aggctcacct tagacatttc ctgccacaga | 960 |
| cttagaatca gccatttctc taaggaccct gattccattt catgagaaat gatagagacc | 1020 |
| acaatcaaaa caagtcatga atttatactg atattttcaa ttcaaattaa agatgaggtt | 1080 |
| tttgctaaat ttttttgagt ttatatttgt atgtcttatg ctgaaaaatc ttgtttccta | 1140 |
| attagtaaca taattattca tttgatgggt aaatatttta gggccgattc tttggtttta | 1200 |

```
tagccaagat accctgttga taaagtcttg tgggagcaat tataagactg gcttattttg    1260
aagcttttta aaaaagacat ccttacctgt tttaactgta gattatatta acttaaatag    1320
gtacagccca cgcttg                                                    1336
```

<210> SEQ ID NO 16
<211> LENGTH: 997
<212> TYPE: DNA
<213> ORGANISM: Artificial Sequence
<220> FEATURE:
<223> OTHER INFORMATION: artificial sequence

<400> SEQUENCE: 16

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg gtcgcgaca tgcagcggga cgcgccaccc cgagcccag ctccggcgcc      360 ccggctcccc gcgccccga tcggggccgc cgctagtagt ggcggcggcg gaggcggggg     420
cagcggcggc ggcggcggag gcgcctctgc agctccggct ccccctggcc tctcgggaac     480
tacaagtccc aggggggcctg gcggtgggcg gcgggcggaa gaggcggggt cggcgccgcg     540
aggccggaag tggccgtgga ggcggaagtg gcgcggccgc ggaggggcct ggagtgcggc     600
ggcggcggga cccggagcag gagcggcggc agcagcgact ggggggcggcg gcggcgcgtt     660 ggaggcggcc ggatccgttt aacgctggtg ggtagggatg agggagggag gggcattgtg     720
atgtacaggg ctgctctgtg agatcaaggg tctcttaagg gtgggagctg gggcagggac     780
tacgagagca gccagatggg ctgaaagtgg aactcaaggg gttctggca cctacctacc     840 tgcttcccgc tggggggtgg ggagttggcc cagagtctta agattgggc agggtggaga     900 ggtgggctct tcctgcttcc cactcatctt atagctttct ttccccagat ccgaattcga     960
gatccaaacc aaggaggaaa ggatatcaca gaggaga                              997
```

<210> SEQ ID NO 17
<211> LENGTH: 1617
<212> TYPE: DNA
<213> ORGANISM: Artificial Sequence
<220> FEATURE:
<223> OTHER INFORMATION: artificial sequence

<400> SEQUENCE: 17

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg gtcgcgaca tgcagcggga cgcgccaccc cgagcccag ctccggcgcc      360 ccggctcccc gcgccccga tcggggccgc cgctagtagt ggcggcggcg gaggcggggg     420
cagcggcggc ggcggcggag gcgcctctgc agctccggct ccccctggcc tctcgggaac     480
tacaagtccc aggggggcctg gcggtgggcg gcgggcggaa gaggcggggt cggcgccgcg     540
```

```
aggccggaag tggccgtgga ggcggaagtg gcgcggccgc ggaggggcct ggagtgcggc    600
ggcggcggga cccggagcag gagcggcggc agcagcgact gggggcggcg gcggcgcgtt    660
ggaggcggcc ggatccgttt aaacggctcg catctctcct tcacgcgccc gccgccctac    720
ctgaggccgc catccacgcc ggttgagtcg cgttctgccg cctcccgcct gtggtgcctc    780
ctgaactgcg tccgccgtct aggtaagttt aaagctcagg tcgagaccgg gcctttgtcc    840
ggcgctccct tggagcctac ctagactcag ccggctctcc acgctttgcc tgaccctgct    900
tgctcaactc tacgtctttg tttcgttttc tgttctgcgc cgttacagat cactagtgtt    960
taaacagagt aatgacatgg ttccttccat cctccaaagg tgaccaataa tagtttgtaa   1020
gtatcattat gaactaatga attttcaaca tatttgatat atttcaatcc attgccatca   1080
ttgttcttat cgatatttga gttggctcac tttgccagta agagtctatt caaattggct   1140
tctgagtcca tttgacacaa cacctttgat ctttgacagt ttccttggtt ttaggtgcta   1200
gatgatttct caggctcacc ttagacattt cctgccacag acttagaatc agccatttct   1260
ctaaggaccc tgattccatt tcatgagaaa tgatagagac cacaatcaaa acaagtcatg   1320
aatttatact gatattttca attcaaatta aagatgaggt ttttgctaaa ttttttttgag   1380 tttatatttg tatgtcttat gctgaaaaat cttgttttcct aattagtaac ataattattc   1440
atttgatggg taaatatttt agggccgatt ctttggtttt atagccaaga taccctgttg   1500
ataaagtctt gtgggagcaa ttataagact ggcttatttt gaagcttttt aaaaaagaca   1560
tccttacctg ttttaactgt agattatatt aacttaaata ggtacagccc acgcttg      1617
```

<210> SEQ ID NO 18
<211> LENGTH: 1275
<212> TYPE: DNA
<213> ORGANISM: Artificial Sequence
<220> FEATURE:
<223> OTHER INFORMATION: artificial sequence

<400> SEQUENCE: 18

```
gcgttacata acttacggta aatggcccgc ctggctgacc gcccaacgac ccccgcccat     60
tgacgtcaat aatgacgtat gttcccatag taacgccaat agggactttc cattgacgtc    120
aatgggtgga gtatttacgg taaactgccc acttggcagt acatcaagtg tatcatatgc    180
caagtacgcc ccctattgac gtcaatgacg gtaaatggcc cgcctggcat tatgcccagt    240
acatgacctt atgggacttt cctacttggc agtacatcta cgtattagtc atcgctatta    300
ccatggcccg gtcgcgaca tgcagcggga cgcgccaccc cgagcccag ctccggcgcc     360 ccggctcccc gcgcccccga tcggggccgc cgctagtagt ggcggcggcg gaggcggggg    420
cagcggcggc ggcggcggag cgcctctgc agctccggct ccccctggcc tctcgggaac    480
tacaagtccc aggggcctg gcggtgggcg gcgggcggaa gaggcgggt cggcgccgcg     540 aggccggaag tggccgtgga ggcggaagtg gcgcggccgc ggaggggcct ggagtgcggc    600
ggcggcggga cccggagcag gagcggcggc agcagcgact gggggcggcg gcggcgcgtt    660
ggaggcggcc ggatccgttt aaacggctcg catctctcct tcacgcgccc gccgccctac    720
ctgaggccgc catccacgcc ggttgagtcg cgttctgccg cctcccgcct gtggtgcctc    780
ctgaactgcg tccgccgtct aggtaagttt aaagctcagg tcgagaccgg gcctttgtcc    840
ggcgctccct tggagcctac ctagactcag ccggctctcc acgctttgcc tgaccctgct    900
tgctcaactc tacgtctttg tttcgttttc tgttctgcgc cgttacagat cactagttaa    960
cgctggtggg tagggatgag ggagggaggg gcattgtgat gtacagggct gctctgtgag   1020
```

```
atcaagggtc tcttaagggt gggagctggg gcagggacta cgagagcagc cagatgggct    1080
gaaagtggaa ctcaagggt  ttctggcacc tacctacctg cttcccgctg ggggtgggg     1140 agttggccca gagtcttaag attggggcag ggtggagagg tgggctcttc ctgcttccca    1200
ctcatcttat agctttcttt ccccagatcc gaattcgaga tccaaaccaa ggaggaaagg    1260
atatcacaga ggaga                                                    1275
```

<210> SEQ ID NO 19
<211> LENGTH: 1660
<212> TYPE: DNA
<213> ORGANISM: Artificial Sequence
<220> FEATURE:
<223> OTHER INFORMATION: artificial sequence

<400> SEQUENCE: 19

```
gcgttacata acttacggta aatggcccgc ctggctgacc gcccaacgac ccccgcccat     60
tgacgtcaat aatgacgtat gttcccatag taacgccaat agggactttc cattgacgtc    120
aatgggtgga gtatttacgg taaactgccc acttggcagt acatcaagtg tatcatatgc    180
caagtacgcc ccctattgac gtcaatgacg gtaaatggcc cgcctggcat tatgcccagt    240
acatgacctt atgggacttt cctacttggc agtacatcta cgtattagtc atcgctatta    300
ccatggcccg ggtcgcgaca tgcagcggga cgcgccaccc cgagcccag ctccggcgcc     360 ccggctcccc gcgcccccga tcggggccgc cgctagtagt ggcggcggcg gaggcggggg    420
cagcggcggc ggcggcggag gcgcctctgc agctccggct cccctggcc tctcgggaac     480 tacaagtccc agggggcctg gcggtgggcg gcgggcggaa gaggcgggt cggcgccgcg     540 aggccggaag tggccgtgga ggcggaagtg gcgcggccgc ggaggggcct ggagtgcggc    600
ggcggcggga cccggagcag gagcggcggc agcagcgact ggggggcggcg gcggcgcgtt   660 ggaggcggcc ggatccgttt aaacagagta atgacatggt tccttccatc ctccaaaggt    720
gaccaataat agtttgtaag tatcattatg aactaatgaa ttttcaacat atttgatata    780
tttcaatcca ttgccatcat tgttcttatc gatatttgag ttggctcact ttgccagtaa    840
gagtctattc aaattggctt ctgagtccat ttgacacaac acctttgatc tttgacagtt    900
tccttggttt taggtgctag atgatttctc aggctcacct tagacatttc ctgccacaga    960
cttagaatca gccatttctc taaggaccct gattccattt catgagaaat gatagagacc    1020
acaatcaaaa caagtcatga atttatactg atatttcaa ttcaaattaa agatgaggtt     1080
tttgctaaat ttttttgagt ttatatttgt atgtcttatg ctgaaaaatc ttgtttccta    1140
attagtaaca taattattca tttgatgggt aaatatttta gggccgattc tttggtttta    1200
tagccaagat accctgttga taaagtcttg tgggagcaat tataagactg gcttattttg    1260
aagcttttta aaaagacat  ccttacctgt tttaactgta gattatatta acttaaatag    1320
gtacagccca cgcttgacta gttaacgctg gtgggtaggg atgagggagg gaggggcatt    1380
gtgatgtaca gggctgctct gtgagatcaa gggtctctta agggtgggag ctgggcagg    1440 gactacgaga gcagccagat gggctgaaag tggaactcaa ggggttctg gcacctacct     1500 acctgcttcc cgctgggggg tggggagttg gcccagagtc ttaagattgg ggcagggtgg    1560
agaggtgggc tcttcctgct tcccactcat cttatagctt tctttcccca gatccgaatt    1620
cgagatccaa accaaggagg aaaggatatc acagaggaga                         1660
```

<210> SEQ ID NO 20

<211> LENGTH: 1941
<212> TYPE: DNA
<213> ORGANISM: Artificial Sequence
<220> FEATURE:
<223> OTHER INFORMATION: artificial sequence

<400> SEQUENCE: 20

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg gtcgcgaca tgcagcggga cgcgccaccc cgagcccag ctccggcgcc      360
ccggctcccc gcgccccga tcggggccgc cgctagtagt ggcggcggcg gaggcggggg     420
cagcggcggc ggcggcggag cgcctctgc agctccggct cccccctggcc tctcgggaac     480
tacaagtccc aggggcctg gcggtgggcg gcgggcggaa gaggcgggt cggcgccgcg      540
aggccggaag tggccgtgga ggcggaagtg gcgcggccgc ggaggggcct ggagtgcggc     600
ggcggcggga cccggagcag gagcggcggc agcagcgact gggggcggcg gcggcgcgtt     660
ggaggcggcc ggatccgttt aaacggctcg catctctcct tcacgcgccc gccgcctac      720
ctgaggccgc catccacgcc ggttgagtcg cgttctgccg cctcccgcct gtggtgcctc     780
ctgaactgcg tccgccgtct aggtaagttt aaagctcagg tcgagaccgg gcctttgtcc     840
ggcgctccct tggagcctac ctagactcag ccggctctcc acgctttgcc tgaccctgct     900
tgctcaactc tacgtctttg tttcgttttc tgttctgcgc cgttacagat cactagtgtt     960
taaacagagt aatgacatgg ttccttccat cctccaaagg tgaccaataa tagtttgtaa    1020
gtatcattat gaactaatga atttttcaaca tatttgatat atttcaatcc attgccatca    1080
ttgttcttat cgatatttga gttggctcac tttgccagta agagtctatt caaattggct    1140
tctgagtcca tttgacacaa cacctttgat cttttgacagt ttccttggtt ttaggtgcta    1200
gatgattttct caggctcacc ttagacattt cctgccacag acttagaatc agccatttct    1260
ctaaggaccc tgattccatt tcatgagaaa tgatagagac cacaatcaaa acaagtcatg    1320
aatttatact gatattttca attcaaatta aagatgaggt ttttgctaaa tttttttgag    1380
tttatatttg tatgtcttat gctgaaaat cttgtttcct aattagtaac ataattattc    1440
atttgatggg taaatatttt agggccgatt cttttggtttt atagccaaga taccctgttg    1500
ataaagtctt gtgggagcaa ttataagact ggcttatttt gaagctttt aaaaaagaca    1560
tccttacctg ttttaactgt agattatatt aacttaaata ggtacagccc acgcttgact    1620
agttaacgct ggtgggtagg gatgagggag ggaggggcat tgtgatgtac agggctgctc    1680
tgtgagatca agggtctctt aagggtggga gctgggcag ggactacgag agcagccaga    1740
tgggctgaaa gtggaactca agggggtttct ggcacctacc tacctgcttc ccgctggggg    1800
gtggggagtt ggcccagagt cttaagattg gggcagggtg gagaggtggg ctcttcctgc    1860
ttcccactca tcttatagct ttcttttcccc agatccgaat tcgagatcca aaccaaggag    1920
gaaaggatat cacagaggag a                                             1941
```

<210> SEQ ID NO 21
<211> LENGTH: 1643
<212> TYPE: DNA
<213> ORGANISM: Artificial Sequence
<220> FEATURE:
<223> OTHER INFORMATION: artificial sequence

<400> SEQUENCE: 21

| | | | | |
|---|---|---|---|---|
| gcgttacata | acttacggta | aatggcccgc | ctggctgacc | gcccaacgac | ccccgcccat | 60 |
| tgacgtcaat | aatgacgtat | gttcccatag | taacgccaat | agggactttc | cattgacgtc | 120 |
| aatgggtgga | gtatttacgg | taaactgccc | acttggcagt | acatcaagtg | tatcatatgc | 180 |
| caagtacgcc | ccctattgac | gtcaatgacg | gtaaatggcc | cgcctggcat | tatgcccagt | 240 |
| acatgacctt | atgggacttt | cctacttggc | agtacatcta | cgtattagtc | atcgctatta | 300 |
| ccatggcccg | ggtcgcgaca | tgcagcggga | cgcgccaccc | cgagcccag | ctccggcgcc | 360 |
| ccggctcccc | gcgccccga | tcggggccgc | cgctagtagt | ggcggcggcg | gaggcggggg | 420 |
| cagcggcggc | ggcggcggag | gcgcctctgc | agctccggct | cccctggcc | tctcgggaac | 480 |
| tacaagtccc | aggggcctg | gcggtgggcg | gcgggcggaa | gaggcggggt | cggcgccgcg | 540 |
| aggccggaag | tggccgtgga | ggcggaagtg | gcgcggccgc | ggagggggcct | ggagtgcggc | 600 |
| ggcggcggga | cccggagcag | gagcggcggc | agcagcgact | gggggcggcg | gcggcgcgtt | 660 |
| ggaggcggcc | ggatccacta | gtcgggtttg | ccgccagaac | acaggtaagt | gccgtgtgtg | 720 |
| gttcccgcgg | gcctggcctc | tttacgggtt | atggcccttg | cgtgccttga | attacttcca | 780 |
| cctggctgca | gtacgtgatt | cttgatcccg | agcttcgggt | tggaagtggg | tgggagagtt | 840 |
| cgaggccttg | cgcttaagga | gccccttcgc | ctcgtgcttg | agttgaggcc | tggcctgggc | 900 |
| gctggggccg | ccgcgtgcga | atctggtggc | accttcgcgc | ctgtctcgct | gctttcgata | 960 |
| agtctctagc | catttaaaat | ttttgatgac | ctgctgcgac | gcttttttttc | tggcaagata | 1020 |
| gtcttgtaaa | tgcgggccaa | gatctgcaca | ctggtatttc | ggttttttggg | gccgcgggcg | 1080 |
| gcgacggggc | ccgtgcgtcc | cagcgcacat | gttcggcgag | gcggggcctg | cgagcgcggc | 1140 |
| caccgagaat | cggacggggg | tagtctcaag | ctggccggcc | tgctctggtg | cctggcctcg | 1200 |
| cgccgccgtg | tatcgccccg | ccctgggcgg | caaggctggc | ccggtcggca | ccagttgcgt | 1260 |
| gagcggaaag | atggccgctt | ccggcccctg | ctgcagggag | ctcaaaatgg | aggacgcggc | 1320 |
| gctcgggaga | gcgggcgggt | gagtcaccca | cacaaaggaa | aagggccttt | ccgtcctcag | 1380 |
| ccgtcgcttc | atgtgactcc | acggagtacc | gggcgccgtc | caggcacctc | gattagttct | 1440 |
| cgagcttttg | gagtacgtcg | tctttaggtt | gggggagg | gttttatgcg | atggagtttc | 1500 |
| cccacactga | gtgggtggag | actgaagtta | ggccagcttg | gcacttgatg | taattctcct | 1560 |
| tggaatttgc | ccttttttgag | tttggatctt | ggttcattct | caagcctcag | acagtggttc | 1620 |
| aaagtttttt | tcttccattt | cag | | | | 1643 |

<210> SEQ ID NO 22
<211> LENGTH: 1051
<212> TYPE: DNA
<213> ORGANISM: Artificial Sequence
<220> FEATURE:
<223> OTHER INFORMATION: artificial sequence

<400> SEQUENCE: 22

| | | | | | |
|---|---|---|---|---|---|
| gcgttacata | acttacggta | aatggcccgc | ctggctgacc | gcccaacgac | ccccgcccat | 60 |
| tgacgtcaat | aatgacgtat | gttcccatag | taacgccaat | agggactttc | cattgacgtc | 120 |
| aatgggtgga | gtatttacgg | taaactgccc | acttggcagt | acatcaagtg | tatcatatgc | 180 |
| caagtacgcc | ccctattgac | gtcaatgacg | gtaaatggcc | cgcctggcat | tatgcccagt | 240 |

```
acatgacctt atgggacttt cctacttggc agtacatcta cgtattagtc atcgctatta    300
ccatggcccg ggtcgcgaca tgcagcggga cgcgccaccc cgagcccag ctccggcgcc     360 ccggctcccc gcgcccccga tcggggccgc cgctagtagt ggcggcggcg gaggcggggg    420
cagcggcggc ggcggcggag gcgcctctgc agctccggct cccctggcc tctcgggaac     480 tacaagtccc aggggcctg cggtgggcg gcgggcggaa gaggcggggt cggcgccgcg      540
aggccggaag tggccgtgga ggcggaagtg gcgcggccgc ggaggggcct ggagtgcggc    600
ggcggcggga cccggagcag gagcggcggc agcagcgact ggggcggcg gcggcgcgtt    660 ggaggcggcc ggatccacta gttcagagag cctcggctag gtagggatc gggactctgg    720 cgggagggcg gcttggtgcg tttgcgggga tgggcggccg cggcaggccc tccgagcgtg    780
gtggagccgt tctgtgagac agccgggtac gagtcgtgac gctggaaggg gcaagcgggt   840
ggtgggcagg aatgcggtcc gccctgcagc aaccggaggg ggagggagaa gggagcggaa  900
aagtctccac cggacgcggc catggctcgg ggggggggg gcagcggagg agcgcttccg    960
gccgacgtct cgtcgctgat tggcttcttt tcctcccgcc gtgtgtgaaa acacaattgt  1020
actaaccttc ttctctttcc tctcctgaca g                                 1051
```

<210> SEQ ID NO 23
<211> LENGTH: 978
<212> TYPE: DNA
<213> ORGANISM: Artificial Sequence
<220> FEATURE:
<223> OTHER INFORMATION: artificial sequence

<400> SEQUENCE: 23

```
gcgttacata acttacggta aatggcccgc ctggctgacc gcccaacgac ccccgcccat    60
tgacgtcaat aatgacgtat gttcccatag taacgccaat agggactttc cattgacgtc  120
aatgggtgga gtatttacgg taaactgccc acttggcagt acatcaagtg tatcatatgc  180
caagtacgcc ccctattgac gtcaatgacg gtaaatggcc cgcctggcat tatgcccagt  240
acatgacctt atgggacttt cctacttggc agtacatcta cgtattagtc atcgctatta  300
ccatggcccg ggtcgcgaca tgcagcggga cgcgccaccc cgagcccag ctccggcgcc   360 ccggctcccc gcgcccccga tcggggccgc cgctagtagt ggcggcggcg gaggcggggg  420
cagcggcggc ggcggcggag gcgcctctgc agctccggct cccctggcc tctcgggaac   480 tacaagtccc aggggcctg cggtgggcg gcgggcggaa gaggcggggt cggcgccgcg    540
aggccggaag tggccgtgga ggcggaagtg gcgcggccgc ggaggggcct ggagtgcggc  600
ggcggcggga cccggagcag gagcggcggc agcagcgact ggggcggcg gcggcgcgtt  660 ggaggcggcc ggatccacta gtcttcgagg ggctcgcatc tctccttcac gcgcccgccg  720
ccctacctga ggccgccatc cacgccggtt gagtcgcgtt ctgccgcctc ccgcctgtgg  780
tgcctcctga actgcgtccg ccgtctaggt aagtttaaag ctcaggtcga ccgggcct    840 ttgtccggcg ctcccttgga gcctacctag actcagccgg ctctccacgc tttgcctgac  900
cctgcttgct caactctacg tctttgtttc gttttctgtt ctgcgccgtt acagatccaa  960
gctgtgaccg gcgcctac                                                978
```

<210> SEQ ID NO 24
<211> LENGTH: 844
<212> TYPE: DNA
<213> ORGANISM: Artificial Sequence
<220> FEATURE:
<223> OTHER INFORMATION: artificial sequence

<400> SEQUENCE: 24

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg ggtcgcgaca tgcagcggga cgcgccaccc cgagcccag ctccggcgcc      360
ccggctcccc gcgcccccga tcggggccgc cgctagtagt ggcggcggcg gaggcggggg     420
cagcggcggc ggcggcggag gcgcctctgc agctccggct ccccctggcc tctcgggaac     480
tacaagtccc aggggggcctg gcggtgggcg gcgggcggaa gaggcggggt cggcgccgcg    540
aggccggaag tggccgtgga ggcggaagtg gcgcggccgc ggaggggcct ggagtgcggc     600
ggcggcggga cccggagcag gagcggcggc agcagcgact gggggcggcg gcggcgcgtt     660
ggaggcggcc ggatccacta gtgcagaagt tggtcgtgag gcactgggca ggtaagtatc     720
aaggttacaa gacaggttta aggagaccaa tagaaactgg gcttgtcgag acagagaaga    780
ctcttgcgtt tctgataggc acctattggt cttactgaca tccactttgc ctttctctcc    840
acag                                                                 844
```

<210> SEQ ID NO 25
<211> LENGTH: 1918
<212> TYPE: DNA
<213> ORGANISM: Artificial Sequence
<220> FEATURE:
<223> OTHER INFORMATION: artificial sequence

<400> SEQUENCE: 25

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg ggtcgcgaca tgcagcggga cgcgccaccc cgagcccag ctccggcgcc      360
ccggctcccc gcgcccccga tcggggccgc cgctagtagt ggcggcggcg gaggcggggg     420
cagcggcggc ggcggcggag gcgcctctgc agctccggct ccccctggcc tctcgggaac     480
tacaagtccc aggggggcctg gcggtgggcg gcgggcggaa gaggcggggt cggcgccgcg    540
aggccggaag tggccgtgga ggcggaagtg gcgcggccgc ggaggggcct ggagtgcggc     600
ggcggcggga cccggagcag gagcggcggc agcagcgact gggggcggcg gcggcgcgtt     660
ggaggcggcc ggatccgttt aaacggctcg catctctcct tcacgcgccc gccgccctac    720
ctgaggccgc catccacgcc ggttgagtcg cgttctgccg cctcccgcct gtggtgcctc    780
ctgaactgcg tccgccgtct aggtaagttt aaagctcagg tcgagaccgg cctttgtcc    840
ggcgctccct tggagcctac ctagactcag ccggctctcc acgctttgcc tgaccctgct    900
tgctcaactc tacgtctttg tttcgttttc tgttctgcgc cgttacagat cactagtcgg    960
gtttgccgcc agaacacagg taagtgccgt gtgtggttcc cgcgggcctg gcctctttac    1020
gggttatggc ccttgcgtgc cttgaattac ttccacctgg ctgcagtacg tgattcttga    1080
```

| | |
|---|---:|
| tcccgagctt cgggttggaa gtgggtggga gagttcgagg ccttgcgctt aaggagcccc | 1140 |
| ttcgcctcgt gcttgagttg aggcctggcc tgggcgctgg ggccgccgcg tgcgaatctg | 1200 |
| gtggcacctt cgcgcctgtc tcgctgcttt cgataagtct ctagccattt aaaattttg | 1260 |
| atgacctgct gcgacgcttt ttttctggca agatagtctt gtaaatgcgg gccaagatct | 1320 |
| gcacactggt atttcggttt ttggggccgc gggcggcgac ggggcccgtg cgtcccagcg | 1380 |
| cacatgttcg gcgaggcggg gcctgcgagc gcggccaccg agaatcggac ggggtagtc | 1440 |
| tcaagctggc cggcctgctc tggtgcctgg cctcgcgccg ccgtgtatcg ccccgccctg | 1500 |
| ggcggcaagg ctggcccggt cggcaccagt tgcgtgagcg gaaagatggc cgcttcccgg | 1560 |
| ccctgctgca gggagctcaa aatggaggac gcggcgctcg ggagagcggg cgggtgagtc | 1620 |
| acccacacaa aggaaaaggg cctttccgtc ctcagccgtc gcttcatgtg actccacgga | 1680 |
| gtaccgggcg ccgtccaggc acctcgatta gttctcgagc ttttggagta cgtcgtctt | 1740 |
| aggttggggg gaggggtttt atgcgatgga gtttccccac actgagtggg tggagactga | 1800 |
| agttaggcca gcttggcact tgatgtaatt ctccttggaa tttgcccttt ttgagtttgg | 1860 |
| atcttggttc attctcaagc ctcagacagt ggttcaaagt ttttttcttc catttcag | 1918 |

<210> SEQ ID NO 26
<211> LENGTH: 1326
<212> TYPE: DNA
<213> ORGANISM: Artificial Sequence
<220> FEATURE:
<223> OTHER INFORMATION: artificial sequence

<400> SEQUENCE: 26

| | |
|---|---:|
| gcgttacata acttacggta aatggcccgc ctggctgacc gcccaacgac ccccgcccat | 60 |
| tgacgtcaat aatgacgtat gttcccatag taacgccaat agggactttc cattgacgtc | 120 |
| aatgggtgga gtatttacgg taaactgccc acttggcagt acatcaagtg tatcatatgc | 180 |
| caagtacgcc ccctattgac gtcaatgacg gtaaatggcc cgcctggcat tatgcccagt | 240 |
| acatgacctt atgggacttt cctacttggc agtacatcta cgtattagtc atcgctatta | 300 |
| ccatggcccg gtcgcgaca tgcagcggga cgcgccaccc cgagcccag ctccggcgcc | 360 |
| ccggctcccc gcgcccccga tcggggccgc cgctagtagt ggcggcggcg gaggcggggg | 420 |
| cagcggcggc ggcggcggag gcgcctctgc agctccggct cccctgcc tctcgggaac | 480 |
| tacaagtccc aggggcctg gcggtgggcg gcgggcggaa gaggcggggt cggcgccgcg | 540 |
| aggccggaag tggccgtgga ggcggaagtg gcgcggccgc ggaggggcct ggagtgcggc | 600 |
| ggcggcggga cccggagcag gagcggcggc agcagcgact gggggcggcg gcggcgcgtt | 660 |
| ggaggcggcc ggatccgttt aaacggctcg catctctcct tcacgcgccc gccgccctac | 720 |
| ctgaggccgc catccacgcc ggttgagtcg cgttctgccg cctcccgcct gtggtgcctc | 780 |
| ctgaactgcg tccgccgtct aggtaagttt aaagctcagg tcgagaccgg cctttgtcc | 840 |
| ggcgctccct tggagcctac ctagactcag ccggctctcc acgctttgcc tgaccctgct | 900 |
| tgctcaactc tacgtctttg tttcgttttc tgttctgcgc cgttacagat cactagttca | 960 |
| gagagcctcg gctaggtagg ggatcggac tctggcggga gggcggcttg gtgcgtttgc | 1020 |
| ggggatgggc ggccgcggca ggccctccga gcgtggtgga gccgttctgt gagacagccg | 1080 |
| ggtacgagtc gtgacgctgg aaggggcaag cgggtggtgg gcaggaatgc ggtccgccct | 1140 |
| gcagcaaccg gaggggagg gagaaggggag cggaaaagtc tccaccggac gcggccatgg | 1200 |
| ctcgggggg gggggcagc ggaggagcgc ttccggccga cgtctcgtcg ctgattggct | 1260 |

```
tcttttcctc cgccgtgtg tgaaaacaca attgtactaa ccttcttctc tttcctctcc   1320
tgacag                                                             1326

<210> SEQ ID NO 27
<211> LENGTH: 1263
<212> TYPE: DNA
<213> ORGANISM: Artificial Sequence
<220> FEATURE:
<223> OTHER INFORMATION: artificial sequence

<400> SEQUENCE: 27
gcgttacata acttacggta aatggcccgc ctggctgacc gcccaacgac ccccgcccat    60
tgacgtcaat aatgacgtat gttcccatag taacgccaat agggactttc cattgacgtc   120
aatgggtgga gtatttacgg taaactgccc acttggcagt acatcaagtg tatcatatgc   180
caagtacgcc ccctattgac gtcaatgacg gtaaatggcc cgcctggcat tatgcccagt   240
acatgacctt atgggacttt cctacttggc agtacatcta cgtattagtc atcgctatta   300
ccatggcccg ggtcgcgaca tgcagcggga cgcgccaccc cgagcccag ctccggcgcc   360 ccggctcccc gcgcccccga tcggggccgc cgctagtagt ggcggcggcg gaggcggggg   420
cagcggcggc ggcggcggag gcgcctctgc agctccggct cccctggcc tctcgggaac   480 tacaagtccc aggggcctg gcggtgggcg cggcggaa gaggcggggt cggcgccgcg   540
aggccggaag tggccgtgga ggcggaagtg gcgcggccgc ggaggggcct ggagtgcggc   600
ggcggcggga cccggagcag gagcggcggc agcagcgact gggggcggcg gcggcgcgtt   660
ggaggcggcc ggatccacta ggatccgttt aaacggctcg catctctcct tcacgcgccc   720
gccgccctac ctgaggccgc catccacgcc ggttgagtcg cgttctgccg cctcccgcct   780
gtggtgcctc ctgaactgcg tccgccgtct aggtaagttt aaagctcagg tcgagaccgg   840
gcctttgtcc ggcgctccct tggagcctac ctagactcag ccggctctcc acgctttgcc   900
tgaccctgct tgctcaactc tacgtctttg tttcgttttc tgttctgcgc cgttacagat   960
cactagtctt cgagggctc gcatctctcc ttcacgcgcc cgccgcccta cctgaggccg  1020
ccatccacgc cggttgagtc gcgttctgcc gcctcccgcc tgtggtgcct cctgaactgc  1080
gtccgccgtc taggtaagtt taaagctcag gtcgagaccg gcctttgtc cggcgctccc  1140 ttggagccta cctagactca gccggctctc cacgctttgc ctgaccctgc ttgctcaact  1200
ctacgtcttt gtttcgtttt ctgttctgcg ccgttacaga tccaagctgt gaccggcgcc  1260
tac                                                               1263

<210> SEQ ID NO 28
<211> LENGTH: 1119
<212> TYPE: DNA
<213> ORGANISM: Artificial Sequence
<220> FEATURE:
<223> OTHER INFORMATION: artificial sequence

<400> SEQUENCE: 28
gcgttacata acttacggta aatggcccgc ctggctgacc gcccaacgac ccccgcccat    60
tgacgtcaat aatgacgtat gttcccatag taacgccaat agggactttc cattgacgtc   120
aatgggtgga gtatttacgg taaactgccc acttggcagt acatcaagtg tatcatatgc   180
caagtacgcc ccctattgac gtcaatgacg gtaaatggcc cgcctggcat tatgcccagt   240
acatgacctt atgggacttt cctacttggc agtacatcta cgtattagtc atcgctatta   300
```

| | |
|---|---:|
| ccatggcccg gtcgcgaca tgcagcggga cgcgccaccc cgagcccag ctccggcgcc | 360 |
| ccggctcccc gcgcccccga tcggggccgc cgctagtagt ggcggcggcg gaggcggggg | 420 |
| cagcggcggc ggcggcggag gcgcctctgc agctccggct cccccctggcc tctcgggaac | 480 |
| tacaagtccc aggggggcctg gcggtgggcg gcgggcggaa gaggcggggt cggcgccgcg | 540 |
| aggccggaag tggccgtgga ggcggaagtg gcgcggccgc ggaggggcct ggagtgcggc | 600 |
| ggcggcggga cccggagcag gagcggcggc agcagcgact gggggcggcg gcggcgcgtt | 660 |
| ggaggcggcc ggatccgttt aaacggctcg catctctcct tcacgcgccc gccgccctac | 720 |
| ctgaggccgc catccacgcc ggttgagtcg cgttctgccg cctcccgcct gtggtgcctc | 780 |
| ctgaactgcg tccgccgtct aggtaagttt aaagctcagg tcgagaccgg gcctttgtcc | 840 |
| ggcgctcccct tggagcctac ctagactcag ccggctctcc acgctttgcc tgaccctgct | 900 |
| tgctcaactc tacgtctttg tttcgttttc tgttctgcgc cgttacagat cactagtgca | 960 |
| gaagttggtc gtgaggcact gggcaggtaa gtatcaaggt tacaagacag gtttaaggag | 1020 |
| accaatagaa actgggcttg tcgagacaga gaagactctt gcgtttctga taggcaccta | 1080 |
| ttggtcttac tgacatccac tttgcctttc tctccacag | 1119 |

<210> SEQ ID NO 29
<211> LENGTH: 2309
<212> TYPE: DNA
<213> ORGANISM: Artificial Sequence
<220> FEATURE:
<223> OTHER INFORMATION: artificial sequence

<400> SEQUENCE: 29

| | |
|---|---:|
| gcgttacata acttacggta aatggcccgc ctggctgacc gcccaacgac ccccgcccat | 60 |
| tgacgtcaat aatgacgtat gttcccatag taacgccaat agggactttc cattgacgtc | 120 |
| aatgggtgga gtatttacgg taaactgccc acttggcagt acatcaagtg tatcatatgc | 180 |
| caagtacgcc ccctattgac gtcaatgacg gtaaatggcc cgcctggcat tatgcccagt | 240 |
| acatgacctt atgggacttt cctacttggc agtacatcta cgtattagtc atcgctatta | 300 |
| ccatggcccg gtcgcgaca tgcagcggga cgcgccaccc cgagcccag ctccggcgcc | 360 |
| ccggctcccc gcgcccccga tcggggccgc cgctagtagt ggcggcggcg gaggcggggg | 420 |
| cagcggcggc ggcggcggag gcgcctctgc agctccggct cccccctggcc tctcgggaac | 480 |
| tacaagtccc aggggggcctg gcggtgggcg gcgggcggaa gaggcggggt cggcgccgcg | 540 |
| aggccggaag tggccgtgga ggcggaagtg gcgcggccgc ggaggggcct ggagtgcggc | 600 |
| ggcggcggga cccggagcag gagcggcggc agcagcgact gggggcggcg gcggcgcgtt | 660 |
| ggaggcggcc ggatccacta gtgtttaaac agagtaatga catggttcct tccatcctcc | 720 |
| aaaggtgacc aataatagtt tgtaagtatc attatgaact aatgaatttt caacatattt | 780 |
| gatatatttc aatccattgc catcattgtt cttatcgata tttgagttgg ctcactttgc | 840 |
| cagtaagagt ctattcaaat tggcttctga gtccatttga cacaacacct ttgatctttg | 900 |
| acagtttcct tggttttagg tgctagatga tttctcaggc tcaccttaga catttcctgc | 960 |
| cacagactta gaatcagcca tttctctaag gaccctgatt ccatttcatg agaaatgata | 1020 |
| gagaccacaa tcaaaacaag tcatgaattt atactgatat tttcaattca aattaaagat | 1080 |
| gaggttttg ctaaatttt ttgagtttat atttgtatgt cttatgctga aaatcttgt | 1140 |
| ttcctaatta gtaacataat tattcatttg atgggtaaat attttagggc cgattctttg | 1200 |
| gttttatagc caagatacccc tgttgataaa gtcttgtggg agcaattata agactggctt | 1260 |

| | |
|---|---|
| attttgaagc tttttaaaaa agacatcctt acctgttta actgtagatt atattaacttt | 1320 |
| aaataggtac agcccacgct tgactagtcg ggtttgccgc cagaacacag gtaagtgccg | 1380 |
| tgtgtggttc ccgcgggcct ggcctcttta cgggttatgg cccttgcgtg ccttgaatta | 1440 |
| cttccacctg gctgcagtac gtgattcttg atcccgagct tcgggttgga agtgggtggg | 1500 |
| agagttcgag gccttgcgct taaggagccc cttcgcctcg tgcttgagtt gaggcctggc | 1560 |
| ctgggcgctg gggccgccgc gtgcgaatct ggtggcacct tcgcgcctgt ctcgctgctt | 1620 |
| tcgataagtc tctagccatt taaaatttt gatgacctgc tgcgacgctt ttttctggc | 1680 |
| aagatagtct tgtaaatgcg ggccaagatc tgcacactgg tatttcggtt tttgggccg | 1740 |
| cgggcggcga cggggcccgt gcgtcccagc gcacatgttc ggcgaggcgg ggcctgcgag | 1800 |
| cgcggccacc gagaatcgga cggggtagt ctcaagctgg ccggcctgct ctggtgcctg | 1860 |
| gcctcgcgcc gccgtgtatc gccccgccct gggcggcaag gctggcccgg tcggcaccag | 1920 |
| ttgcgtgagc ggaaagatgg ccgcttcccg gccctgctgc agggagctca aaatggagga | 1980 |
| cgcggcgctc gggagagcgg gcgggtgagt cacccacaca aggaaaagg gcctttccgt | 2040 |
| cctcagccgt cgcttcatgt gactccacgg agtaccgggc gccgtccagg cacctcgatt | 2100 |
| agttctcgag cttttggagt acgtcgtctt taggttgggg ggagggttt tatgcgatgg | 2160 |
| agtttcccca cactgagtgg gtggagactg aagttaggcc agcttggcac ttgatgtaat | 2220 |
| tctccttgga atttgccctt tttgagtttg gatcttggtt cattctcaag cctcagacag | 2280 |
| tggttcaaag ttttttctt ccatttcag | 2309 |

<210> SEQ ID NO 30
<211> LENGTH: 1717
<212> TYPE: DNA
<213> ORGANISM: Artificial Sequence
<220> FEATURE:
<223> OTHER INFORMATION: artificial sequence

<400> SEQUENCE: 30

| | |
|---|---|
| gcgttacata acttacggta aatggcccgc ctggctgacc gcccaacgac ccccgcccat | 60 |
| tgacgtcaat aatgacgtat gttcccatag taacgccaat agggactttc cattgacgtc | 120 |
| aatgggtgga gtatttacgg taaactgccc acttggcagt acatcaagtg tatcatatgc | 180 |
| caagtacgcc ccctattgac gtcaatgacg gtaaatggcc cgcctggcat tatgcccagt | 240 |
| acatgacctt atgggacttt cctacttggc agtacatcta cgtattagtc atcgctatta | 300 |
| ccatggcccg gtcgcgaca tgcagcggga cgcgccaccc cgagcccag ctccggcgcc | 360 |
| ccggctcccc gcgccccga tcgggccgc cgctagtagt ggcggcggcg gaggcggggg | 420 |
| cagcggcggc ggcggcggag gcgcctctgc agctccggct ccccctggcc tctcgggaac | 480 |
| tacaagtccc aggggcctg gcggtgggcg gcgggcggaa gaggcggggt cggcgccgcg | 540 |
| aggccggaag tggccgtgga ggcggaagtg gcgcggccgc ggaggggcct ggagtgcggc | 600 |
| ggcggcggga cccggagcag gagcggcggc agcagcgact gggggcggcg gcggcgcgtt | 660 |
| ggaggcggcc ggatccacta gtgtttaaac agagtaatga catggttcct tccatcctcc | 720 |
| aaaggtgacc aataatagtt tgtaagtatc attatgaact aatgaatttt caacatattt | 780 |
| gatatatttc aatccattgc catcattgtt cttatcgata tttgagttgg ctcacttgc | 840 |
| cagtaagagt ctattcaaat tggcttctga gtccatttga cacaacacct ttgatctttg | 900 |
| acagtttcct tggtttagg tgctagatga tttctcaggc tcaccttaga catttcctgc | 960 |

```
cacagactta gaatcagcca tttctctaag gaccctgatt ccatttcatg agaaatgata   1020
gagaccacaa tcaaaacaag tcatgaattt atactgatat tttcaattca aattaaagat   1080 gaggttttttg ctaaattttt ttgagtttat atttgtatgt cttatgctga aaaatcttgt   1140
ttcctaatta gtaacataat tattcatttg atgggtaaat attttagggc cgattctttg   1200
gttttatagc caagataccc tgttgataaa gtcttgtggg agcaattata agactggctt   1260
attttgaagc ttttttaaaaa agacatcctt acctgtttta actgtagatt atattaactt   1320
aaataggtac agcccacgct tgactagttc agagagcctc ggctaggtag gggatcggga   1380
ctctggcggg agggcggctt ggtgcgtttg cggggatggg cggccgcggc aggccctccg   1440
agcgtggtgg agccgttctg tgagacagcc gggtacgagt cgtgacgctg aagggggcaa   1500
gcgggtggtg ggcaggaatg cggtccgccc tgcagcaacc ggaggggggag ggagaaggga   1560 gcggaaaagt ctccaccgga cgcggccatg gctcgggggg ggggggggcag cggaggagcg   1620 cttccggccg acgtctcgtc gctgattggc ttctttttcct cccgccgtgt gtgaaaacac   1680
aattgtacta accttcttct ctttcctctc ctgacag                             1717
```

<210> SEQ ID NO 31
<211> LENGTH: 1625
<212> TYPE: DNA
<213> ORGANISM: Artificial Sequence
<220> FEATURE:
<223> OTHER INFORMATION: artificial sequence

<400> SEQUENCE: 31

```
gcgttacata acttacggta aatggcccgc ctggctgacc gcccaacgac ccccgcccat     60
tgacgtcaat aatgacgtat gttcccatag taacgccaat agggactttc cattgacgtc    120
aatgggtgga gtatttacgg taaactgccc acttggcagt acatcaagtg tatcatatgc    180
caagtacgcc ccctattgac gtcaatgacg gtaaatggcc cgcctggcat tatgcccagt    240
acatgacctt atgggacttt cctacttggc agtacatcta cgtattagtc atcgctatta    300
ccatggcccg ggtcgcgaca tgcagcggga cgcgccaccc cgagcccag ctccggcgcc    360 ccggctcccc gcgcccccga tcggggccgc cgctagtagt ggcggcggcg gaggcggggg    420
cagcggcggc ggcggcggag gcgcctctgc agctccggct cccctggcc tctcgggaac    480 tacaagtccc aggggggcctg gcggtggcg gcgggcggaa gaggcggggt cggcgccgcg    540
aggccggaag tggccgtgga ggcggaagtg gcgcggccgc ggagggggcct ggagtgcggc    600 ggcggcggga cccggagcag gagcggcggc agcagcgact gggggcgggcg gcggcgcgtt    660 ggaggcggcc cagagtaatg acatggttcc ttccatcctc caaaggtgac caataatagt    720
ttgtaagtat cattatgaac taatgaattt tcaacatatt tgatatattt caatccattg    780
ccatcattgt tcttatcgat atttgagttg gctcactttg ccagtaagag tctattcaaa    840
ttggcttctg agtccatttg acacaacacc tttgatcttt gacagtttcc ttggttttag    900
gtgctagatg atttctcagg ctcaccttag acatttcctg ccacagactt agaatcagcc    960
atttctctaa ggaccctgat tccatttcat gagaaatgat agagaccaca atcaaaacaa   1020
gtcatgaatt tatactgata ttttcaattc aaattaaaga tgaggttttt gctaaattt   1080 tttgagttta tatttgtatg tcttatgctg aaaaatcttg ttttcctaatt agtaacataa   1140 ttattcattt gatgggtaaa tattttaggg ccgattcttt ggttttatag ccaagatacc   1200
ctgttgataa agtcttgtgg gagcaattat aagactggct tattttgaag cttttttaaaa   1260 aagacatcct tacctgtttt aactgtagat tatattaact taaataggta cagcccacgc   1320
```

```
ttgactagtc ttcgaggggc tcgcatctct ccttcacgcg cccgccgccc tacctgaggc    1380
cgccatccac gccggttgag tcgcgttctg ccgcctcccg cctgtggtgc ctcctgaact    1440
gcgtccgccg tctaggtaag tttaaagctc aggtcgagac cgggcctttg tccggcgctc    1500
ccttggagcc tacctagact cagccggctc tccacgcttt gcctgaccct gcttgctcaa    1560
ctctacgtct ttgtttcgtt ttctgttctg cgccgttaca gatccaagct gtgaccggcg    1620
cctac                                                                1625
```

<210> SEQ ID NO 32
<211> LENGTH: 1491
<212> TYPE: DNA
<213> ORGANISM: Artificial Sequence
<220> FEATURE:
<223> OTHER INFORMATION: artificial sequence

<400> SEQUENCE: 32

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg ggtcgcgaca tgcagcggga cgcgccaccc cgagcccag ctccggcgcc     360 ccggctcccc gcgcccccga tcggggccgc cgctagtagt ggcggcggcg gaggcggggg     420
cagcggcggc ggcggcggag gcgcctctgc agctccggct cccctggcc tctcgggaac     480 tacaagtccc aggggcctg gcggtggcg gcgggcggaa gaggcggggt cggcgccgcg     540
aggccggaag tggccgtgga ggcggaagtg gcgcggccgc ggaggggcct ggagtgcggc     600
ggcggcggga cccggagcag gagcggcggc agcagcgact ggggcggcg gcggcgcgtt     660 ggaggcggcc cagagtaatg acatggttcc ttccatcctc caaaggtgac caataatagt     720
ttgtaagtat cattatgaac taatgaattt tcaacatatt tgatatattt caatccattg     780
ccatcattgt tcttatcgat atttgagttg gctcactttg ccagtaagag tctattcaaa     840
ttggcttctg agtccatttg acacaacacc tttgatcttt gacagtttcc ttggttttag     900
gtgctagatg atttctcagg ctcaccttag acatttcctg ccacagactt agaatcagcc     960
atttctctaa ggaccctgat tccatttcat gagaaatgat agagaccaca atcaaaacaa    1020
gtcatgaatt tatactgata ttttcaattc aaattaaaga tgaggttttt gctaaatttt    1080
tttgagttta tatttgtatg tcttatgctg aaaaatcttg tttcctaatt agtaacataa    1140
ttattcattt gatgggtaaa tatttttaggg ccgattcttt ggttttatag ccaagatacc    1200
ctgttgataa agtcttgtgg gagcaattat aagactggct tattttgaag cttttttaaa    1260
aagacatcct tacctgtttt aactgtagat tatattaact taaataggta cagcccacgc    1320
ttgactagtg cagaagttgg tcgtgaggca ctgggcaggt aagtatcaag gttacaagac    1380
aggtttaagg agaccaatag aaactgggct tgtcgagaca gagaagactc ttgcgtttct    1440
gataggcacc tattggtctt actgacatcc actttgcctt tctctccaca g             1491
```

<210> SEQ ID NO 33
<211> LENGTH: 1964
<212> TYPE: DNA
<213> ORGANISM: Artificial Sequence
<220> FEATURE:

<223> OTHER INFORMATION: artificial sequence

<400> SEQUENCE: 33

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatgcccg gtcgcgaca tgcagcggga cgcgccaccc cgagcccag ctccggcgcc        360
ccggctcccc gcgcccccga tcggggccgc cgctagtagt ggcggcggcg gaggcggggg     420
cagcggcggc ggcggcggag gcgcctctgc agctccggct cccctggcc tctcgggaac      480
tacaagtccc aggggcctg gcgtgggcg gcgggcggaa gaggcggggt cggcgccgcg       540
aggccggaag tggccgtgga ggcggaagtg gcgcggccgc ggagggcct ggagtgcggc      600
ggcggcggga cccggagcag gagcggcggc agcagcgact gggggcggcg gcggcgcgtt    660
ggaggcggcc ggatccgttt aacgctggtg gtagggatg agggagggag gggcattgtg     720
atgtacaggg ctgctctgtg agatcaaggg tctcttaagg gtgggagctg gggcagggac    780
tacgagagca gccagatggg ctgaaagtgg aactcaaggg gtttctggca cctacctacc    840
tgcttcccgc tggggggtgg ggagttggcc cagagtctta agattgggc agggtggaga     900
ggtgggctct tcctgcttcc cactcatctt atagctttct ttccccagat ccgaattcga    960
gatccaaacc aaggaggaaa ggatatcaca gaggagagct agtcgggttt gccgccagaa   1020
cacaggtaag tgccgtgtgt ggttcccgcg ggcctggcct ctttacgggt tatggcccctt  1080
gcgtgccttg aattacttcc acctggctgc agtacgtgat tcttgatccc gagcttcggg   1140
ttggaagtgg gtgggagagt tcgaggcctt gcgcttaagg agccccttcg cctcgtgctt   1200
gagttgaggc ctggcctggg cgctggggcc gccgcgtgcg aatctggtgg caccttcgcg   1260
cctgtctcgc tgctttcgat aagtctctag ccatttaaaa tttttgatga cctgctgcga   1320
cgcttttttt ctggcaagat agtcttgtaa atgcgggcca agatctgcac actggtattt    1380
cggttttttgg ggccgcgggc ggcgacgggg cccgtgcgtc ccagcgcaca tgttcggcga   1440
ggcgggcct gcgagcgcgg ccaccgagaa tcggacgggg gtagtctcaa gctgccggc     1500
ctgctctggt gcctggcctc gcgccgccgt gtatcgcccc gccctgggcg gcaaggctgg   1560
cccggtcggc accagttgcg tgagcggaaa gatggccgct tcccggccct gctgcaggga   1620
gctcaaaatg gaggacgcgg cgctcgggag agcgggcggg tgagtcaccc acacaaagga   1680
aaagggcctt tccgtcctca gccgtcgctt catgtgactc cacggagtac cgggcgccgt   1740
ccaggcacct cgattagttc tcgagctttt ggagtacgtc gtctttaggt tgggggggagg   1800
ggttttatgc gatggagttt ccccacactg agtgggtgga gactgaagtt aggccagctt   1860
ggcacttgat gtaattctcc ttggaatttg ccctttttga gtttggatct tggttcattc   1920
tcaagcctca gacagtggtt caaagttttt ttcttccatt tcag                    1964
```

<210> SEQ ID NO 34
<211> LENGTH: 1372
<212> TYPE: DNA
<213> ORGANISM: Artificial Sequence
<220> FEATURE:
<223> OTHER INFORMATION: artificial sequence

<400> SEQUENCE: 34

```
gcgttacata acttacggta aatggcccgc ctggctgacc gcccaacgac ccccgcccat    60
tgacgtcaat aatgacgtat gttcccatag taacgccaat agggactttc cattgacgtc   120
aatgggtgga gtatttacgg taaactgccc acttggcagt acatcaagtg tatcatatgc   180
caagtacgcc ccctattgac gtcaatgacg gtaaatggcc cgcctggcat tatgcccagt   240
acatgacctt atgggacttt cctacttggc agtacatcta cgtattagtc atcgctatta   300
ccatggcccg ggtcgcgaca tgcagcggga cgcgccaccc cgagcccag ctccggcgcc    360 ccggctcccc gcgccccga tcggggccgc cgctagtagt ggcggcggcg gaggcggggg    420
cagcggcggc ggcggcggag gcgcctctgc agctccggct cccctggcc tctcgggaac    480 tacaagtccc aggggcctg gcggtgggcg gcgggcggaa gaggcggggt cggcgccgcg    540
aggccggaag tggccgtgga ggcggaagtg gcgcggccgc ggaggggcct ggagtgcggc    600
ggcggcggga cccggagcag gagcggcggc agcagcgact ggggggcggcg gcggcgcgtt   660 ggaggcggcc ggatccgttt aacgctggtg gtaggggatg agggagggag gggcattgtg    720
atgtacaggg ctgctctgtg agatcaaggg tctcttaagg gtgggagctg ggcagggac    780 tacgagagca gccagatggg ctgaaagtgg aactcaaggg gtttctggca cctacctacc   840
tgcttcccgc tgggggtgg ggagttggcc cagagtctta agattggggc agggtggaga    900
ggtgggctct tcctgcttcc cactcatctt atagctttct ttccccagat ccgaattcga   960
gatccaaacc aaggaggaaa ggatatcaca gaggagagct agttcagaga gcctcggcta  1020
ggtaggggat cgggactctg gcgggagggc ggcttggtgc gtttgcgggg atgggcggcc  1080
gcggcaggcc ctccgagcgt ggtggagccg ttctgtgaga cagccgggta cgagtcgtga  1140
cgctggaagg ggcaagcggg tggtgggcag gaatgcggtc cgccctgcag caaccggagg  1200
gggagggaga agggagcgga aaagtctcca ccggacgcgg ccatggctcg ggggggggg   1260 ggcagcggag gagcgcttcc ggccgacgtc tcgtcgctga ttggcttctt ttcctcccgc  1320
cgtgtgtgaa aacacaattg tactaacctt cttctctttc ctctcctgac ag          1372
```

<210> SEQ ID NO 35
<211> LENGTH: 1302
<212> TYPE: DNA
<213> ORGANISM: Artificial Sequence
<220> FEATURE:
<223> OTHER INFORMATION: artificial sequence

<400> SEQUENCE: 35

```
gcgttacata acttacggta aatggcccgc ctggctgacc gcccaacgac ccccgcccat    60
tgacgtcaat aatgacgtat gttcccatag taacgccaat agggactttc cattgacgtc   120
aatgggtgga gtatttacgg taaactgccc acttggcagt acatcaagtg tatcatatgc   180
caagtacgcc ccctattgac gtcaatgacg gtaaatggcc cgcctggcat tatgcccagt   240
acatgacctt atgggacttt cctacttggc agtacatcta cgtattagtc atcgctatta   300
ccatggcccg ggtcgcgaca tgcagcggga cgcgccaccc cgagcccag ctccggcgcc    360 ccggctcccc gcgccccga tcggggccgc cgctagtagt ggcggcggcg gaggcggggg    420
cagcggcggc ggcggcggag gcgcctctgc agctccggct cccctggcc tctcgggaac    480 tacaagtccc aggggcctg gcggtgggcg gcgggcggaa gaggcggggt cggcgccgcg    540
aggccggaag tggccgtgga ggcggaagtg gcgcggccgc ggaggggcct ggagtgcggc    600
ggcggcggga cccggagcag gagcggcggc agcagcgact ggggggcggcg gcggcgcgtt   660
```

```
ggaggcggcc ggatccacta gttaacgctg gtgggtaggg atgagggagg gaggggcatt        720
gtgatgtaca gggctgctct gtgagatcaa gggtctctta agggtgggag ctggggcagg        780
gactacgaga gcagccagat gggctgaaag tggaactcaa ggggtttctg gcacctacct        840
acctgcttcc cgctgggggg tggggagttg gcccagagtc ttaagattgg ggcagggtgg        900
agaggtgggc tcttcctgct tcccactcat cttatagctt tctttcccca gatccgaatt        960
cgagatccaa accaaggagg aaaggatatc acagaggaga gctagtcttc gaggggctcg       1020
catctctcct tcacgcgccc gccgccctac ctgaggccgc catccacgcc ggttgagtcg       1080
cgttctgccg cctcccgcct gtggtgcctc ctgaactgcg tccgccgtct aggtaagttt       1140
aaagctcagg tcgagaccgg gcctttgtcc ggcgctccct tggagcctac ctagactcag       1200
ccggctctcc acgctttgcc tgaccctgct tgctcaactc tacgtctttg tttcgttttc       1260
tgttctgcgc cgttacagat ccaagctgtg accggcgcct ac                          1302

<210> SEQ ID NO 36
<211> LENGTH: 1168
<212> TYPE: DNA
<213> ORGANISM: Artificial Sequence
<220> FEATURE:
<223> OTHER INFORMATION: artificial sequence

<400> SEQUENCE: 36
gcgttacata acttacggta aatggcccgc ctggctgacc gcccaacgac ccccgcccat         60
tgacgtcaat aatgacgtat gttcccatag taacgccaat agggactttc cattgacgtc        120
aatgggtgga gtatttacgg taaactgccc acttggcagt acatcaagtg tatcatatgc        180
caagtacgcc ccctattgac gtcaatgacg gtaaatggcc cgcctggcat tatgcccagt        240
acatgacctt atgggacttt cctacttggc agtacatcta cgtattagtc atcgctatta        300
ccatggcccg gtcgcgacat gcagcggga cgcgccaccc cgagcccag ctccggcgcc         360 ccggctcccc gcgcccccga tcggggccgc cgctagtagt ggcggcggcg gaggcggggg        420
cagcggcggc ggcggcggag gcgcctctgc agctccggct cccctggcc tctcgggaac         480 tacaagtccc aggggggcctg gcggtgggcg gcgggcggaa gaggcgggt cggcgccgcg         540 aggccggaag tggccgtgga ggcggaagtg gcgcggccgc ggaggggcct ggagtgcggc        600
ggcggcggga cccggagcag gagcggcggc agcagcgact gggggcggcg gcggcgcgtt        660
ggaggcggcc ggatccacta gttaacgctg gtgggtaggg atgagggagg gaggggcatt        720
gtgatgtaca gggctgctct gtgagatcaa gggtctctta agggtgggag ctggggcagg        780
gactacgaga gcagccagat gggctgaaag tggaactcaa ggggtttctg gcacctacct        840
acctgcttcc cgctgggggg tggggagttg gcccagagtc ttaagattgg ggcagggtgg        900
agaggtgggc tcttcctgct tcccactcat cttatagctt tctttcccca gatccgaatt        960
cgagatccaa accaaggagg aaaggatatc acagaggaga gctagtgcag aagttggtcg       1020
tgaggcactg ggcaggtaag tatcaaggtt acaagacagg tttaaggaga ccaatagaaa       1080
ctgggcttgt cgagacagag aagactcttg cgtttctgat aggcacctat tggtcttact       1140
gacatccact ttgcctttct ctccacag                                          1168

<210> SEQ ID NO 37
<211> LENGTH: 2584
<212> TYPE: DNA
<213> ORGANISM: Artificial Sequence
<220> FEATURE:
<223> OTHER INFORMATION: artificial sequence
```

<400> SEQUENCE: 37

```
gcgttacata acttacggta aatggcccgc ctggctgacc gcccaacgac ccccgcccat    60
tgacgtcaat aatgacgtat gttcccatag taacgccaat agggactttc cattgacgtc   120
aatgggtgga gtatttacgg taaactgccc acttggcagt acatcaagtg tatcatatgc   180
caagtacgcc ccctattgac gtcaatgacg gtaaatggcc cgcctggcat tatgcccagt   240
acatgacctt atgggacttt cctacttggc agtacatcta cgtattagtc atcgctatta   300
ccatggcccg ggtcgcgaca tgcagcggga cgcgccaccc cgagcccag ctccggcgcc    360
ccggctcccc gcgccccga tcggggccgc cgctagtagt ggcggcggcg gaggcggggt    420
cagcggcggc ggcggcggag gcgcctctgc agctccggct cccctggcc tctcgggaac    480
tacaagtccc aggggcctg gcggtgggcg gcgggcggaa gaggcggggt cggcgccgcg    540
aggccggaag tggccgtgga ggcggaagtg gcgcggccgc ggagggcct ggagtgcggc    600
ggcggcggga cccggagcag gagcggcggc agcagcgact gggggcggcg gcggcgcgtt    660
ggaggcggcc ggatccgttt aaacggctcg catctctcct tcacgcgccc gccgccctac    720
ctgaggccgc catccacgcc ggttgagtcg cgttctgccg cctcccgcct gtggtgcctc    780
ctgaactgcg tccgccgtct aggtaagttt aaagctcagg tcgagaccgg gccttttgtcc   840
ggcgctccct tggagcctac ctagactcag ccggctctcc acgctttgcc tgaccctgct    900
tgctcaactc tacgtctttg tttcgttttc tgttctgcgc cgttacagat cactagtgtt    960
taaacagagt aatgacatgg ttccttccat cctccaaagg tgaccaataa tagtttgtaa   1020
gtatcattat gaactaatga atttttcaaca tatttgatat atttcaatcc attgccatca   1080
ttgttcttat cgatatttga gttggctcac tttgccagta agagtctatt caaattggct   1140
tctgagtcca tttgacacaa cacctttgat ctttgacagt ttccttggtt ttaggtgcta   1200
gatgatttct caggctcacc ttagacattt cctgccacag acttagaatc agccatttct   1260
ctaaggaccc tgattccatt tcatgagaaa tgatagagac cacaatcaaa acaagtcatg   1320
aatttatact gatattttca attcaaatta aagatgaggt ttttgctaaa tttttttgag   1380
tttatatttg tatgtcttat gctgaaaaat cttgttttcct aattagtaac ataattattc   1440
atttgatggg taaatatttt agggccgatt cttttggtttt atagccaaga taccctgttg   1500
ataaagtctt gtgggagcaa ttataagact ggcttattt gaagcttttt aaaaaagaca   1560
tccttacctg ttttaactgt agattatatt aacttaaata ggtacagccc acgcttgact   1620
agtcgggttt gccgccagaa cacaggtaag tgccgtgtgt ggttcccgcg ggcctggcct   1680
ctttacgggt tatggccctt gcgtgccttg aattacttcc acctggctgc agtacgtgat   1740
tcttgatccc gagcttcggg ttggaagtgg gtgggagagt tcgaggcctt gcgcttaagg   1800
agccccttcg cctcgtgctt gagttgaggc ctggcctggg cgctggggcc gccgcgtgcg   1860
aatctggtgg caccttcgcg cctgtctcgc tgctttcgat aagtctctag ccatttaaaa   1920
tttttgatga cctgctgcga cgcttttttt ctggcaagat agtcttgtaa atgcgggcca   1980
agatctgcac actggtattt cggttttttgg ggccgcgggc ggcgacgggg cccgtgcgtc   2040
ccagcgcaca tgttcggcga ggcggggcct gcgagcgcgg ccaccgagaa tcggacgggg   2100
gtagtctcaa gctggccggc ctgctctggt gcctggcctc gcgccgccgt gtatcgcccc   2160
gccctgggcg gcaaggctgg cccggtcggc accagttgcg tgagcggaaa gatgccgct    2220
tcccggccct gctgcaggga gctcaaaatg gaggacgcgg cgctcgggag agcgggcggg   2280
```

| | |
|---|---:|
| tgagtcaccc acacaaagga aaagggcctt tccgtcctca gccgtcgctt catgtgactc | 2340 |
| cacggagtac cgggcgccgt ccaggcacct cgattagttc tcgagctttt ggagtacgtc | 2400 |
| gtctttaggt tggggggagg ggttttatgc gatggagttt ccccacactg agtgggtgga | 2460 |
| gactgaagtt aggccagctt ggcacttgat gtaattctcc ttggaatttg ccctttttga | 2520 |
| gtttggatct tggttcattc tcaagcctca gacagtggtt caaagttttt ttcttccatt | 2580 |
| tcag | 2584 |

<210> SEQ ID NO 38
<211> LENGTH: 1992
<212> TYPE: DNA
<213> ORGANISM: Artificial Sequence
<220> FEATURE:
<223> OTHER INFORMATION: artificial sequence

<400> SEQUENCE: 38

| | |
|---|---:|
| gcgttacata acttacggta aatggcccgc ctggctgacc gcccaacgac ccccgcccat | 60 |
| tgacgtcaat aatgacgtat gttcccatag taacgccaat agggactttc cattgacgtc | 120 |
| aatgggtgga gtatttacgg taaactgccc acttggcagt acatcaagtg tatcatatgc | 180 |
| caagtacgcc ccctattgac gtcaatgacg gtaaatggcc cgcctggcat tatgcccagt | 240 |
| acatgacctt atgggacttt cctacttggc agtacatcta cgtattagtc atcgctatta | 300 |
| ccatggcccg ggtcgcgaca tgcagcggga cgcgccaccc cgagcccag ctccggcgcc | 360 |
| ccggctcccc gcgccccga tcggggccgc cgctagtagt ggcggcggcg gaggcggggg | 420 |
| cagcggcggc ggcggcggag gcgcctctgc agctccggct cccctggcc tctcgggaac | 480 |
| tacaagtccc aggggcctg gcggtgggcg gcgggcggaa gaggcgggt cggcgccgcg | 540 |
| aggccggaag tggccgtgga ggcggaagtg gcgcggccgc ggaggggcct ggagtgcggc | 600 |
| ggcggcggga cccggagcag gagcggcggc agcagcgact gggggcggcg cggcgcgtt | 660 |
| ggaggcggcc ggatccgttt aaacggctcg catctctcct tcacgcgccc gccgccctac | 720 |
| ctgaggccgc catccacgcc ggttgagtcg cgttctgccg cctcccgcct gtggtgcctc | 780 |
| ctgaactgcg tccgccgtct aggtaagttt aaagctcagg tcgagaccgg ccttttgtcc | 840 |
| ggcgctccct tggagcctac ctagactcag ccggctctcc acgctttgcc tgaccctgct | 900 |
| tgctcaactc tacgtctttg tttcgttttc tgttctgcgc cgttacagat cactagtgtt | 960 |
| taaacagagt aatgacatgg ttccttccat cctccaaagg tgaccaataa tagtttgtaa | 1020 |
| gtatcattat gaactaatga attttcaaca tatttgatat atttcaatcc attgccatca | 1080 |
| ttgttcttat cgatatttga gttggctcac tttgccagta agagtctatt caaattggct | 1140 |
| tctgagtcca tttgacacaa cacctttgat cttttgacagt ttccttggtt ttaggtgcta | 1200 |
| gatgatttct caggctcacc ttagacattt cctgccacag acttagaatc agccatttct | 1260 |
| ctaaggaccc tgattccatt tcatgagaaa tgatagagac cacaatcaaa acaagtcatg | 1320 |
| aatttatact gatattttca attcaaatta aagatgaggt ttttgctaaa ttttttttgag | 1380 |
| tttatatttg tatgtcttat gctgaaaaat cttgtttcct aattagtaac ataattattc | 1440 |
| atttgatggg taaatatttt agggccgatt cttttggtttt atagccaaga taccctgttg | 1500 |
| ataaagtctt gtgggagcaa ttataagact ggcttatttt gaagcttttt aaaaaagaca | 1560 |
| tccttacctg ttttaactgt agattatatt aacttaaata ggtacagccc acgcttgact | 1620 |
| agttcagaga gcctcggcta ggtaggggat cgggactctg gcgggagggc ggcttggtgc | 1680 |
| gtttgcgggg atgggcggcc gcggcaggcc ctccgagcgt ggtggagccg ttctgtgaga | 1740 |

| | |
|---|---|
| cagccgggta cgagtcgtga cgctggaagg ggcaagcggg tggtgggcag gaatgcggtc | 1800 |
| cgccctgcag caaccggagg gggagggaga agggagcgga aaagtctcca ccggacgcgg | 1860 |
| ccatggctcg ggggggggggg ggcagcggag gagcgcttcc ggccgacgtc tcgtcgctga | 1920 |
| ttggcttctt ttcctcccgc cgtgtgtgaa aacacaattg tactaacctt cttctctttc | 1980 |
| ctctcctgac ag | 1992 |

<210> SEQ ID NO 39
<211> LENGTH: 1929
<212> TYPE: DNA
<213> ORGANISM: Artificial Sequence
<220> FEATURE:
<223> OTHER INFORMATION: artificial sequence

<400> SEQUENCE: 39

| | |
|---|---|
| gcgttacata acttacggta aatggcccgc ctggctgacc gcccaacgac ccccgcccat | 60 |
| tgacgtcaat aatgacgtat gttcccatag taacgccaat agggactttc cattgacgtc | 120 |
| aatgggtgga gtatttacgg taaactgccc acttggcagt acatcaagtg tatcatatgc | 180 |
| caagtacgcc ccctattgac gtcaatgacg gtaaatggcc cgcctggcat tatgcccagt | 240 |
| acatgacctt atgggacttt cctacttggc agtacatcta cgtattagtc atcgctatta | 300 |
| ccatggcccg gtcgcgaca tgcagcggga cgcgccaccc cgagcccag ctccggcgcc | 360 |
| ccggctcccc gcgcccccga tcggggccgc cgctagtagt ggcggcggcg gaggcggggg | 420 |
| cagcggcggc ggcggcggag gcgcctctgc agctccggct cccccctggcc tctcgggaac | 480 |
| tacaagtccc aggggcctg gcgtgggcg gcgggcggaa gaggcggggt cggcgccgcg | 540 |
| aggccggaag tggccgtgga ggcggaagtg gcgcggccgc ggagggcct ggagtgcggc | 600 |
| ggcggcggga cccggagcag gagcggcggc agcagcgact ggggcggcg gcggcgcgtt | 660 |
| ggaggcggcc ggatccacta ggatccgttt aaacggctcg catctctcct tcacgcgccc | 720 |
| gccgccctac ctgaggccgc catccacgcc ggttgagtcg cgttctgccg cctcccgcct | 780 |
| gtggtgcctc ctgaactgcg tccgccgtct aggtaagttt aaagctcagg tcgagaccgg | 840 |
| gcctttgtcc ggcgctccct tggagcctac ctagactcag ccggctctcc acgctttgcc | 900 |
| tgaccctgct tgctcaactc tacgtctttg tttcgttttc tgttctgcgc cgttacagat | 960 |
| cactagtgtt taaacagagt aatgacatgg ttccttccat cctccaaagg tgaccaataa | 1020 |
| tagtttgtaa gtatcattat gaactaatga attttcaaca tatttgatat atttcaatcc | 1080 |
| attgccatca ttgttcttat cgatatttga gttggctcac tttgccagta agagtctatt | 1140 |
| caaattggct tctgagtcca tttgacacaa cacctttgat ctttgacagt tccttggtt | 1200 |
| ttaggtgcta gatgatttct caggctcacc ttagacattt cctgccacag acttagaatc | 1260 |
| agccatttct ctaaggaccc tgattccatt tcatgagaaa tgatagagac cacaatcaaa | 1320 |
| acaagtcatg aatttatact gatattttca attcaaatta aagatgaggt ttttgctaaa | 1380 |
| ttttttttgag tttatatttg tatgtcttat gctgaaaaat cttgtttcct aattagtaac | 1440 |
| ataattattc atttgatggg taaatatttt agggccgatt cttttggtttt atagccaaga | 1500 |
| taccctgttg ataaagtctt gtgggagcaa ttataagact ggcttatttt gaagcttttt | 1560 |
| aaaaaagaca tccttacctg ttttaactgt agattatatt aacttaaata ggtacagccc | 1620 |
| acgcttgact agtcttcgag gggctcgcat ctctccttca cgcgcccgcc gccctacctg | 1680 |
| aggccgccat ccacgccggt tgagtcgcgt tctgccgcct cccgcctgtg gtgcctcctg | 1740 |

| | |
|---|---:|
| aactgcgtcc gccgtctagg taagtttaaa gctcaggtcg agaccgggcc tttgtccggc | 1800 |
| gctcccttgg agcctaccta gactcagccg gctctccacg cttttgcctga ccctgcttgc | 1860 |
| tcaactctac gtctttgttt cgttttctgt tctgcgccgt tacagatcca agctgtgacc | 1920 |
| ggcgcctac | 1929 |

<210> SEQ ID NO 40
<211> LENGTH: 1785
<212> TYPE: DNA
<213> ORGANISM: Artificial Sequence
<220> FEATURE:
<223> OTHER INFORMATION: artificial sequence

<400> SEQUENCE: 40

| | |
|---|---:|
| gcgttacata acttacggta aatggcccgc ctggctgacc gcccaacgac ccccgcccat | 60 |
| tgacgtcaat aatgacgtat gttcccatag taacgccaat agggactttc cattgacgtc | 120 |
| aatgggtgga gtatttacgg taaactgccc acttggcagt acatcaagtg tatcatatgc | 180 |
| caagtacgcc ccctattgac gtcaatgacg gtaaatggcc cgcctggcat tatgcccagt | 240 |
| acatgacctt atgggacttt cctacttggc agtacatcta cgtattagtc atcgctatta | 300 |
| ccatggcccg ggtcgcgaca tgcagcggga cgcgccaccc cgagcccagc tccggcgcc | 360 |
| ccggctcccc gcgccccga tcggggccgc cgctagtagt ggcggcggcg gaggcggggg | 420 |
| cagcggcgga ggcggcggag gcgcctctgc agctccggct cccccctggcc tctcgggaac | 480 |
| tacaagtccc aggggggcctg gcggtgggcg gcgggcggaa gaggcggggt cggcgccgcg | 540 |
| aggccggaag tggccgtgga ggcggaagtg gcgcggccgc ggaggggcct ggagtgcggc | 600 |
| ggcggcggga cccggagcag gagcggcggc agcagcgact gggggcggcg gcggcgcgtt | 660 |
| ggaggcggcc ggatccgttt aaacggctcg catctctcct tcacgcgccc gccgccctac | 720 |
| ctgaggccgc catccacgcc ggttgagtcg cgttctgccg cctcccgcct gtggtgcctc | 780 |
| ctgaactgcg tccgccgtct aggtaagttt aaagctcagg tcgagaccgg cctttgtcc | 840 |
| ggcgctccct tggagcctac ctagactcag ccggctctcc acgctttgcc tgaccctgct | 900 |
| tgctcaactc tacgtctttg tttcgttttc tgttctgcgc cgttacagat cactagtgtt | 960 |
| taaacagagt aatgacatgg ttccttccat cctccaaagg tgaccaataa tagtttgtaa | 1020 |
| gtatcattat gaactaatga attttcaaca tatttgatat atttcaatcc attgccatca | 1080 |
| ttgttcttat cgatatttga gttggctcac tttgccagta agagtctatt caaattggct | 1140 |
| tctgagtcca tttgacacaa caccttttgat cttttgacagt ttccttggtt ttaggtgcta | 1200 |
| gatgatttct caggctcacc ttagacattt cctgccacag acttagaatc agccattct | 1260 |
| ctaaggaccc tgattccatt tcatgagaaa tgatagagac cacaatcaaa acaagtcatg | 1320 |
| aatttatact gatattttca attcaaatta aagatgaggt ttttgctaaa ttttttttgag | 1380 |
| tttatatttg tatgtcttat gctgaaaaat cttgtttcct aattagtaac ataattattc | 1440 |
| atttgatggg taaatatttt agggccgatt ctttggtttt atagccaaga taccctgttg | 1500 |
| ataaagtctt gtgggagcaa ttataagact ggcttatttt gaagcttttt aaaaaagaca | 1560 |
| tccttacctg ttttaactgt agattatatt aacttaaata ggtacagccc acgcttgact | 1620 |
| agtgcagaag ttggtcgtga ggcactgggc aggtaagtat caaggttaca agacaggttt | 1680 |
| aaggagacca atagaaactg ggcttgtcga gacagagaag actcttgcgt ttctgatagg | 1740 |
| cacctattgg tcttactgac atccactttg cctttctctc cacag | 1785 |

<210> SEQ ID NO 41
<211> LENGTH: 2242
<212> TYPE: DNA
<213> ORGANISM: Artificial Sequence
<220> FEATURE:
<223> OTHER INFORMATION: artificial sequence

<400> SEQUENCE: 41

| | |
|---|---|
| gcgttacata acttacggta aatggcccgc ctggctgacc gcccaacgac ccccgcccat | 60 |
| tgacgtcaat aatgacgtat gttcccatag taacgccaat agggactttc cattgacgtc | 120 |
| aatgggtgga gtatttacgg taaactgccc acttggcagt acatcaagtg tatcatatgc | 180 |
| caagtacgcc ccctattgac gtcaatgacg gtaaatggcc cgcctggcat tatgcccagt | 240 |
| acatgacctt atgggacttt cctacttggc agtacatcta cgtattagtc atcgctatta | 300 |
| ccatggcccg gtcgcgaca tgcagcggga cgcgccaccc cgagcccag ctccggcgcc | 360 |
| ccggctcccc gcgccccga tcggggccgc cgctagtagt ggcggcggcg gaggcggggg | 420 |
| cagcggcggc ggcggcggag gcgcctctgc agctccggct ccccctggcc tctcgggaac | 480 |
| tacaagtccc aggggcctg gcggtgggcg gcgggcggaa gaggcgggt cggcgccgcg | 540 |
| aggccggaag tggccgtgga ggcggaagtg gcgcggccgc ggaggggcct ggagtgcggc | 600 |
| ggcggcggga cccggagcag gagcggcggc agcagcgact ggggggcggcg gcggcgcgtt | 660 |
| ggaggcggcc ggatccgttt aaacggctcg catctctcct tcacgcgccc gccgccctac | 720 |
| ctgaggccgc catccacgcc ggttgagtcg cgttctgccg cctcccgcct gtggtgcctc | 780 |
| ctgaactgcg tccgccgtct aggtaagttt aaagctcagg tcgagaccgg cctttgtcc | 840 |
| ggcgctccct tggagcctac ctagactcag ccggctctcc acgctttgcc tgaccctgct | 900 |
| tgctcaactc tacgtctttg tttcgttttc tgttctgcgc cgttacagat cactagttaa | 960 |
| cgctggtggg tagggatgag ggaggagggg gcattgtgat gtacagggct gctctgtgag | 1020 |
| atcaagggtc tcttaagggt gggagctggg gcagggacta cgagagcagc cagatgggct | 1080 |
| gaaagtggaa ctcaaggggt ttctggcacc tacctacctg cttcccgctg ggggtgggg | 1140 |
| agttggccca gagtcttaag attggggcag ggtggagagg tgggctcttc ctgcttccca | 1200 |
| ctcatcttat agctttcttt ccccagatcc gaattcgaga tccaaaccaa ggaggaaagg | 1260 |
| atatcacaga ggagagctag tcgggtttgc cgccagaaca caggtaagtg ccgtgtgtgg | 1320 |
| ttcccgcggg cctggcctct ttacgggtta tggcccttgc gtgccttgaa ttacttccac | 1380 |
| ctggctgcag tacgtgattc ttgatcccga gcttcgggtt ggaagtgggt gggagagttc | 1440 |
| gaggccttgc gcttaaggag ccccttcgcc tcgtgcttga gttgaggcct ggcctgggcg | 1500 |
| ctggggccgc cgcgtgcgaa tctggtggca ccttcgcgcc tgtctcgctg ctttcgataa | 1560 |
| gtctctagcc atttaaaatt tttgatgacc tgctgcgacg ctttttttct ggcaagatag | 1620 |
| tcttgtaaat gcgggccaag atctgcacac tggtatttcg gtttttgggg ccgcgggcgg | 1680 |
| cgacggggcc cgtgcgtccc agcgcacatg ttcgcgagg cggggcctgc gagcgcggcc | 1740 |
| accgagaatc ggacgggggt agtctcaagc tggccggcct gctctggtgc ctggcctcgc | 1800 |
| gccgccgtgt atcgccccgc cctgggcggc aaggctggcc cggtcggcac cagttgcgtg | 1860 |
| agcggaaaga tggccgcttc ccggccctgc tgcaggagc tcaaaatgga ggacgcggcg | 1920 |
| ctcgggagag cgggcgggtg agtcacccac acaaaggaaa agggcctttc cgtcctcagc | 1980 |
| cgtcgcttca tgtgactcca cggagtaccg ggcgccgtcc aggcacctcg attagttctc | 2040 |
| gagcttttgg agtacgtcgt ctttaggttg ggggagggg ttttatgcga tggagtttcc | 2100 |

| ccacactgag tgggtggaga ctgaagttag gccagcttgg cacttgatgt aattctcctt | 2160 |
| ggaatttgcc ctttttgagt ttggatcttg gttcattctc aagcctcaga cagtggttca | 2220 |
| aagttttttt cttccatttc ag | 2242 |

<210> SEQ ID NO 42
<211> LENGTH: 1650
<212> TYPE: DNA
<213> ORGANISM: Artificial Sequence
<220> FEATURE:
<223> OTHER INFORMATION: artificial sequence

<400> SEQUENCE: 42

| gcgttacata acttacggta aatggcccgc ctggctgacc gcccaacgac ccccgcccat | 60 |
| tgacgtcaat aatgacgtat gttcccatag taacgccaat agggactttc cattgacgtc | 120 |
| aatgggtgga gtatttacgg taaactgccc acttggcagt acatcaagtg tatcatatgc | 180 |
| caagtacgcc ccctattgac gtcaatgacg gtaaatggcc cgcctggcat tatgcccagt | 240 |
| acatgacctt atgggacttt cctacttggc agtacatcta cgtattagtc atcgctatta | 300 |
| ccatggcccg gtcgcgaca tgcagcggga cgcgccaccc cgagcccag ctccggcgcc | 360 |
| ccggctcccc gcgccccga tcggggccgc cgctagtagt ggcggcggcg gaggcggggg | 420 |
| cagcggcggc ggcggcggag gcgcctctgc agctccggct cccctggcc tctcgggaac | 480 |
| tacaagtccc aggggcctg gcggtgggcg gcgggcggaa gaggcgggt cggcgccgcg | 540 |
| aggccggaag tggccgtgga ggcggaagtg gcgcggccgc ggaggggcct ggagtgcggc | 600 |
| ggcggcggga cccggagcag gagcggcggc agcagcgact gggggcggcg gcggcgcgtt | 660 |
| ggaggcggcc ggatccgttt aaacggctcg catctctcct tcacgcgccc gccgccctac | 720 |
| ctgaggccgc catccacgcc ggttgagtcg cgttctgccg cctcccgcct gtggtgcctc | 780 |
| ctgaactgcg tccgccgtct aggtaagttt aaagctcagg tcgagaccgg cctttgtcc | 840 |
| ggcgctccct tggagcctac ctagactcag ccggctctcc acgctttgcc tgaccctgct | 900 |
| tgctcaactc tacgtctttg tttcgttttc tgttctgcgc cgttacagat cactagttaa | 960 |
| cgctggtggg tagggatgag ggagggaggg gcattgtgat gtacagggct gctctgtgag | 1020 |
| atcaagggtc tcttaagggt gggagctggg gcagggacta cgagagcagc cagatgggct | 1080 |
| gaaagtggaa ctcaaggggt ttctggcacc tacctacctg cttcccgctg ggggtgggg | 1140 |
| agttggccca gagtcttaag attggggcag ggtggagagg tgggctcttc ctgcttccca | 1200 |
| ctcatcttat agctttcttt ccccagatcc gaattcgaga tccaaaccaa ggaggaaagg | 1260 |
| atatcacaga ggagagctag ttcagagagc ctcggctagg taggggatcg ggactctggc | 1320 |
| gggagggcgg cttggtgcgt ttgcggggat gggcggccgc ggcaggccct ccgagcgtgg | 1380 |
| tggagccgtt ctgtgagaca gccgggtacg agtcgtgacg ctggaagggg caagcgggtg | 1440 |
| gtgggcagga atgcggtccg ccctgcagca accggagggg gagggagaag ggagcggaaa | 1500 |
| agtctccacc ggacgcggcc atggctcggg ggggggggg cagcggagga gcgcttccgg | 1560 |
| ccgacgtctc gtcgctgatt ggcttctttt cctcccgccg tgtgtgaaaa cacaattgta | 1620 |
| ctaaccttct tctctttcct ctcctgacag | 1650 |

<210> SEQ ID NO 43
<211> LENGTH: 1587
<212> TYPE: DNA
<213> ORGANISM: Artificial Sequence
<220> FEATURE:
<223> OTHER INFORMATION: artificial sequence

<400> SEQUENCE: 43

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg ggtcgcgaca tgcagcggga cgcgccaccc cgagcccag ctccggcgcc      360
ccggctcccc gcgcccccga tcggggccgc cgctagtagt ggcggcggcg gaggcggggg     420
cagcggcggc ggcggcggag gcgcctctgc agctccggct cccctggcc tctcgggaac      480
tacaagtccc aggggcctg gcggtggcg gcgggcggaa gaggcggggt cggcgccgcg       540
aggccggaag tggccgtgga ggcggaagtg gcgcggccgc ggaggggcct ggagtgcggc     600
ggcggcggga cccggagcag gagcggcggc agcagcgact gggggcggcg gcggcgcgtt     660
ggaggcggcc ggatccacta ggatccgttt aaacggctcg catctctcct tcacgcgccc     720
gccgccctac ctgaggccgc catccacgcc ggttgagtcg cgttctgccg cctcccgcct     780
gtggtgcctc ctgaactgcg tccgccgtct aggtaagttt aaagctcagg tcgagaccgg     840
gcctttgtcc ggcgctccct ggagcctac ctagactcag ccggctctcc acgctttgcc      900
tgaccctgct tgctcaactc tacgtctttg tttcgttttc tgttctgcgc cgttacagat     960
cactagttaa cgctggtggg tagggatgag ggagggaggg gcattgtgat gtacagggct    1020
gctctgtgag atcaagggtc tcttaagggt gggagctggg gcagggacta cgagagcagc    1080
cagatgggct gaaagtggaa ctcaagggt ttctggcacc tacctacctg cttcccgctg    1140
gggggtgggg agttggccca gagtcttaag attggggcag ggtggagagg tgggctcttc    1200
ctgcttccca ctcatcttat agctttcttt ccccagatcc gaattcgaga tccaaaccaa    1260
ggaggaaagg atatcacaga ggagagctag tcttcgaggg gctcgcatct ctccttcacg    1320
cgcccgccgc cctacctgag gccgccatcc acgccggttg agtcgcgttc tgccgcctcc    1380
cgcctgtggt gcctcctgaa ctgcgtccgc cgtctaggta agtttaaagc tcaggtcgag    1440
accgggcctt tgtccggcgc tcccttggag cctacctaga ctcagccggc tctccacgct    1500
tgcctgacc ctgcttgctc aactctacgt ctttgtttcg ttttctgttc tgcgccgtta    1560
cagatccaag ctgtgaccgg cgcctac                                      1587
```

<210> SEQ ID NO 44
<211> LENGTH: 1443
<212> TYPE: DNA
<213> ORGANISM: Artificial Sequence
<220> FEATURE:
<223> OTHER INFORMATION: artificial sequence

<400> SEQUENCE: 44

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg ggtcgcgaca tgcagcggga cgcgccaccc cgagcccag ctccggcgcc      360
```

```
ccggctcccc gcgcccccga tcggggccgc cgctagtagt ggcggcggcg gaggcggggg    420
cagcggcggc ggcggcggag gcgcctctgc agctccggct cccctggcc tctcgggaac     480 tacaagtccc aggggcctg gcggtgggcg gcgggcggaa gaggcggggt cggcgccgcg     540
aggccggaag tggccgtgga ggcggaagtg gcgcggccgc ggaggggcct ggagtgcggc    600
ggcggcggga cccggagcag gagcggcggc agcagcgact ggggcggcg gcggcgcgtt    660 ggaggcggcc ggatccgttt aaacggctcg catctctcct tcacgcgccc gccgccctac    720
ctgaggccgc catccacgcc ggttgagtcg cgttctgccg cctcccgcct gtggtgcctc    780
ctgaactgcg tccgccgtct aggtaagttt aaagctcagg tcgagaccgg gcctttgtcc    840
ggcgctccct tggagcctac ctagactcag ccggctctcc acgctttgcc tgaccctgct    900
tgctcaactc tacgtctttg tttcgttttc tgttctgcgc cgttacagat cactagttaa    960
cgctggtggg tagggatgag ggaggagggg gcattgtgat gtacagggct gctctgtgag   1020
atcaagggtc tcttaagggt gggagctggg gcagggacta cgagagcagc cagatgggct   1080
gaaagtggaa ctcaagggt ttctggcacc tacctacctg cttcccgctg ggggtgggg    1140 agttggccca gagtcttaag attggggcag ggtggagagg tgggctcttc ctgcttccca   1200
ctcatcttat agctttcttt ccccagatcc gaattcgaga tccaaaccaa ggaggaaagg   1260
atatcacaga ggagagctag tgcagaagtt ggtcgtgagg cactgggcag gtaagtatca   1320
aggttacaag acaggtttaa ggagaccaat agaaactggg cttgtcgaga cagagaagac   1380
tcttgcgttt ctgataggca cctattggtc ttactgacat ccactttgcc tttctctcca   1440
cag                                                                1443

<210> SEQ ID NO 45
<211> LENGTH: 2627
<212> TYPE: DNA
<213> ORGANISM: Artificial Sequence
<220> FEATURE:
<223> OTHER INFORMATION: artificial sequence

<400> SEQUENCE: 45
gcgttacata acttacggta aatggcccgc ctggctgacc gcccaacgac ccccgcccat     60
tgacgtcaat aatgacgtat gttcccatag taacgccaat agggactttc cattgacgtc    120
aatgggtgga gtatttacgg taaactgccc acttggcagt acatcaagtg tatcatatgc    180
caagtacgcc ccctattgac gtcaatgacg gtaaatggcc cgcctggcat tatgcccagt    240
acatgacctt atgggacttt cctacttggc agtacatcta cgtattagtc atcgctatta    300
ccatggcccg gtcgcgaca tgcagcggga cgcgccaccc cgagcccag ctccggcgcc     360 ccggctcccc gcgcccccga tcggggccgc cgctagtagt ggcggcggcg gaggcggggg    420
cagcggcggc ggcggcggag gcgcctctgc agctccggct cccctggcc tctcgggaac    480 tacaagtccc aggggcctg gcggtgggcg gcgggcggaa gaggcggggt cggcgccgcg    540
aggccggaag tggccgtgga ggcggaagtg gcgcggccgc ggaggggcct ggagtgcggc    600
ggcggcggga cccggagcag gagcggcggc agcagcgact ggggcggcg gcggcgcgtt    660 ggaggcggcc ggatccgttt aaacagagta atgacatggt tccttccatc ctccaaaggt    720
gaccaataat agtttgtaag tatcattatg aactaatgaa ttttcaacat atttgatata    780
tttcaatcca ttgccatcat tgttcttatc gatatttgag ttggctcact tgccagtaa    840 gagtctattc aaaattggctt ctgagtccat ttgacacaac accttgatc tttgacagtt    900 tccttggttt taggtgctag atgatttctc aggctcacct tagacatttc ctgccacaga    960
```

-continued

```
cttagaatca gccatttctc taaggaccct gattccattt catgagaaat gatagagacc    1020
acaatcaaaa caagtcatga atttatactg atattttcaa ttcaaattaa agatgaggtt    1080
tttgctaaat ttttttgagt ttatatttgt atgtcttatg ctgaaaaatc ttgtttccta    1140
attagtaaca taattattca tttgatgggt aaatatttta gggccgattc tttggtttta    1200
tagccaagat accctgttga taaagtcttg tgggagcaat tataagactg gcttattttg    1260
aagcttttta aaaagacat ccttacctgt tttaactgta gattatatta acttaaaatag    1320 gtacagccca cgcttgacta gttaacgctg gtgggtaggg atgagggagg gaggggcatt    1380
gtgatgtaca gggctgctct gtgagatcaa gggtctctta agggtgggag ctggggcagg    1440
gactacgaga gcagccagat gggctgaaag tggaactcaa ggggtttctg gcacctacct    1500
acctgcttcc cgctgggggg tggggagttg gcccagagtc ttaagattgg ggcagggtgg    1560
agaggtgggc tcttcctgct tcccactcat cttatagctt tctttcccca gatccgaatt    1620
cgagatccaa accaaggagg aaaggatatc acagaggaga gctagtcggg tttgccgcca    1680
gaacacaggt aagtgccgtg tgtggttccc gcgggcctgg cctctttacg gttatggcc     1740 cttgcgtgcc ttgaattact tccacctggc tgcagtacgt gattcttgat cccgagcttc    1800
gggttggaag tgggtgggag agttcgaggc cttgcgctta aggagcccct tcgcctcgtg    1860
cttgagttga ggcctggcct gggcgctggg ccgccgcgt gcgaatctgg tggcaccttc     1920
gcgcctgtct cgctgctttc gataagtctc tagccattta aaatttttga tgacctgctg    1980
cgacgctttt tttctggcaa gatagtcttg taaatgcggg ccaagatctg cacactggta    2040
tttcggtttt tggggccgcg ggcggcgacg gggcccgtgc gtcccagcgc acatgttcgg    2100
cgaggcgggg cctgcgagcg cggccaccga gaatcgacg ggggtagtct caagctggcc     2160
ggcctgctct ggtgcctggc ctcgcgccgc cgtgtatcgc cccgccctgg gcggcaaggc    2220
tggcccggtc ggcaccagtt gcgtgagcgg aaagatggcc gcttcccggc cctgctgcag    2280
ggagctcaaa atggaggacg cggcgctcgg gagagcgggc gggtgagtca cccacacaaa    2340
ggaaaagggc ctttccgtcc tcagccgtcg cttcatgtga ctccacggag taccgggcgc    2400
cgtccaggca cctcgattag ttctcgagct tttggagtac gtcgtcttta ggttgggggg    2460
aggggtttta tgcgatggag tttcccccaca ctgagtgggt ggagactgaa gttaggccag    2520
cttggcactt gatgtaattc tccttggaat ttgcccttt tgagtttgga tcttggttca     2580
ttctcaagcc tcagacagtg gttcaaagtt ttttcttcc atttcag                   2627
```

<210> SEQ ID NO 46
<211> LENGTH: 1946
<212> TYPE: DNA
<213> ORGANISM: Artificial Sequence
<220> FEATURE:
<223> OTHER INFORMATION: artificial sequence

<400> SEQUENCE: 46

```
gtaacgccaa tagggacttt ccattgacgt caatgggtgg agtatttacg gtaaactgcc     60
cacttggcag tacatcaagt gtatcatatg ccaagtacgc cccctattga cgtcaatgac    120
ggtaaatggc ccgcctggca ttatgcccag tacatgacct tatgggactt tcctacttgg    180
cagtacatct acgtattagt catcgctatt accatggccc gggtcgcgac atgcagcggg    240
acgcgccacc ccgagcccca gctccggcgc cccggctccc cgcgccccg atcgggccg     300 ccgctagtag tggcggcggc ggaggcgggg gcagcggcgg cggcggcgga ggcgcctctg    360
```

```
cagctccggc tcccctggc ctctcgggaa ctacaagtcc caggggcct ggcggtgggc      420 ggcgggcgga agaggcgggg tcggcgccgc gaggccggaa gtggccgtgg aggcggaagt      480
ggcgcggccg cggaggggcc tggagtgcgg cggcggcggg acccggagca ggagcggcgg      540
cagcagcgac tggggcggc ggcggcgcgt tggaggcggc cggatccgtt taaacagagt      600
aatgacatgg ttccttccat cctccaaagg tgaccaataa tagtttgtaa gtatcattat      660
gaactaatga attttcaaca tatttgatat atttcaatcc attgccatca ttgttcttat      720
cgatatttga gttggctcac tttgccagta agagtctatt caaattggct tctgagtcca      780
tttgacacaa cacctttgat ctttgacagt tccttggtt ttaggtgcta gatgatttct      840
caggctcacc ttagacattt cctgccacag acttagaatc agccatttct ctaaggaccc      900
tgattccatt tcatgagaaa tgatagagac cacaatcaaa acaagtcatg aatttatact      960
gatattttca attcaaatta aagatgaggt ttttgctaaa tttttttgag tttatatttg     1020
tatgtcttat gctgaaaaat cttgtttcct aattagtaac ataattattc atttgatggg     1080
taaatatttt agggccgatt ctttggtttt atagccaaga taccctgttg ataaagtctt     1140
gtgggagcaa ttataagact ggcttatttt gaagcttttt aaaaaagaca tccttacctg     1200
ttttaactgt agattatatt aacttaaata ggtacagccc acgcttgact agttaacgct     1260
ggtgggtagg gatgagggag ggaggggcat tgtgatgtac agggctgctc tgtgagatca     1320
agggtctctt aagggtggga gctggggcag ggactacgag agcagccaga tgggctgaaa     1380
gtggaactca aggggtttct ggcacctacc tacctgcttc ccgctgggg gtggggagtt     1440 ggcccagagt cttaagattg ggcagggtg gagaggtggg ctcttcctgc ttcccactca     1500
tcttatagct ttcttttcccc agatccgaat tcgagatcca aaccaaggag gaaaggatat     1560
cacagaggag agctagttca gagagcctcg gctaggtagg ggatcgggac tctggcggga     1620
gggcggcttg gtgcgtttgc ggggatgggc ggccgcggca ggcctccga gcgtggtgga     1680 gccgttctgt gagacagccg ggtacgagtc gtgacgctgg aaggggcaag cgggtggtgg     1740
gcaggaatgc ggtccgccct gcagcaaccg gaggggagg gagaagggag cggaaaagtc     1800
tccaccggac gcggccatgg ctcggggggg ggggggcagc ggaggagcgc ttccggccga     1860
cgtctcgtcg ctgattggct tcttttcctc ccgccgtgtg tgaaaacaca attgtactaa     1920
ccttcttctc tttcctctcc tgacag                                         1946
```

```
<210> SEQ ID NO 47
<211> LENGTH: 1968
<212> TYPE: DNA
<213> ORGANISM: Artificial Sequence
<220> FEATURE:
<223> OTHER INFORMATION: artificial sequence

<400> SEQUENCE: 47
gcgttacata acttacggta aatggcccgc ctggctgacc gcccaacgac ccccgcccat       60
tgacgtcaat aatgacgtat gttcccatag taacgccaat agggactttc cattgacgtc      120
aatgggtgga gtatttacgg taaactgccc acttggcagt acatcaagtg tatcatatgc      180
caagtacgcc ccctattgac gtcaatgacg gtaaatggcc cgcctggcat tatgcccagt      240
acatgacctt atgggacttt cctacttggc agtacatcta cgtattagtc atcgctatta      300
ccatggcccg ggtcgcgaca tgcagcggga gcgccaccc cgagcccag ctccggcgcc      360 ccggctcccc gcgcccccga tcggggccgc cgctagtagt ggcggcggcg gaggcggggg      420
cagcggcggc ggcggcggag gcgcctctgc agctccggct cccctggcc tctcgggaac      480
```

```
tacaagtccc aggggggcctg gcggtgggcg gcgggcggaa gaggcggggt cggcgccgcg      540
aggccggaag tggccgtgga ggcggaagtg gcgcggccgc ggaggggcct ggagtgcggc      600
ggcggcggga cccggagcag gagcggcggc agcagcgact gggggcggcg gcggcgcgtt      660
ggaggcggcc ggatccacta gtgtttaaac agagtaatga catggttcct tccatcctcc      720
aaaggtgacc aataatagtt tgtaagtatc attatgaact aatgaatttt caacatattt      780
gatatatttc aatccattgc catcattgtt cttatcgata tttgagttgg ctcactttgc      840
cagtaagagt ctattcaaat tggcttctga gtccatttga cacaacacct tgatctttg       900 acagtttcct tggttttagg tgctagatga tttctcaggc tcaccttaga catttcctgc      960
cacagactta gaatcagcca tttctctaag gaccctgatt ccatttcatg agaaatgata     1020
gagaccacaa tcaaaacaag tcatgaattt atactgatat tttcaattca aattaaagat     1080 gaggttttg ctaaattttt ttgagtttat atttgtatgt cttatgctga aaaatcttgt      1140
ttcctaatta gtaacataat tattcatttg atgggtaaat attttagggc cgattctttg     1200
gttttatagc caagataccc tgttgataaa gtcttgtggg agcaattata agactggctt     1260
attttgaagc tttttaaaaa agacatcctt acctgtttta actgtagatt atattaactt     1320
aaataggtac agcccacgct tgactagtta acgctggtgg gtagggatga gggagggagg     1380
ggcattgtga tgtacagggc tgctctgtga gatcaagggt ctcttaaggg tgggagctgg     1440
ggcagggact acgagagcag ccagatgggc tgaaagtgga actcaagggg tttctggcac     1500
ctacctacct gcttcccgct gggggggtggg gagttggccc agagtcttaa gattggggca     1560
gggtggagag gtgggctctt cctgcttccc actcatctta tagctttctt tccccagatc     1620
cgaattcgag atccaaacca aggaggaaag gatatcacag aggagagcta gtcttcgagg     1680
ggctcgcatc tctccttcac gcgcccgccg ccctacctga ggccgccatc cacgccggtt     1740
gagtcgcgtt ctgccgcctc ccgcctgtgg tgcctcctga actgcgtccg ccgtctaggt     1800
aagtttaaag ctcaggtcga gaccgggcct ttgtccggcg ctcccttgga gcctacctag     1860
actcagccgg ctctccacgc tttgcctgac cctgcttgct caactctacg tctttgtttc     1920
gttttctgtt ctgcgccgtt acagatccaa gctgtgaccg gcgcctac                 1968
```

<210> SEQ ID NO 48
<211> LENGTH: 1834
<212> TYPE: DNA
<213> ORGANISM: Artificial Sequence
<220> FEATURE:
<223> OTHER INFORMATION: artificial sequence

<400> SEQUENCE: 48

```
gcgttacata acttacggta aatggcccgc ctggctgacc gcccaacgac ccccgcccat       60
tgacgtcaat aatgacgtat gttcccatag taacgccaat agggactttc cattgacgtc      120
aatgggtgga gtatttacgg taaactgccc acttggcagt acatcaagtg tatcatatgc      180
caagtacgcc ccctattgac gtcaatgacg gtaaatggcc cgcctggcat tatgcccagt      240
acatgacctt atgggacttt cctacttggc agtacatcta cgtattagtc atcgctatta      300
ccatggcccg ggtcgcgaca tgcagcggga cgcgccaccc cgagcccag ctccggcgcc       360 ccggctcccc gcgccccga tcggggccgc cgctagtagt ggcggcggcg gaggcggggg       420
cagcggcggc ggcggcggag gcgcctctgc agctccggct ccccctggcc tctcgggaac      480
tacaagtccc aggggggcctg gcggtgggcg gcgggcggaa gaggcggggt cggcgccgcg     540
```

```
aggccggaag tggccgtgga ggcggaagtg gcgcggccgc ggaggggcct ggagtgcggc    600
ggcggcggga cccggagcag gagcggcggc agcagcgact gggggcggcg gcggcgcgtt    660
ggaggcggcc ggatccacta gtgtttaaac agagtaatga catggttcct tccatcctcc    720
aaaggtgacc aataatagtt tgtaagtatc attatgaact aatgaatttt caacatattt    780
gatatatttc aatccattgc catcattgtt cttatcgata tttgagttgg ctcactttgc    840
cagtaagagt ctattcaaat tggcttctga gtccatttga cacaaccct ttgatctttg     900 acagtttcct tggttttagg tgctagatga tttctcaggc tcaccttaga catttcctgc    960
cacagactta gaatcagcca tttctctaag gaccctgatt ccatttcatg agaaatgata   1020
gagaccacaa tcaaaacaag tcatgaattt atactgatat tttcaattca aattaaagat   1080 gaggttttg ctaaattttt ttgagtttat atttgtatgt cttatgctga aaaatcttgt    1140
ttcctaatta gtaacataat tattcatttg atgggtaaat attttagggc cgattctttg   1200
gttttatagc caagataccc tgttgataaa gtcttgtggg agcaattata agactggctt   1260
attttgaagc ttttaaaaa agacatcctt acctgtttta actgtagatt atattaactt    1320
aaataggtac agcccacgct tgactagtta acgctggtgg gtagggatga gggagggagg   1380
ggcattgtga tgtacagggc tgctctgtga gatcaagggt ctcttaaggg tgggagctgg   1440
ggcagggact acgagagcag ccagatgggc tgaaagtgga actcaagggg tttctggcac   1500
ctacctacct gcttcccgct gggggtggg gagttggccc agagtcttaa gattggggca    1560
gggtggagag gtgggctctt cctgcttccc actcatctta tagctttctt tccccagatc   1620
cgaattcgag atccaaacca aggaggaaag gatatcacag aggagagcta gtgcagaagt   1680
tggtcgtgag gcactgggca ggtaagtatc aaggttacaa gacaggttta aggagaccaa   1740
tagaaactgg gcttgtcgag acagagaaga ctcttgcgtt tctgataggc acctattggt   1800
cttactgaca tccactttgc ctttctctcc acag                               1834
```

<210> SEQ ID NO 49
<211> LENGTH: 2908
<212> TYPE: DNA
<213> ORGANISM: Artificial Sequence
<220> FEATURE:
<223> OTHER INFORMATION: artificial sequence

<400> SEQUENCE: 49

```
gcgttacata acttacggta aatggcccgc ctggctgacc gcccaacgac ccccgcccat     60
tgacgtcaat aatgacgtat gttcccatag taacgccaat agggactttc cattgacgtc    120
aatgggtgga gtatttacgg taaactgccc acttggcagt acatcaagtg tatcatatgc    180
caagtacgcc ccctattgac gtcaatgacg gtaaatggcc cgcctggcat tatgcccagt    240
acatgacctt atgggacttt cctacttggc agtacatcta cgtattagtc atcgctatta    300
ccatggcccg gtcgcgaca tgcagcggga cgcgccaccc cgagcccag ctccggcgcc      360 ccggctcccc gcgccccga tcgggccgc gctagtagt ggcggcggcg gaggcggggg       420
cagcggcggc ggcggcggag gcgcctctgc agctccggct ccccctggcc tctcgggaac    480
tacaagtccc agggggcctg gcggtggcg gcggcggaa gaggcgggt cggcgccgcg       540 aggccggaag tggccgtgga ggcggaagtg gcgcggccgc ggaggggcct ggagtgcggc    600
ggcggcggga cccggagcag gagcggcggc agcagcgact gggggcggcg gcggcgcgtt    660
ggaggcggcc ggatccgttt aaacggctcg catctctcct tcacgcgccc gccgccctac    720
ctgaggccgc catccacgcc ggttgagtcg cgttctgccg cctcccgcct gtggtgcctc    780
```

```
ctgaactgcg tccgccgtct aggtaagttt aaagctcagg tcgagaccgg gcctttgtcc      840
ggcgctccct tggagcctac ctagactcag ccggctctcc acgctttgcc tgaccctgct      900
tgctcaactc tacgtctttg tttcgttttc tgttctgcgc cgttacagat cactagtgtt      960
taaacagagt aatgacatgg ttccttccat cctccaaagg tgaccaataa tagtttgtaa     1020
gtatcattat gaactaatga attttcaaca tatttgatat atttcaatcc attgccatca     1080
ttgttcttat cgatatttga gttggctcac tttgccagta agagtctatt caaattggct     1140
tctgagtcca tttgacacaa cacctttgat ctttgacagt ttccttggtt ttaggtgcta     1200 gatgattttct caggctcacc ttagacattt cctgccacag acttagaatc agccatttct     1260
ctaaggaccc tgattccatt tcatgagaaa tgatagagac cacaatcaaa acaagtcatg     1320 aattatact gatattttca attcaaatta aagatgaggt ttttgctaaa ttttttttgag     1380 tttatatttg tatgtcttat gctgaaaaat cttgtttcct aattagtaac ataattattc     1440
atttgatggg taaatatttt agggccgatt ctttggtttt atagccaaga taccctgttg     1500
ataaagtctt gtgggagcaa ttataagact ggcttatttt gaagcttttt aaaaaagaca     1560
tccttacctg ttttaactgt agattatatt aacttaaata ggtacagccc acgcttgact     1620
agttaacgct ggtgggtagg gatgagggag ggaggggcat tgtgatgtac agggctgctc     1680
tgtgagatca agggtctctt aagggtggga gctgggcag ggactacgag agcagccaga     1740
tgggctgaaa gtgaactca aggggtttct ggcacctacc tacctgcttc ccgctggggg     1800
gtggggagtt ggcccagagt cttaagattg gggcagggtg gagaggtggg ctcttcctgc     1860
ttcccactca tcttatagct ttcttttccc agatccgaat tcgagatcca aaccaaggag     1920
gaaaggatat cacagaggag agctagtcgg gtttgccgcc agaacacagg taagtgccgt     1980
gtgtggttcc cgcgggcctg gcctctttac gggttatggc ccttgcgtgc cttgaattac     2040
ttccacctgg ctgcagtacg tgattcttga tcccgagctt cgggttggaa gtgggtggga     2100
gagttcgagg ccttgcgctt aaggagcccc ttcgcctcgt gcttgagttg aggcctggcc     2160
tgggcgctgg ggccgccgcg tgcgaatctg gtggcacctt cgcgcctgtc tcgctgcttt     2220
cgataagtct ctagccattt aaaattttg atgacctgct gcgacgcttt ttttctggca     2280
agatagtctt gtaaatgcgg gccaagatct gcacactggt atttcggttt ttggggccgc     2340
gggcggcgac ggggcccgtg cgtcccagcg cacatgttcg gcgaggcggg gcctgcgagc     2400
gcggccaccg agaatcggac gggggtagtc tcaagctggc cggcctgctc tggtgcctgg     2460
cctcgcgccc ccgtgtatcg ccccgccctg ggcggcaagg ctggcccggt cggcaccagt     2520
tgcgtgagcg gaaagatggc cgcttcccgg ccctgctgca gggagctcaa aatggaggac     2580
gcggcgctcg ggagagcggg cggtgagtc acccacacaa aggaaaaggg cctttccgtc     2640
ctcagccgtc gcttcatgtg actccacgga gtaccgggcg ccgtccaggc acctcgatta     2700
gttctcgagc ttttggagta cgtcgtcttt aggttggggg gagggttttt atgcgatgga     2760
gtttccccac actgagtggg tggagactga agttaggcca gcttggcact tgatgtaatt     2820
ctccttggaa tttgcccttt ttgagtttgg atcttggttc attctcaagc ctcagacagt     2880
ggttcaaagt ttttttcttc catttcag                                        2908
```

<210> SEQ ID NO 50
<211> LENGTH: 2316
<212> TYPE: DNA
<213> ORGANISM: Artificial Sequence
<220> FEATURE:

<223> OTHER INFORMATION: artificial sequence

<400> SEQUENCE: 50

```
gcgttacata acttacggta aatggcccgc ctggctgacc gcccaacgac ccccgcccat    60
tgacgtcaat aatgacgtat gttcccatag taacgccaat agggactttc cattgacgtc   120
aatgggtgga gtatttacgg taaactgccc acttggcagt acatcaagtg tatcatatgc   180
caagtacgcc ccctattgac gtcaatgacg gtaaatggcc cgcctggcat tatgcccagt   240
acatgacctt atgggacttt cctacttggc agtacatcta cgtattagtc atcgctatta   300
ccatggcccg gtcgcgaca tgcagcggga cgcgccaccc cgagcccag ctccggcgcc    360
ccggctcccc gcgccccga tcggggccgc cgctagtagt ggcggcggcg gaggcggggg   420
cagcggcggc ggcggcggag gcgcctctgc agctccggct cccctggcc tctcgggaac   480
tacaagtccc aggggcctg gcggtgggcg gcgggcggaa gaggcggggt cggcgccgcg   540
aggccggaag tggccgtgga ggcggaagtg gcgcggccgc ggaggggcct ggagtgcggc   600
ggcggcggga cccggagcag gagcggcggc agcagcgact gggggcggcg gcggcgcgtt   660
ggaggcggcc ggatccgttt aaacggctcg catctctcct tcacgcgccc gccgccctac   720
ctgaggccgc catccacgcc ggttgagtcg cgttctgccg cctcccgcct gtggtgcctc   780
ctgaactgcg tccgccgtct aggtaagttt aaagctcagg tcgagaccgg gcctttgtcc   840
ggcgctccct tggagcctac ctagactcag ccggctctcc acgctttgcc tgaccctgct   900
tgctcaactc tacgtctttg tttcgttttc tgttctgcgc cgttacagat cactagtgtt   960
taaacagagt aatgacatgg ttccttccat cctccaaagg tgaccaataa tagttttgtaa  1020
gtatcattat gaactaatga attttcaaca tatttgatat atttcaatcc attgccatca  1080
ttgttcttat cgatatttga gttggctcac tttgccagta agagtctatt caaattggct  1140
tctgagtcca tttgacacaa caccttttgat cttttgacagt ttccttggtt ttaggtgcta  1200
gatgattttct caggctcacc ttagacattt cctgccacag acttagaatc agccatttct  1260
ctaaggaccc tgattccatt tcatgagaaa tgatagagac cacaatcaaa acaagtcatg  1320
aatttatact gatattttca attcaaatta aagatgaggt ttttgctaaa tttttttgag  1380
tttatatttg tatgtcttat gctgaaaaat cttgtttcct aattagtaac ataattattc  1440
atttgatggg taaatatttt agggccgatt cttttggtttt atagccaaga taccctgttg  1500
ataaagtctt gtgggagcaa ttataagact ggcttattt gaagctttt aaaaaagaca  1560
tccttacctg ttttaactgt agattatatt aacttaaata ggtacagccc acgcttgact  1620
agttaacgct ggtgggtagg gatgagggag ggaggggcat tgtgatgtac agggctgctc  1680
tgtgagatca agggtctctt aagggtggga gctgggcag ggactacgag agcagccaga  1740
tgggctgaaa gtggaactca agggtttct ggcacctacc tacctgcttc ccgctggggg  1800
gtggggagtt ggcccagagt cttaagattg ggcagggtg gagaggtggg ctcttcctgc  1860
ttcccactca tcttatagct ttcttttcccc agatccgaat tcgagatcca aaccaaggag  1920
gaaaggatat cacagaggag agctagttca gagagcctcg gctaggtagg ggatcgggac  1980
tctggcggga gggcggcttg gtgcgtttgc ggggatgggc ggccgcggca ggccctccga  2040
gcgtggtgga gccgttctgt gagacagccg ggtacgagtc gtgacgctgg aaggggcaag  2100
cgggtggtgg gcaggaatgc ggtccgcccct gcagcaaccg gagggggagg gagaagggag  2160
cggaaaagtc tccaccggac gcggccatgg ctcgggggg ggggggcagc ggaggagcgc  2220
ttccggccga cgtctcgtcg ctgattggct tcttttcctc ccgccgtgtg tgaaaacaca  2280
```
attgtactaa ccttcttctc tttcctctcc tgacag        2316

<210> SEQ ID NO 51
<211> LENGTH: 2253
<212> TYPE: DNA
<213> ORGANISM: Artificial Sequence
<220> FEATURE:
<223> OTHER INFORMATION: artificial sequence

<400> SEQUENCE: 51

| | | | | | |
|---|---|---|---|---|---|
| gcgttacata | acttacggta | aatggcccgc | ctggctgacc | gcccaacgac | ccccgcccat | 60 |
| tgacgtcaat | aatgacgtat | gttcccatag | taacgccaat | agggactttc | cattgacgtc | 120 |
| aatgggtgga | gtatttacgg | taaactgccc | acttggcagt | acatcaagtg | tatcatatgc | 180 |
| caagtacgcc | ccctattgac | gtcaatgacg | gtaaatggcc | cgcctggcat | tatgcccagt | 240 |
| acatgacctt | atgggacttt | cctacttggc | agtacatcta | cgtattagtc | atcgctatta | 300 |
| ccatggcccg | gtcgcgaca | tgcagcggga | cgcgccaccc | cgagcccag | ctccggcgcc | 360 |
| ccggctcccc | gcgccccga | tcggggccgc | cgctagtagt | ggcggcggcg | gaggcggggg | 420 |
| cagcggcggc | ggcggcggag | gcgcctctgc | agctccggct | cccctggcc | tctcgggaac | 480 |
| tacaagtccc | aggggcctg | gcggtgggcg | gcgggcggaa | gaggcggggt | cggcgccgcg | 540 |
| aggccggaag | tggccgtgga | ggcggaagtg | gcgcggccgc | ggaggggcct | ggagtgcggc | 600 |
| ggcggcggga | cccggagcag | gagcggcggc | agcagcgact | ggggcggcg | cggcgcgtt | 660 |
| ggaggcggcc | ggatccacta | ggatccgttt | aaacggctcg | catctctcct | tcacgcgccc | 720 |
| gccgccctac | ctgaggccgc | catccacgcc | ggttgagtcg | cgttctgccg | cctcccgcct | 780 |
| gtggtgcctc | ctgaactgcg | tccgccgtct | aggtaagttt | aaagctcagg | tcgagaccgg | 840 |
| gcctttgtcc | ggcgctccct | tggagcctac | ctagactcag | ccggctctcc | acgctttgcc | 900 |
| tgaccctgct | tgctcaactc | tacgtctttg | tttcgttttc | tgttctgcgc | cgttacagat | 960 |
| cactagtgtt | taaacagagt | aatgacatgg | ttccttccat | cctccaaagg | tgaccaataa | 1020 |
| tagtttgtaa | gtatcattat | gaactaatga | attttcaaca | tatttgatat | atttcaatcc | 1080 |
| attgccatca | ttgttcttat | cgatatttga | gttggctcac | tttgccagta | agagtctatt | 1140 |
| caaattggct | tctgagtcca | tttgacacaa | cacctttgat | cttttgacagt | ttccttggtt | 1200 |
| ttaggtgcta | gatgatttct | caggctcacc | ttagacattt | cctgccacag | acttagaatc | 1260 |
| agccatttct | ctaaggaccc | tgattccatt | tcatgagaaa | tgatagagac | cacaatcaaa | 1320 |
| acaagtcatg | aatttatact | gatattttca | attcaaatta | aagatgaggt | ttttgctaaa | 1380 |
| tttttttgag | tttatatttg | tatgtcttat | gctgaaaaat | cttgtttcct | aattagtaac | 1440 |
| ataattattc | atttgatggg | taaatatttt | agggccgatt | ctttggtttt | atagccaaga | 1500 |
| taccctgttg | ataaagtctt | gtgggagcaa | ttataagact | ggcttatttt | gaagcttttt | 1560 |
| aaaaaagaca | tccttacctg | ttttaactgt | agattatatt | aacttaaata | ggtacagccc | 1620 |
| acgcttgact | agtaacgct | ggtgggtagg | gatgagggag | ggaggggcat | tgtgatgtac | 1680 |
| agggctgctc | tgtgagatca | agggtctctt | aagggtggga | gctggggcag | ggactacgag | 1740 |
| agcagccaga | tgggctgaaa | gtggaactca | agggggtttct | ggcacctacc | tacctgcttc | 1800 |
| ccgctggggg | gtgggagtt | ggcccagagt | cttaagattg | gggcagggtg | gagaggtggg | 1860 |
| ctcttcctgc | ttcccactca | tcttatagct | ttcttcccc | agatccgaat | tcgagatcca | 1920 |
| aaccaaggag | gaaaggatat | cacagaggag | agctagtctt | cgaggggctc | gcatctctcc | 1980 |

```
ttcacgcgcc cgccgcccta cctgaggccg ccatccacgc cggttgagtc gcgttctgcc    2040
gcctcccgcc tgtggtgcct cctgaactgc gtccgccgtc taggtaagtt taaagctcag    2100
gtcgagaccg ggcctttgtc cggcgctccc ttggagccta cctagactca gccggctctc    2160
cacgctttgc ctgaccctgc ttgctcaact ctacgtcttt gtttcgtttt ctgttctgcg    2220
ccgttacaga tccaagctgt gaccggcgcc tac                                 2253

<210> SEQ ID NO 52
<211> LENGTH: 2109
<212> TYPE: DNA
<213> ORGANISM: Artificial Sequence
<220> FEATURE:
<223> OTHER INFORMATION: UBC

<400> SEQUENCE: 52
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg gtcgcgaca tgcagcggga cgcgccaccc cgagcccag ctccggcgcc       360 ccggctcccc gcgccccga tcggggccgc cgctagtagt ggcggcggcg gaggcggggg      420
cagcggcggc ggcggcggag gcgcctctgc agctccggct cccctggcc tctcgggaac      480 tacaagtccc aggggcctg gcggtgggcg gcgggcggaa gaggcggggt cggcgccgcg      540
aggccggaag tggccgtgga ggcggaagtg gcgcggccgc ggagggcct ggagtgcggc      600 ggcggcggga cccggagcag gagcggcggc agcagcgact gggggcggcg gcggcgcgtt      660
ggaggcggcc ggatccgttt aaacggctcg catctctcct tcacgcgccc gccgcctac      720 ctgaggccgc catccacgcc ggttgagtcg cgttctgccg cctcccgcct gtggtgcctc     780
ctgaactgcg tccgccgtct aggtaagttt aaagctcagg tcgagaccgg cctttgtcc     840 ggcgctccct tggagcctac ctagactcag ccggctctcc acgctttgcc tgaccctgct     900
tgctcaactc tacgtctttg tttcgttttc tgttctgcgc cgttacagat cactagtgtt     960
taaacagagt aatgacatgg ttccttccat cctccaaagg tgaccaataa tagttttgtaa   1020 gtatcattat gaactaatga attttcaaca tatttgatat atttcaatcc attgccatca    1080
ttgttcttat cgatatttga gttggctcac tttgccagta agagtctatt caaattggct    1140
tctgagtcca tttgacacaa caccttttgat cttttgacagt ttccttggtt ttaggtgcta    1200
gatgatttct caggctcacc ttagacattt cctgccacag acttagaatc agccatttct    1260
ctaaggaccc tgattccatt tcatgagaaa tgatagagac cacaatcaaa acaagtcatg    1320
aatttatact gatattttca attcaaatta aagatgaggt ttttgctaaa ttttttttgag    1380 tttatatttg tatgtcttat gctgaaaaat cttgtttcct aattagtaac ataattattc    1440
atttgatggg taaatatttt agggccgatt ctttggtttt atagccaaga taccctgttg    1500
ataaagtctt gtgggagcaa ttataagact ggcttatttt gaagcttttt aaaaaagaca    1560
tccttacctg tttttaactgt agattatatt aacttaaata ggtacagccc acgcttgact    1620
agttaacgct ggtgggtagg gatgagggag ggaggggcat tgtgatgtac agggctgctc    1680
tgtgagatca agggtctctt aagggtggga gctgggcag ggactacgag agcagccaga     1740
tgggctgaaa gtgaactca aggggtttct ggcacctacc tacctgcttc ccgctggggg    1800
```

```
gtggggagtt ggcccagagt cttaagattg gggcagggtg gagaggtggg ctcttcctgc    1860
ttcccactca tcttatagct ttctttcccc agatccgaat tcgagatcca aaccaaggag    1920
gaaaggatat cacagaggag agctagtgca gaagttggtc gtgaggcact gggcaggtaa    1980
gtatcaaggt tacaagacag gtttaaggag accaatagaa actgggcttg tcgagacaga    2040
gaagactctt gcgtttctga taggcaccta ttggtcttac tgacatccac tttgcctttc    2100
tctccacag                                                            2109
```

<210> SEQ ID NO 53
<211> LENGTH: 812
<212> TYPE: DNA
<213> ORGANISM: Artificial Sequence
<220> FEATURE:
<223> OTHER INFORMATION: artificial sequence

<400> SEQUENCE: 53

```
gtgagtagcg ggctgctggg ctggccgggg ctttcgtggc cgccgggccg ctcggtggga      60
cggaagcgtg tggagagacc gccaagggct gtagtctggg tccgcgagca aggttgccct     120
gaactggggg ttgggggggag cgcagcaaaa tggcggctgt tcccgagtct tgaatggaag    180
acgcttgtga ggcgggctgt gaggtcgttg aaacaaggtg gggggcatgg tgggcggcaa     240
gaacccaagg tcttgaggcc ttcgctaatg cgggaaagct cttattcggg tgagatgggc     300
tggggcacca tctggggacc ctgacgtgaa gtttgtcact gactggagaa ctcggtttgt     360
cgtctgttgc ggggcggca gttatggcgg tgccgttggg cagtgcaccc gtacctttgg      420
gagcgcgcgc cctcgtcgtg tcgtgacgtc acccgttctg ttggcttata atgcagggtg     480
gggccacctg ccggtaggtg tgcggtaggc ttttctccgt cgcaggacgc agggttcggg     540
cctagggtag gctctcctga atcgacaggc gccggacctc tggtgagggg agggataagt     600
gaggcgtcag tttctttggt cggttttatg tacctatctt cttaagtagc tgaagctccg     660
gttttgaact atgcgctcgg ggttggcgag tgtgttttgt gaagtttttt aggcaccttt     720
tgaaatgtaa tcatttgggt caatatgtaa ttttcagtgt tagactagta aattgtccgc     780
taaattctgg ccgttttgg cttttttgtt ag                                    812
```

<210> SEQ ID NO 54
<211> LENGTH: 1217
<212> TYPE: DNA
<213> ORGANISM: Artificial Sequence
<220> FEATURE:
<223> OTHER INFORMATION: artificial sequence

<400> SEQUENCE: 54

```
gtaggggagc ggaactctgg tgggagggga ggtgcggtgc actgggggga tgggtggcta      60
ggggggccgt ctggtggctt gcggggggttg cctttcccgt gggaagtcgg gaacataatg    120
tttgttacgt tgggagggaa aggggtggct ggatgcaggc ggggagggagg cccgccctgc    180 ggcaaccgga gggggaggga gaagggagcg gaaaatgctc gaaaccggac ggagccattg    240
ctctcgcaga gggaggagcg cttccggcta gcctcttgtc gccgattggc cgtttctcct     300
cccgccgtgt gtgaaaacac aaatggcgta ttctggttgg agtaaagctc ctgtcagtta    360
caccgtcggg agtacgcagc cgcttagcga ctctcgcgtt gccccctggg tggggcgggt     420
aggtaggtgg ggtgtagaga tgctgggtgt gcgggcgcgg ccggcctcct gcggcgggag    480
gggagggtca gtgaaattgg ctctggcgcg ggcgtcctcc cacctccccc ttccttcggg    540
```

```
ggagtcggtt tacccgccgc ctgcttgtct tcgacacctg attggctgtc gaagctgtgg    600
gaccgggccc ttgctactgg ctcgagtctc acatgagcga aaccactgcg cggggcgcgg    660
gggtggcggg gaggcgggcg ttggtacggt cctccccgag gccgagcgcc gcagtgtctg    720
gccccgcgcc cctgcgcaac gtggcaggaa gcgcgcgctg gaggcggggg cgggctgccg    780
gccgagactt ctggatggcg gcggccgcgg ctccgccccg ggttcccacc gcctgaaggg    840
cgagacaagc ccgacctgct acaggcactc gtggggtggg gggaggagcg ggggtcggtc    900
cggctggttt gtgggtggga ggcgcttgtt ctccaaaaac cggcgcgagc tgcaatcctg    960
agggagctgc ggtggaggag gtggagagaa ggccgcaccc ttctgggcag ggggagggga   1020
gtgccgcaat acctttatgg gagttctttg ctgcctcccg tcttgtaagg accgccctgg   1080
gcctggaaga agccctccct cctttcctcc tcgcgtgatc tcgtcatcgc ctccatgtcg   1140
agtcgcttct cgattatggg cgggattctt ttgcctagac aattgtacta accttcttct   1200
ctttcctctc ctgacag                                                  1217

<210> SEQ ID NO 55
<211> LENGTH: 1494
<212> TYPE: DNA
<213> ORGANISM: Artificial Sequence
<220> FEATURE:
<223> OTHER INFORMATION: artificial sequence

<400> SEQUENCE: 55
gcgttacata acttacggta aatggcccgc ctggctgacc gcccaacgac ccccgcccat     60
tgacgtcaat aatgacgtat gttcccatag taacgccaat agggactttc cattgacgtc    120
aatgggtgga gtatttacgg taaactgccc acttggcagt acatcaagtg tatcatatgc    180
caagtacgcc ccctattgac gtcaatgacg gtaaatggcc cgcctggcat tatgcccagt    240
acatgacctt atgggacttt cctacttggc agtacatcta cgtattagtc atcgctatta    300
ccatggcccg gtcgcgaca tgcagcggga cgcgccaccc cgagcccag ctccggcgcc    360 ccggctcccc gcgccccga tcggggccgc cgctagtagt ggcggcggcg gaggcggggg    420
cagcggcggc ggcggcggag gcgcctctgc agctccggct cccctggcc tctcgggaac    480 tacaagtccc agggggcctg gcggtggcg gcgggcggaa gaggcggggt cggcgccgcg    540
aggccggaag tggccgtgga ggcggaagtg gcgcggccgc ggaggggcct ggagtgcggc    600
ggcggcggga cccggagcag gagcggcggc agcagcgact gggggcggcg gcggcgcgtt    660
ggaggcggcc ggatccacta gcgtgagtag cgggctgctg gctggccgg ggcttcgtg    720 gccgccgggc cgctcggtgg gacggaagcg tgtggagaga ccgccaaggg ctgtagtctg    780
ggtccgcgag caaggttgcc ctgaactggg ggttgggggg agcgcagcaa aatggcggct    840
gttcccgagt cttgaatgga agacgcttgt gaggcgggct gtgaggtcgt tgaaacaagg    900 tgggggggcat ggtgggcggc aagaacccaa ggtcttgagg ccttcgctaa tgcgggaaag    960
ctcttattcg ggtgagatgg gctggggcac catctgggga ccctgacgtg aagtttgtca   1020
ctgactggag aactcggttt gtcgtctgtt gcggggcgg cagttatggc ggtgccgttg   1080
ggcagtgcac ccgtaccttt gggagcgcgc gccctcgtcg tgtcgtgacg tcacccgttc   1140
tgttggctta taatgcaggg tggggccacc tgccggtagg tgtgcggtag cttttctcc   1200 gtcgcaggac gcagggttcg ggcctagggt aggctctcct gaatcgacag gcgccggacc   1260
tctggtgagg ggagggataa gtgaggcgtc agtttctttg gtcggtttta tgtacctatc   1320
ttcttaagta gctgaagctc cggttttgaa ctatgcgctc ggggttggcg agtgtgtttt   1380
```

```
gtgaagttttt ttaggcacct tttgaaatgt aatcatttgg gtcaatatgt aattttcagt    1440
gttagactag taaattgtcc gctaaattct ggccgttttt ggcttttttg ttag           1494

<210> SEQ ID NO 56
<211> LENGTH: 1918
<212> TYPE: DNA
<213> ORGANISM: Artificial Sequence
<220> FEATURE:
<223> OTHER INFORMATION: artificial sequence

<400> SEQUENCE: 56
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg ggtcgcgaca tgcagcggga cgcgccaccc cgagcccag  ctccggcgcc     360 ccggctcccc gcgcccccga tcggggccgc cgctagtagt ggcggcggcg gaggcggggg     420
cagcggcggc ggcggcggag gcgcctctgc agctccggct cccc ctggcc tctcgggaac     480 tacaagtccc aggggggcctg gcggtggcg  cgggcggaa gaggcggggt cggcgccgcg     540
aggccggaag tggccgtgga ggcggaagtg gcgcggccgc ggaggggcct ggagtgcggc     600
ggcggcggga cccggagcag gagcggcggc agcagcgact gggggcggcg gcggcgcgtt     660
ggaggcggcc ggatccacta gtctcagaga gcctcggcta ggtagggag cggaactctg      720 gtgggagggg aggtgcggtg cactgggggg atgggtggct aggggggccg tctggtggct     780
tgcgggggtt gccttcccg tgggaagtcg ggaacataat gtttgttacg ttgggaggga     840 aagggtggc tggatgcagg cgggagggag gcccgccctg cggcaaccgg aggggagggg     900
agaagggagc ggaaaatgct cgaaaccgga cggagccatt gctctcgcag agggaggagc     960
gcttccggct agcctcttgt cgccgattgg ccgtttctcc tcccgccgtg tgtgaaaaca    1020
caaatggcgt attctggttg gagtaaagct cctgtcagtt acaccgtcgg gagtacgcag    1080
ccgcttagcg actctcgcgt tgccccctgg gtggggcggg taggtaggtg gggtgtagag    1140
atgctgggtg tgcgggcgcg gccggcctcc tgcggcggga ggggaggtc agtgaaattg    1200 gctctggcgc gggcgtcctc ccaccctccc cttccttcgg gggagtcggt ttacccgccg    1260
cctgcttgtc ttcgacacct gattggctgt cgaagctgtg ggaccgggcc cttgctactg    1320
gctcgagtct cacatgagcg aaaccactgc gcggggcgcg gggtggcgg ggaggcgggc     1380 gttggtacgg tcctcccga ggccgagcgc cgcagtgtct ggccccgcgc ccctgcgcaa     1440
cgtggcagga agcgcgcgct ggaggcgggg gcggctgcc ggccgagact tctggatggc     1500
ggcggccgcg gctccgcccc gggttccac cgcctgaagg gcgagacaag cccgacctgc     1560
tacaggcact cgtgggggtg ggggaggagc ggggtcggt ccggctggtt tgtgggtggg     1620
aggcgcttgt tctccaaaaa ccggcgcgag ctgcaatcct gagggagctg cggtggagga    1680
ggtgagagaa aggccgcacc cttctgggca ggggagggg agtgccgcaa tacctttatg     1740
ggagttcttt gctgcctccc gtcttgtaag gaccgccctg ggcctggaag aagccctccc    1800 tccttttcctc ctcgcgtgat ctcgtcatcg cctccatgtc gagtcgcttc tcgattatgg    1860
gcgggattct tttgcctaga caattgtact aaccttcttc tctttcctct cctgacag      1918
```

<210> SEQ ID NO 57
<211> LENGTH: 1779
<212> TYPE: DNA
<213> ORGANISM: Artificial Sequence
<220> FEATURE:
<223> OTHER INFORMATION: artificial sequence

<400> SEQUENCE: 57

| | | | | | |
|---|---|---|---|---|---|
| gcgttacata | acttacggta | aatggcccgc | ctggctgacc | gcccaacgac | ccccgcccat | 60 |
| tgacgtcaat | aatgacgtat | gttcccatag | taacgccaat | agggactttc | cattgacgtc | 120 |
| aatgggtgga | gtatttacgg | taaactgccc | acttggcagt | acatcaagtg | tatcatatgc | 180 |
| caagtacgcc | ccctattgac | gtcaatgacg | gtaaatggcc | cgcctggcat | tatgcccagt | 240 |
| acatgacctt | atgggacttt | cctacttggc | agtacatcta | cgtattagtc | atcgctatta | 300 |
| ccatggcccg | ggtcgcgaca | tgcagcggga | cgcgccaccc | cgagcccag | ctccggcgcc | 360 |
| ccggctcccc | gcgccccga | tcggggccgc | cgctagtagt | ggcggcggcg | gaggcggggg | 420 |
| cagcggcggc | ggcggcggag | gcgcctctgc | agctccggct | ccccctggcc | tctcgggaac | 480 |
| tacaagtccc | aggggggcctg | gcggtgggcg | gcgggcggaa | gaggcggggt | cggcgccgcg | 540 |
| aggccggaag | tggccgtgga | ggcggaagtg | gcgcggccgc | ggaggggcct | ggagtgcggc | 600 |
| ggcggcggga | cccggagcag | gagcggcggc | agcagcgact | ggggggcggcg | gcggcgcgtt | 660 |
| ggaggcggcc | ggatccgttt | aaacggctcg | catctctcct | tcacgcgccc | gccgccctac | 720 |
| ctgaggccgc | catccacgcc | ggttgagtcg | cgttctgccg | cctcccgcct | gtggtgcctc | 780 |
| ctgaactgcg | tccgccgtct | aggtaagttt | aaagctcagg | tcgagaccgg | gcctttgtcc | 840 |
| ggcgctccct | tggagcctac | ctagactcag | ccggctctcc | acgctttgcc | tgaccctgct | 900 |
| tgctcaactc | tacgtctttg | tttcgttttc | tgttctgcgc | cgttacagat | cactaggatc | 960 |
| cactagcgtg | agtagcgggc | tgctgggctg | gccggggctt | tcgtggccgc | cgggccgctc | 1020 |
| ggtgggacgg | aagcgtgtgg | agagaccgcc | aagggctgta | gtctgggtcc | gcgagcaagg | 1080 |
| ttgccctgaa | ctgggggttg | ggggggagcgc | agcaaaatgg | cggctgttcc | cgagtcttga | 1140 |
| atggaagacg | cttgtgaggc | gggctgtgag | gtcgttgaaa | caaggtgggg | ggcatggtgg | 1200 |
| gcggcaagaa | cccaaggtct | tgaggccttc | gctaatgcgg | gaaagctctt | attcgggtga | 1260 |
| gatgggctgg | ggcaccatct | ggggaccctg | acgtgaagtt | tgtcactgac | tggagaactc | 1320 |
| ggtttgtcgt | ctgttgcggg | ggcggcagtt | atggcggtgc | cgttgggcag | tgcacccgta | 1380 |
| cctttgggag | cgcgcgccct | cgtcgtgtcg | tgacgtcacc | cgttctgttg | gcttataatg | 1440 |
| cagggtgggg | ccacctgccg | gtaggtgtgc | ggtaggcttt | tctccgtcgc | aggacgcagg | 1500 |
| gttcgggcct | agggtaggct | ctcctgaatc | gacaggcgcc | ggacctctgg | tgaggggagg | 1560 |
| gataagtgag | gcgtcagttt | ctttggtcgg | ttttatgtac | ctatcttctt | aagtagctga | 1620 |
| agctccggtt | ttgaactatg | cgctcggggt | tggcgagtgt | gttttgtgaa | gttttttagg | 1680 |
| caccttttga | aatgtaatca | tttgggtcaa | tatgtaattt | tcagtgttag | actagtaaat | 1740 |
| tgtccgctaa | attctggccg | ttttttggctt | ttttgttag | | | 1779 |

<210> SEQ ID NO 58
<211> LENGTH: 2168
<212> TYPE: DNA
<213> ORGANISM: Artificial Sequence
<220> FEATURE:
<223> OTHER INFORMATION: artificial sequence

<400> SEQUENCE: 58

```
gcgttacata acttacggta aatggcccgc ctggctgacc gcccaacgac ccccgcccat    60
tgacgtcaat aatgacgtat gttcccatag taacgccaat agggactttc cattgacgtc   120
aatgggtgga gtatttacgg taaactgccc acttggcagt acatcaagtg tatcatatgc   180
caagtacgcc ccctattgac gtcaatgacg gtaaatggcc cgcctggcat tatgcccagt   240
acatgacctt atgggacttt cctacttggc agtacatcta cgtattagtc atcgctatta   300
ccatggcccg ggtcgcgaca tgcagcggga cgcgccaccc cgagcccag ctccggcgcc    360 ccggctcccc gcgccccga tcggggccgc cgctagtagt ggcggcggcg gaggcggggg   420
cagcggcggc ggcggcggag gcgcctctgc agctccggct ccccctggcc tctcgggaac   480
tacaagtccc aggggggcctg gcggtgggcg gcgggcggaa gaggcgggt cggcgccgcg    540 aggccggaag tggccgtgga ggcggaagtg gcgcggccgc ggaggggcct ggagtgcggc   600
ggcggcggga cccggagcag gagcggcggc agcagcgact gggggcggcg cggcgcgtt    660 ggaggcggcc ggatcctagt gtttaaacag agtaatgaca tggttccttc catcctccaa   720
aggtgaccaa taatagtttg taagtatcat tatgaactaa tgaattttca acatatttga   780
tatatttcaa tccattgcca tcattgttct tatcgatatt tgagttggct cactttgcca   840
gtaagagtct attcaaattg gcttctgagt ccatttgaca caacacctt gatctttgac    900 agtttccttg gttttaggtg ctagatgatt tctcaggctc accttagaca tttcctgcca   960
cagacttaga atcagccatt tctctaagga ccctgattcc atttcatgag aaatgataga  1020
gaccacaatc aaaacaagtc atgaatttat actgatattt tcaattcaaa ttaaagatga  1080
ggtttttgct aaatttttt gagtttatat ttgtatgtct tatgctgaaa aatcttgttt   1140
cctaattagt aacataatta tcatttgat gggtaaatat tttagggccg attcttggt    1200 tttatagcca agataccctg ttgataaagt cttgtgggag caattataag actggcttat  1260
tttgaagctt tttaaaaaag acatccttac ctgttttaac tgtagattat attaacttaa  1320
ataggtacag cccacgcttg actaggatcc actagcgtga gtagcgggct gctgggctgg  1380
ccggggcttt cgtggccgcc gggccgctcg gtgggacgga agcgtgtgga gagaccgcca  1440
agggctgtag tctgggtccg cgagcaaggt tgccctgaac tgggggttgg ggggagcgca  1500
gcaaaatggc ggctgttccc gagtcttgaa tggaagacgc ttgtgaggcg ggctgtgagg  1560
tcgttgaaac aaggtggggg gcatggtggg cggcaagaac ccaaggtctt gaggccttcg  1620
ctaatgcggg aaagctctta ttcgggtgag atgggctggg gcaccatctg ggaccctga   1680 cgtgaagttt gtcactgact ggagaactcg gtttgtcgtc tgttgcgggg gcggcagtta  1740
tggcggtgcc gttgggcagt gcacccgtac ctttgggagc gcgcgccctc gtcgtgtcgt  1800
gacgtcaccc gttctgttgg cttataatgc agggtgggc cacctgccgg taggtgtgcg  1860
gtaggctttt ctccgtcgca ggacgcaggg ttcgggccta gggtaggctc tcctgaatcg  1920
acaggcgccg gacctctggt gaggggaggg ataagtgagg cgtcagtttc tttggtcggt  1980
tttatgtacc tatcttctta agtagctgaa gctccggttt tgaactatgc gctcggggtt  2040
ggcgagtgtg ttttgtgaag ttttttaggc accttttgaa atgtaatcat ttgggtcaat  2100
atgtaatttt cagtgttaga ctagtaaatt gtccgctaaa ttctggccgt ttttggcttt  2160
tttgttag                                                          2168
```

<210> SEQ ID NO 59
<211> LENGTH: 1825
<212> TYPE: DNA

<213> ORGANISM: Artificial Sequence
<220> FEATURE:
<223> OTHER INFORMATION: artificial sequence

<400> SEQUENCE: 59

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg ggtcgcgaca tgcagcggga cgcgccaccc cgagcccag ctccggcgcc     360
ccggctcccc gcgcccccga tcggggccgc cgctagtagt ggcggcggcg gaggcggggg     420
cagcggcggc ggcggcggag gcgcctctgc agctccggct cccctggcc tctcgggaac     480
tacaagtccc aggggcctg gcggtgggcg gcgggcggaa gaggcggggt cggcgccgcg     540
aggccggaag tggccgtgga ggcggaagtg gcgcggccgc ggaggggcct ggagtgcggc     600
ggcggcggga cccggagcag gagcggcggc agcagcgact gggggcggcg gcggcgcgtt     660
ggaggcggcc ggatccgttt aacgctggtg ggtagggatg agggagggag gggcattgtg     720
atgtacaggg ctgctctgtg agatcaaggg tctcttaagg gtgggagctg gggcagggac     780
tacgagagca gccagatggg ctgaaagtgg aactcaaggg gttctggca cctacctacc     840
tgcttcccgc tggggggtgg ggagttggcc cagagtctta agattggggc agggtggaga     900
ggtgggctct tcctgcttcc cactcatctt atagctttct ttccccagat ccgaattcga     960
gatccaaacc aaggaggaaa ggatatcaca gaggagagct aggatccact agcgtgagta    1020
gcgggctgct gggctggccg gggctttcgt ggccgccggg ccgctcggtg ggacggaagc    1080
gtgtggagag accgccaagg gctgtagtct gggtccgcga gcaaggttgc cctgaactgg    1140
gggtgggggg gagcgcagca aaatggcggc tgttcccgag tcttgaatgg aagacgcttg    1200
tgaggcgggc tgtgaggtcg ttgaaacaag gtgggggca tggtgggcgg caagaaccca    1260
aggtcttgag gccttcgcta atgcgggaaa gctcttattc gggtgagatg ggctggggca    1320
ccatctgggg accctgacgt gaagtttgtc actgactgga gaactcggtt tgtcgtctgt    1380
tgcggggcg gcagttatgg cggtgccgtt gggcagtgca cccgtacctt gggagcgcg    1440
cgccctcgtc gtgtcgtgac gtcacccgtt ctgttggctt ataatgcagg gtggggccac    1500
ctgccggtag gtgtgcggta ggcttttctc cgtcgcagga cgcagggttc gggcctaggg    1560
taggctctcc tgaatcgaca ggcgccggac ctctggtgag gggagggata agtgaggcgt    1620
cagtttcttt ggtcggtttt atgtacctat cttcttaagt agctgaagct ccggttttga    1680
actatgcgct cggggttggc gagtgtgttt tgtgaagttt tttaggcacc ttttgaaatg    1740
taatcatttg ggtcaatatg taattttcag tgttagacta gtaaattgtc cgctaaattc    1800
tggccgtttt tggcttttttt gttag                                        1825
```

<210> SEQ ID NO 60
<211> LENGTH: 2447
<212> TYPE: DNA
<213> ORGANISM: Artificial Sequence
<220> FEATURE:
<223> OTHER INFORMATION: artificial sequence

<400> SEQUENCE: 60

```
gcgttacata acttacggta aatggcccgc ctggctgacc gcccaacgac ccccgcccat      60
```

```
tgacgtcaat aatgacgtat gttcccatag taacgccaat agggactttc cattgacgtc      120
aatgggtgga gtatttacgg taaactgccc acttggcagt acatcaagtg tatcatatgc      180
caagtacgcc ccctattgac gtcaatgacg gtaaatggcc cgcctggcat tatgcccagt      240
acatgacctt atgggacttt cctacttggc agtacatcta cgtattagtc atcgctatta      300
ccatggcccg ggtcgcgaca tgcagcggga cgcgccaccc cgagcccag ctccggcgcc       360 ccggctcccc gcgcccccga tcggggccgc cgctagtagt ggcggcggcg gaggcggggg      420
cagcggcggc ggcggcggag gcgcctctgc agctccggct cccctggcc tctcgggaac       480 tacaagtccc aggggggcctg gcggtgggcg gcgggcggaa gaggcggggt cggcgccgcg     540
aggccggaag tggccgtgga ggcggaagtg gcgcggccgc ggagggggcct ggagtgcggc    600 ggcggcggga cccggagcag gagcggcggc agcagcgact ggggggcggcg gcggcgcgtt   660 ggaggcggcc ggatccgttt aaacggctcg catctctcct tcacgcgccc gccgccctac     720
ctgaggccgc catccacgcc ggttgagtcg cgttctgccg cctccgcct gtggtgcctc      780 ctgaactgcg tccgccgtct aggtaagttt aaagctcagg tcgagaccgg cctttgtcc      840 ggcgctccct tggagcctac ctagactcag ccggctctcc acgctttgcc tgaccctgct     900
tgctcaactc tacgtctttg tttcgttttc tgttctgcgc cgttacagat cactagtgtt     960
taaacagagt aatgacatgg ttccttccat cctccaaagg tgaccaataa tagtttgtaa   1020
gtatcattat gaactaatga attttcaaca tatttgatat atttcaatcc attgccatca   1080
ttgttcttat cgatatttga gttggctcac tttgccagta agagtctatt caaattggct   1140
tctgagtcca tttgacacaa cacctttgat ctttgacagt ttccttggtt ttaggtgcta   1200 gatgattct caggctcacc ttagacattt cctgccacag acttagaatc agccatttct    1260
ctaaggaccc tgattccatt tcatgagaaa tgatagagac cacaatcaaa acaagtcatg   1320
aatttatact gatattttca attcaaatta aagatgaggt ttttgctaaa ttttttttgag   1380 tttatatttg tatgtcttat gctgaaaaat cttgtttcct aattagtaac ataattattc   1440
atttgatggg taaatatttt agggccgatt ctttggtttt atagccaaga taccctgttg   1500
ataaagtctt gtgggagcaa ttataagact ggcttatttt gaagcttttt aaaaaagaca   1560
tccttacctg ttttaactgt agattatatt aacttaaata ggtacagccc acgcttgact   1620
agttgatcca ctagcgtgag tagcgggctg ctgggctggc cggggctttc gtggccgccg   1680
ggccgctcgg tgggacggaa gcgtgtggag agaccgccaa gggctgtagt ctgggtccgc   1740
gagcaaggtt gccctgaact gggggttggg gggagcgcag caaaatggcg gctgttcccg   1800
agtcttgaat ggaagacgct tgtgaggcgg gctgtgaggt cgttgaaaca aggtgggggg   1860
catggtgggc ggcaagaacc caaggtcttg aggccttcgc taatgcggga aagctcttat   1920
tcgggtgaga tgggctgggg caccatctgg ggaccctgac gtgaagtttg tcactgactg   1980
gagaactcgg tttgtcgtct gttgcggggg cggcagttat ggcggtgccg ttgggcagtg   2040
cacccgtacc tttgggagcg cgcgccctcg tcgtgtcgtg acgtcacccg ttctgttggc   2100
ttataatgca gggtgggggcc acctgccggt aggtgtgcgg taggctttc tccgtcgcag   2160 gacgcagggt tcgggcctag ggtaggctct cctgaatcga caggcgccgg acctctggtg   2220
aggggaggga taagtgaggc gtcagtttct ttggtcggtt ttatgtacct atcttcttaa   2280
gtagctgaag ctccggtttt gaactatgcg ctcggggttg gcgagtgtgt tttgtgaagt   2340
tttttaggca ccttttgaaa tgtaatcatt tgggtcaata tgtaattttc agtgttagac   2400
```
tagtaaattg tccgctaaat tctggccgtt tttggctttt ttgttag       2447

<210> SEQ ID NO 61
<211> LENGTH: 2447
<212> TYPE: DNA
<213> ORGANISM: Artificial Sequence
<220> FEATURE:
<223> OTHER INFORMATION: artificial sequence

<400> SEQUENCE: 61
gcgttacata acttacggta atggcccgc ctggctgacc gcccaacgac ccccgcccat       60
tgacgtcaat aatgacgtat gttcccatag taacgccaat agggactttc cattgacgtc      120
aatgggtgga gtatttacgg taaactgccc acttggcagt acatcaagtg tatcatatgc      180
caagtacgcc ccctattgac gtcaatgacg gtaaatggcc cgcctggcat tatgcccagt      240
acatgacctt atgggacttt cctacttggc agtacatcta cgtattagtc atcgctatta      300
ccatggcccg gtcgcgaca tgcagcggga cgcgccaccc cgagcccag ctccggcgcc       360 ccggctcccc gcgccccga tcggggccgc cgctagtagt ggcggcggcg gaggcggggg       420
cagcggcggc ggcggcggag gcgcctctgc agctccggct cccctggcc tctcgggaac      480 tacaagtccc aggggcctg gcggtgggcg gcgggcggaa gaggcggggt cggcgccgcg       540
aggccggaag tggccgtgga ggcggaagtg gcgcggccgc ggaggggcct ggagtgcggc       600
ggcggcggga cccggagcag gagcggcggc agcagcgact gggggcggcg gcggcgcgtt       660
ggaggcggcc ggatccgttt aaacggctcg catctctcct tcacgcgccc gccgccctac       720
ctgaggccgc catccacgcc ggttgagtcg cgttctgccg cctcccgcct gtggtgcctc       780
ctgaactgcg tccgccgtct aggtaagttt aaagctcagg tcgagaccgg gcctttgtcc       840
ggcgctccct tggagcctac ctagactcag ccggctctcc acgctttgcc tgaccctgct       900
tgctcaactc tacgtctttg tttcgttttc tgttctgcgc cgttacagat cactagtgtt       960
taaacagagt aatgacatgg ttccttccat cctccaaagg tgaccaataa tagtttgtaa     1020
gtatcattat gaactaatga atttttcaaca tatttgatat atttcaatcc attgccatca     1080
ttgttcttat cgatatttga gttggctcac tttgccagta agagtctatt caaattggct     1140
tctgagtcca tttgacacaa cacctttgat cttttgacagt ttccttggtt ttaggtgcta     1200
gatgatttct caggctcacc ttagacattt cctgccacag acttagaatc agccatttct     1260
ctaaggaccc tgattccatt tcatgagaaa tgatagagac cacaatcaaa acaagtcatg     1320 aattatatact gatattttca attcaaatta aagatgaggt ttttgctaaa ttttttttgag     1380 tttatatttg tatgtcttat gctgaaaaat cttgtttcct aattagtaac ataattattc     1440
atttgatggg taaatatttt agggccgatt ctttggtttt atagccaaga taccctgttg     1500
ataaagtctt gtgggagcaa ttataagact ggcttatttt gaagcttttt aaaaaagaca     1560
tccttacctg ttttaactgt agattatatt aacttaaata ggtacagccc acgcttgact     1620
agttgatcca ctagcgtgag tagcgggctg ctgggctggc cggggctttc gtggccgccg     1680
ggccgctcgg tgggacggaa gcgtgtggag agaccgccaa gggctgtagt ctgggtccgc     1740
gagcaaggtt gccctgaact gggggttggg ggagcgcag caaaatggcg gctgttcccg     1800
agtcttgaat ggaagacgct tgtgaggcgg gctgtgaggt cgttgaaaca aggtgggggg     1860
catggtgggc ggcaagaacc caaggtcttg aggccttcgc taatgcggga aagctcttat     1920
tcgggtgaga tgggctgggg caccatctgg ggacccgac gtgaagtttg tcactgactg     1980
gagaactcgg tttgtcgtct gttgcggggg cggcagttat ggcggtgccg ttgggcagtg     2040

```
caccccgtacc tttgggagcg cgcgccctcg tcgtgtcgtg acgtcacccg ttctgttggc    2100
ttataatgca gggtggggcc acctgccggt aggtgtgcgg taggcttttc tccgtcgcag    2160
gacgcagggt tcgggcctag ggtaggctct cctgaatcga caggcgccgg acctctggtg    2220
aggggaggga taagtgaggc gtcagtttct ttggtcggtt ttatgtacct atcttcttaa    2280
gtagctgaag ctccggtttt gaactatgcg ctcggggttg gcgagtgtgt tttgtgaagt    2340
tttttaggca ccttttgaaa tgtaatcatt tgggtcaata tgtaattttc agtgttagac    2400
tagtaaattg tccgctaaat tctggccgtt tttggctttt ttgttag                  2447
```

<210> SEQ ID NO 62
<211> LENGTH: 2483
<212> TYPE: DNA
<213> ORGANISM: Artificial Sequence
<220> FEATURE:
<223> OTHER INFORMATION: artificial sequence

<400> SEQUENCE: 62

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg gtcgcgaca tgcagcggga cgcgccaccc cgagcccag ctccggcgcc      360 ccggctcccc gcgccccga tcggggccgc cgctagtagt ggcggcggcg gaggcggggg      420
cagcggcggc ggcggcggag gcgcctctgc agctccggct cccccctggcc tctcgggaac    480 tacaagtccc aggggggcctg gcggtgggcg gcgggcggaa gaggcggggt cggcgccgcg    540
aggccggaag tggccgtgga ggcggaagtg gcgcggccgc ggagggggcct ggagtgcggc    600 ggcggcggga cccggagcag gagcggcggc agcagcgact gggggcggcg gcggcgcgtt    660
ggaggcggcc ggatcaaaca gagtaatgac atggttcctt ccatcctcca aaggtgacca    720
ataatagttt gtaagtatca ttatgaacta atgaattttc aacatatttg atatatttca    780
atccattgcc atcattgttc ttatcgatat ttgagttggc tcactttgcc agtaagagtc    840
tattcaaatt ggcttctgag tccatttgac acaacacctt tgatctttga cagtttcctt    900
ggttttaggt gctagatgat ttctcaggct caccttagac atttcctgcc acagacttag    960
aatcagccat ttctctaagg accctgattc catttcatga gaaatgatag agaccacaat   1020
caaaacaagt catgaattta tactgatatt ttcaattcaa attaaagatg aggttttttgc   1080 taaattttttt tgagtttata tttgtatgtc ttatgctgaa aaatcttgtt tcctaattag   1140
taacataatt attcatttga tgggtaaata ttttagggcc gattctttgg ttttatagcc   1200 aagatacccct gttgataaag tcttgtggga gcaattataa gactggctta ttttgaagct   1260
ttttaaaaaa gacatcctta cctgttttaa ctgtagatta tattaactta aataggtaca   1320
gcccacgctt gactagttaa cgctggtggg tagggatgag ggagggaggg gcattgtgat   1380
gtacagggct gctctgtgag atcaagggtc tcttaagggt gggagctggg gcaggacta    1440 cgagagcagc cagatgggct gaaagtggaa ctcaagggggt ttctggcacc tacctacctg   1500
cttcccgctg gggggtgggg agttggccca gagtcttaag attggggcag ggtggagagg   1560
tgggctcttc ctgcttccca ctcatcttat agctttcttt ccccagatcc gaattcgaga   1620
```

| | |
|---|---|
| tccaaaccaa ggaggaaagg atatcacaga ggagagctag gatccactag cgtgagtagc | 1680 |
| gggctgctgg gctggccggg gctttcgtgg ccgccgggcc gctcgtgggg acggaagcgt | 1740 |
| gtggagagac cgccaagggc tgtagtctgg gtccgcgagc aaggttgccc tgaactgggg | 1800 |
| gttgggggga gcgcagcaaa atggcggctg ttcccgagtc ttgaatggaa gacgcttgtg | 1860 |
| aggcgggctg tgaggtcgtt gaaacaaggt gggggggcatg gtgggcggca agaacccaag | 1920 |
| gtcttgaggc cttcgctaat gcgggaaagc tcttattcgg gtgagatggg ctggggcacc | 1980 |
| atctggggac cctgacgtga agtttgtcac tgactggaga actcggtttg tcgtctgttg | 2040 |
| cgggggcgga agttatggcg gtgccgttgg gcagtgcacc cgtacctttg ggagcgcgcg | 2100 |
| ccctcgtcgt gtcgtgacgt cacccgttct gttggcttat aatgcagggt ggggccacct | 2160 |
| gccggtaggt gtgcggtagg cttttctccg tcgcaggacg cagggttcgg gcctagggta | 2220 |
| ggctctcctg aatcgacagg cgccggacct ctggtgaggg gagggataag tgaggcgtca | 2280 |
| gtttctttgg tcggttttat gtacctatct tcttaagtag ctgaagctcc ggttttgaac | 2340 |
| tatgcgctcg gggttggcga gtgtgttttg tgaagttttt taggcacctt ttgaaatgta | 2400 |
| atcatttggg tcaatatgta attttcagtg ttagactagt aaaattgtccg ctaaattctg | 2460 |
| gccgtttttg gcttttttgt tag | 2483 |

<210> SEQ ID NO 63
<211> LENGTH: 2769
<212> TYPE: DNA
<213> ORGANISM: Artificial Sequence
<220> FEATURE:
<223> OTHER INFORMATION: artificial sequence

<400> SEQUENCE: 63

| | |
|---|---|
| gcgttacata acttacggta aatggcccgc ctggctgacc gcccaacgac ccccgcccat | 60 |
| tgacgtcaat aatgacgtat gttcccatag taacgccaat agggactttc cattgacgtc | 120 |
| aatgggtgga gtatttacgg taaactgccc acttggcagt acatcaagtg tatcatatgc | 180 |
| caagtacgcc ccctattgac gtcaatgacg gtaaatggcc cgcctggcat tatgcccagt | 240 |
| acatgacctt atgggacttt cctacttggc agtacatcta cgtattagtc atcgctatta | 300 |
| ccatggcccg ggtcgcgaca tgcagcggga cgcgccaccc cgagcccagc tccggcgcc | 360 |
| ccggctcccc gcgccccga tcggggccgc cgctagtagt ggcggcggcg gaggcggggg | 420 |
| cagcggcggc ggcggcggag gcgcctctgc agctccggct cccctggcc tctcgggaac | 480 |
| tacaagtccc aggggggcctg gcggtggcg gcgggcggaa gaggcggggt cggcgccgcg | 540 |
| aggccggaag tggccgtgga ggcggaagtg gcgcggccgc ggagggggcct ggagtgcggc | 600 |
| ggcggcggga cccggagcag gagcggcggc agcagcgact gggggcgggcg gcggcgcgtt | 660 |
| ggaggcggcc ggatccgttt aaacggctcg catctctcct tcacgcgccc gccgccctac | 720 |
| ctgaggccgc catccacgcc ggttgagtcg cgttctgccg cctcccgcct gtggtgcctc | 780 |
| ctgaactgcg tccgccgtct aggtaagttt aaagctcagg tcgagaccgg gcctttgtcc | 840 |
| ggcgctccct tggagcctac ctagactcag ccggctctcc acgctttgcc tgaccctgct | 900 |
| tgctcaactc tacgtctttg tttcgttttc tgttctgcgc cgttacagat cactagtgtt | 960 |
| taaacagagt aatgacatgg ttccttccat cctccaaagg tgaccaataa tagtttgtaa | 1020 |
| gtatcattat gaactaatga atttcaaca tatttgatat atttcaatcc attgccatca | 1080 |
| ttgttccttat cgatatttga gttggctcac tttgccagta agagtctatt caaattggct | 1140 |
| tctgagtcca tttgacacaa caccttgat ctttgacagt ttccttggtt ttaggtgcta | 1200 |

```
gatgatttct caggctcacc ttagacattt cctgccacag acttagaatc agccatttct   1260
ctaaggaccc tgattccatt tcatgagaaa tgatagagac cacaatcaaa acaagtcatg   1320
aatttatact gatattttca attcaaatta aagatgaggt ttttgctaaa ttttttttgag  1380 tttatatttg tatgtcttat gctgaaaaat cttgtttcct aattagtaac ataattattc   1440
atttgatggg taaatatttt agggccgatt ctttggtttt atagccaaga taccctgttg   1500
ataaagtctt gtgggagcaa ttataagact ggcttattt gaagcttttt aaaaaagaca    1560
tccttacctg ttttaactgt agattatatt aacttaaata ggtacagccc acgcttgact   1620
agttaacgct ggtgggtagg gatgagggag ggaggggcat tgtgatgtac agggctgctc   1680
tgtgagatca agggtctctt aagggtggga gctggggcag ggactacgag agcagccaga   1740
tgggctgaaa gtggaactca aggggtttct ggcacctacc tacctgcttc ccgctggggg   1800
gtggggagtt ggcccagagt cttaagattg ggcagggtg gagaggtggg ctcttcctgc    1860
ttcccactca tcttatagct ttcttttcccc agatccgaat tcgagatcca aaccaaggag  1920
gaaaggatat cacagaggag agctaggatc cactagcgtg agtagcgggc tgctgggctg   1980
gccggggctt tcgtggccgc cgggccgctc ggtgggacgg aagcgtgtgg agagaccgcc   2040
aagggctgta gtctgggtcc gcgagcaagg ttgccctgaa ctgggggttg ggggagcgc    2100 agcaaaatgg cggctgttcc cgagtcttga atggaagacg cttgtgaggc gggctgtgag   2160
gtcgttgaaa caaggtgggg ggcatggtgg gcggcaagaa cccaaggtct tgaggccttc   2220
gctaatgcgg gaaagctctt attcgggtga gatgggctgg ggcaccatct ggggaccctg   2280
acgtgaagtt tgtcactgac tggagaactc ggtttgtcgt ctgttgcggg ggcggcagtt   2340
atggcggtgc cgttgggcag tgcacccgta cctttgggag cgcgcgccct cgtcgtgtcg   2400
tgacgtcacc cgttctgttg gcttataatg cagggtgggg ccacctgccg gtaggtgtgc   2460
ggtaggcttt tctccgtcgc aggacgcagg gttcgggcct agggtaggct tcctgaatc    2520 gacaggcgcc ggacctctgg tgaggggagg gataagtgag gcgtcagttt ctttggtcgg   2580
ttttatgtac ctatcttctt aagtagctga agctccggtt ttgaactatg cgctcggggt   2640
tggcgagtgt gttttgtgaa gtttttttagg cacctttga aatgtaatca tttgggtcaa    2700
tatgtaattt tcagtgttag actagtaaat tgtccgctaa attctggccg tttttggctt   2760
ttttgttag                                                          2769

<210> SEQ ID NO 64
<211> LENGTH: 2193
<212> TYPE: DNA
<213> ORGANISM: Artificial Sequence
<220> FEATURE:
<223> OTHER INFORMATION: artificial sequence

<400> SEQUENCE: 64
gcgttacata acttacggta aatggcccgc ctggctgacc gcccaacgac ccccgcccat     60
tgacgtcaat aatgacgtat gttcccatag taacgccaat agggactttc cattgacgtc    120
aatgggtgga gtatttacgg taaactgccc acttggcagt acatcaagtg tatcatatgc    180
caagtacgcc ccctattgac gtcaatgacg gtaaatggcc cgcctggcat tatgcccagt    240
acatgacctt atgggacttt cctacttggc agtacatcta cgtattagtc atcgctatta    300
ccatggcccg gtcgcgacga tgcagcggga cgcgccaccc cgagcccag ctccggcgcc     360 ccggctcccc gcgccccga tcgggccgc cgctagtagt ggcggcggcg gaggcggggg     420
```

| | |
|---|---|
| cagcggcggc ggcggcggag gcgcctctgc agctccggct ccccctggcc tctcgggaac | 480 |
| tacaagtccc aggggggcctg gcggtgggcg gcgggcggaa gaggcggggt cggcgccgcg | 540 |
| aggccggaag tggccgtgga ggcggaagtg gcgcggccgc ggaggggcct ggagtgcggc | 600 |
| ggcggcggga cccggagcag gagcggcggc agcagcgact gggggcggcg gcggcgcgtt | 660 |
| ggaggcggcc ggatccgttt aaacggctcg catctctcct tcacgcgccc gccgccctac | 720 |
| ctgaggccgc catccacgcc ggttgagtcg cgttctgccg cctcccgcct gtggtgcctc | 780 |
| ctgaactgcg tccgccgtct aggtaagttt aaagctcagg tcgagaccgg gcctttgtcc | 840 |
| ggcgctccct tggagcctac ctagactcag ccggctctcc acgctttgcc tgaccctgct | 900 |
| tgctcaactc tacgtctttg tttcgttttc tgttctgcgc cgttacagat cactagtctc | 960 |
| agagagcctc ggctaggtag gggagcggaa ctctggtggg aggggaggtg cggtgcactg | 1020 |
| gggggatggg tggctagggg ggccgtctgg tggcttgcgg gggttgcctt tcccgtggga | 1080 |
| agtcgggaac ataatgtttg ttacgttggg agggaaaggg gtggctggat gcaggcggga | 1140 |
| gggaggcccg ccctgcggca accggagggg gagggagaag ggagcgggaaa atgctcgaaa | 1200 |
| ccggacggag ccattgctct gcagagggga ggagcgcttc cggctagcct cttgtcgccg | 1260 |
| attggccgtt tctcctcccg ccgtgtgtga aaacacaaat ggcgtattct ggttggagta | 1320 |
| aagctcctgt cagttacacc gtcgggagta cgcagccgct tagcgactct cgcgttgccc | 1380 |
| cctgggtggg gcgggtaggt aggtgggggtg tagagatgct gggtgtgcgg gcgcggccgg | 1440 |
| cctcctgcgg cgggagggga gggtcagtga aattggctct ggcgcgggcg tcctcccacc | 1500 |
| ctcccccttcc ttcggggggag tcggtttacc cgccgcctgc ttgtcttcga cacctgattg | 1560 |
| gctgtcgaag ctgtgggacc gggcccttgc tactggctcg agtctcacat gagcgaaacc | 1620 |
| actgcgcggg gcgcgggggt ggcggggagg cgggcgttgg tacggtcctc cccgaggccg | 1680 |
| agcgccgcag tgtctggccc cgcgcccctg cgcaacgtgg caggaagcgc gcgctggagg | 1740 |
| cgggggcggg ctgccggccg agacttctgg atggcggcgg ccgcggctcc gccccggggtt | 1800 |
| cccaccgcct gaagggcgag acaagcccga cctgctacag gcactcgtgg gggtggggga | 1860 |
| ggagcggggg tcggtccggc tggtttgtgg gtgggaggcg cttgttctcc aaaaaccggc | 1920 |
| gcgagctgca atcctgaggg agctgcggtg gaggaggtgg agagaaggcc gcaccccttct | 1980 |
| gggcagggggg aggggagtgc cgcaataccct ttatgggagt tctttgctgc ctcccgtctt | 2040 |
| gtaaggaccg ccctgggcct ggaagaagcc ctccctcctt tcctcctcgc gtgatctcgt | 2100 |
| catcgcctcc atgtcgagtc gcttctcgat tatgggcggg attcttttgc ctagacaatt | 2160 |
| gtactaacct tcttctcttt cctctcctga cag | 2193 |

<210> SEQ ID NO 65
<211> LENGTH: 2584
<212> TYPE: DNA
<213> ORGANISM: Artificial Sequence
<220> FEATURE:
<223> OTHER INFORMATION: artificial sequence

<400> SEQUENCE: 65

| | |
|---|---|
| gcgttacata acttacggta aatggcccgc ctggctgacc gcccaacgac ccccgcccat | 60 |
| tgacgtcaat aatgacgtat gttcccatag taacgccaat agggactttc cattgacgtc | 120 |
| aatgggtgga gtatttacgg taaactgccc acttggcagt acatcaagtg tatcatatgc | 180 |
| caagtacgcc ccctattgac gtcaatgacg gtaaatggcc cgcctggcat tatgcccagt | 240 |
| acatgacctt atgggacttt cctacttggc agtacatcta cgtattagtc atcgctatta | 300 |

-continued

```
ccatggcccg ggtcgcgaca tgcagcggga cgcgccaccc cgagccccag ctccggcgcc    360
ccggctcccc gcgcccccga tcggggccgc cgctagtagt ggcggcggcg gaggcggggg    420
cagcggcggc ggcggcggag gcgcctctgc agctccggct cccccctggcc tctcgggaac   480 tacaagtccc aggggggcctg gcggtggggcg gcgggcggaa gaggcgggggt cggcgccgcg   540 aggccggaag tggccgtgga ggcggaagtg gcgcggccgc ggaggggcct ggagtgcggc    600
ggcggcggga cccggagcag gagcggcggc agcagcgact gggggcggcg gcggcgcgtt    660
ggaggcggcc ggatccacta gtgtttaaac agagtaatga catggttcct tccatcctcc    720
aaaggtgacc aataatagtt tgtaagtatc attatgaact aatgaatttt caacatattt    780
gatatatttc aatccattgc catcattgtt cttatcgata tttgagttgg ctcactttgc    840
cagtaagagt ctattcaaat tggcttctga gtccatttga cacaacacct ttgatctttg    900
acagtttcct tggttttagg tgctagatga tttctcaggc tcaccttaga catttcctgc    960
cacagactta gaatcagcca tttctctaag gaccctgatt ccatttcatg agaaatgata   1020
gagaccacaa tcaaaacaag tcatgaattt atactgatat tttcaattca aattaaagat   1080 gaggttttttg ctaaattttt ttgagtttat atttgtatgt cttatgctga aaaatcttgt   1140
ttcctaatta gtaacataat tattcatttg atgggtaaat attttagggc cgattctttg   1200
gttttatagc caagatacccc tgttgataaa gtcttgtggg agcaattata agactggctt   1260
attttgaagc ttttttaaaaa agacatcctt acctgtttta actgtagatt atattaactt   1320
aaataggtac agcccacgct tgactagtct cagagagcct cggctaggta ggggagcgga   1380
actctggtgg gagggggaggt gcggtgcact gggggggatgg gtggctaggg gggccgtctg   1440
gtggcttgcg ggggttgcct ttcccgtggg aagtcgggaa cataatgttt gttacgttgg   1500
gagggaaagg ggtggctgga tgcaggcggg agggaggccc gccctgcggc aaccggaggg   1560
ggagggagaa gggagcggaa aatgctcgaa accggacgga gccattgctc tcgcagaggg   1620
aggagcgctt ccggctagcc tcttgtcgcc gattggccgt ttctcctccc gccgtgtgtg   1680
aaaacacaaa tggcgtattc tggttggagt aaagctcctg tcagttacac cgtcgggagt   1740
acgcagccgc ttagcgactc tcgcgttgcc ccctgggtgg ggcgggtagg taggtggggt   1800
gtagagatgc tgggtgtgcg ggcgcggccg gcctcctgcg gcgggagggg agggtcagtg   1860
aaattggctc tggcgcgggc gtcctccccac cctcccctttc cttcggggga gtcggtttac   1920
ccgccgcctg cttgtcttcg acacctgatt ggctgtcgaa gctgtgggac cgggcccttg   1980
ctactggctc gagtctcaca tgagcgaaac cactgcgcgg ggcgcgggggg tggcggggag   2040 gcgggcgttg gtacggtcct ccccgaggcc gagcgccgca gtgtctggcc ccgcgcccct   2100
gcgcaacgtg gcaggaagcg cgcgctgag gcggggggcgg gctgccggcc gagacttctg   2160
gatggcggcg gccgcggctc cgccccgggt tcccaccgcc tgaagggcga gacaagcccg   2220
acctgctaca ggcactcgtg gggggtgggggg aggagcgggg gtcggtccgg ctggtttgtg   2280
ggtgggaggc gcttgttctc caaaaaccgg cgcgagctgc aatcctgagg gagctgcggt   2340
ggaggaggtg gagagaaggc cgcacccttc tgggcagggg gaggggagtg ccgcaatacc   2400
tttatgggag ttctttgctg cctcccgtct tgtaaggacc gccctgggcc tggaagaagc   2460
cctccctcct ttcctcctcg cgtgatctcg tcatcgcctc catgtcgagt cgcttctcga   2520
ttatgggcgg gattcttttg cctagacaat tgtactaacc ttcttctctt tcctctcctg   2580
acag                                                                2584
```

<210> SEQ ID NO 66
<211> LENGTH: 2239
<212> TYPE: DNA
<213> ORGANISM: Artificial Sequence
<220> FEATURE:
<223> OTHER INFORMATION: artificial sequence

<400> SEQUENCE: 66

| | | | | | |
|---|---|---|---|---|---|
| gcgttacata | acttacggta | aatggcccgc | ctggctgacc | gcccaacgac | ccccgcccat | 60 |
| tgacgtcaat | aatgacgtat | gttcccatag | taacgccaat | agggactttc | cattgacgtc | 120 |
| aatgggtgga | gtatttacgg | taaactgccc | acttggcagt | acatcaagtg | tatcatatgc | 180 |
| caagtacgcc | ccctattgac | gtcaatgacg | gtaaatggcc | cgcctggcat | tatgcccagt | 240 |
| acatgacctt | atgggacttt | cctacttggc | agtacatcta | cgtattagtc | atcgctatta | 300 |
| ccatggcccg | ggtcgcgaca | tgcagcggga | cgcgccaccc | cgagcccag | ctccggcgcc | 360 |
| ccggctcccc | gcgccccga | tcggggccgc | cgctagtagt | ggcggcgcg | gaggcggggg | 420 |
| cagcggcggc | ggcggcggag | gcgcctctgc | agctccggct | cccctggcc | tctcgggaac | 480 |
| tacaagtccc | agggggcctg | gcggtgggcg | gcgggcggaa | gaggcgggt | cggcgccgcg | 540 |
| aggccggaag | tggccgtgga | ggcggaagtg | gcgcggccgc | ggagggcct | ggagtgcggc | 600 |
| ggcggcggga | cccggagcag | gagcggcggc | agcagcgact | gggggcggcg | gcggcgcgtt | 660 |
| ggaggcggcc | ggatccgttt | aacgctggtg | gtagggatg | agggagggag | gggcattgtg | 720 |
| atgtacaggg | ctgctctgtg | agatcaaggg | tctcttaagg | gtgggagctg | gggcagggac | 780 |
| tacgagagca | gccagatggg | ctgaaagtgg | aactcaaggg | gtttctggca | cctacctacc | 840 |
| tgcttcccgc | tggggggtgg | ggagttggcc | cagagtctta | agattggggc | agggtggaga | 900 |
| ggtgggctct | tcctgcttcc | cactcatctt | atagctttct | ttccccagat | ccgaattcga | 960 |
| gatccaaacc | aaggaggaaa | ggatatcaca | gaggagagct | agtctcagag | agcctcggct | 1020 |
| aggtagggga | gcggaactct | ggtgggaggg | gaggtgcggt | gcactggggg | gatgggtggc | 1080 |
| tagggggggcc | gtctggtggc | ttgcgggggt | tgccttcc | gtgggaagtc | gggaacataa | 1140 |
| tgttttgttac | gttgggaggg | aaaggggtgg | ctggatgcag | gcgggaggga | ggcccgccct | 1200 |
| gcggcaaccg | gagggggagg | gagaagggag | cggaaaatgc | tcgaaaccgg | acggagccat | 1260 |
| tgctctcgca | gagggaggag | cgcttccggc | tagcctcttg | tcgccgattg | gccgtttctc | 1320 |
| ctcccgccgt | gtgtgaaaac | acaaatggcg | tattctggtt | ggagtaaagc | tcctgtcagt | 1380 |
| tacaccgtcg | ggagtacgca | gccgcttagc | gactctcgcg | ttgcccctg | ggtggggcgg | 1440 |
| gtaggtaggt | ggggtgtaga | gatgctgggt | gtgcgggcgc | ggccggcctc | ctgcggcggg | 1500 |
| aggggagggt | cagtgaaatt | ggctctggcg | cgggcgtcct | cccaccctcc | ccttccttcg | 1560 |
| ggggagtcgg | tttacccgcc | gcctgcttgt | cttcgacacc | tgattggctg | tcgaagctgt | 1620 |
| gggaccgggc | ccttgctact | ggctcgagtc | tcacatgagc | gaaaccactg | cgcggggcgc | 1680 |
| gggggtggcg | gggaggcggg | cgttggtacg | gtcctccccg | aggccgagcg | ccgcagtgtc | 1740 |
| tggccccgcg | cccctgcgca | acgtggcagg | aagcgcgcgc | tggaggcggg | ggcgggctgc | 1800 |
| cggccgagac | ttctggatgg | cggcggccgc | ggctccgccc | cggttcccca | ccgcctgaag | 1860 |
| ggcgagacaa | gcccgacctg | ctacaggcac | tcgtgggggt | gggggaggag | cggggtcgg | 1920 |
| tccggctggt | ttgtgggtgg | gaggcgcttc | ttctccaaaa | accggcgcga | gctgcaatcc | 1980 |
| tgagggagct | gcggtggagg | aggtggagag | aaggccgcac | ccttctggc | aggggagggg | 2040 |
| gagtgccgca | ataccttat | gggagttctt | tgctgcctcc | cgtcttgtaa | ggaccgccct | 2100 |

```
gggcctggaa gaagccctcc ctcctttcct cctcgcgtga tctcgtcatc gcctccatgt    2160
cgagtcgctt ctcgattatg ggcgggattc ttttgcctag acaattgtac taaccttctt    2220
ctctttcctc tcctgacag                                                 2239
```

<210> SEQ ID NO 67
<211> LENGTH: 2859
<212> TYPE: DNA
<213> ORGANISM: Artificial Sequence
<220> FEATURE:
<223> OTHER INFORMATION: artificial sequence

<400> SEQUENCE: 67

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg gtcgcgaca tgcagcggga cgcgccaccc cgagcccag ctccggcgcc       360 ccggctcccc gcgccccga tcggggccgc cgctagtagt ggcggcggcg gaggcggggg      420
cagcggcggc ggcggcggag gcgcctctgc agctccggct cccccctggcc tctcgggaac    480 tacaagtccc aggggggcctg gcgtggggcg gcgggcggaa gaggcgggt cggcgccgcg     540 aggccggaag tggccgtgga ggcggaagtg gcgcggccgc ggagggggcct ggagtgcggc    600 ggcggcggga cccggagcag gagcggcggc agcagcgact ggggcggcg gcggcgcgtt     660 ggaggcggcc ggatccgttt aaacggctcg catctctcct tcacgcgccc gccgccctac    720
ctgaggccgc catccacgcc ggttgagtcg cgttctgccg cctcccgcct gtggtgcctc    780
ctgaactgcg tccgccgtct aggtaagttt aaagctcagg tcgagaccgg gccttttgtcc   840 ggcgctccct tggagcctac ctagactcag ccggctctcc acgctttgcc tgaccctgct    900
tgctcaactc tacgtctttg tttcgttttc tgttctgcgc cgttacagat cactagtgtt    960
taaacagagt aatgacatgg ttccttccat cctccaaagg tgaccaataa tagtttgtaa    1020
gtatcattat gaactaatga attttcaaca tatttgatat atttcaatcc attgccatca    1080
ttgttcttat cgatatttga gttggctcac tttgccagta agagtctatt caaattggct    1140
tctgagtcca tttgacacaa cacctttgat cttttgacagt ttccttggtt ttaggtgcta   1200
gatgatttct caggctcacc ttagacattt cctgccacag acttagaatc agccatttct    1260
ctaaggaccc tgattccatt tcatgagaaa tgatagagac cacaatcaaa acaagtcatg    1320
aatttatact gatattttca attcaaatta aagatgaggt ttttgctaaa ttttttttgag   1380 tttatatttg tatgtcttat gctgaaaaat cttgtttcct aattagtaac ataattattc    1440
atttgatggg taaatatttt agggccgatt ctttggtttt atagccaaga taccctgttg    1500
ataaagtctt gtgggagcaa ttataagact ggcttatttt gaagcttttt aaaaaagaca    1560
tccttacctg ttttaactgt agattatatt aacttaaata ggtacagccc acgcttgact    1620
agtctcagag agcctcggct aggtagggga gcggaactct ggtggagggg gaggtgcggt    1680
gcactggggg gatgggtggc taggggggcc gtctggtggc ttgcggggt tgccttttccc    1740 gtgggaagtc gggaacataa tgtttgttac gttgggaggg aaaggggtgg ctggatgcag    1800
gcgggaggga ggcccgccct gcggcaaccg gagggggagg gagaagggag cggaaaatgc    1860
```

```
tcgaaaccgg acggagccat tgctctcgca gagggaggag cgcttccggc tagcctcttg    1920
tcgccgattg gccgtttctc ctcccgccgt gtgtgaaaac acaaatggcg tattctggtt    1980
ggagtaaagc tcctgtcagt tacaccgtcg ggagtacgca gccgcttagc gactctcgcg    2040 ttgcccctg ggtggggcgg gtaggtaggt ggggtgtaga gatgctgggt gtgcgggcgc     2100
ggccggcctc ctgcggcggg aggggagggt cagtgaaatt ggctctggcg cgggcgtcct    2160
cccaccctcc ccttccttcg ggggagtcgg tttacccgcc gcctgcttgt cttcgacacc    2220
tgattggctg tcgaagctgt gggaccgggc ccttgctact ggctcgagtc tcacatgagc    2280
gaaaccactg cgcggggcgc gggggtggcg gggaggcggg cgttggtacg gtcctccccg    2340
aggccgagcg ccgcagtgtc tggccccgcg ccctgcgca acgtggcagg aagcgcgcgc     2400
tggaggcggg ggcgggctgc cggccgagac ttctggatgg cggcggccgc ggctccgccc    2460
cgggttccca ccgcctgaag ggcgagacaa gcccgacctg ctacaggcac tcgtgggggt    2520
gggggaggag cggggtcgg tccggctggt ttgtgggtgg gaggcgcttg ttctccaaaa     2580
accggcgcga gctgcaatcc tgaggagct gcggtggagg aggtggagag aaggccgcac     2640
ccttctgggc aggggaggg gagtgccgca atacctttat gggagttctt tgctgcctcc     2700
cgtcttgtaa ggaccgccct gggcctggaa gaagccctcc ctcctttcct cctcgcgtga    2760
tctcgtcatc gcctccatgt cgagtcgctt ctcgattatg ggcgggattc ttttgcctag    2820
acaattgtac taaccttctt ctctttcctc tcctgacag                            2859

<210> SEQ ID NO 68
<211> LENGTH: 2517
<212> TYPE: DNA
<213> ORGANISM: Artificial Sequence
<220> FEATURE:
<223> OTHER INFORMATION: artificial sequence

<400> SEQUENCE: 68
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg ggtcgcgaca tgcagcggga cgcgccaccc cgagcccag ctccggcgcc      360 ccggctcccc gcgccccga tcggggccgc cgctagtagt ggcggcggcg gaggcggggg      420
cagcggcggc ggcggcggag gcgcctctgc agctccggct cccctggcc tctcgggaac      480 tacaagtccc aggggcctg gcggtggcg cgggcggaa gaggcgggt cggcgccgcg         540 aggccggaag tggccgtgga ggcggaagtg gcgcggccgc ggaggggcct ggagtgcggc    600
ggcggcggga cccggagcag gagcggcggc agcagcgact gggggcggcg gcggcgcgtt    660
ggaggcggcc ggatccgttt aaacggctcg catctctcct tcacgcgccc gccgccctac   720
ctgaggccgc catccacgcc ggttgagtcg cgttctgccg cctcccgcct gtggtgcctc    780
ctgaactgcg tccgccgtct aggtaagttt aaagctcagg tcgagaccgg ccttttgtcc    840
ggcgctccct tggagcctac ctagactcag ccggctctcc acgctttgcc tgaccctgct    900
tgctcaactc tacgtctttg tttcgttttc tgttctgcgc cgttacagat cactagttaa    960
cgctggtggg tagggatgag ggaggagggg gcattgtgat gtacagggct gctctgtgag   1020
atcaagggtc tcttaagggt gggagctggg gcagggacta cgagagcagc cagatgggct   1080
```

| | | |
|---|---|---|
| gaaagtggaa ctcaaggggt ttctggcacc tacctacctg cttcccgctg ggggtgggg | 1140 | |
| agttggccca gagtcttaag attggggcag ggtggagagg tgggctcttc ctgcttccca | 1200 | |
| ctcatcttat agcttctttt ccccagatcc gaattcgaga tccaaaccaa ggaggaaagg | 1260 | |
| atatcacaga ggagagctag tctcagagag cctcggctag gtaggggagc ggaactctgg | 1320 | |
| tgggagggga ggtgcggtgc actggggga tgggtggcta ggggggccgt ctggtggctt | 1380 | |
| gcggggttg cctttcccgt gggaagtcgg aacataatg tttgttacgt tgggagggaa | 1440 | |
| aggggtggct ggatgcaggc gggagggagg cccgccctgc ggcaaccgga gggggaggga | 1500 | |
| gaagggagcg gaaaatgctc gaaaccggac ggagccattg ctctcgcaga gggaggagcg | 1560 | |
| cttccggcta gcctcttgtc gccgattggc cgtttctcct cccgccgtgt gtgaaaacac | 1620 | |
| aaatggcgta ttctggttgg agtaaagctc ctgtcagtta caccgtcggg agtacgcagc | 1680 | |
| cgcttagcga ctctcgcgtt gcccctggg tgggcgggt aggtaggtgg ggtgtagaga | 1740 | |
| tgctgggtgt gcgggcgcgg ccggcctcct gcggcgggag gggagggtca gtgaaattgg | 1800 | |
| ctctggcgcg ggcgtcctcc caccctcccc ttccttcggg ggagtcggtt tacccgccgc | 1860 | |
| ctgcttgtct tcgacacctg attggctgtc gaagctgtgg gaccgggccc ttgctactgg | 1920 | |
| ctcgagtctc acatgagcga aaccactgcg cggggcgcgg gggtggcggg gaggcgggcg | 1980 | |
| ttggtacggt cctccccgag gccgagcgcc gcagtgtctg gccccgcgcc cctgcgcaac | 2040 | |
| gtggcaggaa gcgcgcgctg gaggcggggg cgggctgccg gccgagactt ctggatggcg | 2100 | |
| gcggccgcgg ctccgccccg ggttcccacc gcctgaaggg cgagacaagc ccgacctgct | 2160 | |
| acaggcactc gtgggggtgg gggaggagcg ggggtcggtc cggctggttt gtgggtggga | 2220 | |
| ggcgcttgtt ctccaaaaac cggcgcgagc tgcaatcctg agggagctgc ggtggaggag | 2280 | |
| gtggagagaa ggccgcaccc ttctgggcag ggggagggga gtgccgcaat acctttatgg | 2340 | |
| gagttctttg ctgcctcccg tcttgtaagg accgccctgg gcctggaaga agccctccct | 2400 | |
| cctttcctcc tcgcgtgatc tcgtcatcgc ctccatgtcg agtcgcttct cgattatggg | 2460 | |
| cgggattctt ttgcctagac aattgtacta accttcttct cttcctctc ctgacag | 2517 | |

<210> SEQ ID NO 69
<211> LENGTH: 2902
<212> TYPE: DNA
<213> ORGANISM: Artificial Sequence
<220> FEATURE:
<223> OTHER INFORMATION: artificial sequence

<400> SEQUENCE: 69

| | | |
|---|---|---|
| gcgttacata acttacggta aatggcccgc ctggctgacc gcccaacgac ccccgcccat | 60 | |
| tgacgtcaat aatgacgtat gttcccatag taacgccaat agggactttc cattgacgtc | 120 | |
| aatgggtgga gtatttacgg taaactgccc acttggcagt acatcaagtg tatcatatgc | 180 | |
| caagtacgcc ccctattgac gtcaatgacg gtaaatggcc cgcctggcat tatgcccagt | 240 | |
| acatgacctt atgggacttt cctacttggc agtacatcta cgtattagtc atcgctatta | 300 | |
| ccatggcccg gtcgcgaca tgcagcggga cgcgccaccc cgagcccag ctccggcgcc | 360 | |
| ccggctcccc gcgccccga tcgggccgc cgctagtagt ggcggcggcg gaggcggggg | 420 | |
| cagcggcggc ggcggcggag gcgcctctgc agctccggct ccccctggcc tctcgggaac | 480 | |
| tacaagtccc aggggcctg gcggtggcg cgggcggaa gaggcggggt cggcgccgcg | 540 | |
| aggccggaag tggccgtgga ggcggaagtg gcgcggccgc ggaggggcct ggagtgcggc | 600 | |

-continued

```
ggcggcggga cccggagcag gagcggcggc agcagcgact gggggcggcg gcggcgcgtt    660
ggaggcggcc ggatccgttt aaacagagta atgacatggt tccttccatc ctccaaaggt    720
gaccaataat agtttgtaag tatcattatg aactaatgaa ttttcaacat atttgatata    780
tttcaatcca ttgccatcat tgttcttatc gatatttgag ttggctcact ttgccagtaa    840
gagtctattc aaattggctt ctgagtccat ttgacacaac acctttgatc tttgacagtt    900
tccttggttt taggtgctag atgatttctc aggctcacct tagacatttc ctgccacaga    960
cttagaatca gccatttctc taaggaccct gattccattt catgagaaat gatagagacc   1020
acaatcaaaa caagtcatga atttatactg atattttcaa ttcaaattaa agatgaggtt   1080
tttgctaaat ttttttgagt ttatatttgt atgtcttatg ctgaaaaatc ttgtttccta   1140
attagtaaca taattattca tttgatgggt aaatatttta gggccgattc tttggtttta   1200
tagccaagat accctgttga taaagtcttg tgggagcaat tataagactg gcttattttg   1260
aagcttttta aaaagacat ccttacctgt tttaactgta gattatatta acttaaatag    1320
gtacagccca cgcttgacta gttaacgctg gtgggtaggg atgagggagg gaggggcatt   1380
gtgatgtaca gggctgctct gtgagatcaa gggtctctta agggtgggag ctggggcagg   1440
gactacgaga gcagccagat gggctgaaag tggaactcaa ggggtttctg gcacctacct   1500
acctgcttcc cgctgggggg tggggagttg gcccagagtc ttaagattgg ggcagggtgg   1560
agaggtgggc tcttcctgct tcccactcat cttatagctt ctttccccca gatccgaatt   1620
cgagatccaa accaaggagg aaaggatatc acagaggaga gctagtctca gagagcctcg   1680
gctaggtagg ggagcggaac tctggtggga ggggaggtgc ggtgcactgg ggggatgggt   1740
ggctaggggg gccgtctggt ggcttgcggg ggttgccttt cccgtgggaa gtcgggaaca   1800
taatgtttgt tacgttggga gggaaagggg tggctggatg caggcgggag ggaggcccgc   1860
cctgcggcaa ccggaggggg agggagaagg gagcggaaaa tgctcgaaac cggacggagc   1920
cattgctctc gcagagggag gagcgcttcc ggctagcctc ttgtcgccga ttggccgttt   1980
ctcctcccgc cgtgtgtgaa acacaaatg gcgtattctg gttggagtaa agctcctgtc    2040
agttacaccg tcgggagtac gcagccgctt agcgactctc gcgttgcccc ctgggtgggg   2100
cgggtaggta ggtggggtgt agagatgctg ggtgtgcggg cgcggccggc ctcctgcggc   2160
gggaggggag ggtcagtgaa attggctctg gcgcgggcgt cctcccaccc tccccttcct   2220
tcgggggagt cggtttaccc gccgcctgct tgtcttcgac acctgattgg ctgtcgaagc   2280
tgtgggaccg ggcccttgct actggctcga gtctcacatg agcgaaacca ctgcgcgggg   2340 cgcggggtg gcggggaggc gggcgttggt acggtcctcc ccgaggccga gcgccgcagt    2400
gtctggcccc gcgcccctgc gcaacgtggc aggaagcgcg cgctggaggc ggggcgggc   2460 tgccggccga gacttctgga tggcggcggc cgcggctccg ccccgggttc ccaccgcctg   2520
aagggcgaga caagcccgac ctgctacagg cactcgtggg ggtgggggag gagcgggggt   2580
cggtccggct ggtttgtggg tggaggcgc ttgttctcca aaaccggcg cgagctgcaa     2640 tcctgaggga gctgcggtgg aggaggtgga gagaaggccg caccctttctg gcaggggga   2700 ggggagtgcc gcaataacctt tatgggagtt ctttgctgcc tcccgtcttg taaggaccgc   2760
cctgggcctg gaagaagccc tccctccttt cctcctcgcg tgatctcgtc atcgcctcca   2820
tgtcgagtcg cttctcgatt atgggcggga ttcttttgcc tagacaattg tactaacctt   2880
cttctctttc ctctcctgac ag                                            2902
```

```
<210> SEQ ID NO 70
<211> LENGTH: 3183
<212> TYPE: DNA
<213> ORGANISM: Artificial Sequence
<220> FEATURE:
<223> OTHER INFORMATION: artificial sequence

<400> SEQUENCE: 70
```

| | | | | | |
|---|---|---|---|---|---|
| gcgttacata | acttacggta | aatggcccgc | ctggctgacc | gcccaacgac | ccccgcccat | 60 |
| tgacgtcaat | aatgacgtat | gttcccatag | taacgccaat | agggactttc | cattgacgtc | 120 |
| aatgggtgga | gtatttacgg | taaactgccc | acttggcagt | acatcaagtg | tatcatatgc | 180 |
| caagtacgcc | ccctattgac | gtcaatgacg | gtaaatggcc | cgcctggcat | tatgcccagt | 240 |
| acatgacctt | atgggacttt | cctacttggc | agtacatcta | cgtattagtc | atcgctatta | 300 |
| ccatggcccg | gtcgcgaca | tgcagcggga | cgcgccaccc | cgagcccag | ctccggcgcc | 360 |
| ccggctcccc | gcgcccccga | tcggggccgc | cgctagtagt | ggcggcggcg | gaggcggggg | 420 |
| cagcggcggc | ggcggcggag | gcgcctctgc | agctccggct | cccccctggcc | tctcgggaac | 480 |
| tacaagtccc | aggggggcctg | gcggtgggcg | gcgggcggaa | gaggcggggt | cggcgccgcg | 540 |
| aggccggaag | tggccgtgga | ggcggaagtg | gcgcggccgc | ggaggggcct | ggagtgcggc | 600 |
| ggcggcggga | cccggagcag | gagcggcggc | agcagcgact | ggggggcggcg | gcggcgcgtt | 660 |
| ggaggcggcc | ggatccgttt | aaacggctcg | catctctcct | tcacgcgccc | gccgccctac | 720 |
| ctgaggccgc | catccacgcc | ggttgagtcg | cgttctgccg | cctcccgcct | gtggtgcctc | 780 |
| ctgaactgcg | tccgccgtct | aggtaagttt | aaagctcagg | tcgagaccgg | cctttgtcc | 840 |
| ggcgctccct | tggagcctac | ctagactcag | ccggctctcc | acgctttgcc | tgaccctgct | 900 |
| tgctcaactc | tacgtctttg | tttcgttttc | tgttctgcgc | cgttacagat | cactagtgtt | 960 |
| taaacagagt | aatgacatgg | ttccttccat | cctccaaagg | tgaccaataa | tagtttgtaa | 1020 |
| gtatcattat | gaactaatga | atttcaaca | tatttgatat | atttcaatcc | attgccatca | 1080 |
| ttgttcttat | cgatatttga | gttggctcac | tttgccagta | agagtctatt | caaattggct | 1140 |
| tctgagtcca | tttgacacaa | cacctttgat | cttttgacagt | ttccttggtt | ttaggtgcta | 1200 |
| gatgatttct | caggctcacc | ttagacattt | cctgccacag | acttagaatc | agccatttct | 1260 |
| ctaaggaccc | tgattccatt | tcatgagaaa | tgatagagac | cacaatcaaa | acaagtcatg | 1320 |
| aatttatact | gatattttca | attcaaatta | aagatgaggt | ttttgctaaa | ttttttttgag | 1380 |
| tttatatttg | tatgtcttat | gctgaaaaat | cttgtttcct | aattagtaac | ataattattc | 1440 |
| atttgatggg | taaatatttt | agggccgatt | cttttggtttt | atagccaaga | taccctgttg | 1500 |
| ataaagtctt | gtgggagcaa | ttataagact | ggcttatttt | gaagcttttt | aaaaaagaca | 1560 |
| tccttacctg | ttttaactgt | agattatatt | aacttaaata | ggtacagccc | acgcttgact | 1620 |
| agttaacgct | ggtgggtagg | gatgagggag | ggaggggcat | tgtgatgtac | agggctgctc | 1680 |
| tgtgagatca | agggtctctt | aagggtggga | gctgggcag | ggactacgag | agcagccaga | 1740 |
| tgggctgaaa | gtggaactca | aggggtttct | ggcacctacc | tacctgcttc | ccgctggggg | 1800 |
| gtggggagtt | ggcccagagt | cttaagattg | gggcagggtg | gagaggtggg | ctcttcctgc | 1860 |
| ttcccactca | tcttatagct | ttcttctcccc | agatccgaat | tcgagatcca | aaccaaggag | 1920 |
| gaaaggatat | cacagaggag | agctagtctc | agagagcctc | ggctaggtag | gggagcggaa | 1980 |
| ctctggtggg | aggggaggtg | cggtgcactg | gggggatggg | tggctagggg | ggccgtctgg | 2040 |
| tggcttgcgg | gggttgcctt | tcccgtggga | agtcgggaac | ataatgtttg | ttacgttggg | 2100 |

| | |
|---|---|
| agggaaaggg gtggctggat gcaggcggga gggaggcccg ccctgcggca accggagggg | 2160 |
| gagggagaag ggagcggaaa atgctcgaaa ccggacggag ccattgctct cgcagaggga | 2220 |
| ggagcgcttc cggctagcct cttgtcgccg attggccgtt tctcctcccg ccgtgtgtga | 2280 |
| aaacacaaat ggcgtattct ggttggagta aagctcctgt cagttacacc gtcgggagta | 2340 |
| cgcagccgct tagcgactct cgcgttgccc cctgggtggg gcgggtaggt aggtggggtg | 2400 |
| tagagatgct gggtgtgcgg gcgcggccgg cctcctgcgg cgggagggga gggtcagtga | 2460 |
| aattggctct ggcgcgggcg tcctcccacc ctccccttcc ttcggggag tcggtttacc | 2520 |
| cgccgcctgc ttgtcttcga cacctgattg gctgtcgaag ctgtgggacc gggcccttgc | 2580 |
| tactggctcg agtctcacat gagcgaaacc actgcgcggg gcgcggggt ggcggggagg | 2640 |
| cgggcgttgg tacggtcctc cccgaggccg agcgccgcag tgtctggccc cgcgcccctg | 2700 |
| cgcaacgtgg caggaagcgc gcgctggagg cggggcggg ctgccggccg agacttctgg | 2760 |
| atggcggcgg ccgcggctcc gccccgggtt cccaccgcct gaagggcgag acaagcccga | 2820 |
| cctgctacag gcactcgtgg gggtggggga ggagcggggg tcggtccggc tggtttgtgg | 2880 |
| gtgggaggcg cttgttctcc aaaaaccggc gcgagctgca atcctgaggg agctgcggtg | 2940 |
| gaggaggtgg agagaaggcc gcacccttct gggcaggggg aggggagtgc cgcaatacct | 3000 |
| ttatgggagt tctttgctgc ctcccgtctt gtaaggaccg ccctgggcct ggaagaagcc | 3060 |
| ctccctcctt tcctcctcgc gtgatctcgt catcgcctcc atgtcgagtc gcttctcgat | 3120 |
| tatgggcggg attcttttgc ctagacaatt gtactaacct tcttctcttt cctctcctga | 3180 |
| cag | 3183 |

<210> SEQ ID NO 71
<211> LENGTH: 961
<212> TYPE: DNA
<213> ORGANISM: Artificial Sequence
<220> FEATURE:
<223> OTHER INFORMATION: EF intron+exon

<400> SEQUENCE: 71

| | |
|---|---|
| cgggtttgcc gccagaacac aggtaagtgc cgtgtgtggt tcccgcgggc ctggcctctt | 60 |
| tacgggttat ggcccttgcg tgccttgaat tacttccacc tggctgcagt acgtgattct | 120 |
| tgatcccgag cttcggggtg gaagtgggtg ggagagttcg aggccttgcg cttaaggagc | 180 |
| cccttcgcct cgtgcttgag ttgaggcctg gcctgggcgc tggggccgcc gcgtgcgaat | 240 |
| ctggtggcac cttcgcgcct gtctcgctgc tttcgataag tctctagcca tttaaaattt | 300 |
| ttgatgacct gctgcgacgc ttttttttctg gcaagatagt cttgtaaatg cgggccaaga | 360 |
| tctgcacact ggtatttcgg ttttttgggc cgcgggcggc gacggggccc gtgcgtccca | 420 |
| gcgcacatgt tcggcgaggc ggggcctgcg agcgcggcca ccgagaatcg gacggggta | 480 |
| gtctcaagct ggccggcctg ctctggtgcc tggcctcgcg ccgccgtgta tcgccccgcc | 540 |
| ctgggcggca aggctggccc ggtcggcacc agttgcgtga gcgaaagat ggccgcttcc | 600 |
| cggccctgct gcagggagct caaaatggag gacgcggcgc tcgggagagc gggcgggtga | 660 |
| gtcacccaca caaaggaaaa gggccttttc gtcctcagcc gtcgcttcat gtgactccac | 720 |
| ggagtaccgg gcgccgtcca ggcacctcga ttagttctcg agcttttgga gtacgtcgtc | 780 |
| tttaggttgg gggagggggt tttatgcgat ggagtttccc cacactgagt gggtggagac | 840 |

```
tgaagttagg ccagcttggc acttgatgta attctccttg gaatttgccc tttttgagtt    900
tggatcttgg ttcattctca agcctcagac agtggttcaa agttttttc ttccatttca    960 g                                                                    961
```

TRANSCRIPTION UNIT AND USE THEREOF IN EXPRESSION VECTORS

BACKGROUND OF THE INVENTION

Field of the Invention

The present invention relates to novel transcription units capable of being used in expression vectors.

Description of the Related Art

At present, the expression of recombinant proteins is still one of the major methods for producing therapeutic proteins, such as pharmacological antibodies.

The nucleic acids coding for the recombinant proteins are generally introduced into an expression vector containing genetic elements allowing the transcription and the translation of these molecules of interest.

SUMMARY OF THE INVENTION

One of the purposes of the invention is to provide a transcription unit making it possible to produce a recombinant protein the gain in productivity of which is neither linked to an antibody targeting a particular antigen and therefore to a given recombinant protein, nor linked to the culture medium.

One of the purposes of the invention is to make available a universal transcription unit making it possible to provide a better transcription and translation ability of a protein of interest compared with the conventional expression vectors for mammal cells such as the rat YB2/0 cell line and related lines, or the CHO cell line and related lines.

One of the other purposes of the invention is to provide a transcription unit making it possible to limit the expression vector size, in order to limit problems with cloning, with the effectiveness of transfection into the expression lines or also with interference between the expression vector and the genome of the recipient line which can lead to genetic instability and extinction of the gene of interest.

Finally, another purpose is to provide a transcription unit devoid of viral promoters, in order to limit the potential health risks.

The present invention relates to transcription units for constructing the expression vectors.

According to a general aspect, the invention relates to a transcription unit constituted by a polynucleotide comprising the following regulatory elements:
(i)—the hCMVie virus enhancer (E2), said enhancer having the nucleotide sequence SEQ ID NO: 1, or
  a nucleotide acid having at least 70% sequence identity with the sequence SEQ ID NO: 1 and essentially having transcription activation properties, and
(ii)—the promoter region of Cyclin-Dependent Kinase 9 (CDK9), said promoter region having the nucleotide sequence SEQ ID NO: 2, or
  a nucleotide acid having at least 70% sequence identity with the sequence SEQ ID NO: 2 and essentially having a transcription promoter activity.

By "regulatory elements" is meant within the meaning of the present invention, non-coding genetic elements making it possible to control the transcription and/or the translation of a nucleic acid coding for a protein of interest.

By "transcription unit" is meant a polynucleotide containing the regulatory elements necessary for the transcription of a nucleic acid of interest to RNA. An RNA polymerase, which makes it possible to synthesize an mRNA from a gene of interest linked to said transcription unit, as well as transcription activation or inhibition factors which modulate the transcription to mRNA in a plus or minus direction, can be bound to such a transcription unit.

By "promoter region" is meant a region of DNA which contains a particular DNA sequence making it possible to initiate the transcription of a gene of particular interest.

Within the meaning of the present invention, the terms "promoter region" and "promoter" can be replaced by each other.

The promoter region contains the zone of the DNA to which the RNA polymerase binds initially, before triggering the synthesis of the RNA.

A promoter is in general close (about twenty to a hundred nucleotides) to the nucleic acid of interest to be controlled and is situated upstream of a gene transcription start site. The presence of a promoter is essential for the transcription of a particular gene.

The promoter of the CDK9 gene represented by the sequence SEQ ID NO: 2 is a GC-rich promoter devoid of TATA box.

"A nucleotide acid having at least 70% sequence identity with the sequence SEQ ID: NO 2 and essentially having a promoter activity" contained in a transcription unit according to the present invention is a nucleotide acid having essentially the same gene transcription initiation ability as that of the promoter region of the CDK9 gene, represented by the sequence SEQ ID NO: 2.

The ability of the promoter region of the CDK9 gene to initiate the transcription of a gene can be determined according to the method described by Liu et al. (*Gene* 252, 51-59 (2000)).

By "enhancer" is meant a segment of DNA which can bind proteins such as the transcription factors in order to stimulate the transcription of a gene. An enhancer is not necessarily close to the gene of interest to be controlled, and can be situated in the 5' or in the 3' end, or even in the middle of the gene to be controlled or in an intron.

The presence of an enhancer in an expression vector makes it possible to increase the level of transcription of a gene.

"A nucleotide acid having at least 70% sequence identity with the sequence SEQ ID: NO 1 and essentially having transcription activation properties" is a nucleotide acid essentially having the same ability to stimulate gene transcription as that of the hCMVie virus enhancer represented by the sequence SEQ ID NO: 1, also denoted E2 hereafter.

The transcription activation properties of a gene can be determined by the use of reporter genes such as luciferase.

Several enhancers can coexist in a transcription unit according to the present invention; this makes it possible to further stimulate gene transcription.

As a result, a transcription unit according to the present invention can comprise:
  the hCMVie virus enhancer, said enhancer having the nucleotide sequence SEQ ID NO: 1 (E2), or a nucleotide acid having at least 70% sequence identity with the sequence SEQ ID NO: 1 and essentially having transcription activation properties, and
  at least one other enhancer chosen from an SV40 enhancer and an Eµ enhancer.

In the above and hereafter, the identity percentage between two sequences of nucleic acids can be calculated according to the following formula:

$$\frac{\text{the number of the identical residues} \times 100}{\text{the number of residues of the shortest sequence}}$$

In a particular embodiment of the invention, the enhancer is situated upstream of the promoter region. In other words, the enhancer is situated at the 5' end of the DNA of the promoter region, in order to facilitate the cloning of the coding sequences in the expression vector. The enhancer is a non-positional genetic element.

In a more particular embodiment of the invention, a transcription unit according to the present invention is constituted by a polynucleotide comprising the following regulatory elements:
  (i)—the hCMVie virus enhancer (E2), said enhancer having the nucleotide sequence SEQ ID NO: 1, or
    a nucleotide acid having at least 70% sequence identity with the sequence SEQ ID NO: 1 and essentially having transcription activation properties, and
  (ii)—the promoter region of Cyclin-Dependent Kinase 9 (CDK9), said promoter region having the nucleotide sequence SEQ ID NO: 2, or
    a nucleotide acid having at least 70% sequence identity with the sequence SEQ ID: NO 2 and essentially having a promoter activity, the enhancer being situated upstream of the promoter region.

A transcription unit according to the present invention can also comprise a nucleotide acid situated downstream of the promoter region and upstream of the translation initiation site, said nucleotide acid comprising at least one of the 5' untranslated regions (5' UTR) chosen from the following:
  (i)—the regulatory R region of the 5' Long Terminal Repeat (LTR) (RU-5') of the HTLV-1 virus having the nucleotide sequence SEQ ID NO: 3 (U1), or
    a nucleotide acid having at least 70% sequence identity with the sequence SEQ ID NO: 3,
  (ii)—the 5' UTR region of the NF-κB Repressing Factor (NRF) gene having the nucleotide sequence SEQ ID NO: 4 (U2), or
    a nucleotide acid having at least 70% sequence identity with the sequence SEQ ID NO: 4,
  (iii)—the 5' UTR region of the eukaryotic Initiation Factor 4GI (eIF4GI) gene having the nucleotide sequence SEQ ID NO: 5 (U3), or
    a nucleotide acid having at least 70% sequence identity with the sequence SEQ ID NO: 5,
the abovementioned nucleotide acids having at least 70% sequence identity with one of the sequences represented by the sequences SEQ ID NO: 3, SEQ ID NO: 4 or SEQ ID NO: 5 and essentially having mRNA stabilization and translation facilitator properties.

The mRNA stabilization and translation facilitator properties can be measured by Fritz et al. (*Sci. STKE*, 5 Dec. 2000 Vol. 2000, Issue 61, p. p11) and Ross et al. (*Microbiol Rev.* 1995 September; 59(3):423-50).

The facilitation of the translation can be carried out by comparing the quantity of mRNA which remains constant analyzed by q-RT-PCR while showing an increase in the protein level.

The 5' untranslated region in a gene corresponds to the portion of the messenger RNA (mRNA) placed upstream of the translation initiation site. This region allows ribosome binding and can be involved in regulating the expression of the gene concerned.

The translation initiation site is a triplet of nucleotides which directs the initiation of the protein translation. This triplet is often the triplet ATG.

"The nucleotide acids having at least 70% sequence identity with one of the sequences represented by the sequences SEQ ID NO: 3, SEQ ID NO: 4 or SEQ ID NO: 5" contained in the transcription units according to the present invention allow ribosome binding and mRNA stabilization.

The abovementioned nucleotide acid situated downstream of the promoter region and upstream of the translation initiation site can comprise a single 5' UTR region chosen from:
  (i)—the R region of the Long Terminal Repeat (LTR) of the HTLV-1 virus having the nucleotide sequence SEQ ID NO: 3 (U1), or
    a nucleotide acid having at least 70% sequence identity with the sequence SEQ ID NO: 3,
  (ii)—the 5' UTR region of the NF-κB Repressing Factor (NRF) gene having the nucleotide sequence SEQ ID NO: 4 (U2), or
    a nucleotide acid having at least 70% sequence identity with the sequence SEQ ID NO: 4,
  (iii)—the 5' UTR region of the eukaryotic Initiation Factor 4GI (eIF4GI) gene having the nucleotide sequence SEQ ID NO: 5 (U3), or
    a nucleotide acid having at least 70% sequence identity with the sequence SEQ ID NO: 5.

By a 5'UTR region "situated downstream of the promoter region and upstream of the translation initiation site" is meant a 5'UTR region situated after the 3' end of the DNA of the promoter region and before the 5' end of the DNA of the translation initiation site.

The abovementioned nucleotide acid situated downstream of the promoter region and upstream of the translation initiation site can comprise two 5'UTR regions.

The presence of two or more 5'UTR regions in a transcription unit according to the invention makes it possible to accumulate or synergize the positive effects on the stability of the mRNA and the translation efficiency.

An abovementioned nucleotide acid used in a transcription unit according to the present invention can comprise the R region of the Long Terminal Repeat (LTR) of the HTLV-1 virus and the 5' UTR region of the NF-κB Repressing Factor (NRF) gene, said nucleotide acid being represented by the sequence SEQ ID NO: 6, or being a nucleotide acid having at least 70% sequence identity with the sequence SEQ ID NO: 6.

An abovementioned nucleotide acid used in a transcription unit according to the present invention can also comprise the R region of the Long Terminal Repeat (LTR) of the HTLV-1 virus and the 5' UTR region of the eukaryotic Initiation Factor 4GI (eIF4GI) gene, said nucleotide acid being represented by the sequence SEQ ID NO: 7, or being a nucleotide acid having at least 70% sequence identity with the sequence SEQ ID NO: 7.

An abovementioned nucleotide acid used in a transcription unit according to the present invention can also comprise the 5' UTR region of the NF-κB Repressing Factor (NRF) gene and the 5' UTR region of the eukaryotic Initiation Factor 4GI (eIF4GI) gene, said nucleotide acid being represented by the sequence SEQ ID NO: 8 or being a nucleotide acid having at least 70% sequence identity with the sequence SEQ ID NO: 8.

The abovementioned nucleotide acid situated downstream of the promoter region and upstream of the translation initiation site can also comprise three 5'UTR regions, namely the R region of the Long Terminal Repeat (LTR) of the HTLV-1 virus, the 5' UTR region of the NF-κB Repressing Factor (NRF) gene and the 5' UTR region of the eukaryotic Initiation Factor 4GI (eIF4GI) gene, said nucleotide acid being represented by the sequence SEQ ID NO: 9 or being a nucleotide acid having at least 70% sequence identity with the sequence SEQ ID NO: 9.

In a particular embodiment of the invention, a transcription unit according to the present invention is constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID: NO 2 and essentially having a promoter activity, and (iii) the R region of the Long Terminal Repeat (LTR) of the HTLV-1 virus represented by the nucleotide sequence SEQ ID NO: 3, or a nucleotide acid having at least 70% sequence identity with the sequence SEQ ID NO: 3, said 5' UTR region being situated downstream of the promoter region and upstream of the translation initiation site.

The advantages of the combined elements are supplied with a potential synergy between the 5'UTR region and the other elements in a transcription unit.

In a more particular embodiment, a transcription unit according to the invention is constituted by a polynucleotide comprising a nucleotide acid represented by the sequence SEQ ID NO: 14 and constituted by:

(i) the hCMVie virus enhancer represented by the sequence SEQ ID NO: 1, (ii) the promoter region of the CDK9 gene represented by the sequence SEQ ID NO: 2, and (iii) the 5'UTR region of the LTR of the HTLV-1 virus, represented by the sequence SEQ ID NO: 3, or by a nucleotide acid having at least 70% sequence identity with the sequence SEQ ID NO: 14.

In another particular embodiment of the invention, a transcription unit according to the present invention is constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID: NO 2 and essentially having a promoter activity, and (iii) the 5' UTR region of the NF-κB Repressing Factor (NRF) gene represented by the nucleotide sequence SEQ ID NO: 4, or a nucleotide acid having at least 70% sequence identity with the sequence SEQ ID NO: 4, said 5' UTR region being situated downstream of the promoter region and upstream of the translation initiation site.

In a more particular embodiment, a transcription unit according to the invention is constituted by a polynucleotide comprising a nucleotide acid represented by the sequence SEQ ID NO: 15 and constituted by:

(i) the hCMVie virus enhancer represented by the sequence SEQ ID NO: 1, (ii) the promoter region of the CDK9 gene represented by the sequence SEQ ID NO: 2, and (iii) the 5' UTR region of the NRF gene, represented by the sequence SEQ ID NO: 4, or a nucleotide acid having at least 70% sequence identity with the sequence SEQ ID NO: 15.

In another particular embodiment of the invention, a transcription unit according to the present invention is constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID: NO 2 and essentially having a promoter activity, and (iii) the 5' UTR region of the eukaryotic Initiation Factor 4GI (eIF4GI) gene represented by the nucleotide sequence SEQ ID NO: 5, or a nucleotide acid having at least 70% sequence identity with the sequence SEQ ID NO: 5, said 5' UTR region being situated downstream of the promoter region and upstream of the translation initiation site.

In a more particular embodiment, a transcription unit according to the invention is constituted by a polynucleotide comprising a nucleotide acid represented by the sequence SEQ ID NO: 16 and constituted by:

(i) the hCMVie virus enhancer represented by the sequence SEQ ID NO: 1, (ii) the promoter region of the CDK9 gene represented by the sequence SEQ ID NO: 2, and (iii) the 5' UTR region of the eIF4GI gene represented by the sequence SEQ ID NO: 5, or by a nucleotide acid having at least 70% sequence identity with the sequence SEQ ID NO: 16.

In another particular embodiment of the invention, a transcription unit according to the present invention can comprise two 5'UTR regions. Such a transcription unit is constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the R region of the Long Terminal Repeat (LTR) of the HTLV-1 virus represented by the nucleotide sequence SEQ ID NO: 3, or a nucleotide acid having at least 70% sequence identity with the sequence SEQ ID NO: 3, and (iv) the 5' UTR region of the NF-κB Repressing Factor (NRF) gene represented by the nucleotide sequence SEQ ID NO: 4, or a nucleotide acid having at least 70% sequence identity with the sequence SEQ ID NO: 4, the 5' UTR regions being situated downstream of the promoter region and upstream of the translation initiation site.

In a more particular embodiment, a transcription unit according to the invention is constituted by a polynucleotide comprising a nucleotide acid represented by the sequence SEQ ID NO: 17 and constituted by:

(i) the hCMVie virus enhancer represented by the sequence SEQ ID NO: 1, (ii) the promoter region of the CDK9 gene represented by the sequence SEQ ID NO: 2, and (iii) the 5' UTR region represented by the sequence SEQ ID NO: 6, or by a nucleotide acid having at least 70% sequence identity with the sequence SEQ ID NO: 17.

In another particular embodiment of the invention, a transcription unit according to the present invention can comprise two 5'UTR regions. Such a transcription unit is constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID: NO 2 and essentially having a promoter activity, (iii) the R region of the Long Terminal Repeat (LTR) of the HTLV-1 virus having the nucleotide sequence SEQ ID NO: 3, or a nucleotide acid having at least 70% sequence identity with the sequence SEQ ID NO: 3, and (iv) the 5' UTR region of the eukaryotic Initiation Factor 4GI (eIF4GI) gene having the nucleotide sequence SEQ ID NO: 5, or a nucleotide acid having at least 70% sequence identity with the sequence SEQ ID NO: 5, the 5' UTR regions being situated downstream of the promoter region and upstream of the translation initiation site.

In a more particular embodiment, a transcription unit according to the invention is constituted by a polynucleotide comprising a nucleotide acid represented by the sequence SEQ ID NO: 18 and constituted by:

(i) the hCMVie virus enhancer represented by the sequence SEQ ID NO: 1, (ii) the promoter region of the CDK9 gene represented by the sequence SEQ ID NO: 2, and (iii) the 5' UTR region represented by the sequence SEQ ID NO: 7, or by a nucleotide acid having at least 70% sequence identity with the sequence SEQ ID NO: 18.

In another particular embodiment of the invention, a transcription unit according to the present invention can comprise two 5'UTR regions. Such a transcription unit is constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID: NO 2 and essentially having a promoter activity, (iii) the 5' UTR region of the NF-κB Repressing Factor (NRF) gene having the nucleotide sequence SEQ ID NO: 4, or a nucleotide acid having at least 70% sequence identity with the sequence SEQ ID NO: 4, and (iv) the 5' UTR region of the eukaryotic Initiation Factor 4GI (eIF4GI) gene having the nucleotide sequence SEQ ID NO: 5, or a nucleotide acid having at least 70% sequence identity with the sequence SEQ ID NO: 5, the 5' UTR regions being situated downstream of the promoter region and upstream of the translation initiation site.

In a more particular embodiment, a transcription unit according to the invention is constituted by a polynucleotide comprising a nucleotide acid represented by the sequence SEQ ID NO: 19 and constituted by:

(i) the hCMVie virus enhancer represented by the sequence SEQ ID NO: 1, (ii) the promoter region of the CDK9 gene represented by the sequence SEQ ID NO: 2, and (iii) the 5' UTR region represented by the sequence SEQ ID NO: 8, or by a nucleotide acid having at least 70% sequence identity with the sequence SEQ ID NO: 19.

In another particular embodiment of the invention, a transcription unit according to the present invention can comprise three 5'UTR regions. Such a transcription unit is constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID: NO 2 and essentially having a promoter activity, (iii) the R region of the Long Terminal Repeat (LTR) of the HTLV-1 virus having the nucleotide sequence SEQ ID NO: 3, or a nucleotide acid having at least 70% sequence identity with the sequence SEQ ID NO: 3, (iv) the 5' UTR region of the NF-κB Repressing Factor (NRF) gene having the nucleotide sequence SEQ ID NO: 4, or a nucleotide acid having at least 70% sequence identity with the sequence SEQ ID NO: 4, and (v) the 5' UTR region of the eukaryotic Initiation Factor 4GI (eIF4GI) gene having the nucleotide sequence SEQ ID NO: 5, or a nucleotide acid having at least 70% sequence identity with the sequence SEQ ID NO: 5, the 5' UTR regions being situated downstream of the promoter region and upstream of the translation initiation site.

In a more particular embodiment, a transcription unit according to the invention is constituted by a polynucleotide comprising a nucleotide acid represented by the sequence SEQ ID NO: 20 and constituted by:

(i) the hCMVie virus enhancer represented by the sequence SEQ ID NO: 1, (ii) the promoter region of the CDK9 gene represented by the sequence SEQ ID NO: 2, and (iii) the 5' UTR region represented by the sequence SEQ ID NO: 9, or by a nucleotide acid having at least 70% sequence identity with the sequence SEQ ID NO: 20.

A transcription unit according to the present invention can also comprise one or more introns situated downstream of said promoter region.

By "intron" is meant a non-coding part of a gene. An intron is often situated between two exons. After the transcription, this part is excised from the pre-messenger RNA (splicing of the introns) in order to produce the messenger RNA. The presence of a heterologous intron makes it possible to optimize the expression of the exogenous genes in a DNA construction. In fact the latter can contain regulatory elements which can stabilize the mRNA or promote its transcription.

In the construction of a transcription unit according to the present invention, one or more introns can be situated:

(i) downstream of the 5' UTR region and upstream of the translation initiation site, and/or (ii) downstream of the promoter and upstream of the 5'UTR region, and/or (iii) after the translation initiation site and within a coding sequence, and/or (iv) between the stop codon of the coding sequence and the polyadenylation signal.

When an intron is situated after the translation initiation site and within a coding sequence, it is important not to change the mRNA reading frame during the translation and to preserve the donor and acceptor sites as well as the branch site sequence (UAUAAC) allowing splicing by the spliceosome.

By "an intron situated downstream of said promoter region" is meant an intron situated towards the 3' region of the DNA of the promoter region.

Said intron can be chosen from the following:
the intron of the Elongation Factor 1α (EF1α) gene having the nucleotide sequence SEQ ID NO: 10, or a nucleotide acid having at least 70% sequence identity with the sequence SEQ ID NO: 10, such as the sequence SEQ ID NO: 71.
the murine ROSA intron having the nucleotide sequence SEQ ID NO: 11, or a nucleotide acid having at least 70% sequence identity with the sequence SEQ ID NO: 11,
5'-Long Terminal Repeat (5'-LTR) intron of the HTLV-1 virus having the nucleotide sequence SEQ ID NO: 12, or a nucleotide acid having at least 70% sequence identity with the sequence SEQ ID NO: 12,
pCI-neo chimeric intron having the nucleotide sequence SEQ ID NO: 13, or a nucleotide acid having at least 70% sequence identity with the sequence SEQ ID NO: 13,
ubiquitin gene intron having the nucleotide sequence SEQ ID NO: 53, or a nucleotide acid having at least 70% sequence identity with the sequence SEQ ID NO: 53,
human ROSA gene intron having the nucleotide sequence SEQ ID NO: 54, or a nucleotide acid having at least 70% sequence identity with the sequence SEQ ID NO: 54.

The nucleotide acid represented by the sequence SEQ ID NO: 10 is denoted in the present application by "EF1α" or "EFss".

The nucleotide acid represented by the sequence SEQ ID NO: 71 is denoted in the present application by "EF1α with exon" or "EF". This nucleotide acid contains the EF1α intron of the sequence SEQ ID NO: 10 and an exonic sequence in the 5' region.

A transcription unit according to the present invention can comprise:
(i) the hCMVie virus enhancer represented by the nucleotide sequence SEQ ID NO: 1, or a nucleotide acid having at least 70% sequence identity with the sequence SEQ ID NO: 1 and essentially having transcription activation properties,
(ii) a promoter region of Cyclin-Dependent Kinase 9 (CDK9), said promoter region having the nucleotide sequence SEQ ID NO: 2, or a nucleotide acid having at least 70% sequence identity with the sequence SEQ ID NO: 2 and essentially having a promoter activity, and
(iii) an intron chosen from:
the intron of the Elongation Factor 1α (EF1α) gene having the nucleotide sequence SEQ ID NO: 10, or a nucleotide acid having at least 70% sequence identity with the sequence SEQ ID NO: 10,
the murine ROSA intron having the nucleotide sequence SEQ ID NO: 11, or a nucleotide acid having at least 70% sequence identity with the sequence SEQ ID NO: 11,
the 5'LTR intron of the HTLV-1 virus having the nucleotide sequence SEQ ID NO: 12, or a nucleotide acid having at least 70% sequence identity with the sequence SEQ ID NO: 12,
the pCI-neo chimeric intron having the nucleotide sequence SEQ ID NO: 13, or a nucleotide acid having at least 70% sequence identity with the sequence SEQ ID NO: 13,
ubiquitin gene intron having the nucleotide sequence SEQ ID NO: 53, or a nucleotide acid having at least 70% sequence identity with the sequence SEQ ID NO: 53,
human ROSA gene intron having the nucleotide sequence SEQ ID NO: 54, or a nucleotide acid having at least 70% sequence identity with the sequence SEQ ID NO: 54.
said enhancer being situated in the 5' or in the 3' end of the transcription unit, or within the coding sequence in an intron;
said intron being situated:
(i) downstream of the 5' UTR region and upstream of the translation initiation site, or
(ii) downstream of the promoter and upstream of the 5'UTR region, or
(iii) after the translation initiation site and within the coding sequence, or
(iv) between the stop codon of the coding sequence and the polyadenylation signal.

A particular embodiment of the invention relates to a transcription unit constituted by a polynucleotide comprising the following regulatory elements:
(i) the hCMVie virus enhancer represented by the nucleotide sequence SEQ ID NO: 1, or a nucleotide acid having at least 70% sequence identity with the sequence SEQ ID NO: 1 and essentially having transcription activation properties, and
(ii) the promoter region of Cyclin-Dependent Kinase 9 (CDK9) represented by the nucleotide sequence SEQ ID NO: 2, or a nucleotide acid having at least 70% sequence identity with the sequence SEQ ID: NO 2 and essentially having a promoter activity, and
(iii) the intron of the Elongation Factor 1α (EF1α) gene having the nucleotide sequence SEQ ID NO: 10, or a nucleotide acid having at least 70% sequence identity with the sequence SEQ ID NO: 10.

In a more particular embodiment of the invention, a transcription unit according to the invention is constituted by a polynucleotide comprising a nucleotide acid represented by the sequence SEQ ID NO: 21 and constituted by:
(i) the hCMVie virus enhancer represented by the nucleotide sequence SEQ ID NO: 1,
(ii) the promoter region of the CDK9 gene represented by the nucleotide sequence SEQ ID NO: 2, and
(iii) the intron of the EF1α gene represented by the nucleotide sequence SEQ ID NO: 10, or by a nucleotide acid having at least 70% sequence identity with the sequence SEQ ID NO: 21.

A particular embodiment of the invention relates to a transcription unit constituted by a polynucleotide comprising the following regulatory elements:
(i) the hCMVie virus enhancer represented by the nucleotide sequence SEQ ID NO: 1, or a nucleotide acid having at least 70% sequence identity with the sequence SEQ ID NO: 1 and essentially having transcription activation properties, and
(ii) the promoter region of Cyclin-Dependent Kinase 9 (CDK9) represented by the nucleotide sequence SEQ ID NO: 2, or a nucleotide acid having at least 70% sequence identity with the sequence SEQ ID: NO 2 and essentially having a promoter activity, and (iii) the murine ROSA intron having the nucleotide sequence SEQ ID NO: 11, or a nucleotide acid having at least 70% sequence identity with the sequence SEQ ID NO: 11.

In a more particular embodiment of the invention, a transcription unit according to the invention is constituted by a polynucleotide comprising a nucleotide acid represented by the sequence SEQ ID NO: 22 and constituted by:

(i) the hCMVie virus enhancer represented by the nucleotide sequence SEQ ID NO: 1, (ii) the promoter region of the CDK9 gene represented by the nucleotide sequence SEQ ID NO: 2, and (iii) the murine ROSA intron having the nucleotide sequence SEQ ID NO: 11, or by a nucleotide acid having at least 70% sequence identity with the sequence SEQ ID NO: 22.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, and (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, and (iii) the 5'LTR intron of the HTLV-1 virus having the nucleotide sequence SEQ ID NO: 12, or a nucleotide acid having at least 70% sequence identity with the sequence SEQ ID NO: 12.

In a more particular embodiment of the invention, a transcription unit according to the invention is constituted by a polynucleotide comprising a nucleotide acid represented by the sequence SEQ ID NO: 23 and constituted by:

(i) the hCMVie virus enhancer represented by the nucleotide sequence SEQ ID NO: 1, (ii) the promoter region of the CDK9 gene represented by the nucleotide sequence SEQ ID NO: 2, and (iii) the 5'LTR intron of the HTLV-1 virus having the nucleotide sequence SEQ ID NO: 12, or a nucleotide acid having at least 70% sequence identity with the sequence SEQ ID NO: 12.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, and (ii) the promoter region of Cyclin-Dependent Kinase 9 (CDK9) represented by the nucleotide sequence SEQ ID NO: 2, or a nucleotide acid having at least 70% sequence identity with the sequence SEQ ID: NO 2 and essentially having a promoter activity, and (iii) the pCI-neo intron having the nucleotide sequence SEQ ID NO: 13, or a nucleotide acid having at least 70% sequence identity with the sequence SEQ ID NO: 13.

In a more particular embodiment of the invention, a transcription unit according to the invention is constituted by a polynucleotide comprising a nucleotide acid represented by the sequence SEQ ID NO: 24 and constituted by:

(i) the hCMVie virus enhancer represented by the nucleotide sequence SEQ ID NO: 1, (ii) the promoter region of the CDK9 gene represented by the nucleotide sequence SEQ ID NO: 2, and (iii) the pCI-neo chimeric intron represented by the nucleotide sequence SEQ ID NO: 13, or by a nucleotide acid having at least 70% sequence identity with the sequence SEQ ID NO: 24.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, and (ii) the promoter region of Cyclin-Dependent Kinase 9 (CDK9) represented by the nucleotide sequence SEQ ID NO: 2, or a nucleotide acid having at least 70% sequence identity with the sequence SEQ ID: NO 2 and essentially having a promoter activity, and (iii) the ubiquitin gene intron having the nucleotide sequence SEQ ID NO: 53, or a nucleotide acid having at least 70% sequence identity with the sequence SEQ ID NO: 55.

In a more particular embodiment of the invention, a transcription unit according to the invention is constituted by a polynucleotide comprising a nucleotide acid represented by the sequence SEQ ID NO: 55 and constituted by:

(i) the hCMVie virus enhancer represented by the nucleotide sequence SEQ ID NO: 1, (ii) the promoter region of the CDK9 gene represented by the nucleotide sequence SEQ ID NO: 2, and (iii) the ubiquitin gene intron represented by the nucleotide sequence SEQ ID NO: 53, or by a nucleotide acid having at least 70% sequence identity with the sequence SEQ ID NO: 55.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, and (ii) the promoter region of Cyclin-Dependent Kinase 9 (CDK9) represented by the nucleotide sequence SEQ ID NO: 2, or a nucleotide acid having at least 70% sequence identity with the sequence SEQ ID: NO 2 and essentially having a promoter activity, and (iii) the human ROSA intron having the nucleotide sequence SEQ ID NO: 54, or a nucleotide acid having at least 70% sequence identity with the sequence SEQ ID NO: 54.

In a more particular embodiment of the invention, a transcription unit according to the invention is constituted by a polynucleotide comprising a nucleotide acid represented by the sequence SEQ ID NO: 56 and constituted by:

(i) the hCMVie virus enhancer represented by the nucleotide sequence SEQ ID NO: 1, (ii) the promoter region of the CDK9 gene represented by the nucleotide sequence SEQ ID NO: 2, and (iii) the human ROSA intron represented by the nucleotide sequence SEQ ID NO: 54, or by a nucleotide acid having at least 70% sequence identity with the sequence SEQ ID NO: 56.

A transcription unit according to the present invention can comprise:
(i) the hCMVie virus enhancer represented by the nucleotide sequence SEQ ID NO: 1, or a nucleotide acid having at least 70% sequence identity with the sequence SEQ ID NO: 1 and essentially having transcription activation properties,
(ii) a promoter region of Cyclin-Dependent Kinase 9 (CDK9), said promoter region having the nucleotide sequence SEQ ID NO: 2, or a nucleotide acid having at least 70% sequence identity with the sequence SEQ ID NO: 2 and essentially having a promoter activity, or
(iii) at least one of the 5' untranslated regions (5' UTR) chosen from:
  the R region of the Long Terminal Repeat (LTR) of the HTLV-1 virus having the nucleotide sequence SEQ ID NO: 3, or a nucleotide acid having at least 70% sequence identity with the sequence SEQ ID NO: 3,
  the 5' UTR region of the NF-κB Repressing Factor (NRF) gene having the nucleotide sequence SEQ ID NO: 4, or a nucleotide acid having at least 70% sequence identity with the sequence SEQ ID NO: 4,
  the 5' UTR region of the eukaryotic Initiation Factor 4GI (eIF4GI) gene having the nucleotide sequence SEQ ID NO: 5, or a nucleotide acid having at least 70% sequence identity with the sequence SEQ ID NO: 5, and
(iv) at least one intron chosen from:
  the intron of the Elongation Factor 1α (EF1α) gene having the nucleotide sequence SEQ ID NO: 10, or a nucleotide acid having at least 70% sequence identity with the sequence SEQ ID NO: 10,
  the murine ROSA intron having the nucleotide sequence SEQ ID NO: 11, or a nucleotide acid having at least 70% sequence identity with the sequence SEQ ID NO: 11,
  5'LTR intron of the HTLV-1 virus having the nucleotide sequence SEQ ID NO: 12, or a nucleotide acid having at least 70% sequence identity with the sequence SEQ ID NO: 12,
  the pCI-neo chimeric intron having the nucleotide sequence SEQ ID NO: 13, or a nucleotide acid having at least 70% sequence identity with the sequence SEQ ID NO: 13,
  ubiquitin gene intron having the nucleotide sequence SEQ ID NO: 53, or a nucleotide acid having at least 70% sequence identity with the sequence SEQ ID NO: 53,
  human ROSA gene intron having the nucleotide sequence SEQ ID NO: 54, or a nucleotide acid having at least 70% sequence identity with the sequence SEQ ID NO: 54
said enhancer being situated in the 5' or in the 3' end of the transcription unit, between the promoter and the 5'UTR region or in a intron;
said promoter region being situated upstream of the 5'UTR region;
said introns being situated:
  (i) downstream of the 5' UTR region and upstream of the translation initiation site, and/or
  (ii) downstream of the promoter and upstream of the 5'UTR region, and/or
  (iii) after the translation initiation site and within the coding sequence, and/or
  (iv) between the stop codon of the coding sequence and the polyadenylation signal.

A particular embodiment of the invention relates to a transcription unit constituted by a polynucleotide comprising the following regulatory elements:
(i) the hCMVie virus enhancer represented by the nucleotide sequence SEQ ID NO: 1, or a nucleotide acid having at least 70% sequence identity with the sequence SEQ ID NO: 1 and essentially having transcription activation properties,
(ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity,
(iii) the R region of the Long Terminal Repeat (LTR) of the HTLV-1 virus having the nucleotide sequence SEQ ID NO: 3, or a nucleotide acid having at least 70% sequence identity with the sequence SEQ ID NO: 3, and
(iv) the intron of the Elongation Factor 1α (EF1α) gene having the nucleotide sequence SEQ ID NO: 10, or a nucleotide acid having at least 70% sequence identity with the sequence SEQ ID NO: 10.

In a more particular embodiment of the invention, a transcription unit according to the invention is constituted by a polynucleotide comprising a nucleotide acid represented by the sequence SEQ ID NO: 25 and constituted by:
(i) the hCMVie virus enhancer represented by the nucleotide sequence SEQ ID NO: 1,
(ii) the promoter region of Cyclin-Dependent Kinase 9 (CDK9) represented by the nucleotide sequence SEQ ID NO: 2,
(iii) the R region of the LTR of the HTLV-1 virus having the nucleotide sequence SEQ ID NO: 3, and
(iv) the intron of the Elongation Factor 1α (EF1α) gene having the nucleotide sequence SEQ ID NO: 10,
or by a nucleotide acid having at least 70% sequence identity with the sequence SEQ ID NO: 25.

A particular embodiment of the invention relates to a transcription unit constituted by a polynucleotide comprising the following regulatory elements:
(i) the hCMVie virus enhancer represented by the nucleotide sequence SEQ ID NO: 1, or a nucleotide acid having at least 70% sequence identity with the sequence SEQ ID NO: 1 and essentially having transcription activation properties,
(ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity,
(iii) the R region of the Long Terminal Repeat (LTR) of the HTLV-1 virus having the nucleotide sequence SEQ ID NO: 3, or a nucleotide acid having at least 70% sequence identity with the sequence SEQ ID NO: 3, and
(iv) the murine ROSA intron having the nucleotide sequence SEQ ID NO: 11, or a nucleotide acid having at least 70% sequence identity with the sequence SEQ ID NO: 11.

In a more particular embodiment of the invention, a transcription unit according to the invention is constituted by a polynucleotide comprising a nucleotide acid represented by the sequence SEQ ID NO: 26 and constituted by:
(i) the hCMVie virus enhancer represented by the nucleotide sequence SEQ ID NO: 1,
(ii) the promoter region of Cyclin-Dependent Kinase 9 (CDK9) represented by the nucleotide sequence SEQ ID NO: 2,
(iii) the R region of the LTR of the HTLV-1 virus having the nucleotide sequence SEQ ID NO: 3, and
(iv) the murine ROSA intron having the nucleotide sequence SEQ ID NO: 11,
or by a nucleotide acid having at least 70% sequence identity with the sequence SEQ ID NO: 26.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially having transcription activation properties, and (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the R region of the Long Terminal Repeat (LTR) of the HTLV-1 virus having the nucleotide sequence SEQ ID NO: 3, or a nucleotide acid having at least 70% sequence identity with the sequence SEQ ID NO: 3, and (iv) the 5'LTR intron of the HTLV-1 virus having the nucleotide sequence SEQ ID NO: 12, or a nucleotide acid having at least 70% sequence identity with the sequence SEQ ID NO: 12.

In a more particular embodiment of the invention, a transcription unit according to the invention is constituted by a polynucleotide comprising a nucleotide acid represented by the sequence SEQ ID NO: 27 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the R region of the LTR of the HTLV-1 virus having the nucleotide sequence SEQ ID NO: 3, and (iv) the 5'LTR intron of the HTLV-1 virus having the nucleotide sequence SEQ ID NO: 12, or by a nucleotide acid having at least 70% sequence identity with the sequence SEQ ID NO: 27.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, and (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the R region of the Long Terminal Repeat (LTR) of the HTLV-1 virus having the nucleotide sequence SEQ ID NO: 3, or a nucleotide acid having at least 70% sequence identity with the sequence SEQ ID NO: 3, and (iv) pCI-neo chimeric intron having the nucleotide sequence SEQ ID NO: 13, or a nucleotide acid having at least 70% sequence identity with the sequence SEQ ID NO: 13.

In a more particular embodiment of the invention, a transcription unit according to the invention is constituted by a polynucleotide comprising a nucleotide acid represented by the sequence SEQ ID NO: 28 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the R region of the LTR of the HTLV-1 virus having the nucleotide sequence SEQ ID NO: 3, and (iv) pCI-neo chimeric intron having the nucleotide sequence SEQ ID NO: 13, or by a nucleic acid having at least 70% sequence identity with the sequence SEQ ID NO: 28.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, and (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the R region of the Long Terminal Repeat (LTR) of the HTLV-1 virus having the nucleotide sequence SEQ ID NO: 3, or a nucleotide acid having at least 70% sequence identity with the sequence SEQ ID NO: 3, and (iv) ubiquitin gene intron having the nucleotide sequence SEQ ID NO: 53, or a nucleotide acid having at least 70% sequence identity with the sequence SEQ ID NO: 53.

In a more particular embodiment of the invention, a transcription unit according to the invention is constituted by a polynucleotide comprising a nucleotide acid represented by the sequence SEQ ID NO: 57 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the R region of the LTR of the HTLV-1 virus having the nucleotide sequence SEQ ID NO: 3, and (iv) ubiquitin gene intron having the nucleotide sequence SEQ ID NO: 53, or by a nucleotide acid having at least 70% sequence identity with the sequence SEQ ID NO: 57.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially having transcription activation properties, and (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the R region of the Long Terminal Repeat (LTR) of the HTLV-1 virus having the nucleotide sequence SEQ ID NO: 3, or a nucleotide acid having at least 70% sequence identity with the sequence SEQ ID NO: 3, and (iv) human ROSA gene intron represented by the nucleotide sequence SEQ ID NO: 54, or a nucleotide acid having at least 70% sequence identity with the sequence SEQ ID NO: 54.

In a more particular embodiment of the invention, a transcription unit according to the invention is constituted by a polynucleotide comprising a nucleotide acid represented by the sequence SEQ ID NO: 64 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the R region of the LTR of the HTLV-1 virus having the nucleotide sequence SEQ ID NO: 3, and (iv) human ROSA gene intron represented by the nucleotide sequence SEQ ID NO: 54, or by a nucleotide acid having at least 70% sequence identity with the sequence SEQ ID NO: 64.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region of the NF-κB Repressing Factor (NRF) gene having the nucleotide sequence SEQ ID NO: 4, or a nucleotide acid having at least 70% sequence identity with the sequence SEQ ID NO: 4, and (iv) the intron of the Elongation Factor 1α (EF1α) gene having the nucleotide sequence SEQ ID NO: 10, or a nucleotide acid having at least 70% sequence identity with the sequence SEQ ID NO: 10.

In a more particular embodiment of the invention, a transcription unit according to the invention is constituted by a polynucleotide comprising a nucleotide acid represented by the sequence SEQ ID NO: 29 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region of the NF-κB Repressing Factor (NRF) gene having the nucleotide sequence SEQ ID NO: 4, and (iv) the intron of the Elongation Factor 1α (EF1α) gene having the nucleotide sequence SEQ ID NO: 10, or by a nucleotide acid having at least 70% sequence identity with the sequence SEQ ID NO: 29.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region of the NF-κB Repressing Factor (NRF) gene having the nucleotide sequence SEQ ID NO: 4, or a nucleotide acid having at least 70% sequence identity with the sequence SEQ ID NO: 4, and (iv) the murine ROSA intron having the nucleotide sequence SEQ ID NO: 11, or a nucleotide acid having at least 70% sequence identity with the sequence SEQ ID NO: 11.

In a more particular embodiment of the invention, a transcription unit according to the invention is constituted by a polynucleotide comprising a nucleotide acid represented by the sequence SEQ ID NO: 30 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region of the NF-κB Repressing Factor (NRF) gene having the nucleotide sequence SEQ ID NO: 4, and (iv) the murine ROSA intron having the nucleotide sequence SEQ ID NO: 11, or by a nucleotide acid having at least 70% sequence identity with the sequence SEQ ID NO: 30.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region of the NF-κB Repressing Factor (NRF) gene having the nucleotide sequence SEQ ID NO: 4, or a nucleotide acid having at least 70% sequence identity with the sequence SEQ ID NO: 4, and (iv) the 5'LTR intron of the HTLV-1 virus having the nucleotide sequence SEQ ID NO: 12, or a nucleotide acid having at least 70% sequence identity with the sequence SEQ ID NO: 12.

In a more particular embodiment of the invention, a transcription unit according to the invention is constituted by a polynucleotide comprising a nucleotide acid represented by the sequence SEQ ID NO: 31 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region of the NF-κB Repressing Factor (NRF) gene having the nucleotide sequence SEQ ID NO: 4, and (iv) the intron of the 5'LTR gene of the HTLV-1 virus having the nucleotide sequence SEQ ID NO: 12, or by a nucleotide acid having at least 70% sequence identity with the sequence SEQ ID NO: 31.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, and (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region of the NF-κB Repressing Factor (NRF) gene having the nucleotide sequence SEQ ID NO: 4, or a nucleotide acid having at least 70% sequence identity with the sequence SEQ ID NO: 4, and (iv) pCI-neo chimeric intron having the nucleotide sequence SEQ ID NO: 13, or a nucleotide acid having at least 70% sequence identity with the sequence SEQ ID NO: 13.

In a more particular embodiment of the invention, a transcription unit according to the invention is constituted by a polynucleotide comprising a nucleotide acid represented by the sequence SEQ ID NO: 32 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region of the NF-κB Repressing Factor (NRF) gene having the nucleotide sequence SEQ ID NO: 4, and (iv) pCI-neo chimeric intron having the nucleotide sequence SEQ ID NO: 13, or by a nucleotide acid having at least 70% sequence identity with the sequence SEQ ID NO: 32.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, and (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region of the NF-κB Repressing Factor (NRF) gene having the nucleotide sequence SEQ ID NO: 4, or a nucleotide acid having at least 70% sequence identity with the sequence SEQ ID NO: 4, and (iv) ubiquitin gene intron having the nucleotide sequence SEQ ID NO: 53, or a nucleotide acid having at least 70% sequence identity with the sequence SEQ ID NO: 53.

In a more particular embodiment of the invention, a transcription unit according to the invention is constituted by a polynucleotide comprising a nucleotide acid represented by the sequence SEQ ID NO: 58 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region of the NF-κB Repressing Factor (NRF) gene having the nucleotide sequence SEQ ID NO: 4, and (iv) ubiquitin gene intron having the nucleotide sequence SEQ ID NO: 53, or by a nucleotide acid having at least 70% sequence identity with the sequence SEQ ID NO: 58.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, and (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region of the NF-κB Repressing Factor (NRF) gene having the nucleotide sequence SEQ ID NO: 4, or a nucleotide acid having at least 70% sequence identity with the sequence SEQ ID NO: 4, and (iv) human ROSA gene intron represented by the nucleotide sequence SEQ ID NO: 54, or a nucleotide acid having at least 70% sequence identity with the sequence SEQ ID NO: 54.

In a more particular embodiment of the invention, a transcription unit according to the invention is constituted by a polynucleotide comprising a nucleotide acid represented by the sequence SEQ ID NO: 65 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region of the NF-κB Repressing Factor (NRF) gene having the nucleotide sequence SEQ ID NO: 4, and (iv) human ROSA gene intron represented by the nucleotide sequence SEQ ID NO: 54, or by a nucleotide acid having at least 70% sequence identity with the sequence SEQ ID NO: 65.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region of the eukaryotic Initiation Factor 4GI (eIF4GI) gene having the nucleotide sequence SEQ ID NO: 5, or a nucleotide acid having at least 70% sequence identity with the sequence SEQ ID NO: 5, and (iv) the intron of the Elongation Factor 1α (EF1α) gene having the nucleotide sequence SEQ ID NO: 10, or a nucleotide acid having at least 70% sequence identity with the sequence SEQ ID NO: 10.

In a more particular embodiment of the invention, a transcription unit according to the invention is constituted by a polynucleotide comprising a nucleotide acid represented by the sequence SEQ ID NO: 33 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region of the eukaryotic Initiation Factor 4GI (eIF4GI) gene having the nucleotide sequence SEQ ID NO: 5, and (iv) the intron of the Elongation Factor 1α (EF1α) gene having the nucleotide sequence SEQ ID NO: 10, or by a nucleotide acid having at least 70% sequence identity with the sequence SEQ ID NO: 33.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region of the eukaryotic Initiation Factor 4GI (eIF4GI) gene having the nucleotide sequence SEQ ID NO: 5, or a nucleotide acid having at least 70% sequence identity with the sequence SEQ ID NO: 5, and (iv) the murine ROSA intron having the nucleotide sequence SEQ ID NO: 11, or a nucleotide acid having at least 70% sequence identity with the sequence SEQ ID NO: 11.

In a more particular embodiment of the invention, a transcription unit according to the invention is constituted by a polynucleotide comprising a nucleotide acid represented by the sequence SEQ ID NO: 34 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region of the eukaryotic Initiation Factor 4GI (eIF4GI) gene having the nucleotide sequence SEQ ID NO: 5, and (iv) the murine ROSA intron having the nucleotide sequence SEQ ID NO: 11, or by a nucleotide acid having at least 70% sequence identity with the sequence SEQ ID NO: 34.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, and (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region of the eukaryotic Initiation Factor 4GI (eIF4GI) gene having the nucleotide sequence SEQ ID NO: 5, or a nucleotide acid having at least 70% sequence identity with the sequence SEQ ID NO: 5, and (iv) the 5'LTR intron of the HTLV-1 virus having the nucleotide sequence SEQ ID NO: 12, or a nucleotide acid having at least 70% sequence identity with the sequence SEQ ID NO: 12.

In a more particular embodiment of the invention, a transcription unit according to the invention is constituted by a polynucleotide comprising a nucleotide acid represented by the sequence SEQ ID NO: 35 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region of the eukaryotic Initiation Factor 4GI (eIF4GI) gene having the nucleotide sequence SEQ ID NO: 5, and (iv) the 5'LTR intron of the HTLV-1 virus having the nucleotide sequence SEQ ID NO: 12, or by a nucleotide acid having at least 70% sequence identity with the sequence SEQ ID NO: 35.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, and (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region of the eukaryotic Initiation Factor 4GI (eIF4GI) gene having the nucleotide sequence SEQ ID NO: 5, or a nucleotide acid having at least 70% sequence identity with the sequence SEQ ID NO: 5, and (iv) pCI-neo chimeric intron having the nucleotide sequence SEQ ID NO: 13, or a nucleotide acid having at least 70% sequence identity with the sequence SEQ ID NO: 13.

In a more particular embodiment of the invention, a transcription unit according to the invention is constituted by a polynucleotide comprising a nucleotide acid represented by the sequence SEQ ID NO: 36 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region of the eukaryotic Initiation Factor 4GI (eIF4GI) gene having the nucleotide sequence SEQ ID NO: 5, and (iv) pCI-neo chimeric intron having the nucleotide sequence SEQ ID NO: 13, or by a nucleotide acid having at least 70% sequence identity with the sequence SEQ ID NO: 36.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, and (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region of the eukaryotic Initiation Factor 4GI (eIF4GI) gene having the nucleotide sequence SEQ ID NO: 5, or a nucleotide acid having at least 70% sequence identity with the sequence SEQ ID NO: 5, and (iv) ubiquitin gene intron having the nucleotide sequence SEQ ID NO: 53, or a nucleotide acid having at least 70% sequence identity with the sequence SEQ ID NO: 53.

In a more particular embodiment of the invention, a transcription unit according to the invention is constituted by a polynucleotide comprising a nucleotide acid represented by the sequence SEQ ID NO: 59 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region of the eukaryotic Initiation Factor 4GI (eIF4GI) gene having the nucleotide sequence SEQ ID NO: 5, and (iv) ubiquitin gene intron having the nucleotide sequence SEQ ID NO: 53, or by a nucleotide acid having at least 70% sequence identity with the sequence SEQ ID NO: 59.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, and (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region of the eukaryotic Initiation Factor 4GI (eIF4GI) gene having the nucleotide sequence SEQ ID NO: 5, or a nucleotide acid having at least 70% sequence identity with the sequence SEQ ID NO: 5, and (iv) human ROSA gene intron represented by the nucleotide sequence SEQ ID NO: 54, or a nucleotide acid having at least 70% sequence identity with the sequence SEQ ID NO: 54.

In a more particular embodiment of the invention, a transcription unit according to the invention is constituted by a polynucleotide comprising a nucleotide acid represented by the sequence SEQ ID NO: 66 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region of the eukaryotic Initiation Factor 4GI (eIF4GI) gene having the nucleotide sequence SEQ ID NO: 5, and (iv) human ROSA gene intron represented by the nucleotide sequence SEQ ID NO: 54, or by a nucleotide acid having at least 70% sequence identity with the sequence SEQ ID NO: 66.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region represented by the sequence SEQ ID NO: 6, or a nucleotide acid having at least 70% sequence identity with the sequence SEQ ID NO: 6, (iv) the intron of the Elongation Factor 1α (EF1α) gene having the nucleotide sequence SEQ ID NO: 10, or a nucleotide acid having at least 70% sequence identity with the sequence SEQ ID NO: 10.

In a more particular embodiment of the invention, a transcription unit according to the invention is constituted by a polynucleotide comprising a nucleotide acid represented by the sequence SEQ ID NO: 37 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region represented by the nucleotide sequence SEQ ID NO: 6, and (iv) the intron of the Elongation Factor 1α (EF1α) gene having the nucleotide sequence SEQ ID NO: 11, or by a nucleotide acid having at least 70% sequence identity with the sequence SEQ ID NO: 37.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region represented by the sequence SEQ ID NO: 6, or a nucleotide acid having at least 70% sequence identity with the sequence SEQ ID NO: 6, and (iv) the murine ROSA intron having the nucleotide sequence SEQ ID NO: 11, or a nucleotide acid having at least 70% sequence identity with the sequence SEQ ID NO: 11.

In a more particular embodiment of the invention, a transcription unit according to the invention is constituted by a polynucleotide comprising a nucleotide acid represented by the sequence SEQ ID NO: 38 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region represented by the nucleotide sequence SEQ ID NO: 6, and (iv) the murine ROSA intron having the nucleotide sequence SEQ ID NO: 11, or by a nucleotide acid having at least 70% sequence identity with the sequence SEQ ID NO: 38.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region represented by the sequence SEQ ID NO: 6, or a nucleotide acid having at least 70% sequence identity with the sequence SEQ ID NO: 6, and (iv) the 5'LTR intron of the HTLV-1 virus having the nucleotide sequence SEQ ID NO: 12, or a nucleotide acid having at least 70% sequence identity with the sequence SEQ ID NO: 12.

In a more particular embodiment of the invention, a transcription unit according to the invention is constituted by a polynucleotide comprising a nucleotide acid represented by the sequence SEQ ID NO: 39 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region represented by the nucleotide sequence SEQ ID NO: 6, and (iv) the 5'LTR intron of the HTLV-1 virus having the nucleotide sequence SEQ ID NO: 12, or by a nucleotide acid having at least 70% sequence identity with the sequence SEQ ID NO: 39.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region represented by the sequence SEQ ID NO: 6, or a nucleotide acid having at least 70% sequence identity with the sequence SEQ ID NO: 6, and (iv) the pCI-neo chimeric intron having the nucleotide sequence SEQ ID NO: 13, or a nucleotide acid having at least 70% sequence identity with the sequence SEQ ID NO: 13.

In a more particular embodiment of the invention, a transcription unit according to the invention is constituted by a polynucleotide comprising a nucleotide acid represented by the sequence SEQ ID NO: 40 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region represented by the nucleotide sequence SEQ ID NO: 6, and (iv) the pCI-neo chimeric intron having the nucleotide sequence SEQ ID NO: 13, or by a nucleotide acid having at least 70% sequence identity with the sequence SEQ ID NO: 40.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region represented by the sequence SEQ ID NO: 6, or a nucleotide acid having at least 70% sequence identity with the sequence SEQ ID NO: 6, and (iv) ubiquitin gene intron having the nucleotide sequence SEQ ID NO: 53, or a nucleotide acid having at least 70% sequence identity with the sequence SEQ ID NO: 53.

In a more particular embodiment of the invention, a transcription unit according to the invention is constituted by a polynucleotide comprising a nucleotide acid represented by the sequence SEQ ID NO: 60 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region represented by the nucleotide sequence SEQ ID NO: 6, and (iv) ubiquitin gene intron having the nucleotide sequence SEQ ID NO: 53, or by a nucleotide acid having at least 70% sequence identity with the sequence SEQ ID NO: 60.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region represented by the sequence SEQ ID NO: 6, or a nucleotide acid having at least 70% sequence identity with the sequence SEQ ID NO: 6, and (iv) human ROSA gene intron having the nucleotide sequence SEQ ID NO: 54, or a nucleotide acid having at least 70% sequence identity with the sequence SEQ ID NO: 54.

In a more particular embodiment of the invention, a transcription unit according to the invention is constituted by a polynucleotide comprising a nucleotide acid represented by the sequence SEQ ID NO: 67 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region represented by the nucleotide sequence SEQ ID NO: 6, and (iv) human ROSA gene intron having the nucleotide sequence SEQ ID NO: 54, or by a nucleotide acid having at least 70% sequence identity with the sequence SEQ ID NO: 67.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region represented by the sequence SEQ ID NO: 7, or a nucleotide acid having at least 70% sequence identity with the sequence SEQ ID NO: 7, and (iv) the intron of the Elongation Factor 1α (EF1α) gene having the nucleotide sequence SEQ ID NO: 10, or a nucleotide acid having at least 70% sequence identity with the sequence SEQ ID NO: 10.

In a more particular embodiment of the invention, a transcription unit according to the invention is constituted by a polynucleotide comprising a nucleotide acid represented by the sequence SEQ ID NO: 41 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region represented by the nucleotide sequence SEQ ID NO: 7, and (iv) the intron of the Elongation Factor 1α (EF1α) gene having the nucleotide sequence SEQ ID NO: 10, or by a nucleotide acid having at least 70% sequence identity with the sequence SEQ ID NO: 41.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region represented by the sequence SEQ ID NO: 7, or a nucleotide acid having at least 70% sequence identity with the sequence SEQ ID NO: 7, and (iv) the murine ROSA intron having the nucleotide sequence SEQ ID NO: 11, or a nucleotide acid having at least 70% sequence identity with the sequence SEQ ID NO: 11.

In a more particular embodiment of the invention, a transcription unit according to the invention is constituted by a polynucleotide comprising a nucleotide acid represented by the sequence SEQ ID NO: 42 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region represented by the nucleotide sequence SEQ ID NO: 7, and (iv) the murine ROSA intron having the nucleotide sequence SEQ ID NO: 11, or by a nucleotide acid having at least 70% sequence identity with the sequence SEQ ID NO: 42.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region represented by the sequence SEQ ID NO: 7, or a nucleotide acid having at least 70% sequence identity with the sequence SEQ ID NO: 7, and (iv) the 5'LTR intron of the HTLV-1 virus having the nucleotide sequence SEQ ID NO: 12, or a nucleotide acid having at least 70% sequence identity with the sequence SEQ ID NO: 12.

In a more particular embodiment of the invention, a transcription unit according to the invention is constituted by a polynucleotide comprising a nucleotide acid represented by the sequence SEQ ID NO: 43 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region represented by the nucleotide sequence SEQ ID NO: 7, and (iv) the 5'LTR intron of the HTLV-1 virus having the nucleotide sequence SEQ ID NO: 12, or by a nucleotide acid having at least 70% sequence identity with the sequence SEQ ID NO: 43.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region represented by the sequence SEQ ID NO: 7, or a nucleotide acid having at least 70% sequence identity with the sequence SEQ ID NO: 7, and (iv) the pCI-neo chimeric intron having the nucleotide sequence SEQ ID NO: 13, or a nucleotide acid having at least 70% sequence identity with the sequence SEQ ID NO: 13.

In a more particular embodiment of the invention, a transcription unit according to the invention is constituted by a polynucleotide comprising a nucleotide acid represented by the sequence SEQ ID NO: 44 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region represented by the nucleotide sequence SEQ ID NO: 7, and (iv) the pCI-neo chimeric intron having the nucleotide sequence SEQ ID NO: 13, or by a nucleotide acid having at least 70% sequence identity with the sequence SEQ ID NO: 44.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region represented by the sequence SEQ ID NO: 7, or a nucleotide acid having at least 70% sequence identity with the sequence SEQ ID NO: 7, and (iv) the ubiquitin gene intron having the nucleotide sequence SEQ ID NO: 53, or a nucleotide acid having at least 70% sequence identity with the sequence SEQ ID NO: 53.

In a more particular embodiment of the invention, a transcription unit according to the invention is constituted by a polynucleotide comprising a nucleotide acid represented by the sequence SEQ ID NO: 61 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region represented by the nucleotide sequence SEQ ID NO: 7, and (iv) the ubiquitin gene intron having the nucleotide sequence SEQ ID NO: 53, or by a nucleotide acid having at least 70% sequence identity with the sequence SEQ ID NO: 61.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region represented by the sequence SEQ ID NO: 7, or a nucleotide acid having at least 70% sequence identity with the sequence SEQ ID NO: 7, and (iv) human ROSA gene intron having the nucleotide sequence SEQ ID NO: 54, or a nucleotide acid having at least 70% sequence identity with the sequence SEQ ID NO: 54.

In a more particular embodiment of the invention, a transcription unit according to the invention is constituted by a polynucleotide comprising a nucleotide acid represented by the sequence SEQ ID NO: 68 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region represented by the nucleotide sequence SEQ ID NO: 7, and (iv) human ROSA gene intron having the nucleotide sequence SEQ ID NO: 54, or by a nucleotide acid having at least 70% sequence identity with the sequence SEQ ID NO: 68.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, and (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region represented by the sequence SEQ ID NO: 8, or a nucleotide acid having at least 70% sequence identity with the sequence SEQ ID NO: 8, and (iv) the intron of the Elongation Factor 1α (EF1α) gene having the nucleotide sequence SEQ ID NO: 10, or a nucleotide acid having at least 70% sequence identity with the sequence SEQ ID NO: 10.

In a more particular embodiment of the invention, a transcription unit according to the invention is constituted by a polynucleotide comprising a nucleotide acid represented by the sequence SEQ ID NO: 45 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region represented by the nucleotide sequence SEQ ID NO: 8, and (iv) the intron of the Elongation Factor 1α (EF1α) gene having the nucleotide sequence SEQ ID NO: 10, or by a nucleotide acid having at least 70% sequence identity with the sequence SEQ ID NO: 45.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region represented by the sequence SEQ ID NO: 8, or a nucleotide acid having at least 70% sequence identity with the sequence SEQ ID NO: 8, (iv) the murine ROSA intron having the nucleotide sequence SEQ ID NO: 11, or a nucleotide acid having at least 70% sequence identity with the sequence SEQ ID NO: 11.

In a more particular embodiment of the invention, a transcription unit according to the invention is constituted by a polynucleotide comprising a nucleotide acid represented by the sequence SEQ ID NO: 46 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region represented by the nucleotide sequence SEQ ID NO: 8, and (iv) the murine ROSA intron having the nucleotide sequence SEQ ID NO: 11, or by a nucleotide acid having at least 70% sequence identity with the sequence SEQ ID NO: 46.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region represented by the sequence SEQ ID NO: 8, or a nucleotide acid having at least 70% sequence identity with the sequence SEQ ID NO: 8, and (iv) the 5'LTR intron of the HTLV-1 virus having the nucleotide sequence SEQ ID NO: 12, or a nucleotide acid having at least 70% sequence identity with the sequence SEQ ID NO: 12.

In a more particular embodiment of the invention, a transcription unit according to the invention is constituted by a polynucleotide comprising a nucleotide acid represented by the sequence SEQ ID NO: 47 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region represented by the nucleotide sequence SEQ ID NO: 8, and (iv) the 5'LTR intron of the HTLV-1 virus having the nucleotide sequence SEQ ID NO: 12, or by a nucleotide acid having at least 70% sequence identity with the sequence SEQ ID NO: 47.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region represented by the sequence SEQ ID NO: 8, or a nucleotide acid having at least 70% sequence identity with the sequence SEQ ID NO: 8, and (iv) the pCI-neo chimeric intron having the nucleotide sequence SEQ ID NO: 13, or a nucleotide acid having at least 70% sequence identity with the sequence SEQ ID NO: 13.

In a more particular embodiment of the invention, a transcription unit according to the invention is constituted by a polynucleotide comprising a nucleotide acid represented by the sequence SEQ ID NO: 48 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region represented by the nucleotide sequence SEQ ID NO: 8, and (iv) the pCI-neo chimeric intron having the nucleotide sequence SEQ ID NO: 13, or by a nucleotide acid having at least 70% sequence identity with the sequence SEQ ID NO: 48.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region represented by the sequence SEQ ID NO: 8, or a nucleotide acid having at least 70% sequence identity with the sequence SEQ ID NO: 8, and (iv) ubiquitin gene intron having the nucleotide sequence SEQ ID NO: 53, or a nucleotide acid having at least 70% sequence identity with the sequence SEQ ID NO: 53.

In a more particular embodiment of the invention, a transcription unit according to the invention is constituted by a polynucleotide comprising a nucleotide acid represented by the sequence SEQ ID NO: 62 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region represented by the nucleotide sequence SEQ ID NO: 8, and (iv) ubiquitin gene intron having the nucleotide sequence SEQ ID NO: 53, or by a nucleotide acid having at least 70% sequence identity with the sequence SEQ ID NO: 62.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region represented by the sequence SEQ ID NO: 8, or a nucleotide acid having at least 70% sequence identity with the sequence SEQ ID NO: 8, and (iv) human ROSA gene intron having the nucleotide sequence SEQ ID NO: 54, or a nucleotide acid having at least 70% sequence identity with the sequence SEQ ID NO: 54.

In a more particular embodiment of the invention, a transcription unit according to the invention is constituted by a polynucleotide comprising a nucleotide acid represented by the sequence SEQ ID NO: 69 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region represented by the nucleotide sequence SEQ ID NO: 8, and (iv) human ROSA gene intron having the nucleotide sequence SEQ ID NO: 54, or by a nucleotide acid having at least 70% sequence identity with the sequence SEQ ID NO: 69.

A particular embodiment of the invention relates to a transcription unit constituted by a polynucleotide comprising the following regulatory elements:
(i) the hCMVie virus enhancer represented by the nucleotide sequence SEQ ID NO: 1, or a nucleotide acid having at least 70% sequence identity with the sequence SEQ ID NO: 1 and essentially having transcription activation properties,
(ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity,
(iii) the 5' UTR region represented by the sequence SEQ ID NO: 9, or a nucleotide acid having at least 70% sequence identity with the sequence SEQ ID NO: 9, and
(iv) the intron of the Elongation Factor 1α (EF1α) gene having the nucleotide sequence SEQ ID NO: 10, or a nucleotide acid having at least 70% sequence identity with the sequence SEQ ID NO: 10.

In a more particular embodiment of the invention, a transcription unit according to the invention is constituted by a polynucleotide comprising a nucleotide acid represented by the sequence SEQ ID NO: 49 and constituted by:
(i) the hCMVie virus enhancer represented by the nucleotide sequence SEQ ID NO: 1,
(ii) the promoter region of Cyclin-Dependent Kinase 9 (CDK9) represented by the nucleotide sequence SEQ ID NO: 2,
(iii) the 5' UTR region represented by the nucleotide sequence SEQ ID NO: 9, and
(iv) the intron of the Elongation Factor 1α (EF1α) gene having the nucleotide sequence SEQ ID NO: 10,
or by a nucleotide acid having at least 70% sequence identity with the sequence SEQ ID NO: 49.

A particular embodiment of the invention relates to a transcription unit constituted by a polynucleotide comprising the following regulatory elements:
(i) the hCMVie virus enhancer represented by the nucleotide sequence SEQ ID NO: 1, or a nucleotide acid having at least 70% sequence identity with the sequence SEQ ID NO: 1 and essentially having transcription activation properties,
(ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity,
(iii) the 5' UTR region represented by the sequence SEQ ID NO: 9, or a nucleotide acid having at least 70% sequence identity with the sequence SEQ ID NO: 9, and
(iv) the murine ROSA intron having the nucleotide sequence SEQ ID NO: 11, or a nucleotide acid having at least 70% sequence identity with the sequence SEQ ID NO: 11.

In a more particular embodiment of the invention, a transcription unit according to the invention is constituted by a polynucleotide comprising a nucleotide acid represented by the sequence SEQ ID NO: 50 and constituted by:
(i) the hCMVie virus enhancer represented by the nucleotide sequence SEQ ID NO: 1,
(ii) the promoter region of Cyclin-Dependent Kinase 9 (CDK9) represented by the nucleotide sequence SEQ ID NO: 2,
(iii) the 5' UTR region represented by the nucleotide sequence SEQ ID NO: 9, and
(iv) the murine ROSA intron having the nucleotide sequence SEQ ID NO: 11,
or by a nucleotide acid having at least 70% sequence identity with the sequence SEQ ID NO: 50.

A particular embodiment of the invention relates to a transcription unit constituted by a polynucleotide comprising the following regulatory elements:
(i) the hCMVie virus enhancer represented by the nucleotide sequence SEQ ID NO: 1, or a nucleotide acid having at least 70% sequence identity with the sequence SEQ ID NO: 1 and essentially having transcription activation properties,
(ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity,
(iii) the 5' UTR region represented by the sequence SEQ ID NO: 9, or a nucleotide acid having at least 70% sequence identity with the sequence SEQ ID NO: 9, and
(iv) the 5'LTR intron of the HTLV-1 virus having the nucleotide sequence SEQ ID NO: 12, or a nucleotide acid having at least 70% sequence identity with the sequence SEQ ID NO: 12.

In a more particular embodiment of the invention, a transcription unit according to the invention is constituted by a polynucleotide comprising a nucleotide acid represented by the sequence SEQ ID NO: 51 and constituted by:
(i) the hCMVie virus enhancer represented by the nucleotide sequence SEQ ID NO: 1,
(ii) the promoter region of Cyclin-Dependent Kinase 9 (CDK9) represented by the nucleotide sequence SEQ ID NO: 2,
(iii) the 5' UTR region represented by the nucleotide sequence SEQ ID NO: 9, and
(iv) the 5'LTR intron of the HTLV-1 virus having the nucleotide sequence SEQ ID NO: 12,
or by a nucleotide acid having at least 70% sequence identity with the sequence SEQ ID NO: 51.

A particular embodiment of the invention relates to a transcription unit constituted by a polynucleotide comprising the following regulatory elements:
(i) the hCMVie virus enhancer represented by the nucleotide sequence SEQ ID NO: 1, or a nucleotide acid having at least 70% sequence identity with the sequence SEQ ID NO: 1 and essentially having transcription activation properties,
(ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity,
(iii) the 5' UTR region represented by the sequence SEQ ID NO: 9, or a nucleotide acid having at least 70% sequence identity with the sequence SEQ ID NO: 9, and
(iv) the pCI-neo chimeric intron having the nucleotide sequence SEQ ID NO: 13, or a nucleotide acid having at least 70% sequence identity with the sequence SEQ ID NO: 13.

In a more particular embodiment of the invention, a transcription unit according to the invention is constituted by a polynucleotide comprising a nucleotide acid represented by the sequence SEQ ID NO: 52 and constituted by:
(i) the hCMVie virus enhancer represented by the nucleotide sequence SEQ ID NO: 1,
(ii) the promoter region of Cyclin-Dependent Kinase 9 (CDK9) represented by the nucleotide sequence SEQ ID NO: 2, (iii) the 5' UTR region represented by the nucleotide sequence SEQ ID NO: 9, and (iv) the pCI-neo chimeric intron having the nucleotide sequence SEQ ID NO: 13, or by a nucleotide acid having at least 70% sequence identity with the sequence SEQ ID NO: 52.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region represented by the sequence SEQ ID NO: 9, or a nucleotide acid having at least 70% sequence identity with the sequence SEQ ID NO: 9, and (iv) ubiquitin gene intron having the nucleotide sequence SEQ ID NO: 53, or a nucleotide acid having at least 70% sequence identity with the sequence SEQ ID NO: 53.

In a more particular embodiment of the invention, a transcription unit according to the invention is constituted by a polynucleotide comprising a nucleotide acid represented by the sequence SEQ ID NO: 63 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region represented by the nucleotide sequence SEQ ID NO: 9, and (iv) ubiquitin gene intron having the nucleotide sequence SEQ ID NO: 53, or by a nucleotide acid having at least 70% sequence identity with the sequence SEQ ID NO: 63.

A particular embodiment of the invention relates to a transcription unit constituted by a polynucleotide comprising the following regulatory elements:

(i) the hCMVie virus enhancer represented by the nucleotide sequence SEQ ID NO: 1, or a nucleotide acid having at least 70% sequence identity with the sequence SEQ ID NO: 1 and essentially having transcription activation properties, (ii) the promoter region of Cyclin-Dependent Kinase 9 (CDK9) represented by the nucleotide sequence SEQ ID NO: 2, or a nucleotide acid having at least 70% sequence identity with the sequence SEQ ID NO: 2 and essentially having a promoter activity, (iii) the 5' UTR region represented by the sequence SEQ ID NO: 9, or a nucleotide acid having at least 70% sequence identity with the sequence SEQ ID NO: 9, and (iv) human ROSA gene intron having the nucleotide sequence SEQ ID NO: 54, or a nucleotide acid having at least 70% sequence identity with the sequence SEQ ID NO: 54.

In a more particular embodiment of the invention, a transcription unit according to the invention is constituted by a polynucleotide comprising a nucleotide acid represented by the sequence SEQ ID NO: 70 and constituted by:

(i) the hCMVie virus enhancer represented by the nucleotide sequence SEQ ID NO: 1, (ii) the promoter region of Cyclin-Dependent Kinase 9 (CDK9) represented by the nucleotide sequence SEQ ID NO: 2, (iii) the 5' UTR region represented by the nucleotide sequence SEQ ID NO: 9, and (iv) human ROSA gene intron having the nucleotide sequence SEQ ID NO: 54, or by a nucleotide acid having at least 70% sequence identity with the sequence SEQ ID NO: 70.

In an advantageous embodiment, the present invention relates to a transcription unit, in which the promoter region is that of CDK9, the 5' UTR region is that of the eIF4GI gene (U3) and the intron is that of the EF1α gene, said transcription unit having the nucleotide sequence SEQ ID NO: 33, or a nucleotide sequence having at least 70% identity with the sequence SEQ ID NO: 33 and allowing a volume production of a protein of interest greater than that obtained with the combination of the CMV enhancer associated with the promoter region of CDK9.

By a "volume production" is meant a quantity of protein expressed in weight per volume unit (g/L) also called protein titre or concentration of the protein of interest.

The present invention also relates to an expression vector comprising at least one transcription unit as defined above and at least one cloning site allowing the integration of a nucleic acid coding for a protein of interest.

Said nucleic acid can be a genomic DNA, a complementary DNA (cDNA), a synthetic nucleic acid or a chimeric nucleic acid.

By "cloning site", is meant a short segment of DNA which comprises one or more restriction sites, recognized respectively by one or more restriction enzymes and allowing the insertion of a nucleotide sequence of interest.

The present invention also relates to an expression vector comprising at least one transcription unit as defined above and at least one site for the site-specific recombination allowing the integration of a nucleotide acid coding for a protein of interest.

Said nucleotide acid can be a genomic DNA or a complementary DNA (cDNA).

By "site for the site-specific recombination", is meant a short segment of DNA which is recognized by a recombinase, such as the loxP site which is recognized by Cre recombinase, the xis site which is recognized by the integrase Int, the FRT site which is recognized by the FLP recombinase.

An expression vector according to the present invention can moreover comprise a eukaryotic resistance gene, a bacterial resistance gene, a bacterial origin of replication and a dedicated gene amplification unit.

A eukaryotic resistance gene can be a gene resistant to Geneticin (G418), Blasticidin, zeocin, A bacterial resistance gene can be a gene resistant to ampicillin, Kanamycin, Puromycin, Blasticidin, Zeocin.

A bacterial origin of replication (Ori) is a particular DNA sequence of bacterial origin allowing the initiation of the replication of the genetic material such as an expression vector and making it possible to determine in the bacterium the number of copies of vector per bacterium. Such an origin of replication can be chosen from Ori-P, Ori-C, Ori-fl, ColE1, pSC101 Ori, p15A Ori, pACYC Ori, SV40 Ori, pMB1 Ori, pUC ori.

By "a dedicated gene amplification unit", is meant any unit making it possible to carry out gene amplification and/or significant enrichment with highly productive cells. Most often, this unit allows the expression of a gene resistant to an inhibitor acting in a dose-dependent manner; by increasing the dose of inhibitor, cell variants expressing the resistance gene more strongly, in particular following gene amplification or integration into a strong expression site, are selected. Most often the genes close to this unit are also genetically amplified and/or have an increased expression. Such a unit can be the dhfr (dihydrofolate reductase) gene, the inhibitor of which is methotrexate or the glutamine synthetase gene the inhibitor of which is methionyl sulphoximine, a system of amplification of gene fragments which is based on the selection of transformants resistant to methotrexate (MTX). It requires the prior introduction of a transcription unit comprising the nucleic acid coding for the enzyme DHFR (dihydrofolate reductase) into the expression vector for the production of the recombinant molecule of interest (SHITARI et al., 1994)

A recombinant protein of interest capable of being produced by a vector according to the invention is a protein that is natural or modified in its primary sequence and chosen from the group constituted by the proteins involved in the coagulation cascade or an immunoglobulin, metabolic enzymes, cytokines, chemokines, hormones, growth factors or complement factors and any fusion protein.

An objective of the present invention is to provide host cells comprising an expression vector as described in the present invention.

Said host cells can be a mammalian cell line such as a YB2/0 cell line (N° ATCC: CRL-1662), or a CHO cell line.

The present invention also relates to the use of an expression vector described above for transfecting a host cell.

Another objective of the present invention is to make available an expression system comprising an expression vector according to the present invention and a host cell as described above, allowing the expression of a protein of interest encoded by a nucleotide acid.

The present invention also relates to the use of an expression vector comprising at least one transcription unit according to the present invention in a host cell as described above for producing a protein encoded by a nucleotide acid, said protein being produced with a higher titre than in the reference expression vector comprising at least one RSV promoter, a chimeric intron originating from the pCI-neo vector, a polyadenylation sequence, a eukaryotic resistance gene, a bacterial resistance gene, a bacterial origin of replication and a dedicated gene amplification unit, said reference vector comprising the same nucleotide sequence.

A subject of the present invention is also a method for the in vitro production of a recombinant protein of interest comprising the stages of:
  introduction of the expression vector comprising at least one transcription unit according to the present invention and a nucleotide sequence in genomic form or in the form of cDNA coding for a protein of interest into a host cell,
  selection and identification of the host cells obtained in the previous stage expressing said protein of interest in a stable manner,
  extraction and purification of said protein of interest.

In another particular embodiment, the production method according to the present invention comprises the stages of:
  introduction of the expression vector comprising at least one transcription unit according to the present invention and a nucleotide sequence in genomic form or in the form of cDNA coding for a protein of interest into a host cell by transient transfection,
  extraction and purification of said protein of interest.

Such a recombinant protein can be a protein involved in the coagulation cascade or a immunoglobulin, metabolic enzymes, cytokines, chemokines, hormones, growth factors or complement factors and any fusion protein.

A method according to the present invention can moreover comprise a stage of selection and identification of the host cells obtained expressing said protein of interest in a stable manner.

BRIEF DESCRIPTION OF THE DRAWING FIGURES

The present invention is illustrated by the figures and the examples below. However, the present invention is in no way limited to the figures and examples below.

Figures

Figure 18:
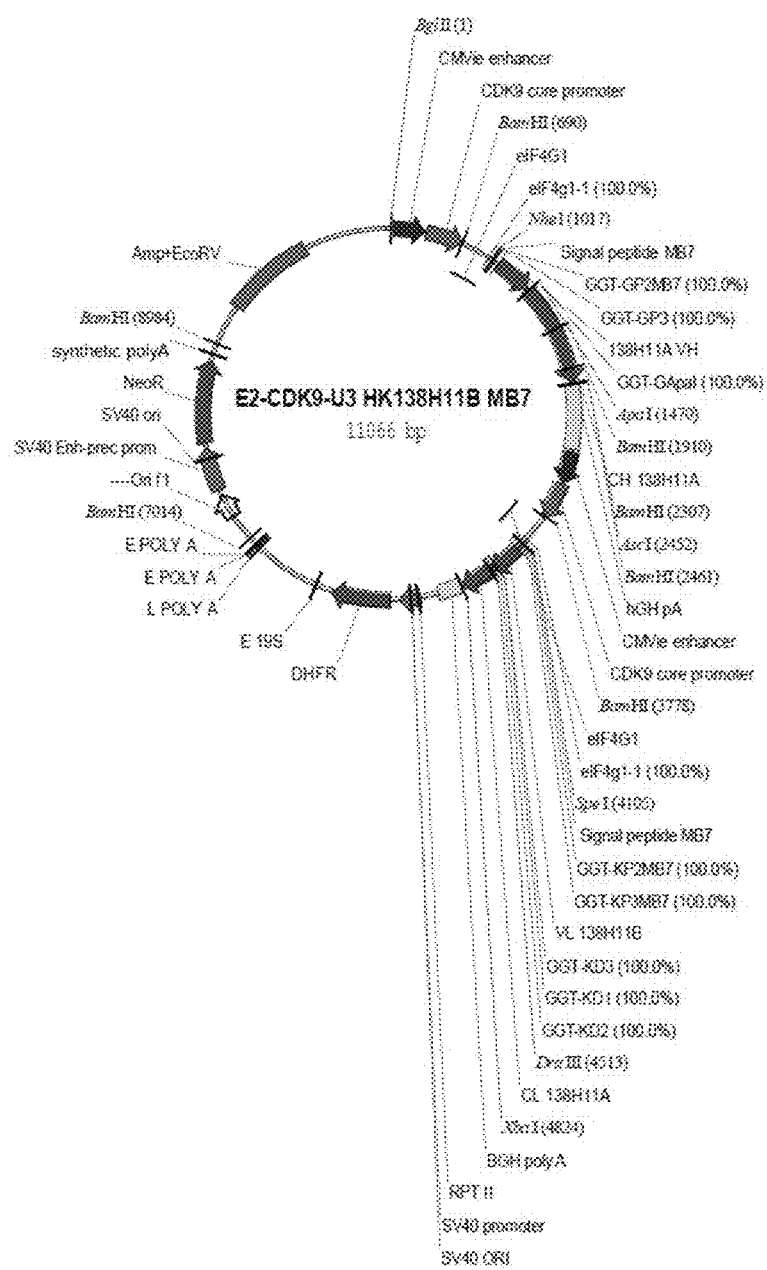

FIG. 18 illustrates the E2-CDK9-U3-HK138H11B_MB7 vector comprising the light chain with the signal peptide MB7 and the heavy chain with the signal peptide MB7 of the anti-GGT antibody 138H11B the light chain with the signal peptide MB7 and the heavy chain with the signal peptide MB7 of the anti-GGT antibody 138H11B. The transcription units of interest are dependent on the (hCMVie) enhancer E2 of the CDK9 promoter and the 5'UTR region of the eIF4G1 gene (U3)

Figure 19:
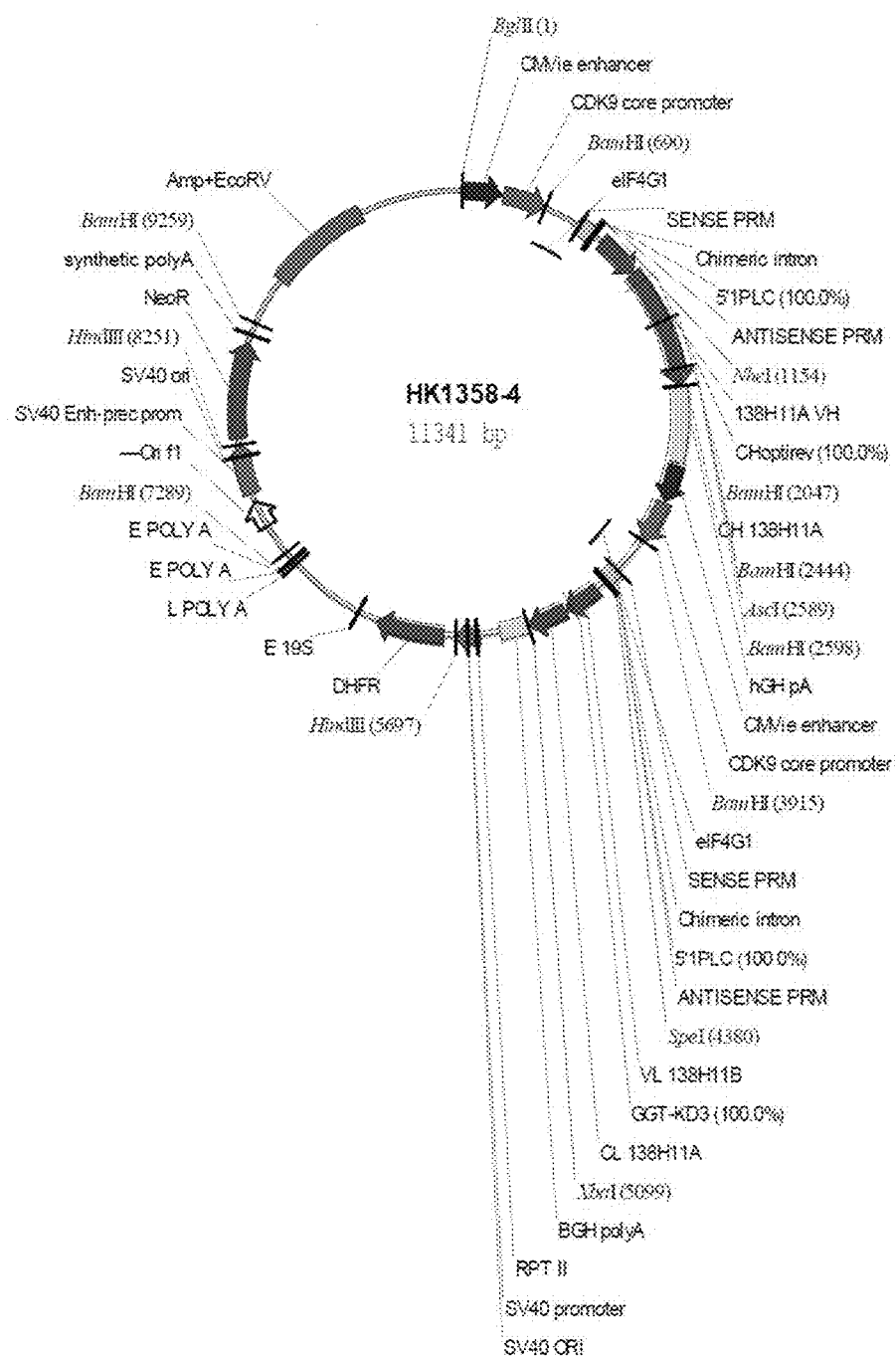

FIG. 19 illustrates the HK1358-4 vector comprising the light chain with the signal peptide MB7 and the heavy chain with the signal peptide MB7 of the anti-GGT antibody 138H11B. The transcription units of interest are dependent on the (hCMVie) enhancer E2 of the CDK9 promoter, the 5'UTR region of the eIF4G1 gene (U3) and the pCI-neo chimeric intron.

Figure 20:
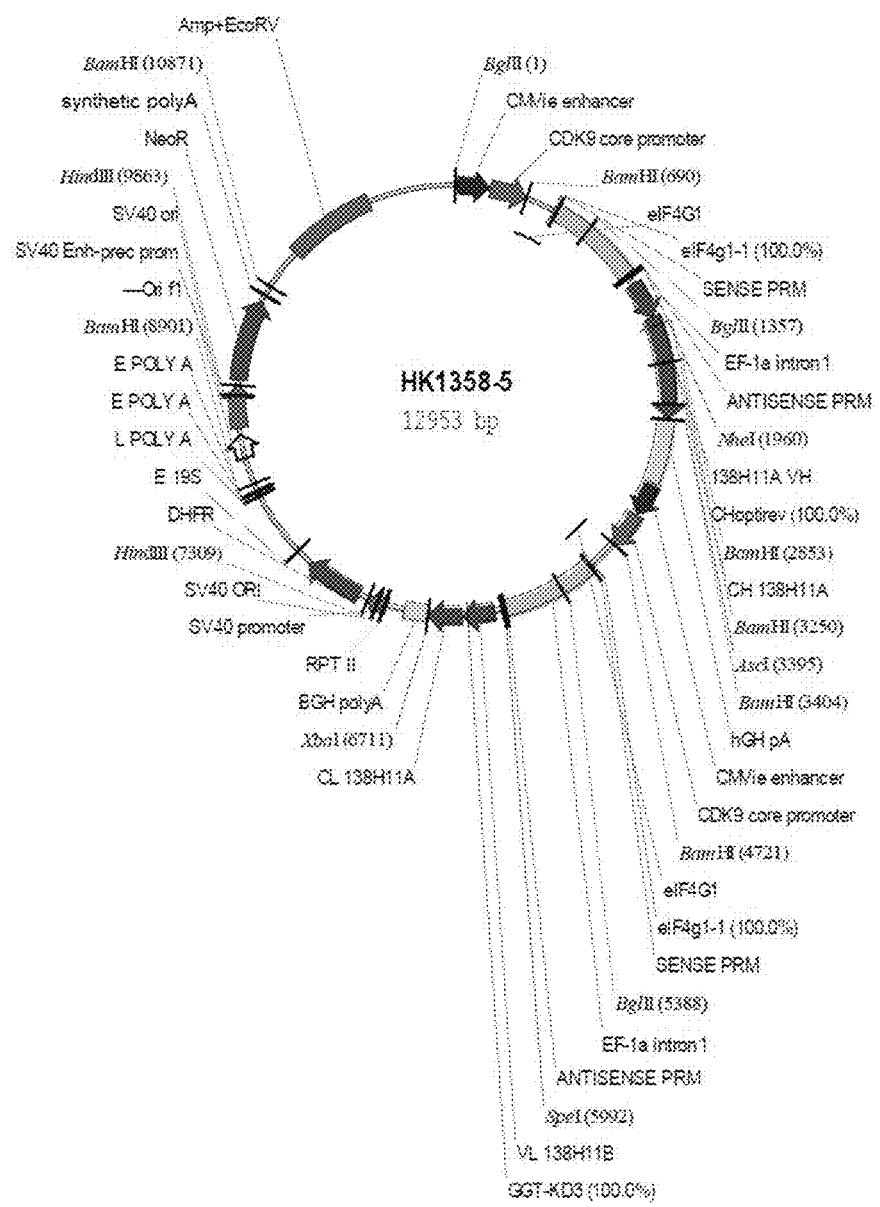

FIG. 20 illustrates the HK1358-5 vector comprising the light chain with the signal peptide MB7 and the heavy chain with the signal peptide MB7 of the anti-GGT antibody 138H11B. The transcription units of interest are dependent on the (hCMVie) enhancer E2 of the CDK9 promoter, the 5'UTR region of the eIF4G1 gene (U3) and the EF1α intron.

Figure 21:
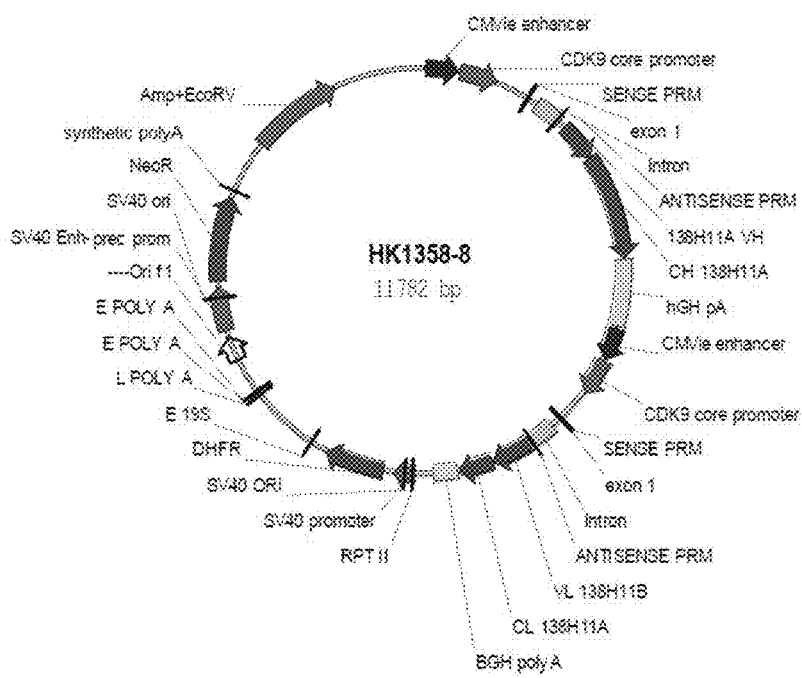

FIG. 21 illustrates the HK1358-8 vector comprising the light chain with the signal peptide MB7 and the heavy chain with the signal peptide MB7 of the anti-GGT antibody 138H11B. The transcription units of interest are dependent on the (hCMVie) enhancer E2 of the CDK9 promoter, the 5'UTR region of the eIF4G1 gene (U3) and the mROSA intron.

Figure 22:
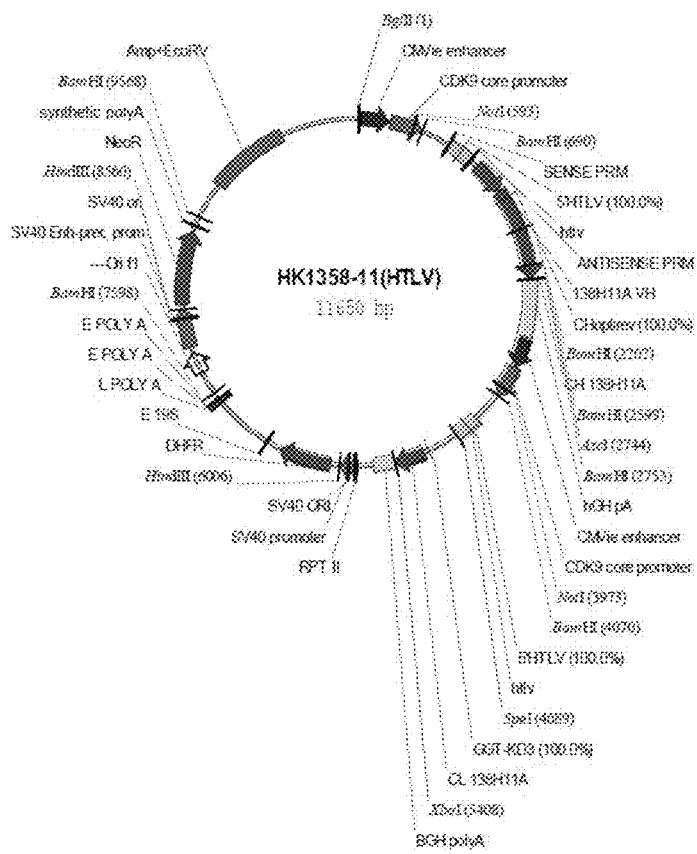

FIG. 22 illustrates the HK1358-11 vector comprising the light chain with the signal peptide MB7 and the heavy chain with the signal peptide MB7 of the anti-GGT antibody 138H11B. The transcription units of interest are dependent on the (hCMVie) enhancer E2 of the CDK9 promoter, the 5'UTR region of the eIF4G1 gene (U3) and the 5'LTR intron HTLV1.

Figure 23:
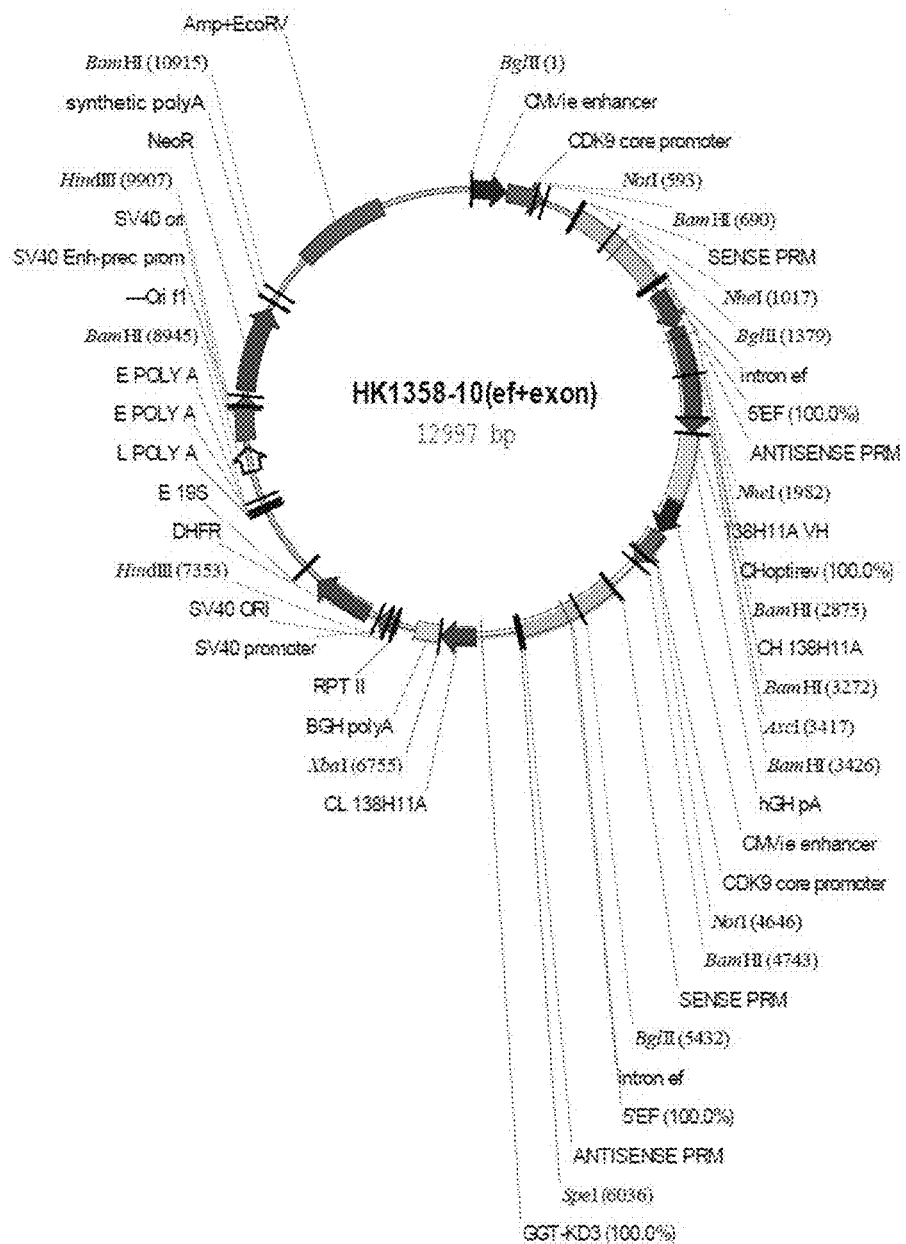

FIG. 23 illustrates the HK1358-10 vector comprising the light chain with the signal peptide MB7 and the heavy chain with the signal peptide MB7 of the anti-GGT antibody 138H11B. The transcription units of interest are dependent on the (hCMVie) enhancer E2 of the CDK9 promoter, the 5'UTR region of the eIF4G1 gene (U3) and the intron pEF with exon.

Figure 24:
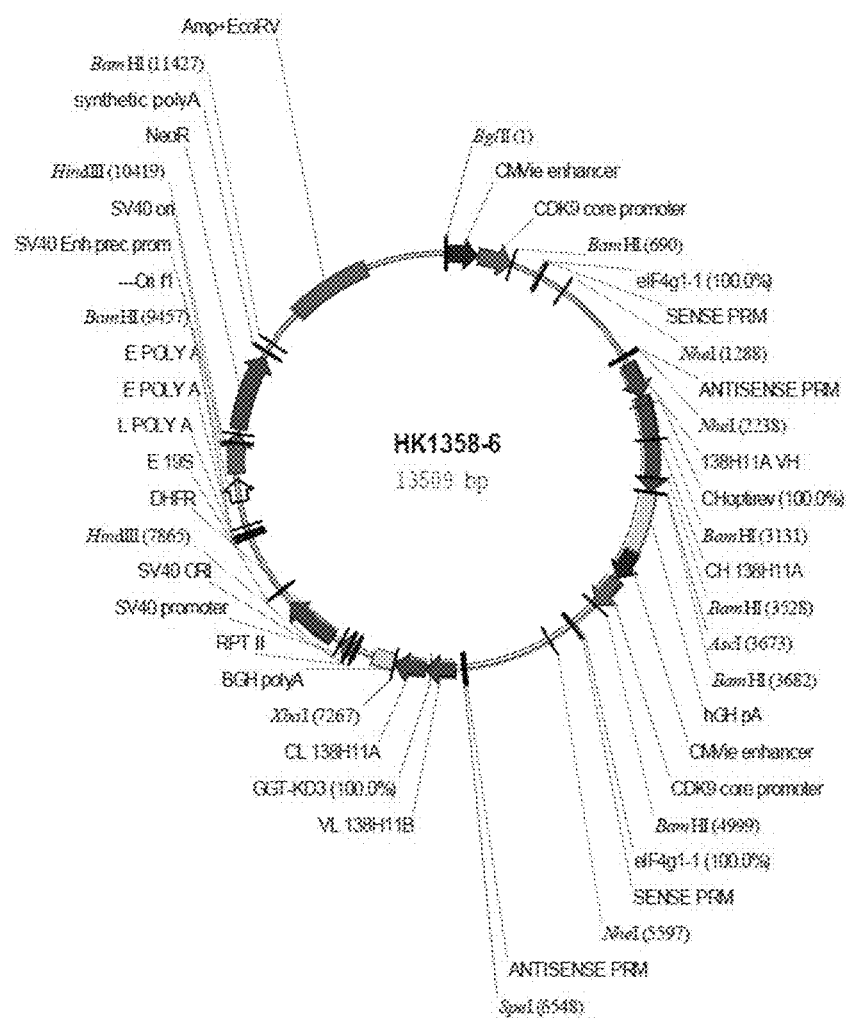

FIG. 24 illustrates the HK1358-6 vector comprising the light chain with the signal peptide MB7 and the heavy chain with the signal peptide MB7 of the anti-GGT antibody 138H11B. The transcription units of interest are dependent on the (hCMVie) enhancer E2 of the CDK9 promoter, the 5'UTR region of the eIF4G1 gene (U3) and the human ROSA intron.

Figure 25:
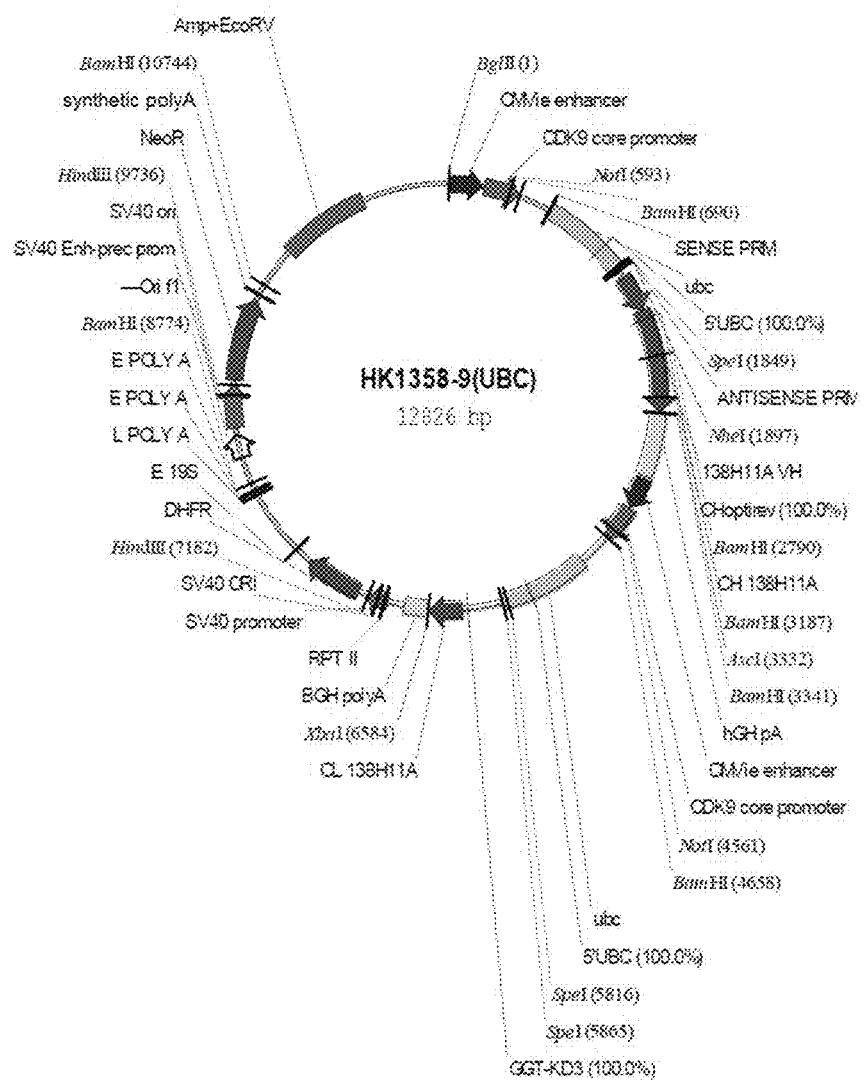
Figure 20:
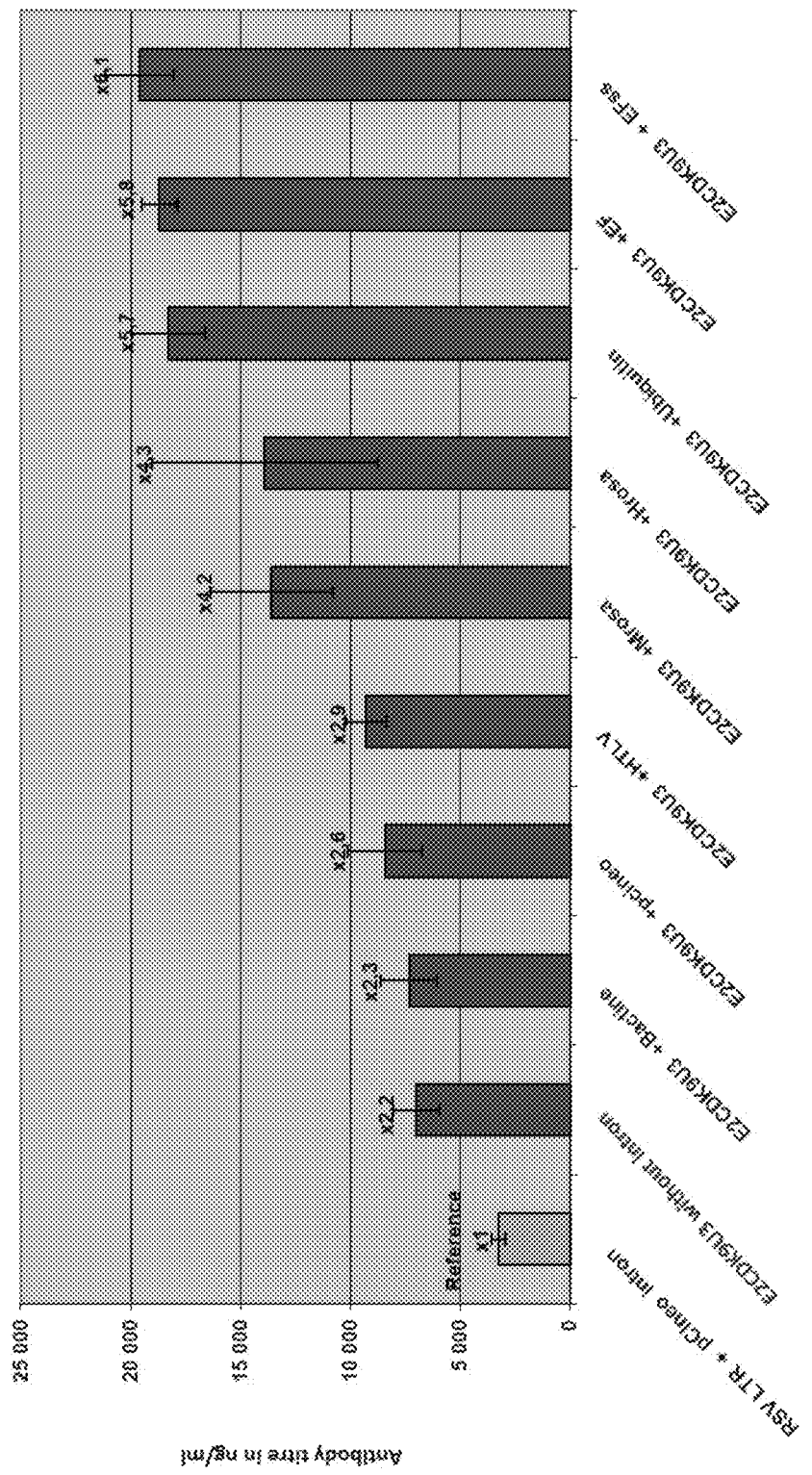

FIG. 25 illustrates the HK1358-9 vector comprising the light chain with the signal peptide MB7 and the heavy chain with the signal peptide MB7 of the anti-GGT antibody 138H11B. The transcription units of interest are dependent on the (hCMVie) enhancer E2 of the CDK9 promoter, the 5'UTR region of the eIF4G1 gene (U3) and the ubiquitin gene intron.

FIG. 26 illustrates the productivity of the anti-GGT antibody (138H11B) in the E2CDK9U3 context with different introns, in stable pools in medium with serum, in comparison with the reference RSV LTR+pCI neo intron. "EF" corresponds to the intron represented by the sequence SEQ ID NO: 71. "EFss" corresponds to the intron represented by the sequence SEQ ID NO: 10.

Figure 27:
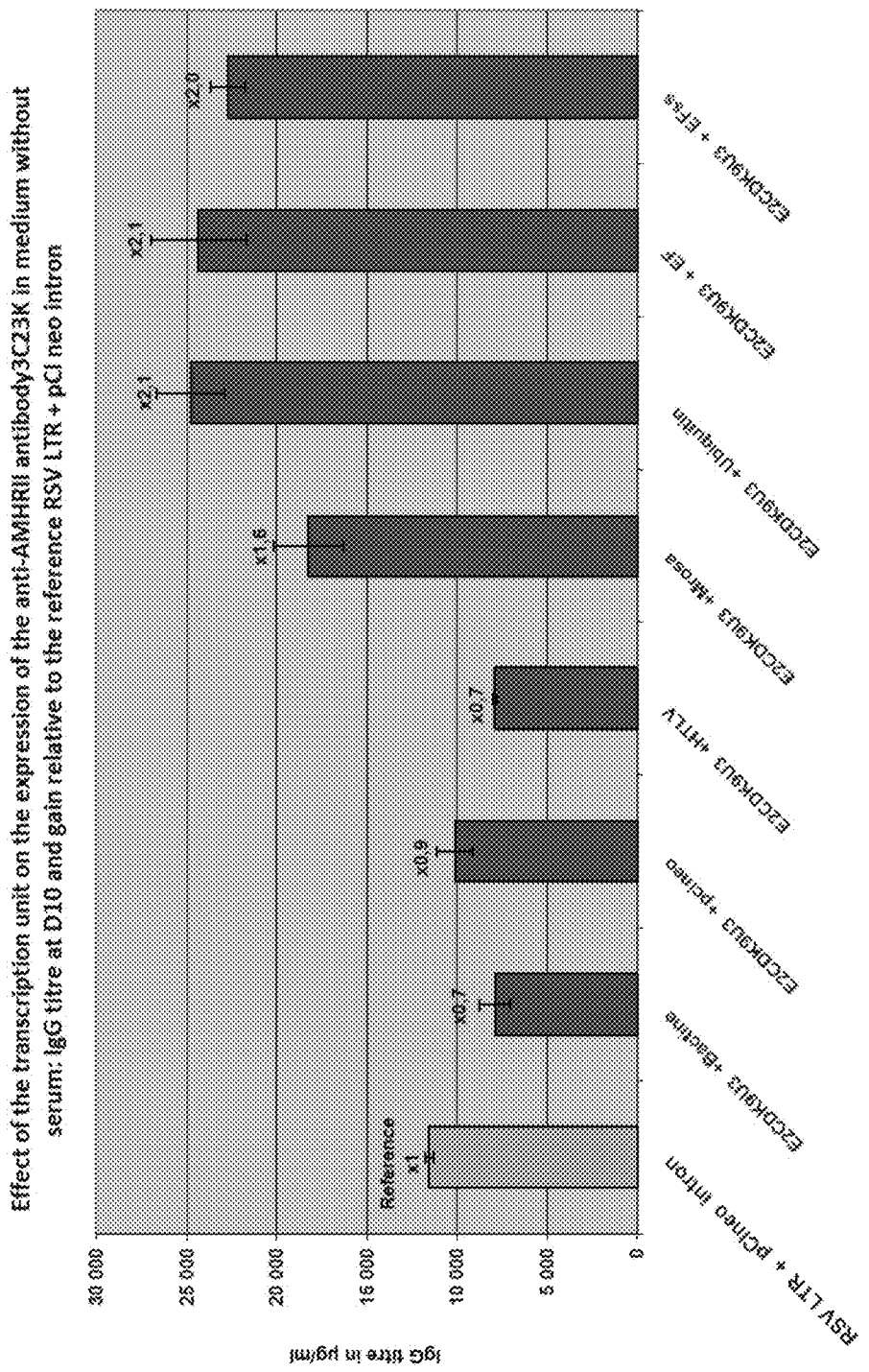

FIG. 27 illustrates the productivity of the anti-AMHRII antibody (3C23K) in the E2CDK9U3 context with different introns, in pools in medium without serum, in comparison with the reference RSV LTR+pCI neo intron. "EF" corresponds to the intron represented by the sequence SEQ ID NO: 71. "EFss" corresponds to the intron represented by the sequence SEQ ID NO: 10.

Figure 28:
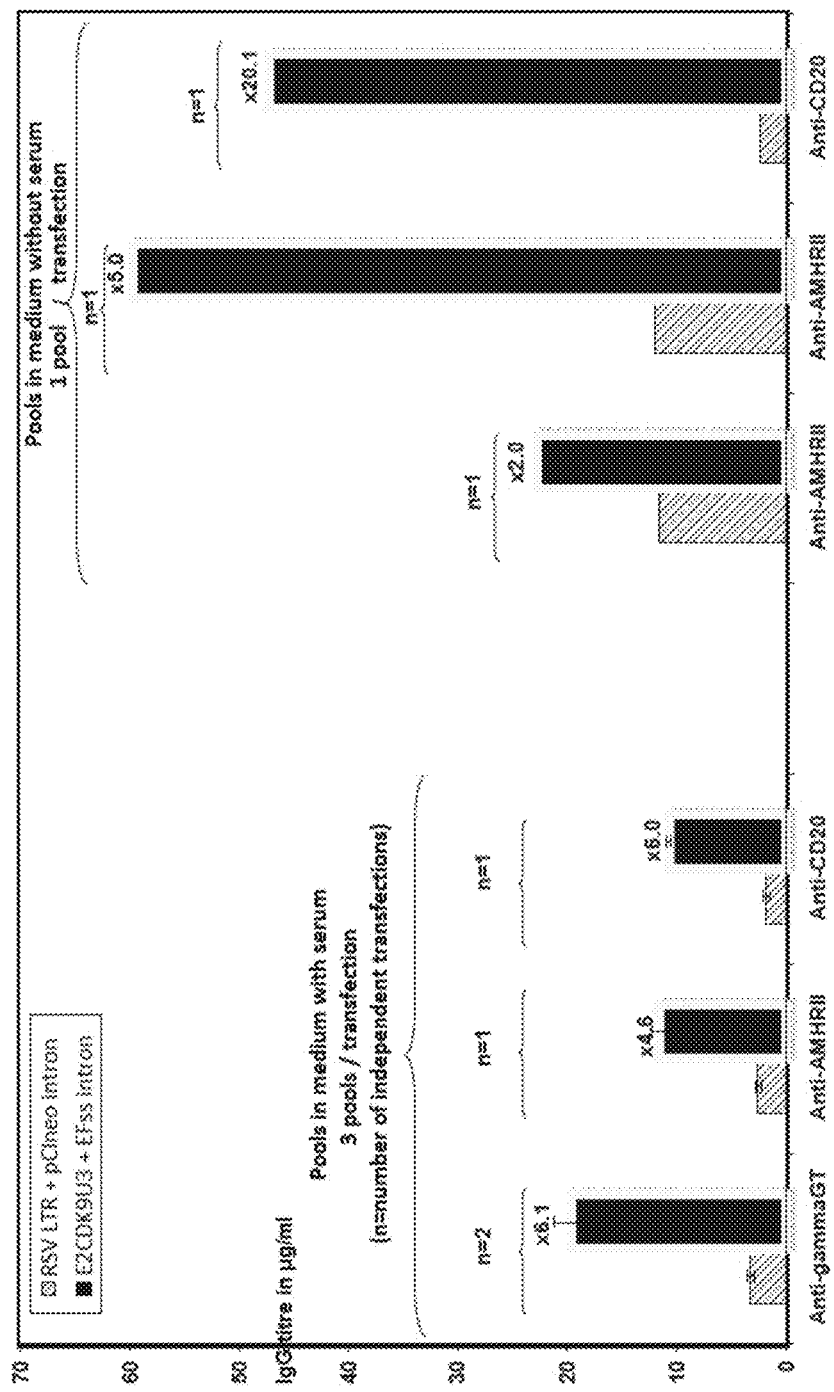

FIG. 28 illustrates the productivity of the 3 antibodies anti-GGT (138H11B), anti-AMHRII (3C23K) and anti-CD20 (R603) in the E2CDK9U3 and EFss intron context, in comparison with the reference RSV LTR+pCI neo intron.

Figure 29:
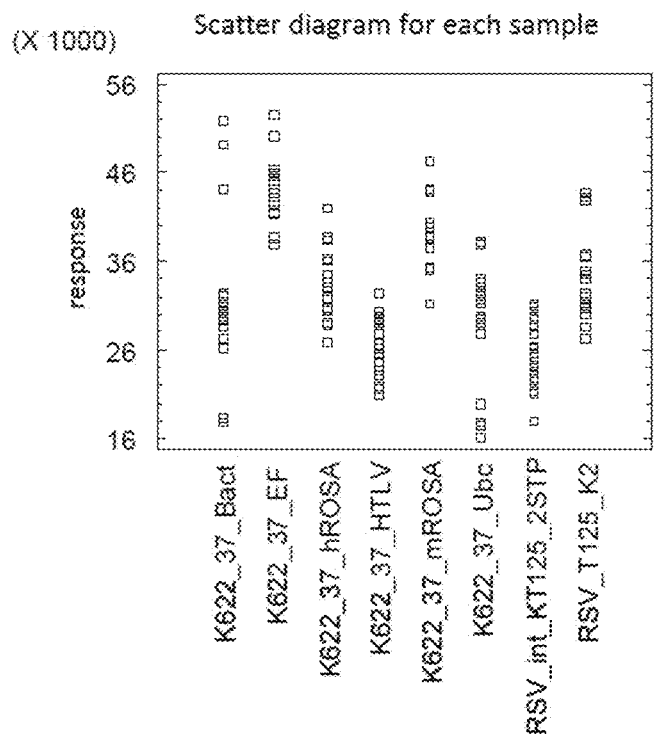

FIG. 29 illustrates the comparison of the effect of different introns in combination with the RSV LTR on the expression in transient transfection of the free kappa chain of the anti-Rh(D) T125 antibody into the CHO—S line evaluated by transient transfection. The columns of dots, from left to right, represent the level of expression of the free kappa chain under the control of the introns: β-actin (Bact), EF1α, mROSA, hROSA, 5'-LTR HTLV1, ubiquitin (ubc), pCI neo respectively. The reference vector is RSV_T125_K2. The y-axis represents the concentration of free kappa chains in the culture medium.

Figure 30:
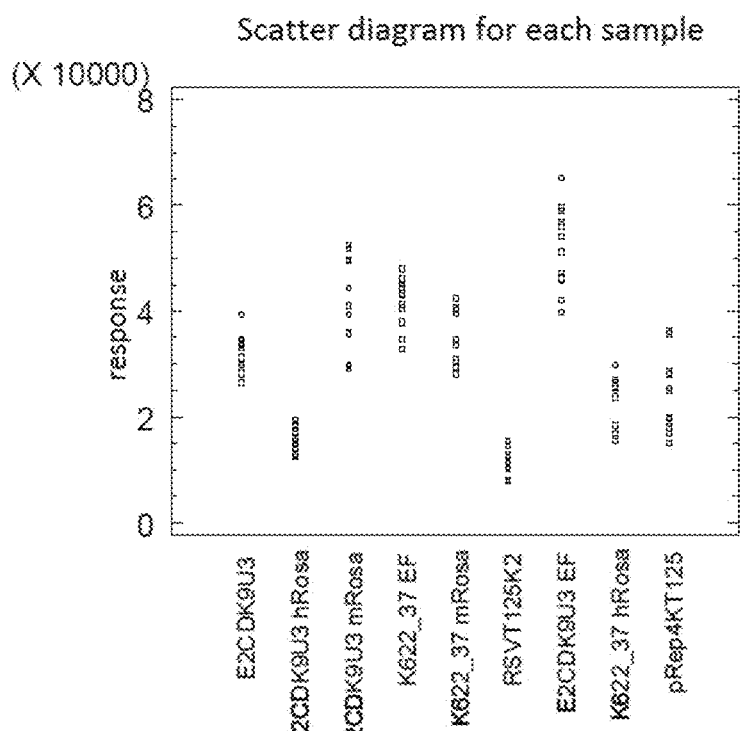

FIG. 30 illustrates the comparison of the effect of different introns in combination with the transcription unit E2-CDK9-U3 or the RSV LTR on the expression of the free kappa chain of the anti-Rh(D) antibody T125 in the CHO—S line evaluated by transient transfection. The columns of dots, from left to right, represent respectively the level of expression of the free kappa chain under the control of the combinations: E2-CDK9-U3 without intron, E2-CDK9-U3 with hROSA intron, E2-CDK9-U3 with mROSA intron, RSV LTR with EF1α intron, RSV LTR with mROSA intron, E2-CDK9-U3 with EF1α intron, RSV LTR with hROSA intron. The reference vectors are RSV_T125_K2 and pRep4KT125. The y-axis represents the concentration of free kappa chains in the culture medium. E2 represents the hCMVie enhancer. U3 corresponds to the 5'UTR region of the eIF4G1 gene.

Figure 31:
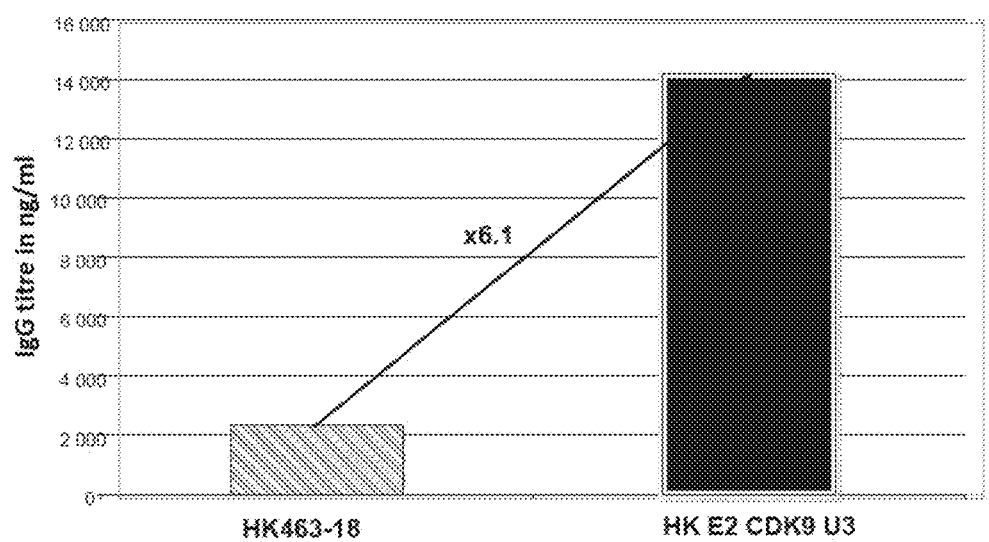

FIG. 31 illustrates the comparison of the expression in stable pools of transfectants expressing the anti-Rh(D) IgG in the CHO—S line as a function of the vector (E2CDK9U3/RSV LTR pCIneo intron) and more precisely the productivity in stable pools of the whole anti-Rh(D) antibody T125 with the vector containing the transcription unit E2-CDK9-U3 (HK E2 CDK9 U3) in comparison with the reference RSV LTR with pCIneo intron (HK463-18). E2 represents the hCMVie enhancer. U3 corresponds to the 5'UTR region of the eIF4G1 gene.

Figure 32:
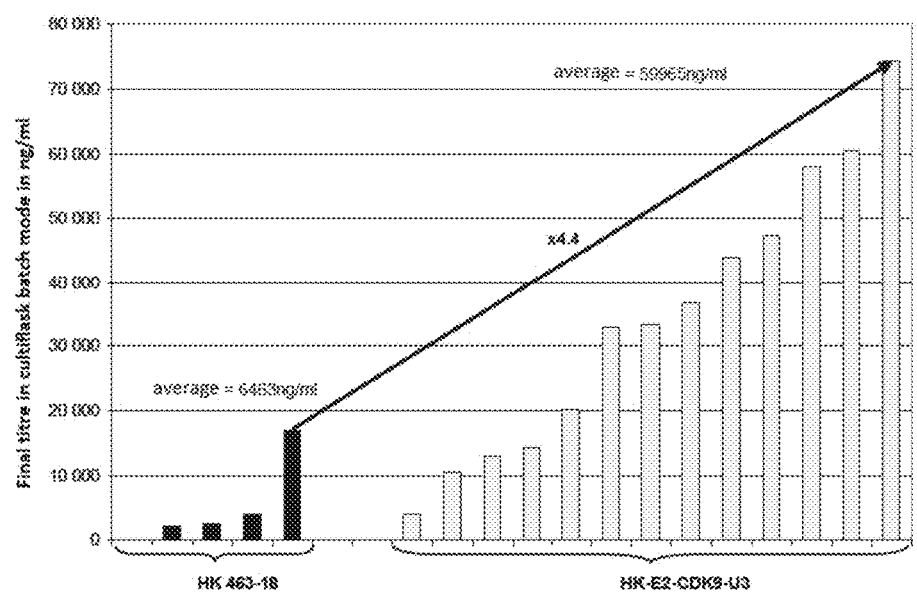

FIG. 32 is a distribution diagram of the transfectants expressing the anti-Rh(D) IgG in the CHO—S line as a function of the vector (E2CDK9U3/RSV LTR pCI neo intron). This diagram illustrates the productivity of clones producing the whole anti-Rh(D) antibody T125 with the vector containing the transcription unit E2-CDK9-U3 (HK E2 CDK9 U3) in comparison with the reference RSV LTR intron with pCI neo (HK463-18).

Figure 33:
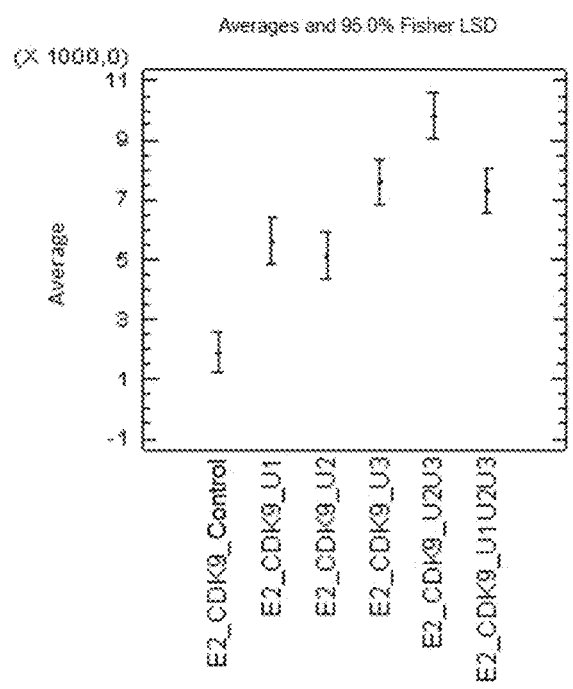

FIG. 33 illustrates the comparison of the average titres of T125 kappa chains obtained in the YB2/0 line from the vectors containing different transcription units according to the invention, namely E2-CDK9-U1, E2-CDK9-U2, E2-CDK9-U3, E2-CDK9-U2U3, E2-CDK9-U1U2U3. The 6 averages obtained are compared in order to determine which are significantly different from each other (multiple-range tests).

Figure 34:
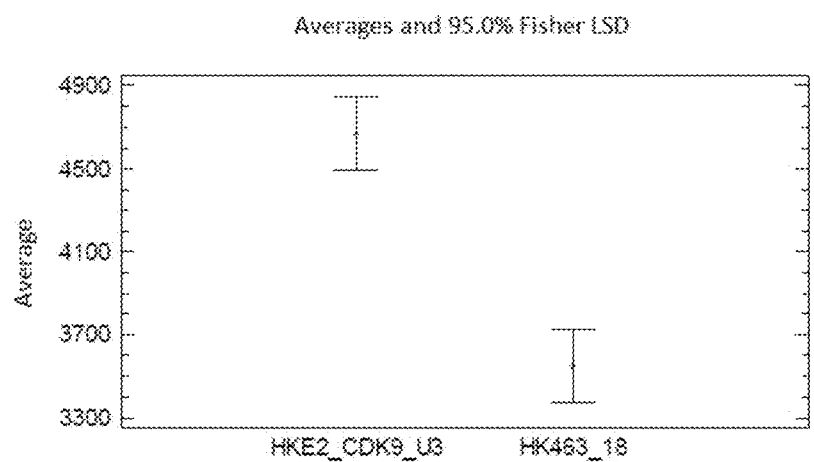

FIG. 34 illustrates the comparison of the average titres of whole anti-Rh(D) immunoglobulin obtained in the YB2/0 line from the E2-CDK9-U3 vector and from the HK463-18 reference vector containing RSV+pCIneo intron. The averages obtained are compared in order to determine if they are significantly different from each other (multiple-range test).

Figure 35:
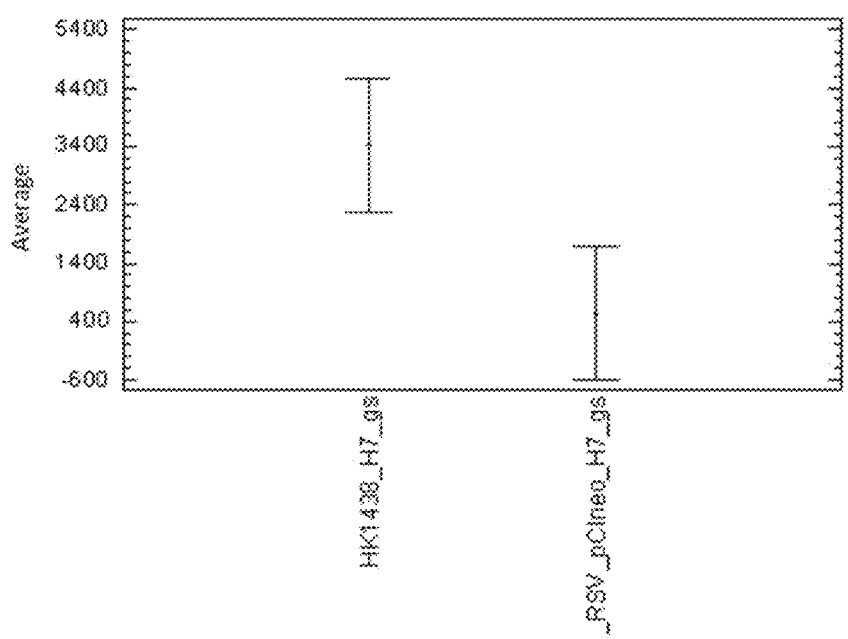

FIG. 35 illustrates the comparison of the average titres of the anti-CD71 immunoglobulin (H7) obtained in the YB2/0 line from the E2-CDK9-U3 vector containing the EF1α intron with that obtained from the RSV_pCLneo reference vector also containing the EF intron. The averages obtained are compared in order to determine which are significantly different from each other (multiple-range tests).

DETAILED DESCRIPTION OF THE INVENTION

EXAMPLES

1. Materials and Methods
1.1. Transient Transfection

In YB2/0, the parental cells are seeded the day before the transfection (D−1) at $2^E5$ cv/ml in EMS (Invitrogen, medium made to order)+5% FCS (Invitrogen) in a flask. On the day of the electroporation (D0), centrifugation of $4^E6$ cells per 4-mm cuvette (Biorad) taken up in 100 μl of buffer V (Cell line nucleofector kitV, Lonza) which are nucleofected by AMAXA with 4 μg of plasmid DNA using the T020 programme of the device. The cells are cultured in P6-well plates at 37° C., 7% of $CO_2$ in 3 ml of EMS medium+5% of FCS. The supernatants are collected for ELISA assay on D+5.

In CHO—S, the sequences to be expressed are evaluated by transient transfection according to the protocol of the FreeStyle kit (Invitrogen). The parental cells are seeded 24 h before the transfection (D−1) in an Erlenmeyer flask (VWR) at $6^E5$ cv/ml in FreeStyle CHO EM (Fisher Bioblock scientific) and incubated under stirring at 120 rpm, 37° C., 8% $CO_2$. On the day of the transfection a FreeStyle MAX Reagent (Fisher Bioblock Scientific)/DNA complex, at a ratio of 1:1, is formed in Opti Pro SFM (Invitrogen). The complex is then deposited on the cells in suspension previously centrifuged and taken up at $1^E6$ cv/ml in FreeStyle CHO EM in a cultiflask (Sartorius) (5 ml) and incubated at 200 rpm at 37° C., 8% $CO_2$. The supernatants are collected on D+5 for evaluation of the level of molecules secreted in the medium.

1.2. Stable Transfection
1.2.1 Stable Transfection of the YB2/0 Line in Medium with Serum The cells must have stabilized growth and be thawed for at least 4 weeks in EMS (LFB) medium+5% FCS in an F150 (80 ml) flasks. The cells are subcultured the previous day at 2E5 cv/ml in EMS medium+5% FCS.

On the day of the electroporation, the cells are electroporated by Gene Pulser Xcell (BioRad) with a voltage of 230 V and capacitance of 960 μF in 4-mm cuvettes (Biorad) with 5E6 cv (qsf 500 μl of electroporation buffer from the electrobuffer kit (Ozyme) containing the linearized plasmid DNA). After electroporation, plating is carried out in 24-well plates (P24) (25,000 cells/well) in EMS medium+5% FCS.

On D+3: Placing in selective medium in order to obtain the following final concentrations: EMS+5% FCS+G418 1 mg/ml+1% phenol red On D+7: Renewal of the plates with the corresponding medium.

On D+10: When the cells are close to confluence, make 3 pools from 8 P24 wells, reculture the cells at 2E5 cv/ml in F25 and carry out maximum production (max prod on D+7), the supernatant being collected and assayed with the Fast ELYSA kit (RD-biotech).

1.2.2 Stable Transfection of the YB2/0 Line in Medium without Serum

The cells must have stabilized growth and be thawed for at least 3 weeks, in EMABPRO1 medium (LFB) in a cultiflask under stirring at 250 rpm. The cells are recultured the previous day at 3E5 cv/ml in EMABPRO1 medium.

On the day of the electroporation, the cells are electroporated by Gene Pulser Xcell (BioRad) with a voltage of 230 V and a capacitance of 950 μF in 4-mm cuvettes (Biorad) with 5E6 cv (qsf 500 μl of electroporation buffer from the electrobuffer kit (Ozyme) containing the linearized plasmid DNA). After electroporation, the cells are taken up at 3E5 cv/ml in EMABPRO1 medium in an F75 culture flask.

On D+3: Placing in selective medium in order to obtain the following final concentrations: EMABPRO1+ LFB additive for low density cell cloning LDCC+G418 1 mg/ml.

On D+10: if the cell density is greater than 6E5 cv/ml, reculture the cells at 3E5 cv/ml EMABPRO1+G418 1 mg/ml in F25, otherwise dilute it by half in EMABPRO1+ LFB for LDCC additive+G418 1 mg/ml.

Starting from D+12 and 3 times per week: if the cell density is greater than 6E5 cv/ml, reculture the cells at 3E5 cv/ml in F25.

Starting from D+17 and if the viability is greater than 80%, carry out a production in simplified fed-batch mode: inoculation of the cultiflasks at $3^E5$ cv/ml, culture under stirring at 250 rpm, addition of a glucose and glutamine feed on D+3, D+5 and D+7.

The supernatant is collected on D+10 and assayed with the Fast ELYSA kit (RD-biotech).

1.2.3 Stable Transfection of the CHO—S Line

The evaluations are carried out on pools of transfectants ("transfection in stable pools") in order to compare the different constructions on the base of an average expression level on a large number of transfectants (several thousand) as well as on the best clones selected by ClonePixFL on these pools.

1.2.3.1. Obtaining the Pools and Evaluations in Pools

The CHO—S line is cultured in Freestyle CHO EM medium+8 mM of glutamine, in a flask at 37° C., 8% CO2, under stirring at 135 rpm.

The cells are recultured the previous day at $6 \times 10^5$ cell/ml.

On the day of the electroporation, the cells are electroporated by Gene Pulser Xcell (BioRad) with a voltage of 300 V and capacitance of 500 µF in 4-mm cuvettes (Biorad) with 5E6 cv (qsf 500 µl of electroporation buffer from the electrobuffer kit (Ozyme) containing the linearized plasmid DNA). After electroporation the cells are taken up at 3E5 cv/ml in an F75 culture flask.

On D+3: Placing in selective medium in order to obtain the following final concentrations: Freestyle CHO EM+LFB additives for low density cell cloning LDCC+G418 1 mg/ml.

On D+10: Dilution by half in Freestyle CHO EM+LFB additives for low density cell cloning LDCC+G418 1 mg/ml.

Starting from D+12 and 3 times per week: if the cell density is greater than 6E5 cv/ml, reculture the cells at 3E5 cv/ml in F25.

Starting from D+17 reculture in a F25 or F75 flask in Freestyle CHO EM+G418 1 mg/ml.

Starting from D+25, carry out batch-mode production: inoculate the F25 at $3^E5$ cv/ml in Freestyle CHO EM+G418 1 mg/ml (production in pools).

The supernatant is collected on D+12 and assayed with the Fast ELYSA kit (RD-biotech).

1.2.3.2. Obtaining Clones and Evaluations of the Clones

The pools of cells obtained previously are plated in semi-solid medium (CloneMedia CHO—Molecular Devices) in the presence of fluorescent detection antibodies.

The clones that are the greatest producers of each pool are selected firstly as a function of their fluorescence intensity (screening and picking by ClonePix$^{FL}$) then as a function of their P24 saturation titre.

The best clones are then evaluated in batch-mode production by inoculation of cultiflasks at $3^E5$ cv/ml in Freestyle CHO EM+G418 1 mg/ml and culture under stirring at 250 rpm.

The supernatant is collected when the viability is less than 50% and assayed with the Fast ELYSA kit (RD-biotech).

1.3. Evaluation of the Level of Recombinant Protein Secreted

The evaluation of the level of free kappa chain of the anti-Rh(D) antibody T125 as well as the production of anti-CD20, anti-AMHRII or anti-GGT IgG1 are determined by the Enzyme-linked immunosorbent assay (ELISA) technique.

The free kappa chain present in the culture supernatant is captured over 2 h by a goat anti-human kappa antibody (Caltag Lab) which is adsorbed on 96-well plates. The captured antibody is then revealed by a biotinylated goat anti-human kappa chain (Pierce) followed by the addition of peroxidase-coupled streptavidin (Pierce). Between each stage 4 washings are carried out in order to remove the proteins and reagents not involved in the formation of the complex. The revelation is carried out by the addition of the enzyme substrate OPD (Sigma) and the reaction is stopped with 1N HCl. The reading is carried out spectrophotometrically at 492 nm. The antibody concentration is determined in comparison with a standard range.

The IgG1s produced in transient and stable transfections are evaluated with the Fast ELYSA kit (RD-biotech) according to supplier's instructions. The optical density is read spectrophotometrically at 450 nm. The antibody concentration is determined in comparison with a standard range contained in the kit.

1.4. Statistical Analyses

The free Kappa chain or whole immunoglobulin production results are compared with values standardized by the median values from one experiment to another. The statistical analyses are carried out using the STATGRAPHICS Centurion XV software. Multiple-range tests are applied to the data with the 95.0% LSD method. The data pairs have statistically significant differences with a 95.0% confidence level.

Example 1

Figure 1:
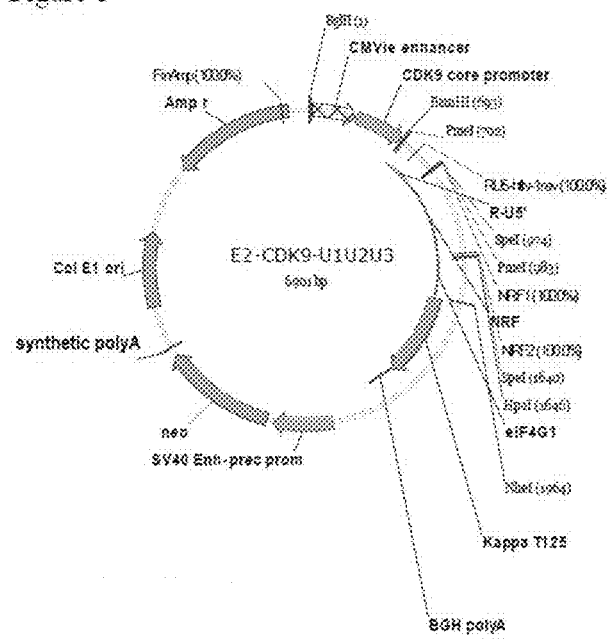
FIG. 1 illustrates the E2-CDK9-U1U2U3 vector comprising a transcription unit comprising the hCMVie enhancer (E2), the promoter region of the CDK9 gene, the R region of the LTR of the HTLV-1 virus (U1), the 5'UTR region of the NRF gene (U2) and the 5'UTR region of the eIF4G1 gene (U3).

Construction of the E2-CDK9-U1U2U3 Vector (FIG. 1)

Digestion of the E2-CDK9 vector with BamHI and NheI
Recovery of the fragment of 5630 bases, removal of the fragment of 204 bases
Digestion of the synthetic insert with BamHI and NheI
Recovery on gel of the insert of 1271 bases
Ligation and obtaining of E2-CDK9-U1U2U3
Screening of the bacterial clones by a suitable technique such as PCR, using appropriate primers Example 2

Figure 2:
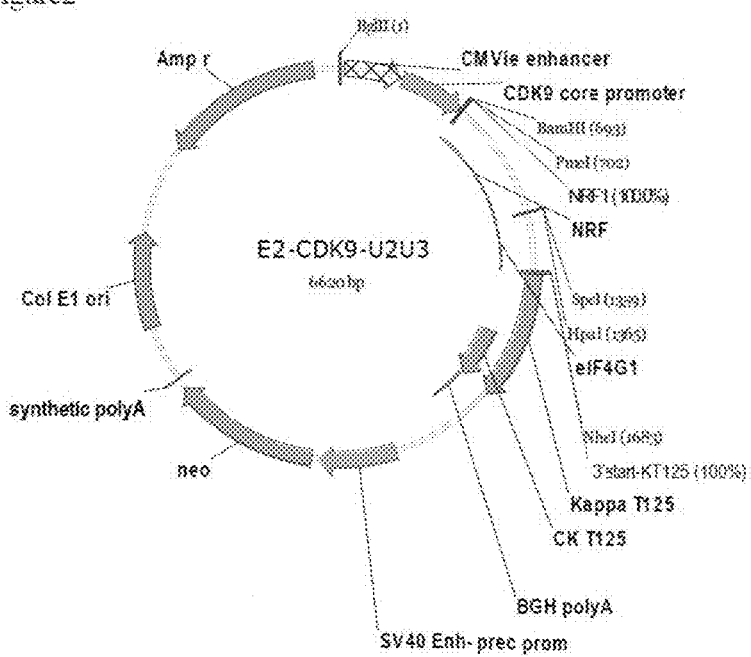
FIG. 2 illustrates the E2-CDK9-U2U3 vector comprising a transcription unit comprising the hCMVie enhancer, the promoter region of the CDK9 gene, the 5'UTR region of the NRF gene and the 5'UTR region of the eIF4G1 gene.

Construction of the E2-CDK9-U2U3 Vector (FIG. 2)

PmeI digestion on E2-CDK9-U1U2U3
Recovery of the fragment of 6620 bases; removal of the fragment of 281 bases
Ligation and obtaining of E2-CDK9-U2U3
Screening of the bacterial clones by a suitable technique such as PCR, using appropriate primers Example 3

Figure 3:
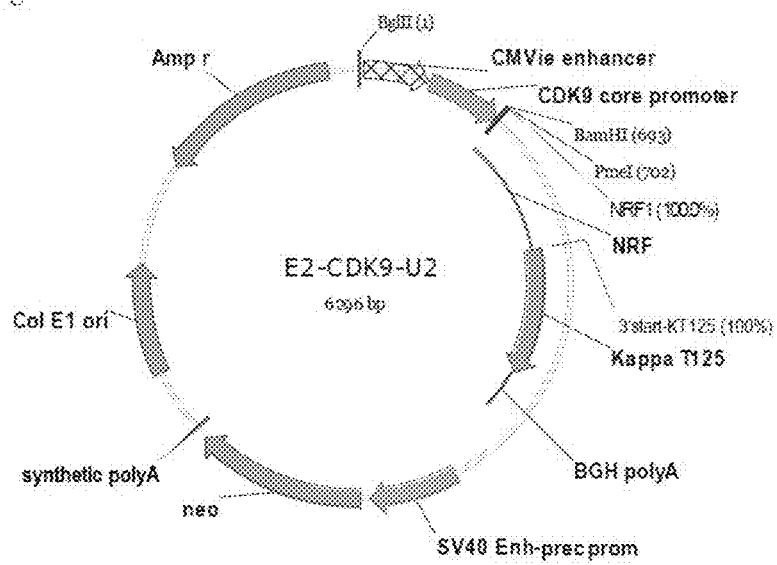
FIG. 3 illustrates the E2-CDK9-U2 vector comprising a transcription unit comprising the hCMVie enhancer, the promoter region of the CDK9 gene and the 5'UTR region of the NRF gene.

Construction of the E2-CDK9-U2 Vector (FIG. 3)

SpeI+NheI digestion of E2-CDK9-U2U3
Recovery on gel of the fragment of 6296 bases, removal of the fragment of 324 bases
Ligation and obtaining of E2-CDK9-U2
Screening of the bacterial clones by a suitable technique such as PCR, using appropriate primers Example 4

Figure 4:
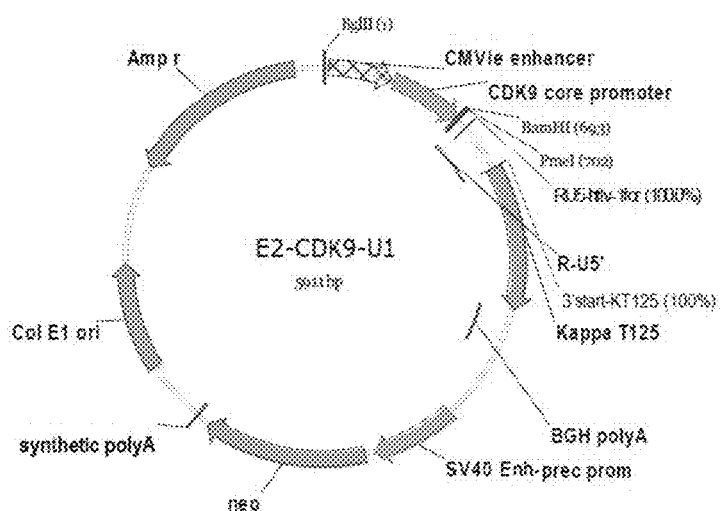
FIG. 4 illustrates the E2-CDK9-U1 vector comprising a transcription unit comprising the hCMVie enhancer, the promoter region of the CDK9 gene and the R region of the LTR of the HTLV-1 virus.

Construction of the E2-CDK9-U1 Vector (FIG. 4)

SpeI+NheI digestion of E2-CDK9-U1U2U3
Recovery on gel of the fragment of 5911 bases, removal of the fragment of 990 bases
Ligation and obtaining of E2-CDK9-U1
Screening of the bacterial clones by a suitable technique such as PCR, using appropriate primers

Example 5

Figure 5:
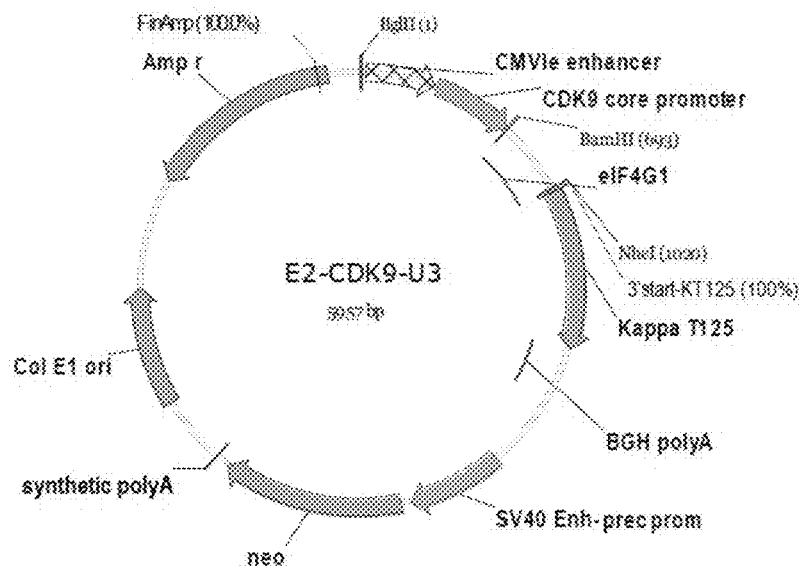
FIG. 5 illustrates the E2-CDK9-U3 vector comprising a transcription unit comprising the hCMVie enhancer, the promoter region of the CDK9 gene, and the 5'UTR region of the eIF4G1 gene.

Construction of the E2-CDK9-U3 Vector (FIG. 5)

Digestion HpaI+PmeI on E2-CDK9-U1U2U3
Recovery on gel of the fragment of 5957 bases, removal of the fragment of 944 bases
Ligation and obtaining of E2-CDK9-U3
Screening of the bacterial clones by a suitable technique such as PCR, using appropriate primers

Example 6

Figure 6:
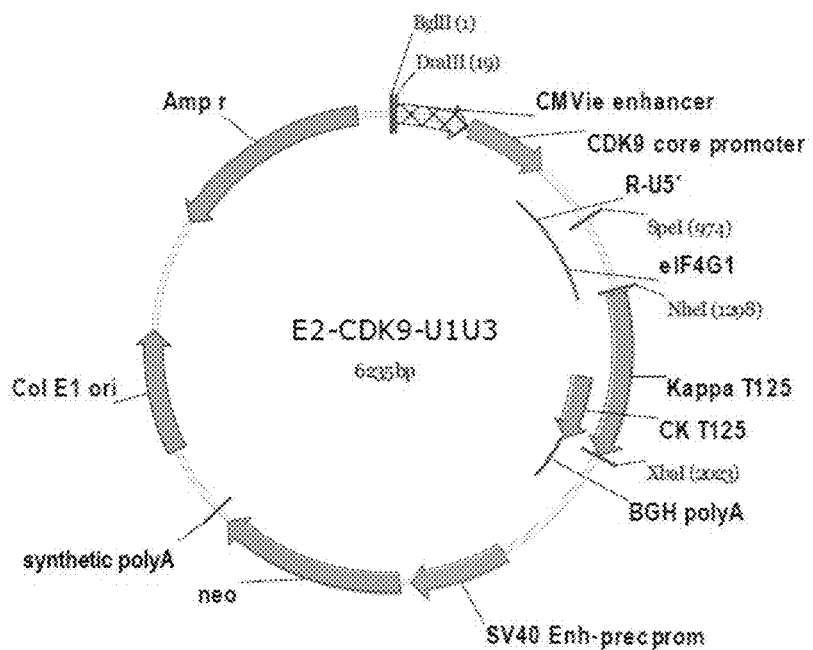
FIG. 6 illustrates the E2-CDK9-U1U3 vector comprising a transcription unit comprising the hCMVie enhancer, the promoter region of the CDK9 gene, the R region of the LTR of the HTLV-1 virus and the 5'UTR region of the eIF4G1 gene.

Construction of the E2-CDK9-U1U3 Vector (FIG. 6)

SpeI digestion on E2-CDK9-U1U2U3 in order to release the 5'UTR U2 region
Recovery on gel of the fragment of 6235 bases, removal of the fragment of 666 bases
Ligation and obtaining of E2-CDK9-U1U3
Screening of the bacterial clones by a suitable technique such as PCR, using appropriate primers

Example 7

Figure 7:
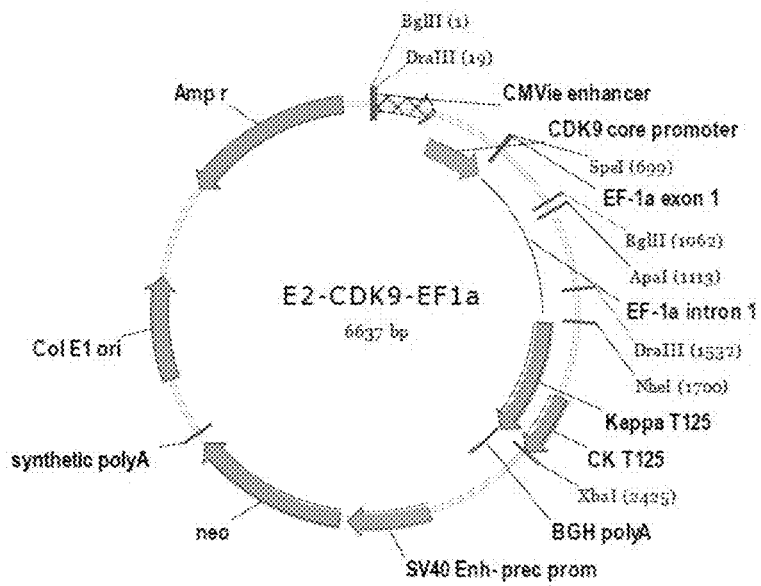
FIG. 7 illustrates the E2-CDK9-EF1α vector comprising a transcription unit comprising the hCMVie enhancer, the promoter region of the CDK9 gene and the first intron of the EF1α gene.

Construction of the E2-CDK9-EF1α Vector (FIG. 7)

SpeI+NheI digestion of E2-CDK9
Recovery on gel of the fragment of 5636 bases, removal of the fragment of 198 bases
Digestion of the synthetic insert with SpeI and NheI
Recovery on gel of the insert of 1001 bases
Ligation and obtaining of E2-CDK9-EF1α
Screening of the bacterial clones by a suitable technique such as PCR, using appropriate primers

Example 8

Figure 8:
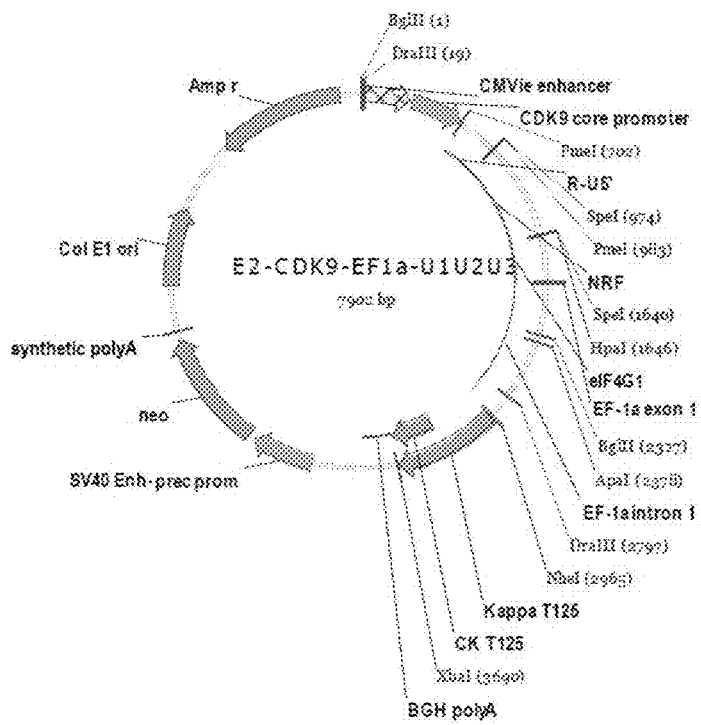
FIG. 8 illustrates the E2-CDK9-U1U2U3-EF1α vector comprising a transcription unit comprising the hCMVie enhancer, the promoter region of the CDK9 gene, the R region of the LTR of the HTLV-1 virus, the 5'UTR region of the NRF gene, the 5'UTR region of the eIF4G1 gene and the first intron of the EF1α gene.

Construction of the E2-CDK9-EF1α-U1U2U3 Vector (FIG. 8)

Digestion SpeI+BamHI of E2-CDK9-EF1α
Recovery on gel of the fragment of ??? bases, removal of the fragment of ???bases
Digestion of the synthetic insert with BamHI and NheI
Recovery on gel of the insert of 1271 bases
Ligation and obtaining of E2-CDK9-EF1α-U1U2U3
Screening of the bacterial clones by a suitable technique such as PCR, using appropriate primers

Example 9

Figure 9:
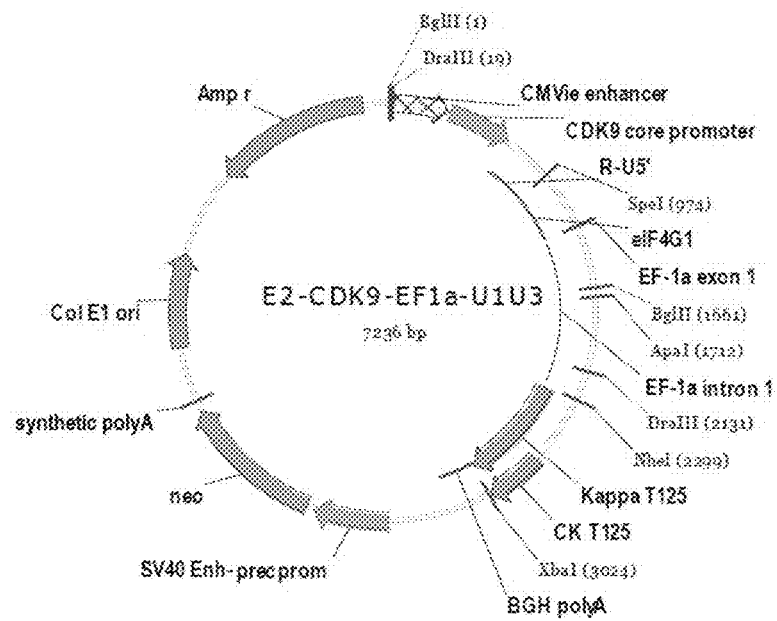
FIG. 9 illustrates the E2-CDK9-U1U3-EF1α vector comprising a transcription unit comprising the hCMVie enhancer, the promoter region of the CDK9 gene, the R region of the LTR of the HTLV-1 virus, the 5'UTR region of the eIF4G1 gene and the first intron of the EF1α gene.

Construction of the E2-CDK9-EF1α-U1U3 Vector (FIG. 9)

SpeI digestion on E2-CDK9-EF1α-U1U2U3
Recovery of the fragment of 7236 bases and removal of the fragment of 666 bases
Ligation and obtaining of E2-CDK9-EF1α-U1U3
Screening of the bacterial clones by a suitable technique such as PCR, using appropriate primers

Example 10

Figure 10:
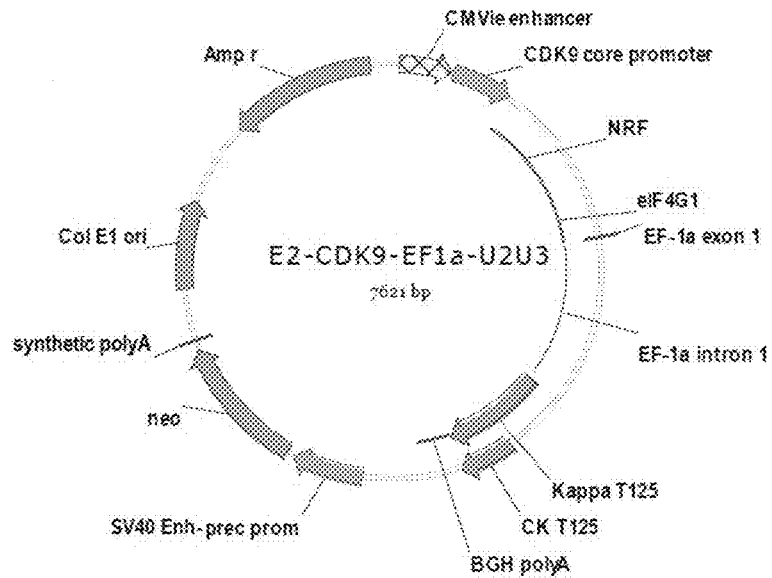
FIG. 10 illustrates the E2-CDK9-U2U3-EF1α vector comprising a transcription unit comprising the hCMVie enhancer, the promoter region of the CDK9 gene, the 5'UTR region of the NRF gene, the 5'UTR region of the eIF4G1 gene and the first intron of the EF1α gene.

Construction of the E2-CDK9-EF1α-U2U3 Vector (FIG. 10)

HpaI/PmeI digestion on E2-CDK9-EF1α-U1U2U3
Recovery of the fragment of 7230 bases; removal of the fragment of 672 bases
Ligation and obtaining of E2-CDK9-EF1α-U2U3
Screening of the bacterial clones by a suitable technique such as PCR, using appropriate primers

Example 11

Figure 11:
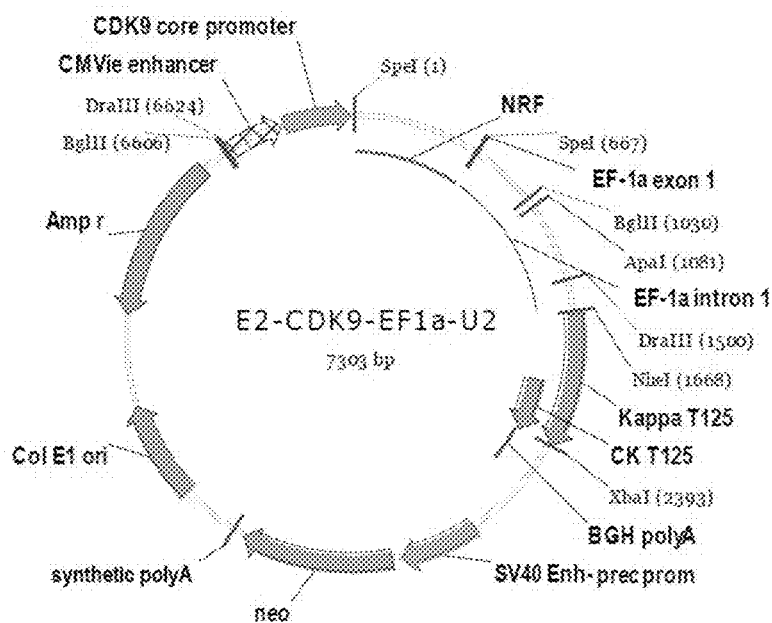
FIG. 11 illustrates the E2-CDK9-U2-EF1α vector comprising a transcription unit comprising the hCMVie enhancer, the promoter region of the CDK9 gene, the 5'UTR region of the NRF gene and the first intron of the EF1α gene.

Construction of the E2-CDK9-EF1α-U2 Vector (FIG. 11)

SpeI digestion of E2-CDK9-EF1α
Recovery on gel of the fragment of 6637 bases,
Digestion of the synthetic insert with SpeI
Recovery on gel of the insert of 666 bases
Ligation and obtaining of E2-CDK9-EF1α-U2
Screening of the bacterial clones by a suitable technique such as PCR, using appropriate primers

Example 12

Figure 12A:
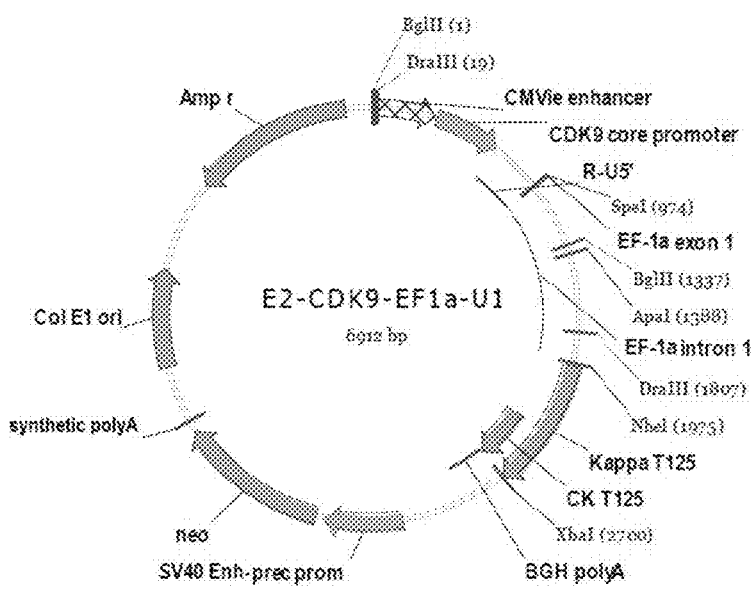
FIG. 12A illustrates the E2-CDK9-U1-EF1α vector comprising a transcription unit comprising the hCMVie enhancer, the promoter region of the CDK9 gene, the R region of the LTR of the HTLV-1 virus and the first intron of the EF1α gene.
Figure 12B:
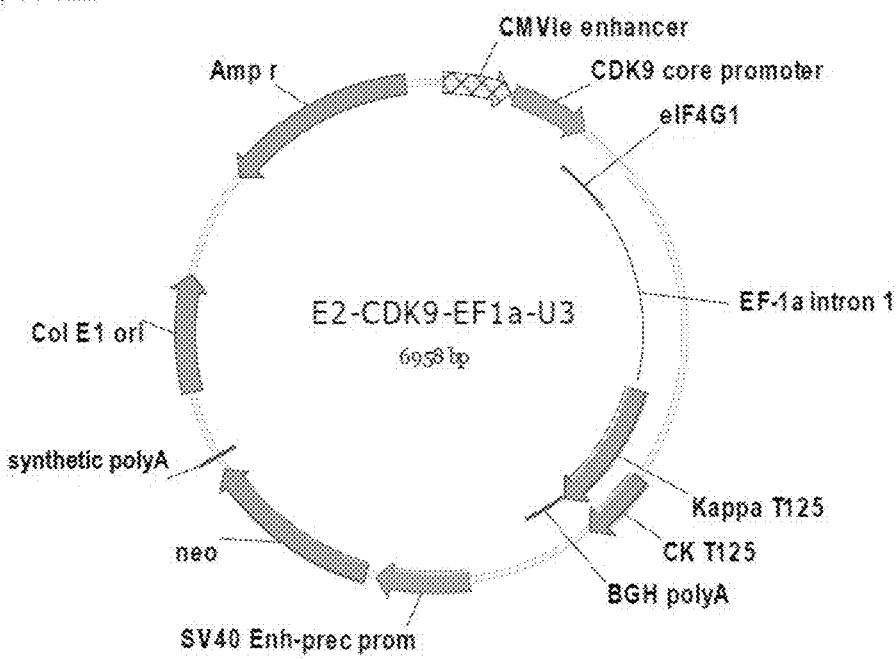
FIG. 12B illustrates the E2-CDK9-U3-EF1α vector, comprising a transcription unit comprising the hCMVie enhancer, the promoter region of the CDK9 gene, the 5'UTR region of the eIF4G1 gene and the first intron of the EF1α gene.

Construction of the E2-CDK9-EF1α-U1 Vector (FIG. 12A)

BamI+SpeI digestion of E2-CDK9-EF1α
Recovery on gel
Digestion of the synthetic insert with BamI+SpeI
Recovery on gel of the insert of 947 bases
Ligation and obtaining of E2-CDK9-EF1α-U1
Screening of the bacterial clones by a suitable technique such as PCR, using appropriate primers

Example 13

Figure 13:
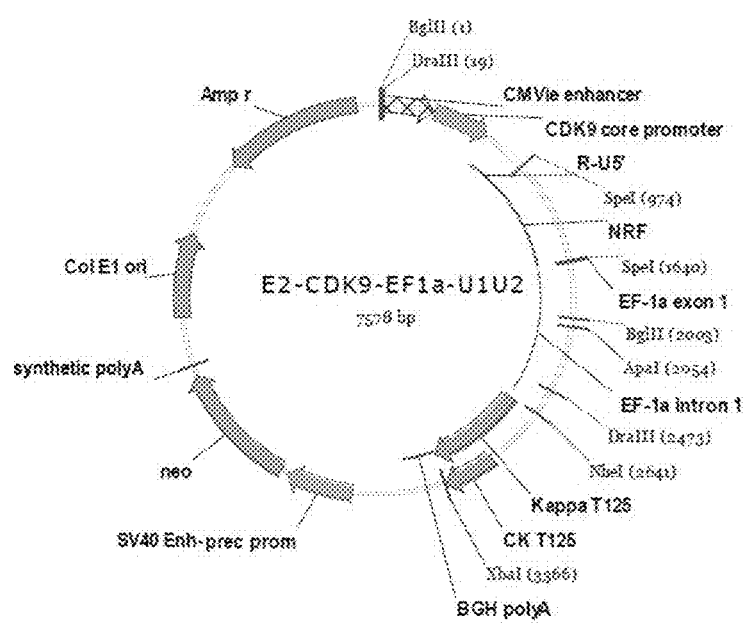
FIG. 13 illustrates the E2-CDK9-U1U2-EF1α vector comprising a transcription unit comprising the hCMVie enhancer, the promoter region of the CDK9 gene, the first intron of the EF1α gene, the R region of the LTR of the HTLV-1 virus and the 5'UTR region of the NRF gene.

Construction of the E2-CDK9-EF1α-U1U2 Vector (FIG. 13)

SpeI digestion of E2-CDK9-EF1α-U1
Recovery on gel of the fragment of 9612 bases
Digestion of the synthetic insert by SpeI
Recovery on gel of the insert of 947 bases
Ligation and obtaining of E2-CDK9-EF1α-U1U2
Screening of the bacterial clones by a suitable technique such as PCR, using appropriate primers

Example 14

Construction of the E2-CDK9-U3-HK138H11B Vector for the Expression of the Anti-GGT Antibody in YB2/0

The E2-CDK9-U3-HK138H11B MB7 vector is constructed for the expression in stable pools of the anti-GGT chimeric antibody 138H11_B in the YB2/0 line taking account of the results of 5' RACE sequencing of the hybridoma source.

The nucleotide acid of the heavy chain of the antibody 138H11 and the nucleotide acid of the light chain of said antibody are cloned in the CHK622-21 vector.

Cloning of the Light Chains of the Antibody 138H11 without Signal Peptide

Figure 14:
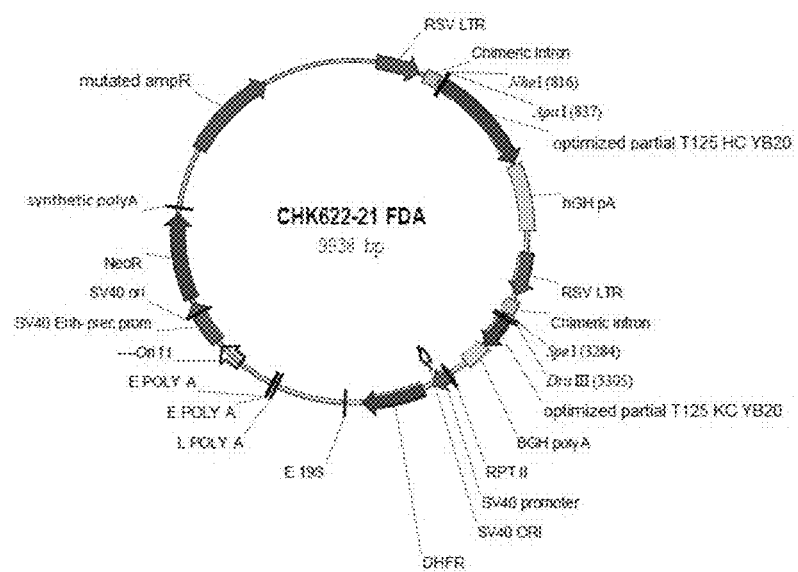
FIG. 14 illustrates the CHK622-21 bicistronic vector for expressing an IgG1/K. The transcription units of interest are dependent on the RSV LTR promoter in combination with the pCI-neo chimeric intron.

Digestion of the CHK622-21 vector (FIG. 14) with DraIII and SpeI

Recovery of a fragment of 9917 bp by nucleospin extract.

1st PCR of 15 dimer cycles with TAQ Proof Reading using the primers GGT-KP1 (acagctcttactagtgccgccaccatggacatgagggtgccagctcagctgctgggac) and GGT-KP2 (ctggatgtcgcatctagcgcctggcagccacagcagcagcagtcccagcagctgag) in order to obtain a fragment of 99 bp 2nd PCR of 15 cycles using the primers GGT-KP3 (gcgctagatgcgacatccagatgacacaatctagctcctctttcagtgtgag) and GGT-KD3 (CAAAAGTCCAGGGTGTGGACAGATAC) in order to obtain a fragment of 306 bp 3rd PCR of 15 dimer cycles using the primers GGT-KD1 (CACCCTGGACTTTTGGCGGAGGGACCAAGCTGGAAATCAAAAG) and GGT-KD2 (GAAAGATGAAGACACTTGGTGCAGCCACGGTTCTTTTGATTTCC) in order to obtain a fragment of 75 bp Purification on gel and nucleospin extract of the product obtained by the 2nd PCR Purification and nucleospin extract of the products obtained by the 1st PCR1 and the 3rd PCR3

Assembly of the 3 fragments by PCR with the primers GGT-KP1 and GGT-KD2 in order to obtain a fragment of 445 bp.

Digestion of the fragment of 445 bp with DraIII+SpeI and recovery of a fragment of 420 bp by purification and nucleospin extract Ligation of said digested fragment in the digested CHK622-21 vector in order to obtain the CHK622-21_138H11B vector of 10337 bp Screening by PCR with the primers 5'1PLC and GGT-KP2 which gives an amplicon of 143 bp.

Cloning of the Light Chains of the Antibody 138H11 with Signal Peptide MB7

Digestion of the CHK622-21 vector with DraIII and SpeI

Recovery of a fragment of 9917 bp by nucleospin extract.

1st PCR of 15 dimer cycles with TAQ Proof Reading using the primers GGT-KP1MB7 (tacagctcttactagtgccgccaccatgcgatggagctggatcttcctg) and GGT-KP2MB7 (atctggatgtcggcgttggcgctggtgatgctcagcagcagcaggaagatc) in order to obtain a fragment of 90 bp 2nd PCR of 15 cycles using the primers GGT-KP3MB7 (gccaacgccgacatccagatgacacaatctagctcctctttcagtgtgag) and GGT-KD3 in order to obtain a fragment of 304 bp 3rd PCR of 15 dimer cycles using the primers GGT-KD1 and GGT-KD2 in order to obtain a fragment of 75 bp Purification on gel and nucleospin extract of the product obtained by the 2nd PCR Purification and nucleospin extract of the products obtained by the 1st PCR1 and the 3rd PCR3

Assembly of the 3 fragments by PCR with the primers GGT-KP1MB7 and GGT-KD2 in order to obtain a fragment of 434 bp.

Digestion of the fragment of 434 bp with DraIII+SpeI and recovery of a fragment of 408 bp by purification and nucleospin extract Ligation of said digested fragment in the digested CHK622-21 vector in order to obtain the vector CHK622-21_138H11B_MB7 of 10325 bp Screening by PCR with the primers 5'1PLC and GGT-KP2 which gives an amplicon of 133 bp.

Cloning of the Heavy Chains of the Antibody 138H11 without Signal Peptide

Digestion of the CHK622-21_138H11B vector with NheI and ApaI

Recovery of a fragment of 10316 bp by nucleospin extract.

1st PCR of 15 cycles using the primers GGT-GP1 (tacagctcttgctagcgccgccaccatg) and GGT-GP2 (caccagctgcacttggcactgcaccccctccaggatg) in order to obtain a fragment of 97 bp 2nd PCR of 15 cycles using the primers GGT-GP3 (caagtgcagctggtggagagcggcggaaccctggtgaag) and GGT-GApaI (gggggaacacggatgggcccttagtg) in order to obtain a fragment of 400 bp Purification and nucleospin extract of the products obtained by the two PCRs Assembly of the 3 fragments by PCR with the primers GGT-GP1 and GGT-GApaI in order to obtain a fragment of 482 bp.

Figure 15:
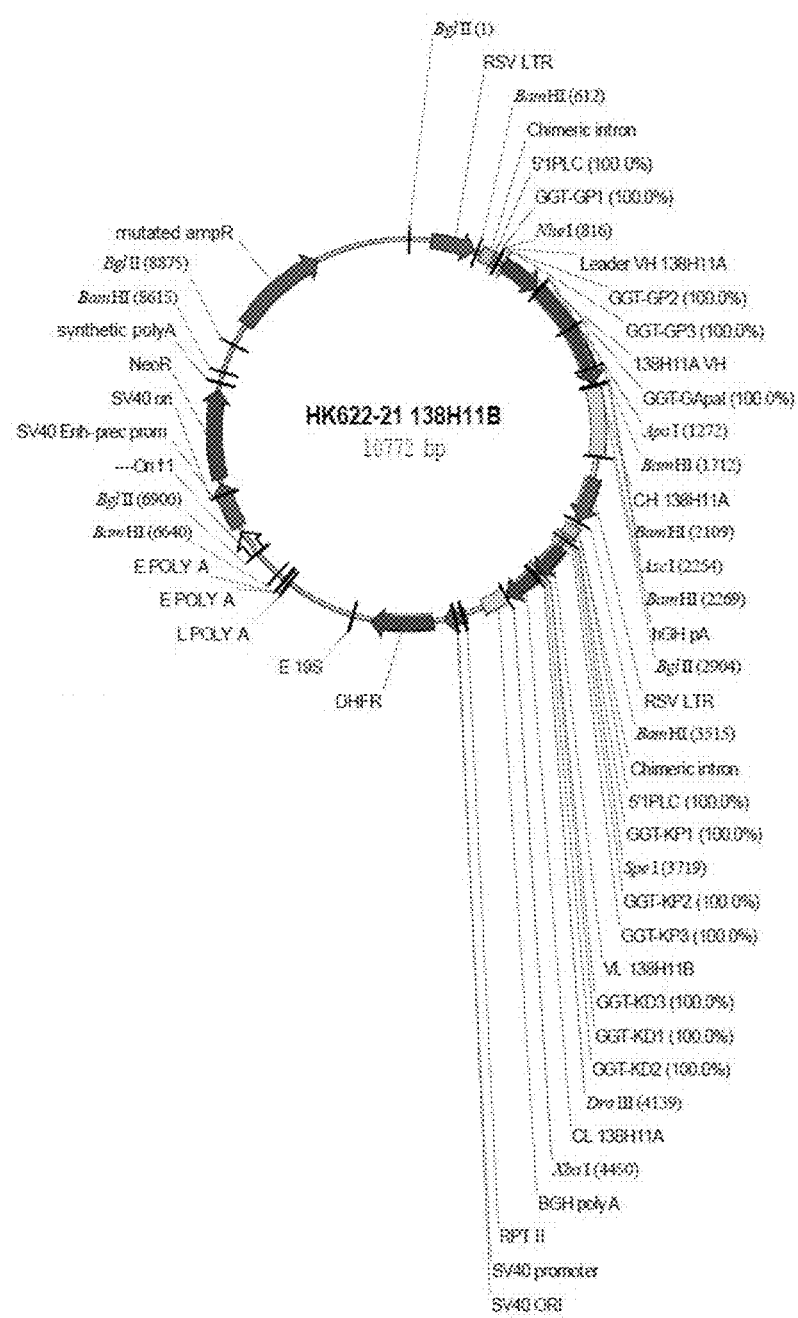
FIG. 15 illustrates the HK622-21_138H11B vector comprising the light chain and the heavy chain of the anti-GGT antibody 138H11B. The transcription units of interest are dependent on the RSV LTR promoter in combination with the pCI-neo chimeric intron.

Digestion of the fragment of 482 bp with NheI and ApaI and recovery of a fragment of 456 bp by purification and nucleospin extract Ligation of said digested fragment in the digested CHK622-21 vector in order to obtain the vector HK622-21_138H11B of 10772 bp (FIG. 15)

Screening by PCR with the appropriate primers which gives an amplicon of 604 bp

Cloning of the Heavy Chains of the Antibody 138H11 with Signal Peptide MB7

Digestion of the CHK622-21_138H11B_MB7 vector with NheI and ApaI

Recovery of a fragment of 10304 bp by nucleospin extract

1st PCR of 15 cycles using the primers GGT-GP1MB7 (tacagctcttgctagcgccgccaccatgcgatggagctggatcttcctgctgctgctgag) and GGT-GP2MB7 (caccagctgcacttgggcgttggcgctggtgatgctcagcagcagcaggaagatc) in order to obtain a fragment of 94 bp 2nd PCR of 15 cycles using the primers GGT-GP3 and GGT-GApaI in order to obtain a fragment of 400 bp Purification and nucleospin extract of the products obtained by the two PCRs Assembly of the 3 fragments by PCR with the primers GGT-GP1 and GGT-GApaI in order to obtain a fragment of 479 bp.

Figure 16:
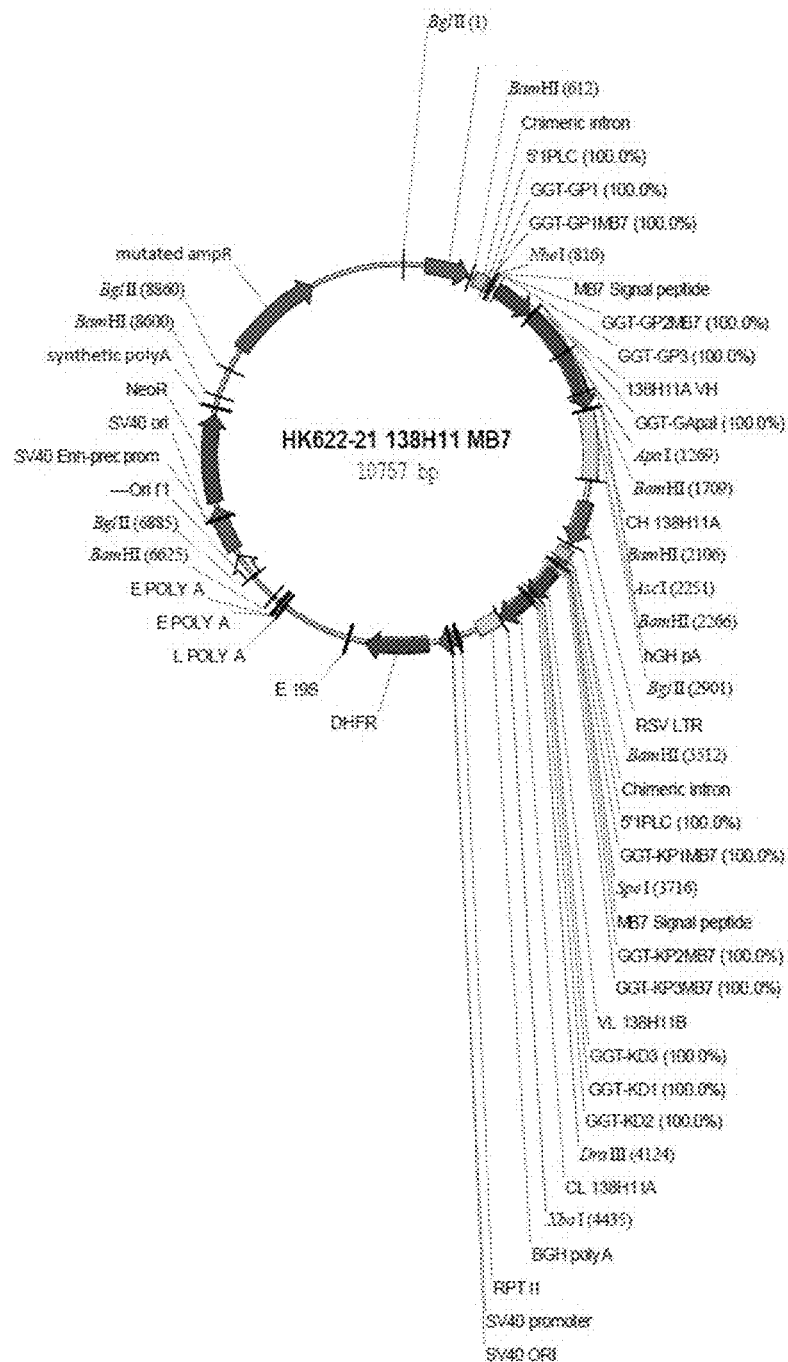
FIG. 16 illustrates the HK622-21_138H11B_MB7 vector comprising the light chain with the signal peptide MB7 and the heavy chain with the signal peptide MB7 of the anti-GGT antibody 138H11B. The transcription units of interest are dependent on the RSV LTR promoter in combination with the pCI-neo chimeric intron.

Digestion of the fragment of 479 bp with NheI and ApaI and recovery of a fragment of 453 bp by purification and nucleospin extract Ligation of said digested fragment in the digested CHK622-21 vector in order to obtain the HK622-21_138H11B_MB7 vector of 10757 bp (FIG. 16)

Screening by PCR with the appropriate primers which gives an amplicon of 601 bp.

Figure 17:
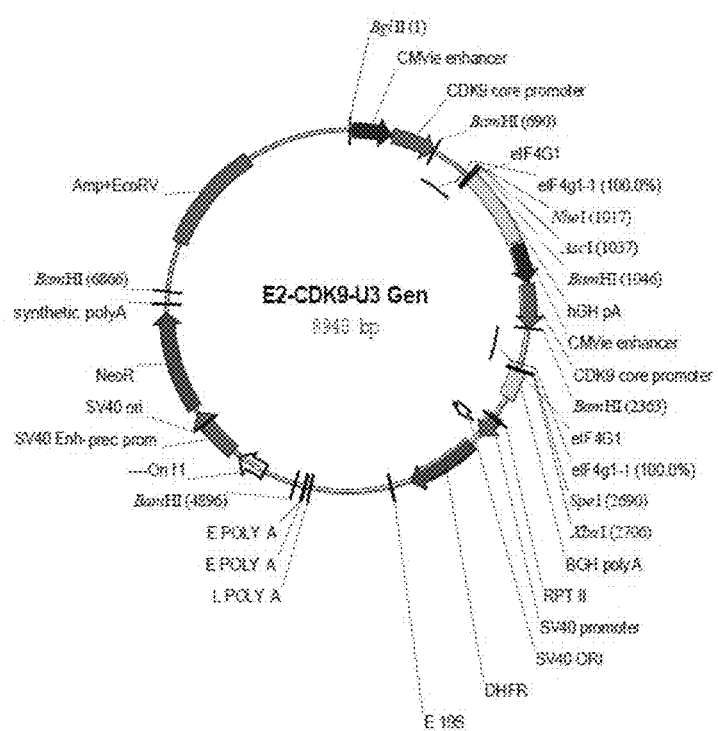
FIG. 17 illustrates the E2-CDK9-U3-Gen bicistronic vector for expressing an IgG1/K. The transcription units of interest are dependent on the (hCMVie) enhancer E2 of the CDK9 promoter and the 5'UTR region of the eIF4G1 gene (U3).

Cloning of the Heavy Chains of the Antibody 138H11 with Signal Peptide MB7 in the E2-CDK9-U3-Gen Generic Vector Digestion of the E2-CDK9-U3-Gen vector (FIG. 17) with NheI and AseI Recovery of a fragment of 8928 bp by nucleospin extract Digestion of the HK622-21_138H11B_MB7 vector with NheI and AseI Recovery of a fragment of 1435 bp by nucleospin extract Ligation of said digested fragment in the digested E2-CDK9-U3-Gen vector in order to obtain the E2-CDK9-U3-H138H11B_MB7 vector Screening by PCR with the appropriate primers which gives an amplicon of 512 bp Cloning of the Light Chains of the Antibody 138H11 with Signal Peptide MB7 in the E2-CDK9-U3-Gen Generic Vector Digestion of the E2-CDK9-U3-H138H11B_MB7 vector with SpeI and XbaI
Dephosphorylation of the digested vector and recovery of a fragment of 10347 bp by nucleospin extract
Digestion of the HK622-21_138H11B_MB7 vector with SpeI and XbaI
Recovery of a fragment of 709 bp by nucleospin extract
Ligation of said digested fragment in the digested E2-CDK9-U3-Gen vector in order to obtain the E2-CDK9-U3-HK138H11B MB7 vector (FIG. 18)
Screening by PCR with the appropriate primers which gives an amplicon of 407 bp Example 15

Construction of the E2-CDK9-U3-pCI-Neo-HK138H11B Vector

The HK1358-4 vector (FIG. 19), in which the pCI-neo chimeric intron is inserted into the E2-CDK9-U3-HK138H11B MB7 vector, is constructed for the expression in stable pools of the anti-GGT 138H11_B chimeric antibody in the YB2/0 line.

Cloning of the pCI-Neo Chimeric Intron in the E2-CDK9-U3-HK138H11B MB7 Vector

The E2-CDK9-U3-HK138H11B MB7 vector is digested by NheI and SpeI. Two fragments of 7978 bp and 3088 bp are obtained by nucleospin extract. The nucleotide acid of the pCI-neo chimeric intron is amplified from the CHK622-21 vector using the primers P1pCiNeo-NheI (acagaggagctaggtaagtatcaaggttacaagac) and P2p-pCI-neo-NheI (tacgcattgagctagctgtggagagaaaggcaaagtg) giving an amplicon of 163 bp and the primers P1pCiNeo-SpeI (acagaggagaactaggtaagtatcaaggttacaagac) and P2p-pCI-neo-SpeI (cagccacagtactagctgtggagagaaaggcaaagtg) which gives an amplicon of 164 bp.

The PCRs are carried out with the KAPA HiFi enzyme. Each primer is made up of 15 bases complementary to the sequence of the E2-CDK9-U3-HK138H11B_MB7 vector at the insertion site and some twenty bases belonging to the sequence of the intron to be reinserted.

An additional base was added in order to recreate the insertion site.

The pCI-neo chimeric intron is inserted into the digested E2-CDK9-U3-HK138H11B MB7 vector by the IN-FUSION method. The IN-FUSION method is a method described in the commercial kit from Ozyme (ref. 639690).

The two fragments of 163 bp and 164 bp obtained by PCR, as well as the digested E2-CDK9-U3-HK138H11B MB7 vector are assembled in a single stage in order to obtain the HK1358-4 vector. The insertion of the intron into the vector is verified by the 5'1PLC/CHoptiREV primers which gives an amplicon of 570 bp and the 5'PLC/GGT KD3 primers which gives an amplicon of 387 bp.

Example 16

Construction of the E2-CDK9-U3-pEF Vector

The HK1358-5 vector (FIG. 20), in which the EF1α intron is inserted into the E2-CDK9-U3-HK138H11B MB7 vector, is constructed for the expression in stable pools of the anti-GGT 138H11_B chimeric antibody in the YB2/0 line.

The E2-CDK9-U3-HK138H11B MB7 vector is digested by NheI and SpeI. Two fragments of 7978 bp and 3088 bp are obtained by nucleospin extract. The nucleotide acid of the EF1α intron is amplified from the K622-37EF vector using the primers P1EF-NheI (ACAGAGGAGAGCTAGG-TAAGTGCCGTGTGTGGTTCC) and P22-pEF-NheI (tggtggcggcgctagctgaaatggaagaaaaaaactttgaac) which gives an amplicon of 969 bp and the primers P1pEF-SpeI (ACA-GAGGAGAACTAGGTAAGTGCCGTGTGTGGTTCC) and P22-pEF-SpeI (tggtggcggcactagtctgaaatggaagaaaaaaactttgaac) which gives an amplicon of 970 bp.

The EF1α intron is inserted into the digested E2-CDK9-U3-HK138H11B MB7 vector by the IN-FUSION method.

The two fragments of 969 bp and 970 bp obtained by PCR, as well as the digested E2-CDK9-U3-HK138H11B MB7 vector are assembled in a single stage in order to obtain the HK1358-5 vector. The insertion of the intron into the vector is verified by the eIF4g1-1/CHoptiREV primers which gives an amplicon of 1534 bp and the eIF4g1-1/GGT KD3 primers which gives an amplicon of 1351 bp.

Example 17

Construction of the E2-CDK9-U3-mROSA Vector

The HK1358-8 vector (FIG. 21), in which the mROSA intron is inserted into the E2-CDK9-U3-HK138H11B MB7 vector, is constructed for the expression in stable pools of the anti-GGT 138H11_B chimeric antibody in the YB2/0 line.

The E2-CDK9-U3-HK138H11B MB7 vector is digested by NheI and SpeI. Two fragments of 7978 bp and 3088 bp are obtained by nucleospin extract. The nucleotide acid of the mROSA intron is amplified from the K622-37 mRosa vector using the P1p-mROSA-NheI (acagaggagagctaggtaggggatcgggactctgg) and P22-hROSA-NheI (tggtggcggcgctagctgtcaggagaggaaagagaag) primers which gives an amplicon of 381 bp and the P1pmROSA-SpeI (acagaggagaactaggtaggggatcgggactctgg) and P22-hROSA-SpeI (tggtggcggcactagtctgtcaggagaggaaagagaag) primers which gives an amplicon of 382 bp.

The mROSA intron is inserted into the digested E2-CDK9-U3-HK138H11B MB7 vector by the IN-FUSION method.

The two fragments of 381 bp and 382 bp obtained by PCR, as well as the digested E2-CDK9-U3-HK138H11B MB7 vector are assembled in a single stage in order to obtain the HK1358-8 vector. The insertion of the intron into the vector is verified by the eIF4g1-1/CHoptiREV primers which gives an amplicon of 949 bp and the eIF4g1-1/GGT KD3 primers which gives an amplicon of 765 bp.

Example 18

Construction of the E2-CDK9-U3-HTLV1 Vector

The HK1358-11 vector (FIG. 22), in which the 5'-LTR HTLV1 intron is inserted into the E2-CDK9-U3-HK138H11B MB7 vector, is constructed for the expression in stable pools of the anti-GGT 138H11_B chimeric antibody in the YB2/0 line.

The E2-CDK9-U3-HK138H11B MB7 vector is digested by NheI and SpeI. Two fragments of 7978 bp and 3088 bp are obtained by nucleospin extract. The nucleotide acid of the HCLV-1 intron is amplified from the K622-37 HTLV vector using the P1htlv-NheI (acagaggagagctagggctcg-catctctccttcac) and P22-htlv-NheI (tggtggcggcgctagGTAG-GCGCCGGTCACAGC) primers which gives an amplicon of 318 bp and the P1htlv-SpeI (acagaggagaactaggctcg-catctctccttcac) and P22-htlv-SpeI (tggtggcggcactagtGTAG-GCGCCGGTCACAGC) primers which gives an amplicon of 318 bp.

The 5'-LTR HTLV1 intron is inserted into the digested E2-CDK9-U3-HK138H11B MB7 vector by the IN-FUSION method.

The two fragments of 318 bp obtained by PCR, as well as the digested E2-CDK9-U3-HK138H11B MB7 vector are assembled in a single stage in order to obtain the HK1358-11 vector. The insertion of the intron into the vector is verified by the 5'HTLV/CHoptiREV primers which gives an amplicon of 519 bp and the 5'HTLV/GGT KD3 primers which gives an amplicon of 702 bp.

Example 19

Construction of the E2-CDK9-U3-pEF-Exon Vector

The HK1358-10 vector (FIG. 23), in which the EF1α intron with exon bases is inserted into the E2-CDK9-U3-HK138H11B MB7 vector, is constructed for the expression in stable pools of the anti-GGT 138H11_B chimeric antibody in the YB2/0 line.

The E2-CDK9-U3-HK138H11B MB7 vector is digested by NheI and SpeI. Two fragments of 7978 bp and 3088 bp are obtained by nucleospin extract. The nucleotide acid of the EF1α-exon intron is amplified from the K622-37 EF vector using the P12EF-NheI (ACAGAGGA-GAGCTAGCGGGTTTGCCGCCAGAACACAG) and P22-pEF-NheI (TGGTGGCGGCGCTAGCTGAAATG-GAAGAAAAAAACTTTGAAC) primers which gives an amplicon of 991 bp and the P12EF-SpeI (ACAGAGGA-GAACTAGCGGGTTTGCCGCCAGAACACAG) and P22-pEF-SpeI (TGGTGGCGGCACTAGTCTGAAATG-GAAGAAAAAAACTTTGAAC) primers which gives an amplicon of 992 bp.

The EF1α-exon intron is inserted into the digested E2-CDK9-U3-HK138H11B MB7 vector by the IN-FUSION method.

The two fragments of 991 bp and 992 bp obtained by PCR, as well as the digested E2-CDK9-U3-HK138H11B MB7 vector are assembled in a single stage in order to obtain the HK1358-10 vector. The insertion of the intron into the vector is verified by the 5'EF/CHoptiREV primers which gives an amplicon of 843 bp and the 5'EF1/GGT KD3 primers which gives an amplicon of 1023 bp.

Example 20

Construction of the E2-CDK9-U3-hROSA Vector

The HK1358-6 vector (FIG. 24), in which the hROSA intron is inserted into the E2-CDK9-U3-HK138H11B MB7 vector, is constructed for the expression in stable pools of the anti-GGT 138H11_B chimeric antibody in the YB2/0 line.

The E2-CDK9-U3-HK138H11B MB7 vector is digested by NheI and SpeI. Two fragments of 7978 bp and 3088 bp are obtained by nucleospin extract. The nucleotide acid of the hROSA intron is amplified from the vector K622-37hROSA using P1hROSA-NheI (acagaggagagctagg-taggggagcggaactctggtg) and P22-hROSA-NheI (tggtggcg-gcgctagctgtcaggagaggaaagagaag) which gives an amplicon of 1247 bp and the P1hROSA-SpeI (acagaggagaactagg-taggggagcggaactctggtg) and P22-hROSA-SpeI (tggtggcg-gcactagtctgtcaggagaggaaagagaag) primers which gives an amplicon of 1248 bp.

The hROSA intron is inserted into the digested E2-CDK9-U3-HK138H11B MB7 vector by the IN-FUSION method.

The two fragments of 1247 bp and 1248 bp obtained by PCR, as well as the digested E2-CDK9-U3-HK138H11B MB7 vector are assembled in a single stage in order to obtain the HK1358-6 vector. The insertion of the intron into the vector is verified by the appropriate primers which gives an amplicon of 1812 bp and the elF4g1-1/GGT KD3 primers which gives an amplicon of 1629 bp.

Example 21

Construction of the E2-CDK9-U3-UBC Vector

The HK1358-9 vector (FIG. 25), in which the ubiquitin gene intron is inserted into the E2-CDK9-U3-HK138H11B MB7 vector, is constructed for the expression in stable pools of the anti-GGT 138H11_B chimeric antibody in the YB2/0 line.

The E2-CDK9-U3-HK138H11B MB7 vector is digested by NheI and SpeI. Two fragments of 7978 bp and 3088 bp are obtained by nucleospin extract. The nucleotide acid of the UbC intron is amplified from the K622-37UBC vector using the P12UBC-NheI (ACAGAGGAGAGCTAGAGT-TCCGTCGCAGCCGGGATTTG) and P22-UBC-NheI (tg-gtggcggcgctagCTAACAAAAAAGCCAAAAACGGC) primers which gives an amplicon of 906 bp and the P1UBC-SpeI (acagaggagaactaGTGAGTAGCGGGCTGCTGG) and P22-UBC-SpeI (tggtggcggcactagtCTAACAAAAAAGC-CAAAAACGGC) primers which gives an amplicon of 906 bp.

The ubiquitin intron is inserted into the digested E2-CDK9-U3-HK138H11B MB7 vector by the IN-FUSION method.

The two fragments of 906 bp and 906 bp obtained by PCR, as well as the digested E2-CDK9-U3-HK138H11B MB7 vector are assembled in a single stage in order to obtain the HK1358-6 vector. The insertion of the intron into the vector is verified by the appropriate primers which gives an amplicon of 830 bp and the 5'UBC/GGT KD3 which gives giving an amplicon of 1629 bp.

Example 22

Production of Two Whole Anti-GGT and Anti-AMHRII Antibodies, By the Vectors Containing the Transcription Unit E2CDK9U3 with Different Introns The whole anti-GGT (138H11B MB7) and anti-AMHRII (3C23K) antibodies were produced from stable pools in YB2/0, in medium with serum and without serum respectively, by the vectors in the context of E2CDK9U3 with the EF1α intron with exon (EF), the EF1α intron without exon (EFss), the ubiquitin intron, the hROSA intron, the mROSA intron, the 5'LTR intron HTLV1, the pCI-neo chimeric intron, the β-actin intron, or without introns respectively. The antibody titres obtained with these vectors are shown in FIGS. 26 and 27.

The gain provided by the E2CDK9U3+intron structure is estimated by comparison with a reference vector coding for the same IgG but with a TU structure comprising the RSV LTR+pCIneo intron instead of the E2CDK9U3+intron structure.

FIG. 26 illustrates the productivity of the anti-GGT antibody (138H11B) in the context of E2CDK9U3 with different introns, in pools in medium with serum, in comparison with the reference RSV LTR+pCI neo intron. It shows in particular that:

the combination of E2CDK9U3 without additional intron already provides a substantial gain (×2.2) compared with RSV LTR+pCI neo intron.

all the introns tested provide an additional gain with the E2CDK9U3 combination: somewhat modest in the case of the beta-actin, pCIneo and HTLV introns, fairly significant in the case of the murine and human ROSA introns, very significant in the case of the ubiquitin and EF introns (with or without the small 5' exon) allowing maximum gains of approximately 6× in relation to the reference RSV LTR+pCI neo intron.

FIG. 27 shows in particular that:

The overall hierarchy of the introns in combination with E2CDK9U3 is maintained in relation to the test with the anti-GGT antibody. In particular, the EF (with and without exon) and ubiquitin introns are the strongest (approximately ×2 compared with the reference RSV LTR+pCI neo intron), the mROSA intron retains a significant effect (×1.6). The hROSA intron was not tested in this test.

The gains in relation to the reference RSV LTR+pCI neo intron are less significant in this test, with no identified cause. However, the hierarchy of the introns is not called into question and subsequent tests with the same antibody to be expressed and the same method in medium without serum, have shown higher gains similar to those obtained in medium with serum (×5 for the EFss intron; cf FIG. 28).

Example 23

Production of Three Different Antibodies in YB2/0, with and Without Serum, by a Vector Containing the Transcription Unit E2CDK9U3+EFss (or EF)

The sequences coding for three antibodies: anti-CD20 (R603), anti-GGT (138H11B MB7) and anti-AMHRII (3C23K) were integrated into a vector containing the transcription unit E2CDK9U3+EFss. These vectors, as well as their vector homologues except that the transcription unit is under the control of the RSV LTR+pCI neo intron (reference control) instead of E2CDK9U3+EFss, were expressed in pools, with and without serum in the case of anti-CD20 and anti-AMHRII, with serum in the case of anti-GGT, in independent transfections.

The gain provided by the E2CDK9U3+EF intron structure is estimated by comparison with the reference vector coding for the same IgG but with a TU structure comprising the RSV LTR+pCIneo intron instead of the E2CDK9U3+ EF intron structure.

FIG. 28 illustrates the productivity of the anti-GGT (138H11B), anti-AMHRII (3C23K) and anti-CD20 (R603) antibodies in the E2CDK9U3+EFss intron context, in comparison with the reference RSV LTR+pCI neo intron.

It shows in particular that the E2CDK9U3+ EFss intron combination still provides a significant gain in relation to RSV LTR+pCI neo intron: from 4.6 to 6.1× in the case of the three antibodies in medium with serum. In medium without serum, in the case of the two antibodies tested, the results are more variable but also show a significant effect of the E2CDK9U3+ EFss intron combination (the lowest gain of 2× is that already shown in FIG. 27).

Example 24

Comparison of the Introns in Combination with the RSV LTR

The introns to be tested: (Bact (β-actin), EF1α, mROSA, hROSA, 5'-LTR HTLV1, ubc (ubiquitin) are inserted into the expression vector K622_37, comprising the RSV LTR, in order to produce the light kappa chain of the antibody T125. The gain in productivity of the vectors thus constructed is compared with that of the reference vectors RSV_int_KT125_2STP and RSV_T125_K2.

The results obtained from 3 transfections carried out over 3 different weeks are illustrated in FIG. 29 and make it possible to observe significant differences between the introns.

A multiple comparison is carried out for the Ig light chain production averages (ng/mL) obtained with the different introns in the CHO—S line (Table 1). The method currently used to discriminate between the averages is Fisher's least significant difference (LSD) procedure. Multiple-range tests are carried out with the 95.0% LSD method. These pairs have statistically significant differences at the 95.0% confidence level.

TABLE 1

|   | Effective | Average | Homogeneous group |
|---|---|---|---|
| RSV_int_KT125_2STP | 18 | 25506.3 | X |
| K622_37_HTLV | 18 | 26511.3 | X |
| K622_37_Ubc | 18 | 28790.0 | XX |
| K622_37_Bact | 17 | 31992.3 | XX |
| K622_37_hROSA | 18 | 33561.0 | X |
| RSV_T125_K2 | 16 | 34362.8 | X |
| K622_37_mROSA | 15 | 38874.8 | X |
| K622_37_EF | 14 | 44104.4 | X |

Five homogeneous groups are identified using columns of Xs. The EF1α intron is significantly more effective. The mROSA intron is situated in second position. The other introns have no positive effect in combination with the RSV LTR.

Example 25

Comparison of the Transcription Units in the E2-CDK9-U3 and RSV LTR Contexts

The different transcription units to be tested are tested for the production of the light kappa chain of the T125 antibody. The gain in productivity of the vectors thus constructed is compared with that of the reference vectors pRep4KT125 and RSV_T125_K2.

The results obtained from 3 transfections carried out over different 3 weeks are illustrated in FIG. 30 and make it possible to observe significant differences between the combinations tested.

A multiple comparison is carried out for the averages (ng/mL) of Ig light chain production obtained with the different combinations in the CHO—S line (Table 2). The method currently used in order to discriminate between the averages is Fisher's least significant difference (LSD) procedure. Multiple-range tests are carried out with the 95.0% LSD method. These pairs have statistically significant differences at the 95.0% confidence level.

TABLE 2

|   | Effective | Average | Homogeneous group |
|---|---|---|---|
| RSVT125K2 | 12 | 10940.2 | X |
| E2CDK9U3_hRosa | 12 | 15847.6 | X |
| K622_37_hRosa | 12 | 23340.0 | X |
| pRep4KT125 | 12 | 23843.2 | X |
| E2CDK9U3 | 12 | 31903.9 | X |

TABLE 2-continued

|  | Effective | Average | Homogeneous group |
|---|---|---|---|
| K622_37_mRosa | 12 | 35041.1 | X |
| E2CDK9U3_mRosa | 12 | 40688.4 | X |
| K622_37_EF | 12 | 41708.2 | X |
| E2CDK9U3_EF | 12 | 51907.2 | X |

Five homogeneous groups are identified using columns of Xs.

The combination of E2-CDK9-U3 with the EF1α is intron significantly most effective. In the E2-CDK9-U3 context, the EF1α intron thus provides a gain of 63%.

The RSV LTR with EF intron and E2-CDK9-U3 with mROSA intron combinations are also significantly very effective.

To a lesser extent, the other combinations tested are more effective than the reference RSV T125 K2.

Example 26

Production of the Whole Anti-Rh(D) Antibody (HK) by Vectors Containing E2CDK9U3 in the CHO—S Cells The whole anti-Rh(D) antibodies (HK) are produced in the CHO—S cells transfected by the vectors containing a transcription unit of structure E2-CDK9-U3 and in the CHO—S cells transfected by the vector containing a transcription unit of structure RSV-pCI-neo intron (reference vector) respectively.

Table 3 below shows the assay results for the whole anti-Rh(D) antibodies produced by pools of cells transfected by the vector HK463-18 or by the vector HK E2-CDK9-U3. FIG. 31 illustrates these results.

TABLE 3

F6-2 = pool originating from transfection with
HK463-18, F11-2 = pool originating from
transfection with HK E2-CDK9-U3

| Pool | Medium | Type of batch production | IgG ELISA assay in ng/ml | Gain E2CDK9U3/ RSV + pCI intron |
|---|---|---|---|---|
| F6-2 | Freestyle + G418 | D + 12 F25 | 2 324 |  |
| F11-2 | Freestyle + G418 | D + 12 F25 | 14 193 | 6.1 |

The transcription unit E2CDK9U3 makes it possible to obtain a gain in productivity of the order of 6 times higher than that obtained with the reference vector.

Table 4 below shows the assay results for the whole anti-Rh(D) antibodies produced by the best clones (originating from the screening method described in materials and methods, on a limited number of colonies) originating from the pools previously described, transfected by the HK463-18 vector or by the HK E2-CDK9-U3 vector. FIG. 32 illustrates these results.

TABLE 4

| | cultiflask | |
|---|---|---|
| name of the vector | Max Prod D-1 IgG ELISA in ng/ml | max prod IgG ELISA in ng/ml |
| HK 463-18 | NA | <min |
| HK 463-18 | NA | 2,071 |
| HK 463-18 | NA | 2,732 |
| HK 463-18 | NA | 4,110 |
| HK 463-18 | NA | 16,937 |
| HK-E2-CDK9-U3 | NA | 4,061 |
| HK-E2-CDK9-U3 | NA | 10,585 |
| HK-E2-CDK9-U3 | 6 863 | 13,235 |
| HK-E2-CDK9-U3 | 13 389 | 14,221 |
| HK-E2-CDK9-U3 | 21 318 | 20,203 |
| HK-E2-CDK9-U3 | 29 860 | 33,069 |
| HK-E2-CDK9-U3 | 37 611 | 33,402 |
| HK-E2-CDK9-U3 | NA | 36,830 |
| HK-E2-CDK9-U3 | NA | 43,851 |
| HK-E2-CDK9-U3 | NA | 47,315 |
| HK-E2-CDK9-U3 | 58 007 | 58,007 |
| HK-E2-CDK9-U3 | 47 056 | 60,304 |
| HK-E2-CDK9-U3 | 61 902 | 74,233 |

Example 27

Production of the T125 Kappa Chain in the YB2/0 Cells

The T125 kappa chain was expressed in the YB2/0 line transiently transfected by different vectors containing different transcription unit constructions according to the present invention. The transcription unit constructions tested, as well as the expression results obtained are shown in FIG. 33.

Example 28

Production of Whole Anti-Rh(D) Antibodies (HK) by Vectors Containing E2CDK9U3 in the YB2/0 Cells The whole anti-Rh(D) antibodies (HK) are produced in the YB2/0 cells in stable transfection by the vectors containing a transcription unit of structure E2-CDK9-U3 or by the vector containing a transcription unit of structure RSV-pCI-neo intron (reference vector) respectively. The anti-Rh (D) antibody expression result in μg/mL is shown in FIG. 34.

Example 29

Production of the Whole Anti-CD71 Antibody (H7) in the YB2/0 Cells by Vectors Containing E2CDK9U3

The anti-CD71 antibodies are produced in the YB2/0 cells transfected by a vector containing the transcription unit E2-CDK9-U3 and the EF intron or by the reference vector containing RSV-pCI-neo intron respectively. The anti-CD71 antibody expression result in μg/mL is shown in FIG. 35.

The invention claimed is:

1. A transcription unit comprising a polynucleotide comprising the following regulatory elements:
   a. the hCMVie virus enhancer, said enhancer having the nucleotide sequence SEQ ID NO: 1, or a nucleic acid having at least 70% sequence identity with the sequence SEQ ID NO: 1 and having transcription activation activity,
   b. the promoter region of Cyclin-Dependent Kinase 9 (CDK9), said promoter region haying the nucleotide sequence SEQ ID NO: 2, or a nucleic acid having at least 70% sequence identity with the sequence of SEQ ID NO: 2 and having a promoter activity,
   c. a nucleotide sequence situated downstream of said promoter region and upstream of the translation initiation site, said nucleotide sequence comprising the 5' untranslated region (5' UTR) of the eukaryotic Initiation Factor 4G1 (eIF4GI) gene, said 5' UTR having the nucleotide sequence SEQ ID NO: 5, or a nucleic acid having at least 70% sequence identity with the sequence of SEQ ID NO: 5 and having mRNA stabilization and translation facilitator activitites, and
   d. the intron of the Elongation Factor 1a (EFla) gene having the nucleotide sequence SEQ ID NO: 10, or a nucleic acid having at least 70% sequence identity with the sequence of SEQ ID NO: 10, said intron being situated downstream of said 5' UTR region and upstream of the transcription initiation site,
   said transcription unit having the nucleotide sequence SEQ ID NO: 33, or a nucleotide add haying at least 70% sequence identity with the sequence SEQ ID NO: 33, and having said transcription activation activity, said promoter activity, and said mRNA stabilization and translation facilitator activity,
   wherein said transcription unit is capable of generating a volume production of a protein of interest greater than that obtained with a combination of said CMVie virus enhancer combined with said promoter region of CDK9 alone.

2. An expression vector comprising at least one transcription unit as defined according to claim 1 and at least one cloning site allowing the integration of a nucleotide acid coding for a protein of interest.

3. An expression vector comprising at least one transcription unit as defined according to claim 1 and at least one site for the site-specific recombination allowing the integration of a nucleotide acid coding for a protein of interest.

4. The expression vector according to claim 2, also comprising a eukaryotic resistance gene, a bacterial resistance gene, a bacterial origin of replication and a dedicated gene amplification unit.

5. The expression vector according to claim 2, in which said protein of interest is chosen from the group constituted by the proteins participating in coagulation or an immunoglobulin, cytokines, hormones, growth factors or complement factors and any fusion protein.

6. A host cell comprising an expression vector as defined in claim 2.

7. The host cell according to claim 6, said host cell being the YB2/0 cell line.

8. An expression system comprising an expression vector as defined according to claim 2 and a host cell comprising said expression vector allowing the expression of a protein of interest encoded by a nucleotide acid.

* * * * *